US012692293B2

(12) United States Patent
Dell 'Accio et al.

(10) Patent No.: US 12,692,293 B2
(45) Date of Patent: Jul. 28, 2026

(54) AGRIN POLYPEPTIDE AND USES THEREOF

(71) Applicant: QUEEN MARY UNIVERSITY OF LONDON, London (GB)

(72) Inventors: Francesco Dell 'Accio, London (GB); Suzanne Elizabeth Ruane, London (GB)

(73) Assignee: Queen Mary University of London, London (GB)

( * ) Notice: Subject to any disclaimer, the term of this patent is extended or adjusted under 35 U.S.C. 154(b) by 622 days.

(21) Appl. No.: 18/021,721

(22) PCT Filed: Aug. 17, 2021

(86) PCT No.: PCT/GB2021/052126
§ 371 (c)(1),
(2) Date: Feb. 16, 2023

(87) PCT Pub. No.: WO2022/038346
PCT Pub. Date: Feb. 24, 2022

(65) Prior Publication Data
US 2024/0025955 A1 Jan. 25, 2024

(30) Foreign Application Priority Data

Aug. 17, 2020 (GB) ..................................... 2012804

(51) Int. Cl.
| | |
|---|---|
| *A61K 38/17* | (2006.01) |
| *A61P 19/02* | (2006.01) |
| *C07K 14/47* | (2006.01) |
| *C12N 5/077* | (2010.01) |
| *A61K 38/00* | (2006.01) |

(52) U.S. Cl.
CPC .......... *C07K 14/4725* (2013.01); *A61K 38/17* (2013.01); *A61P 19/02* (2018.01); *C12N 5/0655* (2013.01); *A61K 38/00* (2013.01); *C12N 2501/998* (2013.01)

(58) Field of Classification Search
CPC ..... C07K 14/4725; C07K 14/47; A61K 38/17
See application file for complete search history.

(56) References Cited

U.S. PATENT DOCUMENTS

2009/0054300 A1* 2/2009 Abbas ..................... A61P 35/02
435/320.1
2015/0031057 A1* 1/2015 Hettwer ................ G01N 33/68
435/23

FOREIGN PATENT DOCUMENTS

CN 109734790 A 5/2019
WO 2005051988 A2 6/2005

OTHER PUBLICATIONS

R&D Systems, product No. 6624-AG (Feb. 6, 2018).*
Written Opinion of the International Searching Authority and International Search Report; European Patent Office D-80298 Munich, Germany, International application No. PCTGB20211052126; Date of mailing of the international search report: Dec. 10, 2021.
Aug. 11, 2005 (Aug. 11, 2005), "Human PRO polypeptide Seq ID No 391 .", retrieved from EBI accession No. GSP:AEA23849 Database accession No. AEA23849.
Eldridge Suzanne et al: "Agrin mediates chondrocyte homeostasis and requires both LRP4 and a-dystroglycan to enhance cartilage formation in vitro and in vivo", Annals of the Rheumatic Diseases, vol. 75, No. 6, Jun. 1, 2016 (Jun. 1, 2016), pp. 1228-1235, XP055846961.
Grässel Susanne et al: "Recent advances in the treatment of osteoarthritis", FI OOOresearch, vol. 9, Jan. 1, 2020 (Jan. 1, 2020), p. 325, XP055868457, DOI: 1 0.1 2688/f1OOOresearch.221 15.1.
Eldridge Suzanne E et al: "Agrin induces long-term osteochondral regeneration by supporting repair morphogenesis", Sci. Transl. Med, vol. 12, No. 559, Sep. 2, 2020 (Sep. 2, 2020), p. eaax9086, XP055846954.
Kingwell Katie: "Doubling down on osteoarthritis", Nature Reviews Drug Discovery, Nature Publishing Group, GB, vol. 19, No. 1 1 , Oct. 2, 2020 (Oct. 2, 2020), p. 753, XP037282807, ISSN: 1474-1776, DOI: 1 0.1 038/D41573-020-00174-1.

* cited by examiner

Primary Examiner — Xiaozhen Xie
(74) Attorney, Agent, or Firm — Klarquist Sparkman, LLP

(57) ABSTRACT

The present invention relates to novel polypeptides, which are derived from a human agrin or a variant of a human agrin. The invention also concerns uses of the polypeptides and compositions comprising the polypeptides.

14 Claims, 63 Drawing Sheets
Specification includes a Sequence Listing.

Bovine chondrocytes

Bovine chondrocytes

Bovine chondrocytes

Fig. 3H
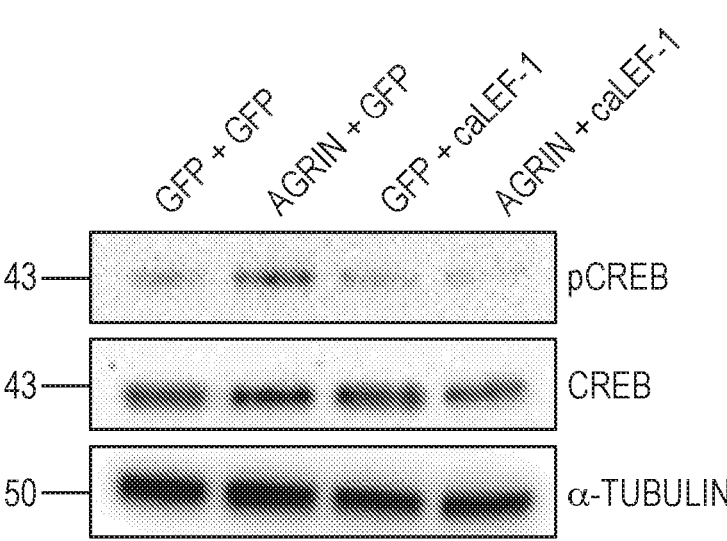
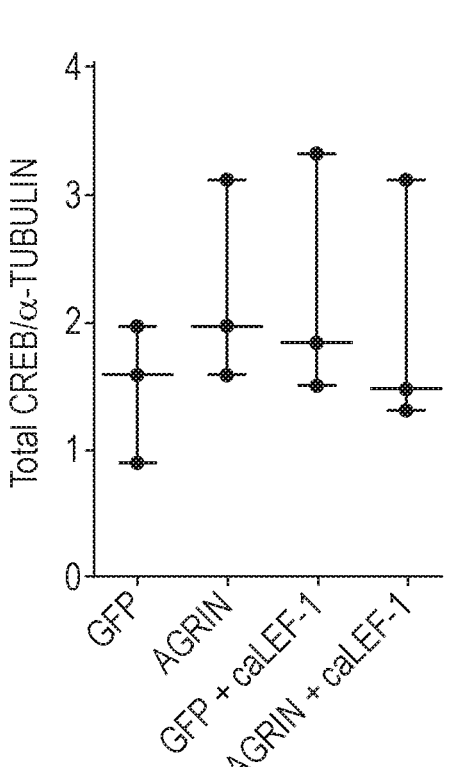
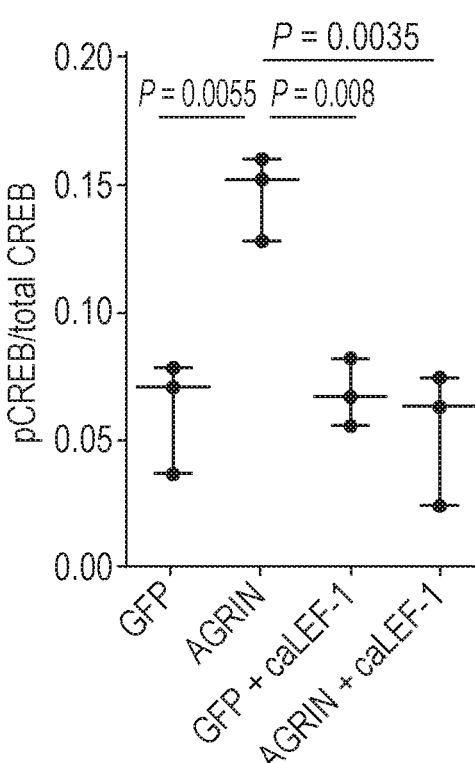

C28/I2 cells

C28/I2 cells

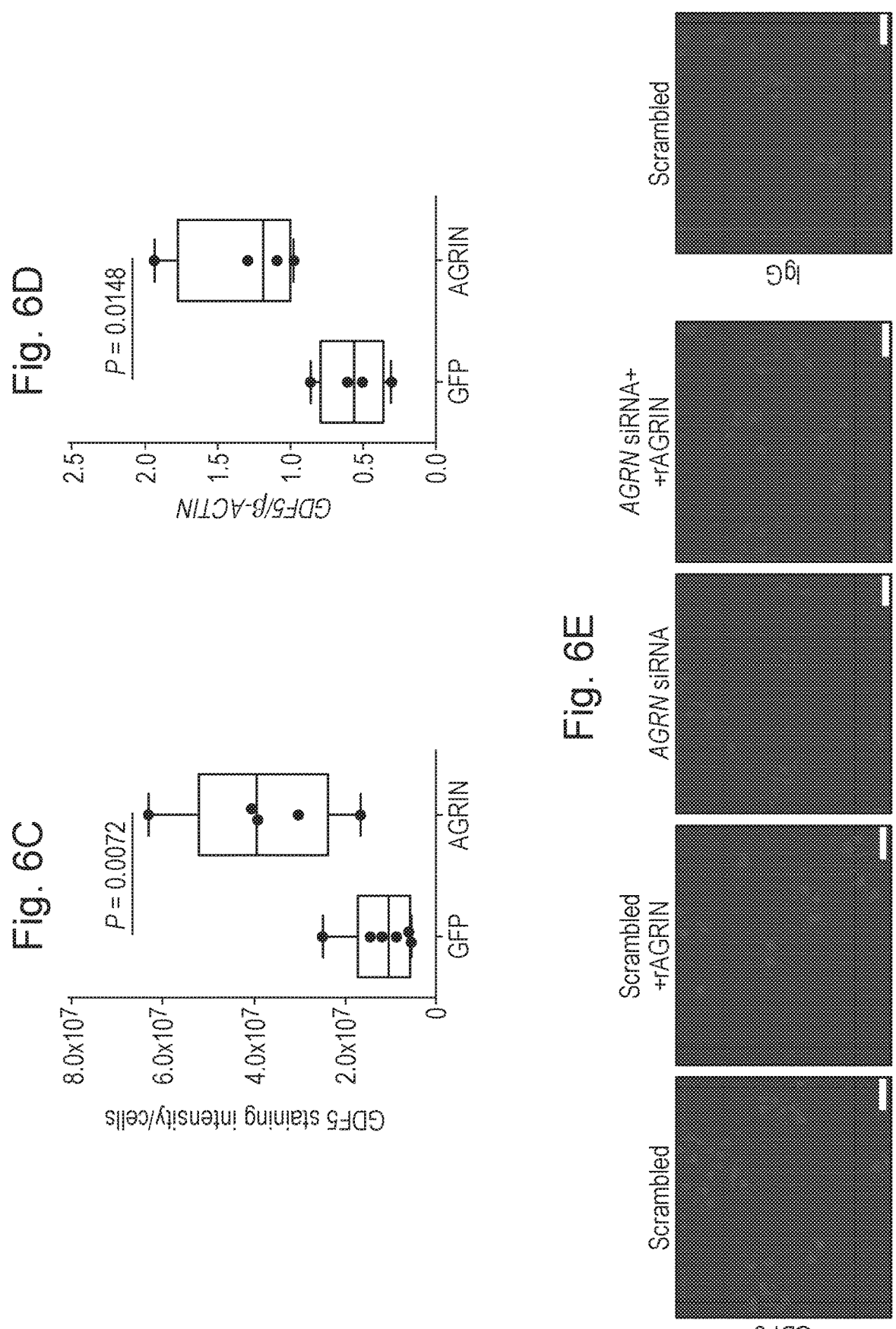

Fig. 6F
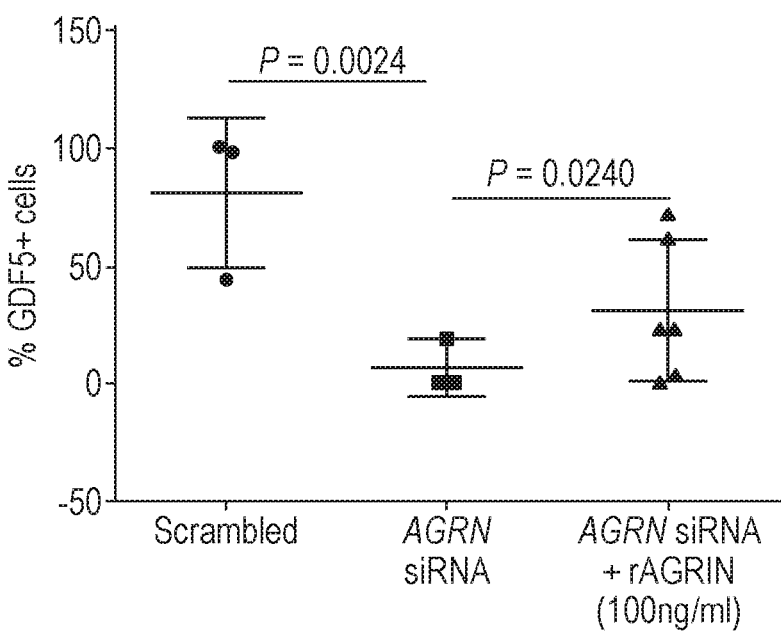
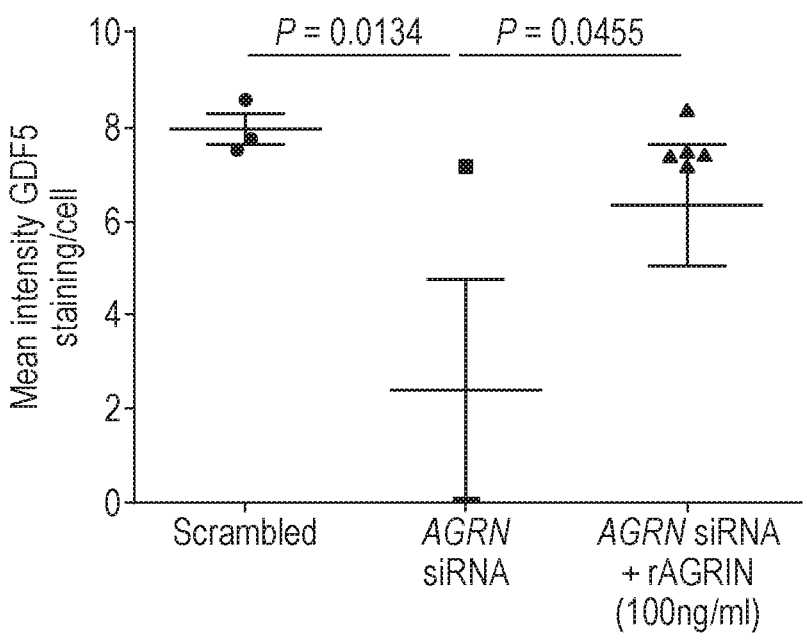

Fig. 6I          C28/I2 cells
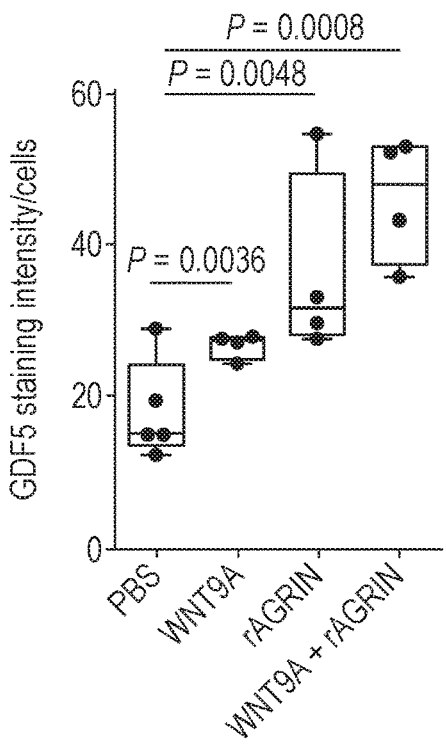
Fig. 6J          HEK293 cells
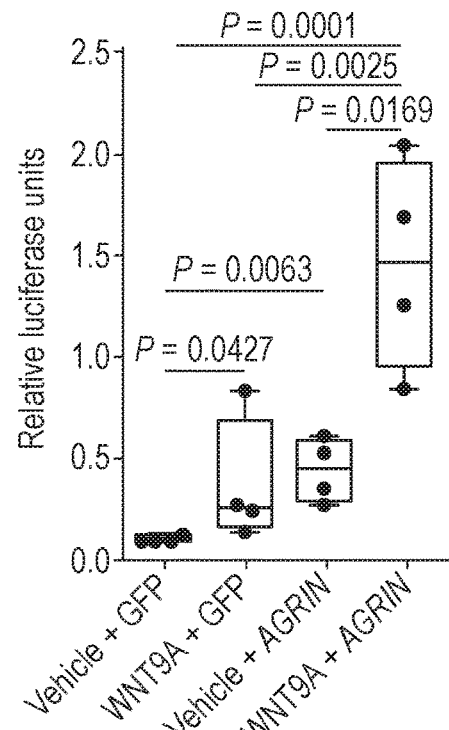

Fig. 6K
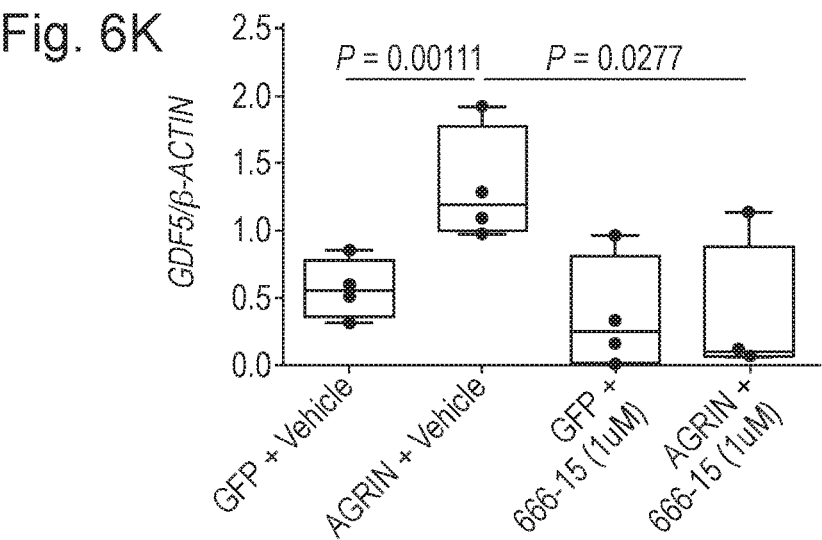
Fig. 6L
Fig. 6M
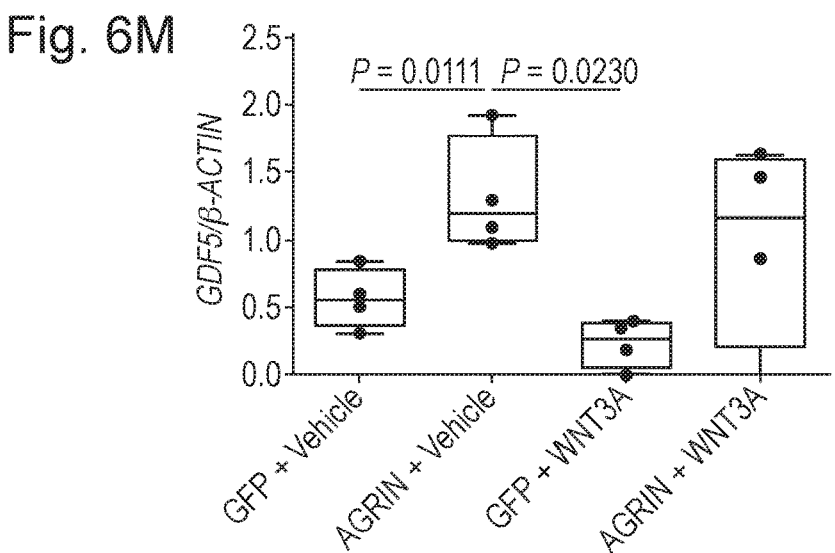

Repair mesenchyme

Synovial membrane

Fig. 8A
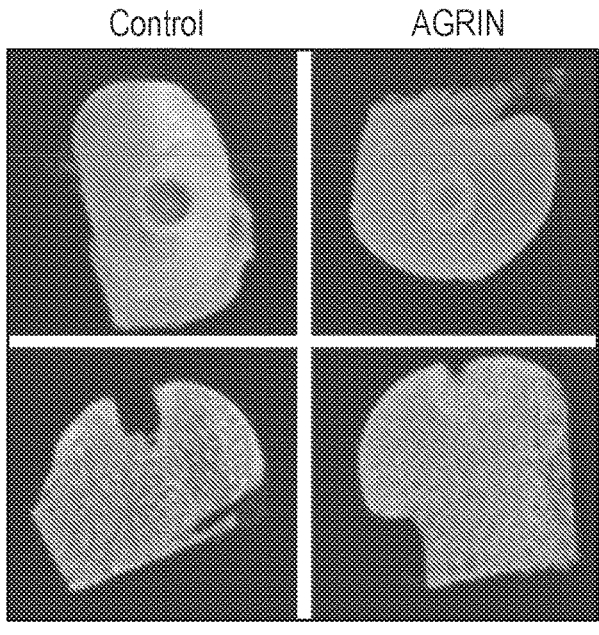
Fig. 8B
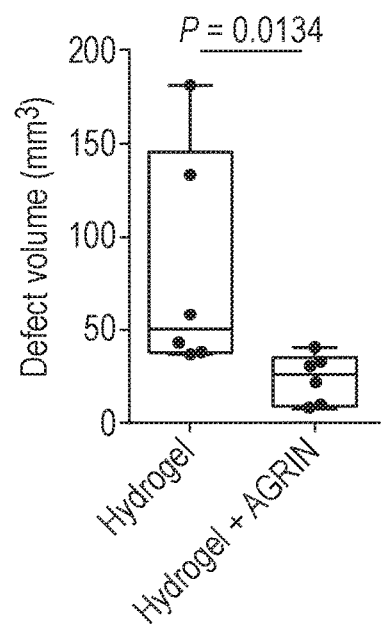
Fig. 8C
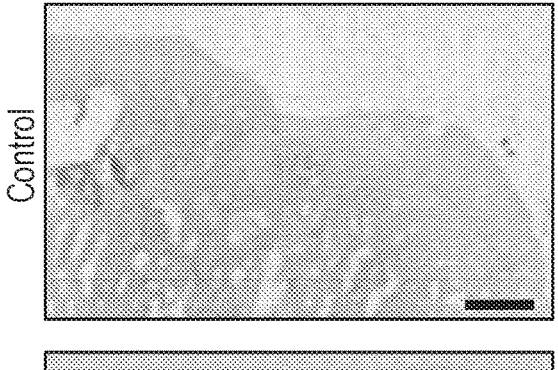
Fig. 8D
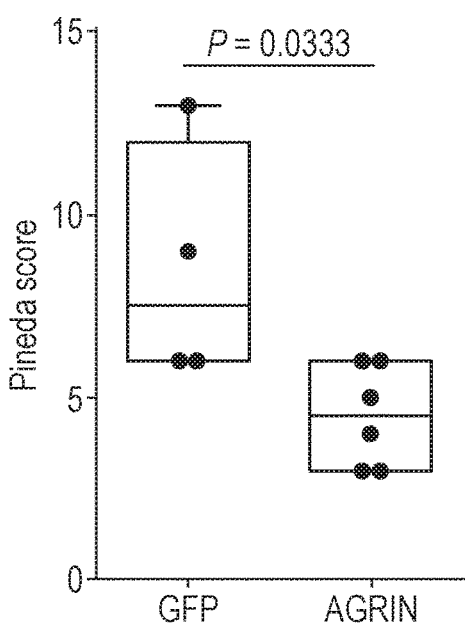

Unoperated 1 mm

Untreated

500 μm

Fig. 14C
3 weeks post surgery
PBS
rAGRIN
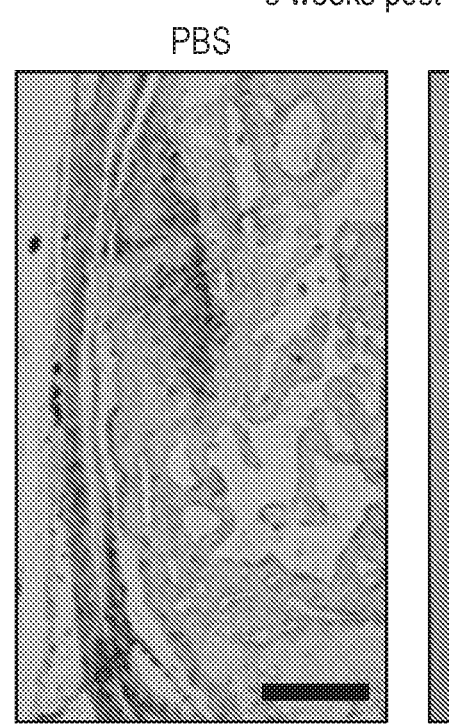 
Fig. 14D
Synovial membrane
$P = 0.062$
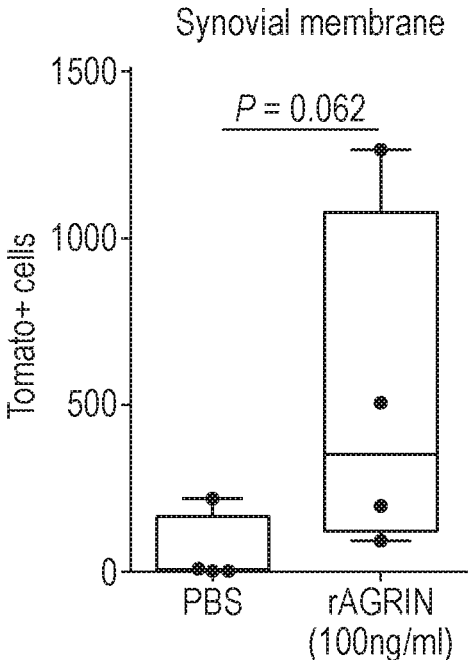
Fig. 14E
Repair mesenchyme
$P = 0.0047$
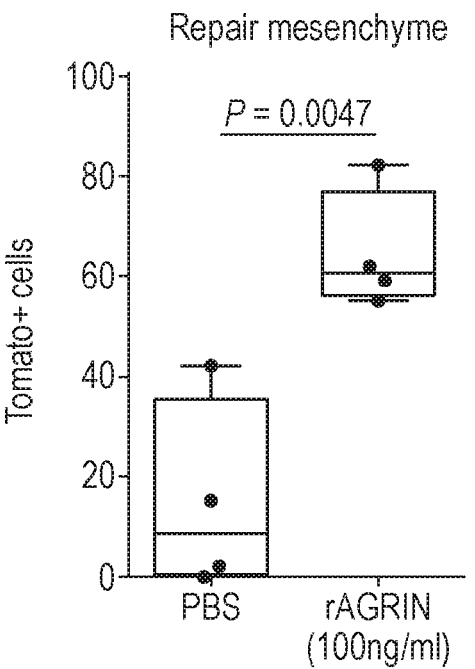

Fig. 18A
Fig. 18B
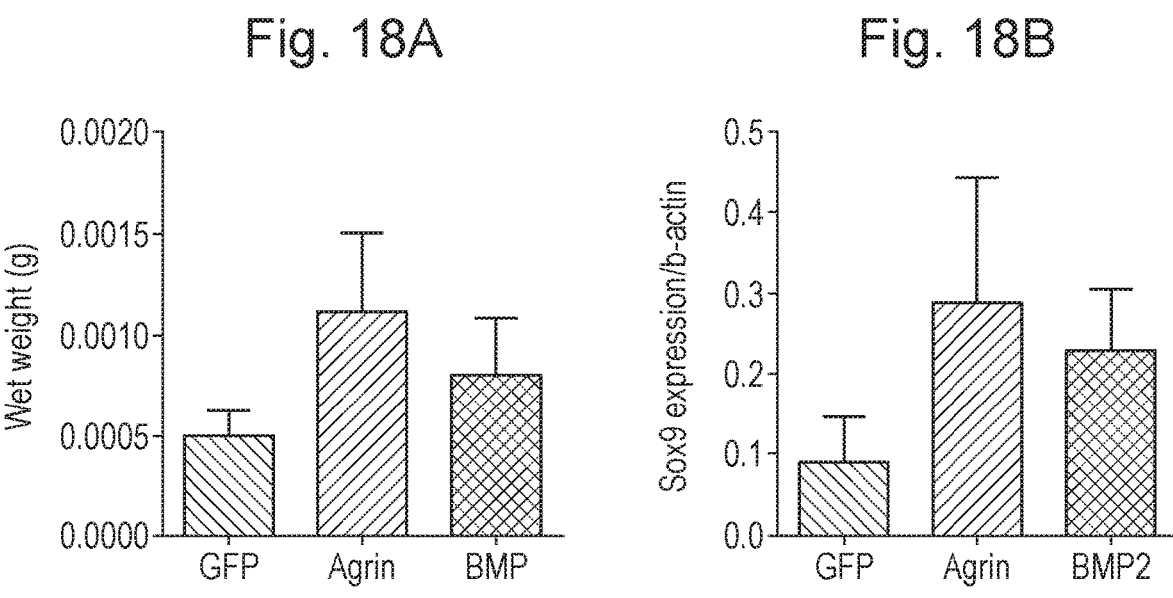
Fig. 18C
Fig. 18D
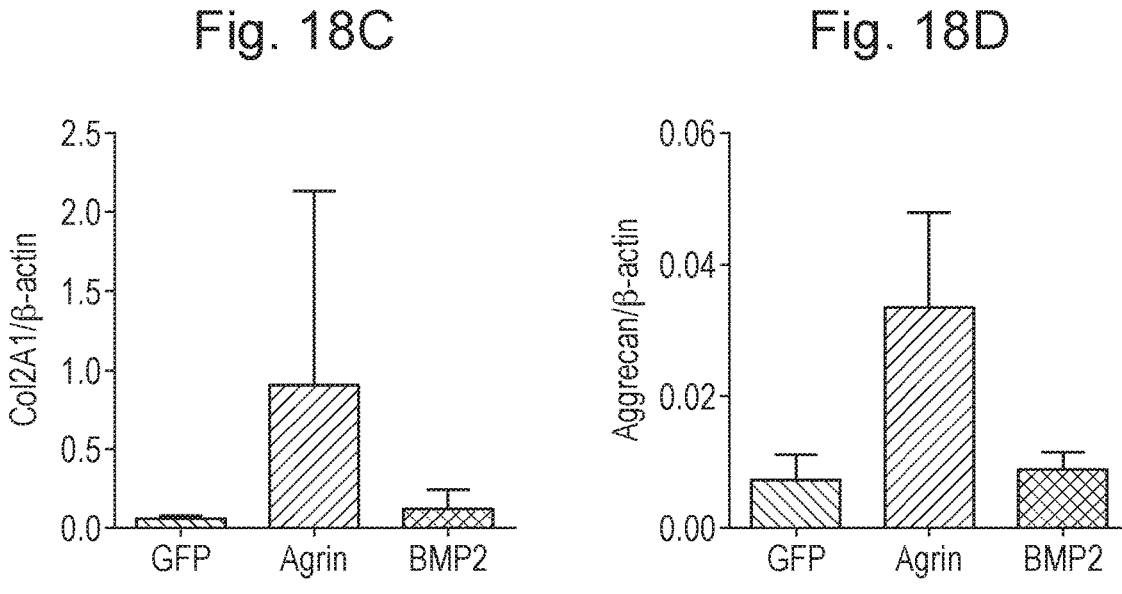

Agrin
(Recombinant rat non-neuronal)

Agrin
(Recombinant rat non-neuronal)

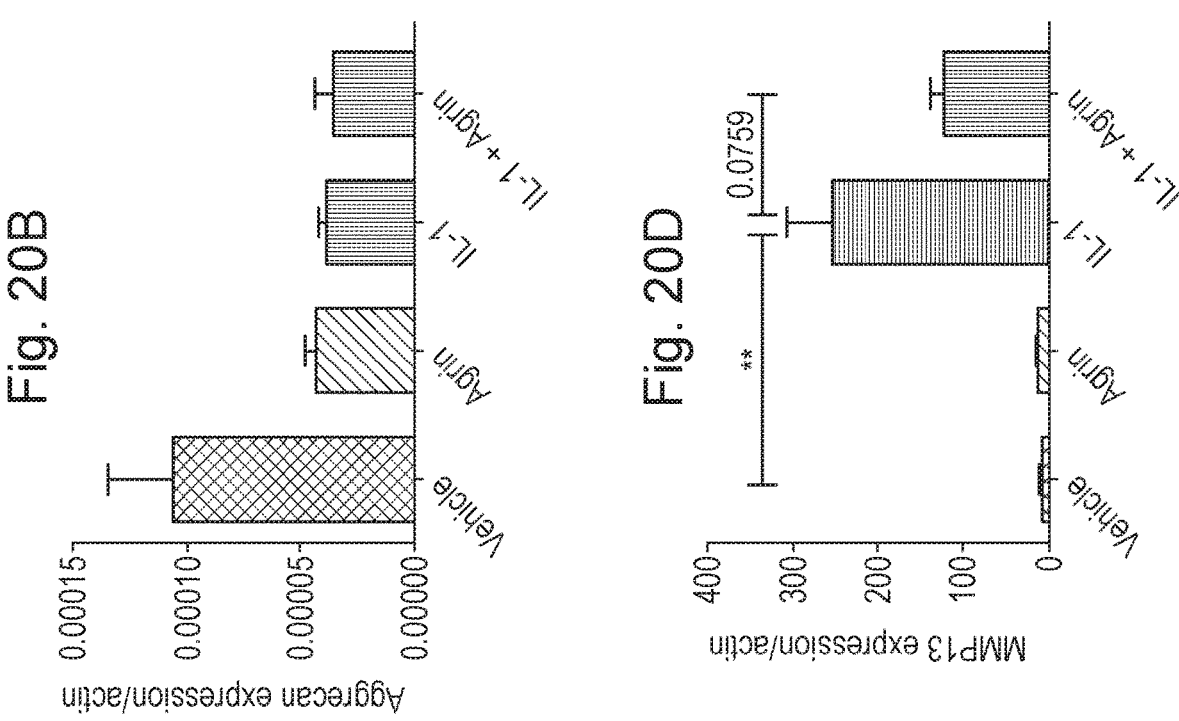
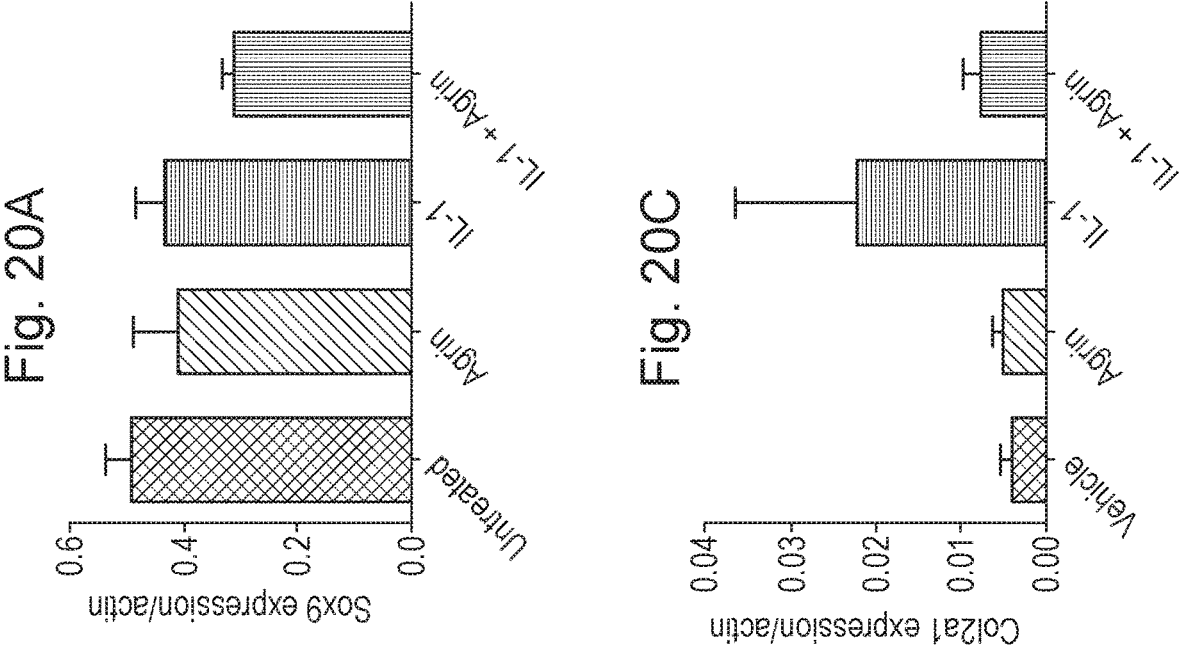

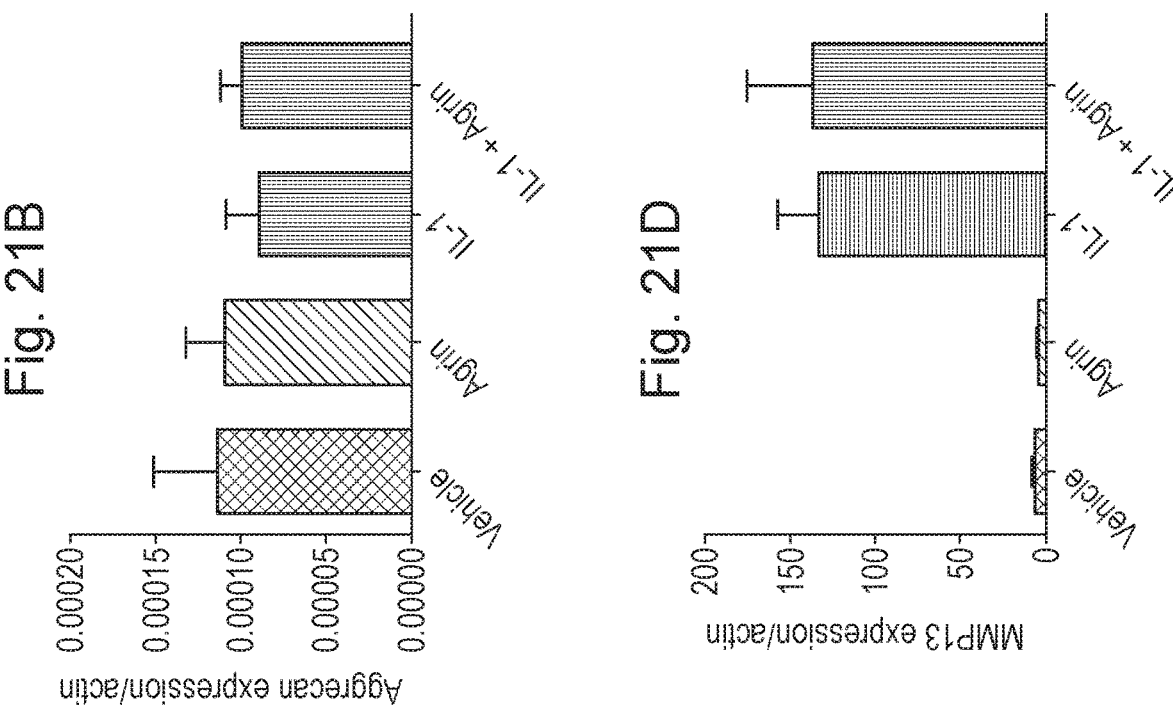
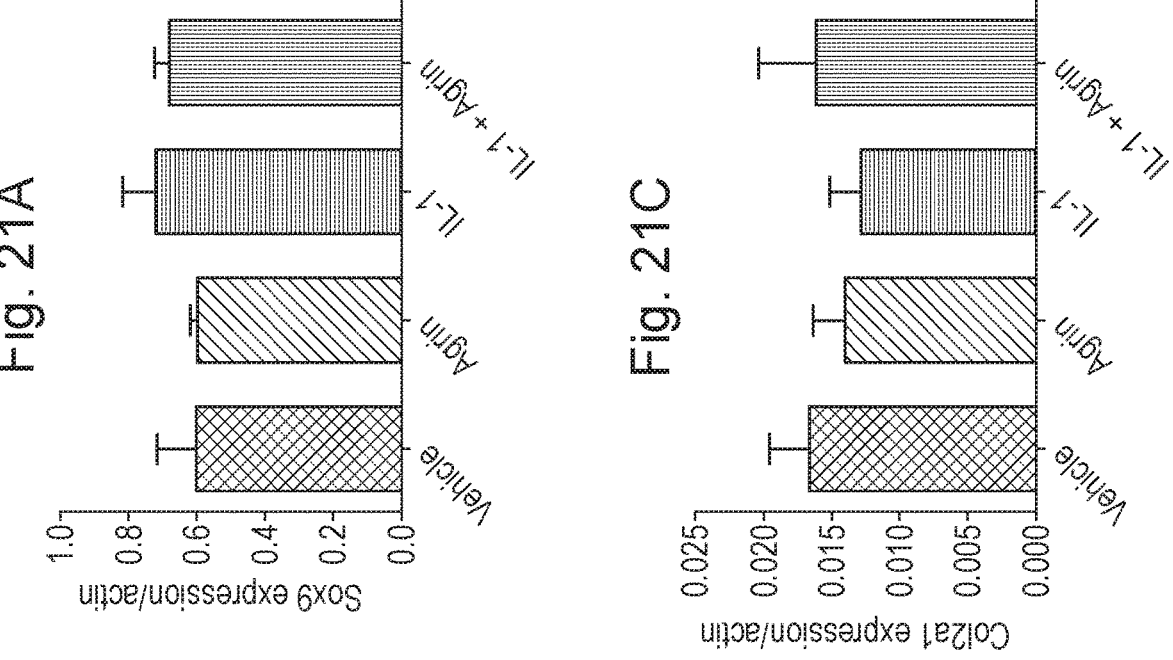

Fig. 28A
hSM-MSCs
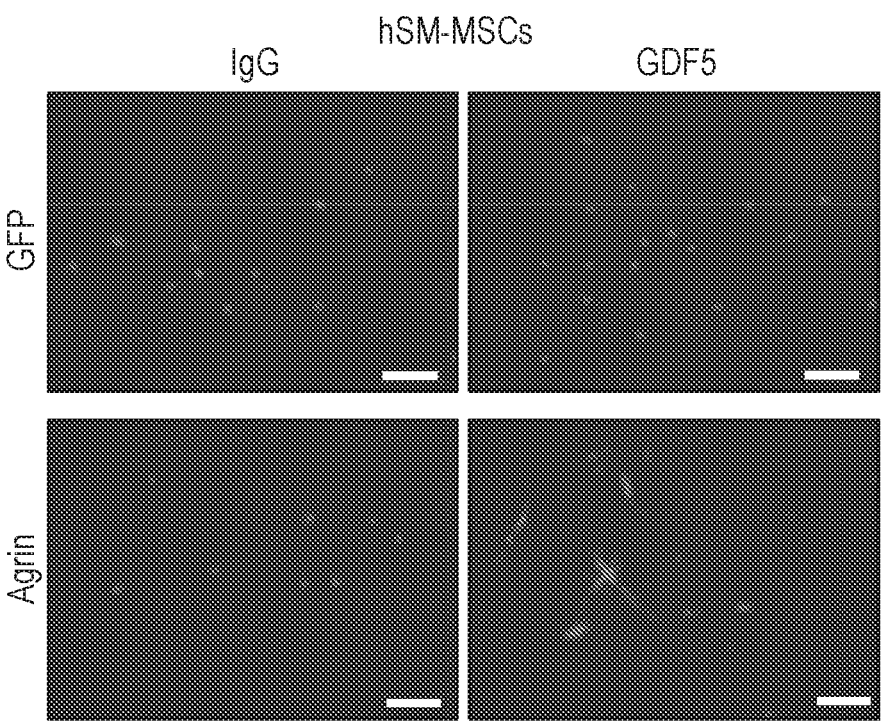
Fig. 28B
C28/I2 cells
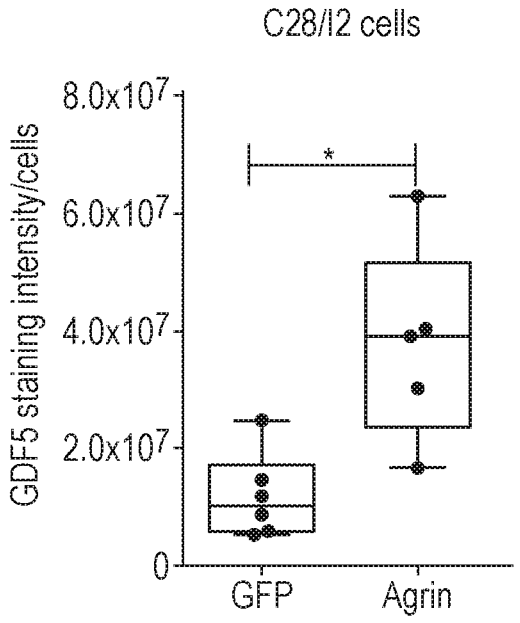
Fig. 28C
C28/I2 cells 100k OVCR3 cells per well (48 well plate - plated 24hrs and stimulate 24hrs)

Agrin-induced CREB activation

AGRIN POLYPEPTIDE AND USES THEREOF

FIELD OF THE INVENTION

The present invention relates to novel polypeptides, which are derived from a human agrin or a variant of a human agrin. The invention also concerns uses of the polypeptides and compositions comprising the polypeptides.

BACKGROUND OF THE INVENTION

Articular cartilage overlies subchondral bone at the joint surface and enables the frictionless movement of joints. Whereas bone has a high turnover and heals well, cartilage is avascular, has a low turnover, and often fails to repair after injury. This results in further cartilage loss and osteoarthritis, the most common form of arthritis, which causes pain and disability. Currently, there is no pharmacological therapy to restore cartilage or slow cartilage loss. Osteoarthritis is therefore, along with cardiovascular disease, the leading cause of chronic disability, costing around 1.5-2% of the gross domestic product (GDP) for westernized countries.

Joint surface defects are common and, when exceeding a critical size, heal poorly. When successful, the repair of small osteochondral defects involves trafficking of specialized mesenchymal stem cells (MSCs) ontogenetically derived from the growth differentiation factor 5 (GDF5)-expressing cells of the embryonic joint interzone to the injury site. During embryonic development, MSCs are recruited from SOX9-expressing progenitor cells, transiently express GDF5, and give rise to the articular cartilage, menisci, and ligaments. In adulthood, GDF5-lineage progenitor cells persist in the synovial membrane (SM-MSCs). At the bottom of the defect, the repair cartilage is invaded by vessels and replaced by bone through endochondral bone formation, which proceeds towards the surface of the defect and stops at the level of the osteochondral junction. The most superficial layer of cartilage remains avascular and is resistant to endochondral bone formation. Although this morphogenetic process takes place over several weeks in rodents and several months in humans, at the molecular level, the mesenchyme becomes patterned long before morphological changes become obvious. Such patterning displays striking similarity to that of developing joints during embryonic morphogenesis.

During skeletal development, the chondrogenic mesenchyme forming the skeletal templates becomes segmented by the joint interzones, where specific molecular markers—including WNT9A and GDF5, a member of the bone morphogenetic protein (BMP) family of morphogens—indicate the location where joints will form. Through the process of cavitation, a fissure forms in the center of the joint interzones, eventually separating the skeletal elements. Meanwhile, the center of the cartilaginous template undergoes vascular invasion and chondrocytes undergo hypertrophy (expressing markers such as COL10A1) and are eventually replaced by bone. In the long bones, this process starts at the center (diaphysis) and proceeds towards the growth plate. Secondary ossification centers then form near the joints, in the epiphysis, to form the subchondral spongiosa containing bone marrow. The last few layers of chondrocytes closest to the joint cavity are spared from undergoing endochondral bone formation and form the articular cartilage. Lineage tracking experiments have established that the cells that form the articular cartilage (which persists throughout life), and those of the epiphyseal cartilage (destined to be replaced by bone), derive from distinct lineages, the former expressing GDF5 during embryonic joint formation.

Members of the WNT family of morphogens (WNT4, WNT9A, and WNT16) are the earliest markers of the joint interzone. The activation of the WNT pathway is both required and sufficient to initiate the process of joint morphogenesis. The ectopic expression of Wnt9a was shown to trigger the ectopic expression of other joint interzone markers including Gdf5. During development, WNT signaling prevents the premature differentiation of the joint interzone cells into mature chondrocytes. In adulthood, WNT signaling maintains a population of chondroprogenitors at the surface of the cartilage by preventing their differentiation into mature chondrocytes. Due to its anti-chondrogenic effect however, excessive activation of WNT signaling within the joint predisposes to osteoarthritis.

WNTs are secreted signaling molecules involved in the regulation of cell proliferation, polarity, morphogenesis and differentiation during both development and adulthood. In the absence of WNTs, the intracellular protein β-catenin is constitutively phosphorylated by GSK-3β and is degraded through the proteasome pathway. In the presence of so called "canonical" WNTs such as WNT1, WNT3A, or WNT8, the heterodimerization of frizzled (FZD) receptors and their co-receptors LRP5 and 6 results in de-activation of GSK-3β and consequent stabilization of β-catenin. Stabilized β-catenin is transported to the nucleus where it interacts with the transcription factors TCF/LEF and activates transcription of target genes. Other WNT ligands, such as WNT5A, activate other calcium-dependent pathways, collectively denominated "non-canonical". One of these non-canonical pathways is mediated by the intracellular kinase CaMKII and the transcription factor CREB. In many cells, including articular chondrocytes, activation of the non-canonical WNT signaling results in inhibition of the canonical pathway.

The present inventors have found that agrin, a signaling proteoglycan (encoded by the gene AGRN) best known for its role at the neuromuscular junction, where it stabilizes the clustering of the acetylcholine receptors by binding to its receptor LRP4, is an orchestrator of repair morphogenesis at the joint surface by modulating multiple signaling pathways. Agrin is composed of a large N-terminal portion that binds to components of the basal membrane and a biologically active C-terminal portion encompassing three globular domains separated by EGF-like repeats. Agrin is expressed in a splice isoform devoid of the y and z motifs, playing a role not only in differentiation of mature articular chondrocytes but also in chondrogenesis and in the repair of osteochondral defects.

SUMMARY OF THE INVENTION

The invention provides a soluble polypeptide comprising the amino acid sequence of SEQ ID NO: 2 and having the ability to induce chondrocyte differentiation and/or chondrogenesis, which polypeptide is a fragment of a human agrin or of a variant of a human agrin.

The invention also provides a polynucleotide which encodes a polypeptide of the invention.

The invention also provides a composition comprising a polypeptide of the invention and/or a polynucleotide of the invention, which comprises at least one pharmaceutically acceptable diluent, carrier or preservative.

The invention also provides a method of treating or preventing a disease or condition in a subject, the method comprising administering to the subject a polypeptide of the invention, a polynucleotide of the invention, or the composition of the invention.

The invention also provides a method for inducing stem cells, wherein the method comprises contacting the stem cells with a polypeptide of the invention, a polynucleotide of the invention, or a composition of the invention.

5

Figure 1A:
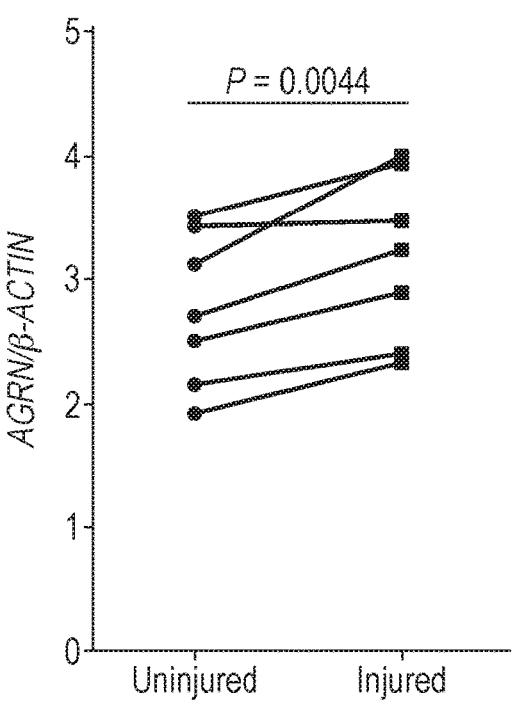
FIG. 1 shows that Agrin is upregulated after cartilage injury, induces chondrogenesis in MSCs, and is chondrogenic in joint-resident MSCs. (A) RT-PCR for AGRN of human adult articular cartilage explants after mechanical injury or in control conditions (n=7), paired t-test P=0.0044. (B) AGRIN immunostaining of human adult articular cartilage explants after mechanical injury or in control conditions; bars 50 μm, counterstained with DAPI. (C) Quantification of AGRIN staining normalized for number of cells (n=3), paired t-test P=0.0222. (D) RT-PCR for AGRN in C28/I2 chondrocytes treated for 3 days with IL-1β (20 ng/ml, n=9, t-test P<0.0001) or (E) TNF-α (20 ng/ml, n=8, t-test P=0.0080). (F) Alcian blue staining and spectrophotometric quantitation of glycosaminoglycans in micromasses of SM-MSCs over a feeder of growth-arrested COS7 cells overexpressing AGRIN (n=8), GFP (n=7), or TGF-β (n=8) for 6 days, one way ANOVA with Tukey's HSD post-hoc GFP vs AGRIN P<0.0001, GFP vs TGF-β P=0.0028, AGRIN vs TGF-β P<0.0001; bars 0.5 mm (G) RT-PCR for SOX9 of SM-MSC micromasses overexpressing AGRIN or GFP (n=4), t-test P=0.0402.
Figure 1B:
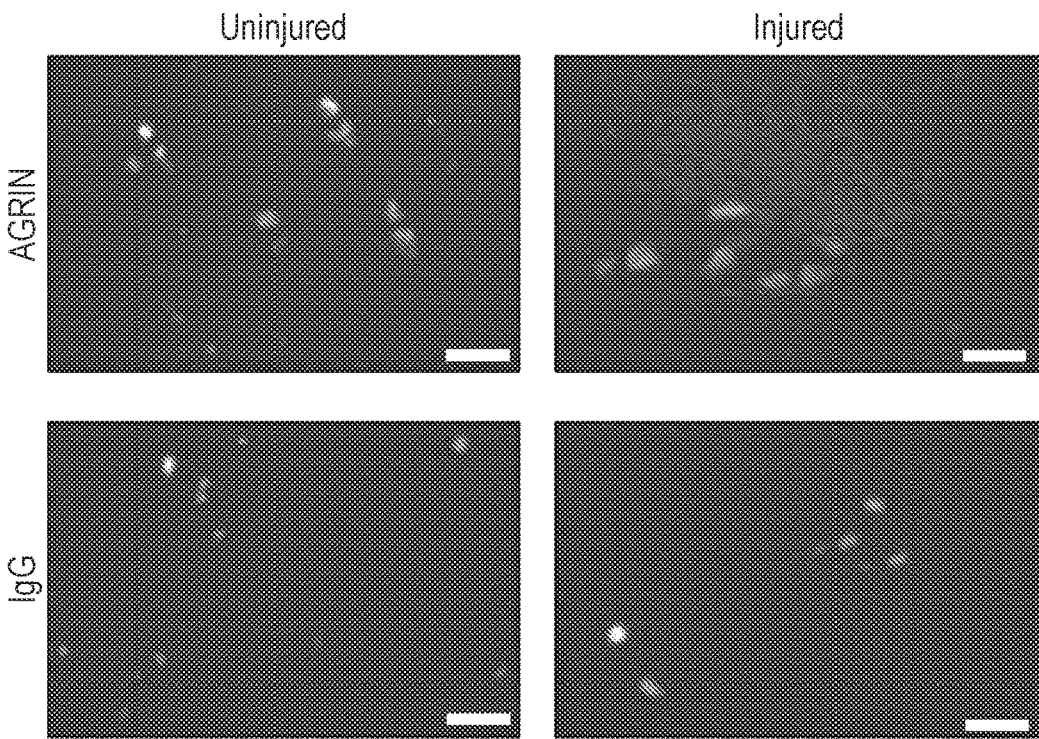
Figure 1C:
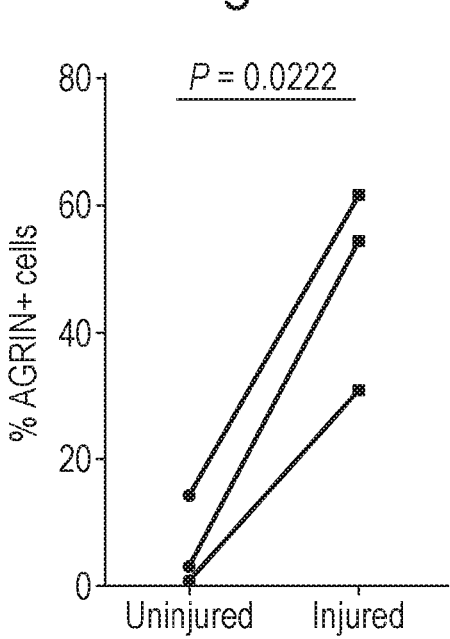
Figure 1D:
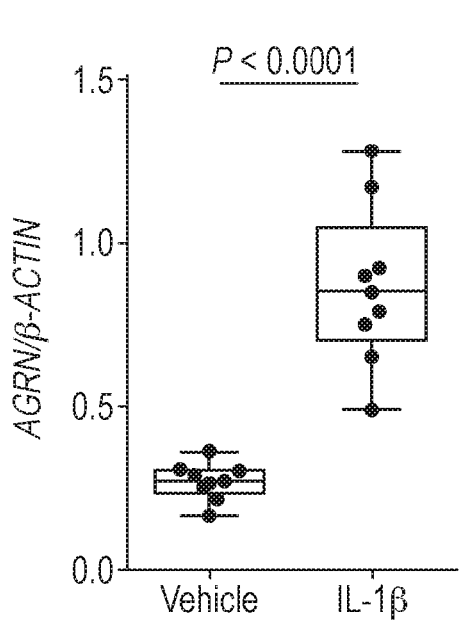
Figure 1E:
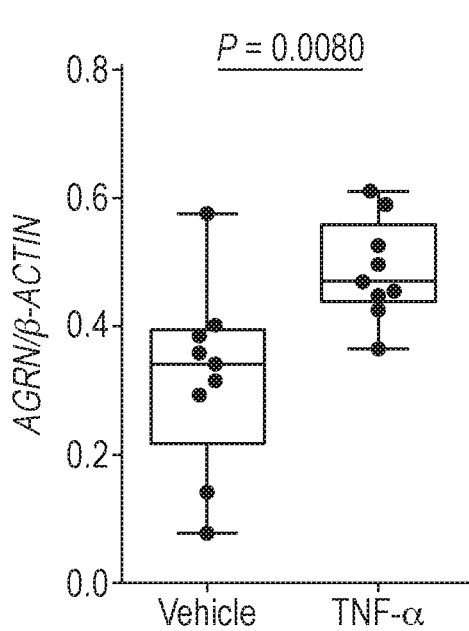
Figure 1F:
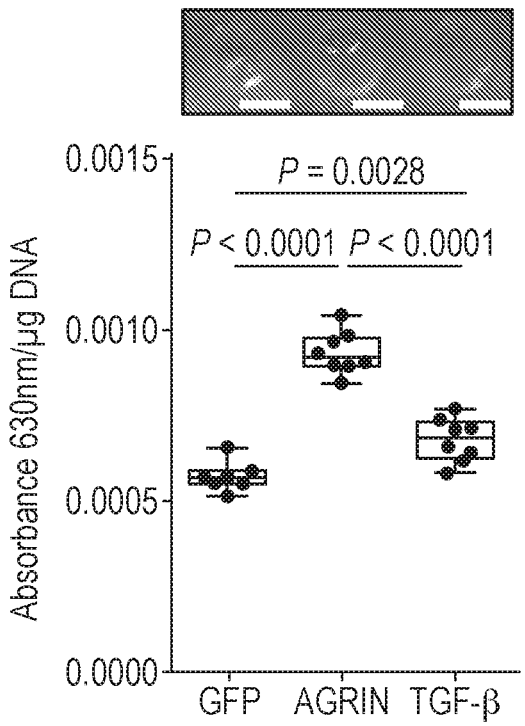
Figure 1G:
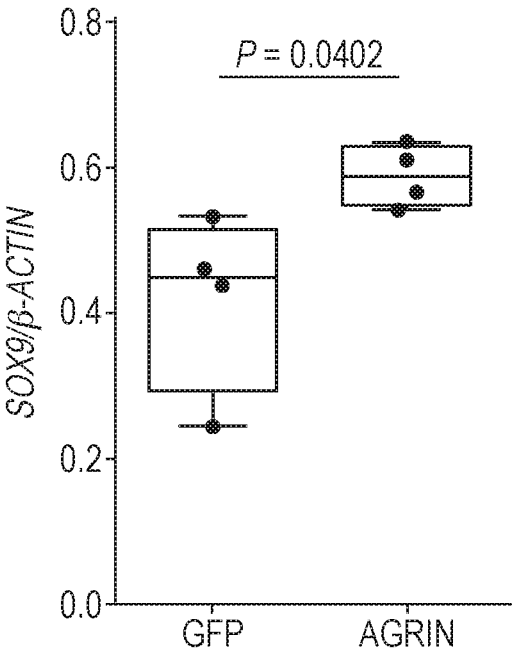

FIG. 5 shows that Agrin supports repair morphogenesis and articular cartilage formation in vivo. (A) Representative safranin 0 staining of the femoral condyle of C57BL/6 mice 8 weeks after the generation of an osteochondral defect filled with a collagen gel containing either AGRIN or GFP (n=4); bars 200 μm. The dotted lines represent the approximate location of the original defect. M=meniscus; F=Femur; T=tibia (B) Quantification of Safranin 0 staining in the repair cartilage layer (n=4). T-test after logarithmic transformation P=0.041. (C) Pineda score of osteochondral defect repair after 8 weeks (lower scores indicate better repair) (n=4), Mann-Whitney U test, P=0.0140. (D) Histomorphometric quantification of the residual bone defect. (n=4; Welch Two Sample t-test following log transformation; P=0.008714). (E) Quantification of the non-differentiated (fibroblast-like) portion of the repair mesenchyme (n=4; Welch Two Sample t-test following log transformation; P=0.0021).

FIG. 6 shows that Agrin supports GDF5 expression in synovial membrane MSCs. (A and B) GDF5 immunocytochemistry of SM-MSCs (A) or C28/I2 cells (B) transfected with AGRIN or GFP and cultured in monolayer for 24 hrs (n=4); bars 50 μm. DAPI counterstain. (C) Quantification of GDF5 staining intensity in (B) normalized by number of cells; t-test P=0.0072. (D) RT-PCR for GDF5 in C28/I2 cells transfected with AGRIN or GFP and cultured for 3 days in micromass (n=4); t-test P=0.0148. (E) GDF5 immunocytochemistry of C28/I2 cells cultured in monolayer for 24 hrs following transfection with Scrambled or AGRN siRNA in the presence or absence of rAGRIN (a soluble polypeptide of the invention); bars 50 (F) Quantification of % GDF5+ cells (E) Scrambled n=3; AGRN siRNA n=3; AGRN siRNA+rAGRIN n=6) one-way ANOVA Scrambled vs AGRN siRNA P=0.0024, AGRN siRNA vs AGRN siRNA+rAGRIN P=0.024; and mean intensity per cell, one-way ANOVA using generalized linear model followed by pairwise comparison within each Scrambled vs AGRN siRNA P=0.0134, AGRN siRNA vs AGRN siRNA+rAGRIN P=0.0455. (G) RT-PCR for GDF5 in C28/I2 cells transfected with Scrambled or AGRN siRNA cultured for 3 days in micromass (n=4); t-test P=0.0358. (H) Immunostaining for GDF5 in C28/I2 chondrocytes treated with recombinant AGRIN (300 ng/ml) and/or WNT9A (200 ng/ml) for 24 hrs; bars 50 μm; and (I) quantification (n=4); one-way ANOVA with Tukey test for multiple comparisons P=0.0008; PBS vs WNT9A P=0.0036, PBS vs rAGRIN P=0.0048, PBS vs WNT9A+AGRIN P=0.0008. (J) CREB reporter assay in HEK293 cells treated with recombinant AGRIN (300 ng/ml) and/or WNT9A (200 ng/ml) (n=4); one-way ANOVA with Tukey test for multiple comparisons P=Vehicle+GFP vs WNT9A+GFP P=0.0427630, Vehicle+GFP vs Vehicle+AGRIN P=Vehicle+GFP vs WNT9A+AGRIN P<0.0001, Vehicle+AGRIN vs WNT9A+AGRIN P=0.0169, WNT9A+GFP vs WNT9A+AGRIN P=0.0025. (K to M) RT-PCR for GDF55 mRNA in C28/I2 cells transfected with AGRIN or GFP plasmids, cultured in micromass for 4 days and treated in the presence of (K) 666-15 (1 μM) or vehicle or (L) co-transfected with caLEF1 plasmid or (M) recombinant WNT3A (200 ng/ml) (n=4); one-way ANOVA with Tukey's HSD post-hoc (K) GFP vs AGRIN P=0.0111, AGRIN+ vehicle vs AGRIN666-15 P=0.0277, (L) GFP vs AGRIN P=0.0111, AGRIN vs GFP+caLEF1 P=0.0003, AGRIN vs AGRIN+caLEF1 P=0.00033, (M) AGRIN+vehicle vs GFP+ WNT3A P=0.0230.

FIG. 7 shows that Agrin-induced joint surface repair is associated with increased recruitment of Gdf5-lineage joint stem cells and CREB phosphorylation in the repair mesenchyme. (A) Pineda score of Gdf5:Tom transgenic mice 8 weeks after the generation of an osteochondral defect filled with either Agrin or GFP (n=9 GFP, n=10 AGRIN; Mann-Whitney U test; P=0.01994). (B) Immunohistochemistry for Tomato in the defect of Gdf5:Tom transgenic mice 3 weeks after the generation of an osteochondral defect filled with a collagen gel containing either AGRIN or GFP; sm=synovial membrane; rm=repair mesenchyme (n=6). Boxed region shown at higher magnification below; bars 50 (C) Quantification of Tom+ cells in the repair mesenchyme and (D) in the synovial membrane; t-test (C) P=0.0002, (D) P=0.0398. (E) Safranin 0 (left panels) and immunofluorescence (right) for Tomato (red) and Collagen type 2 (green) 8 weeks post-surgery. Boxed region shown at higher magnification below; bars 100 μm Immunohistochemistry (F) and quantification (G) of phospho-CREB in the repair mesenchyme of Gdf5;Tom mice treated with AGRIN or control, 3 weeks after the generation of an osteochondral defect (n=3); phosphatase treatment was used as staining control; (F) Welch two sample t-test of squared values P=0.04058; bars 100 μm.

Figure 8E:
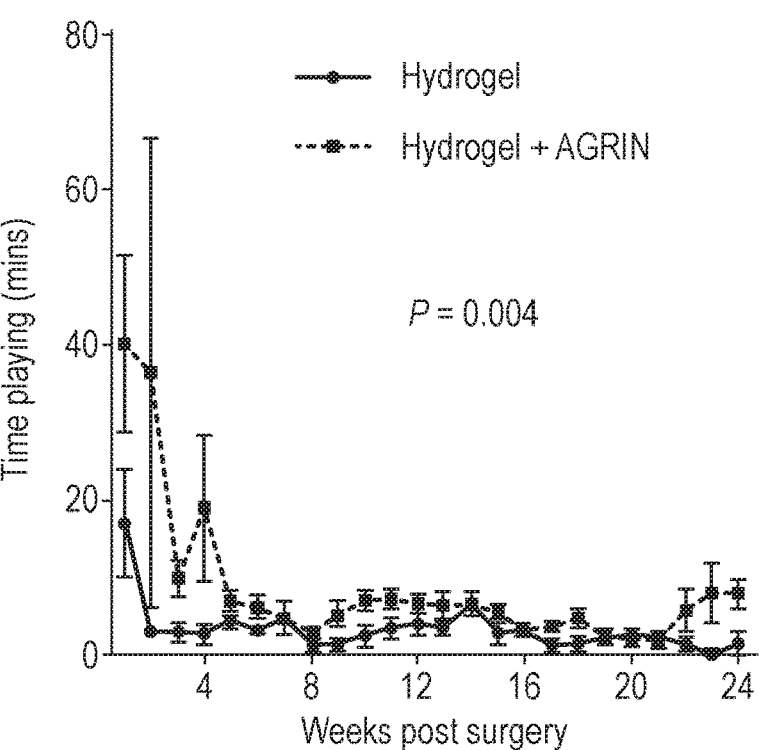
Figure 8F:
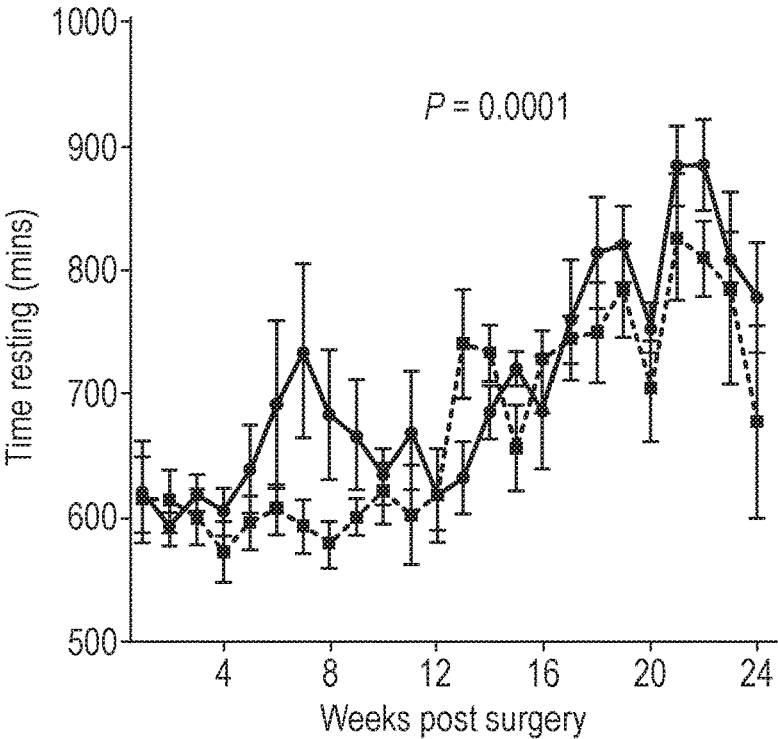
Figure 8G:
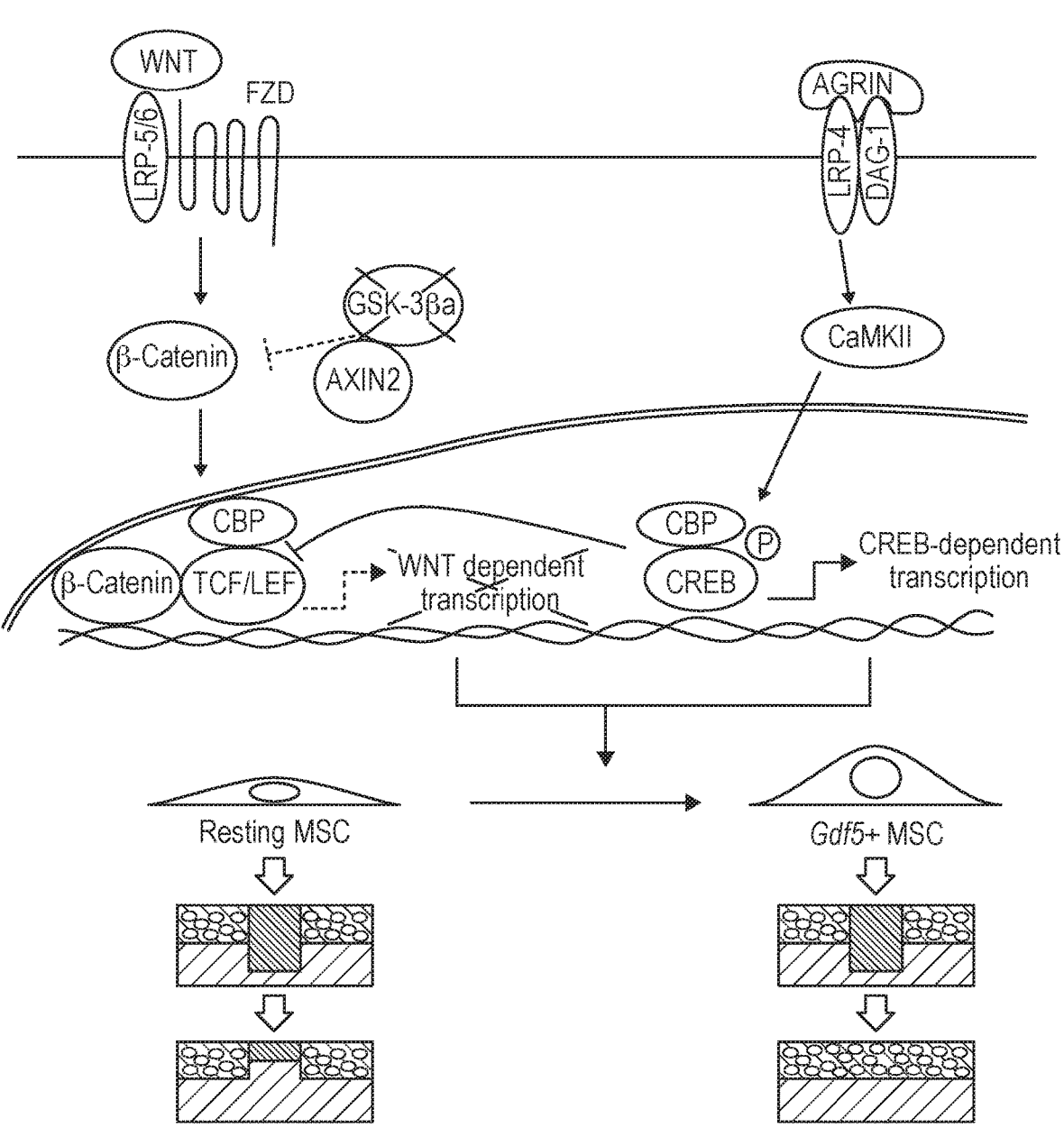

FIG. 8 shows that a single administration of Agrin in critical size joint surface defects in sheep regenerates the articular cartilage. Sheep underwent the generation of an osteochondral defect that was filled with a collagen gel containing AGRIN or GFP and killed after 6 months (n=6). (A) Representative μCT images of defects at 6-month timepoint and (n=6). (B) quantification of the residual non-calcified defect area (n=6 control and n=5 Agrin; Welch t-test after log transformation, P=0.0134). (C) Safranin 0 staining of the joint surface defect area, bars 200 μm. (D) Pineda score (n=4 controls and n=6 AGRIN; Mann-Whitney U test P=0.0333. (E) Time spent playing (two-way ANOVA, Treatment P=0.00495) and (F) time spent resting (two-way ANOVA, Treatment P=0.00043). (G) AGRIN promotes the morphogenesis of the repair mesenchyme at the site of cartilage injury. This process involves the activation of CREB-dependent upregulation of Gdf5 and suppression of WNT signaling downstream of β-catenin.

FIG. 9. (A) Microarray human chondrocytes—(mined from GEO accession GSE75181[30]), p<0.0001. (B) RT-PCR for DKK1 in C28/I2 cells transfected with Scrambled or AGRN siRNA cultured for 3 days in micromass (n=4).

Figure 10:
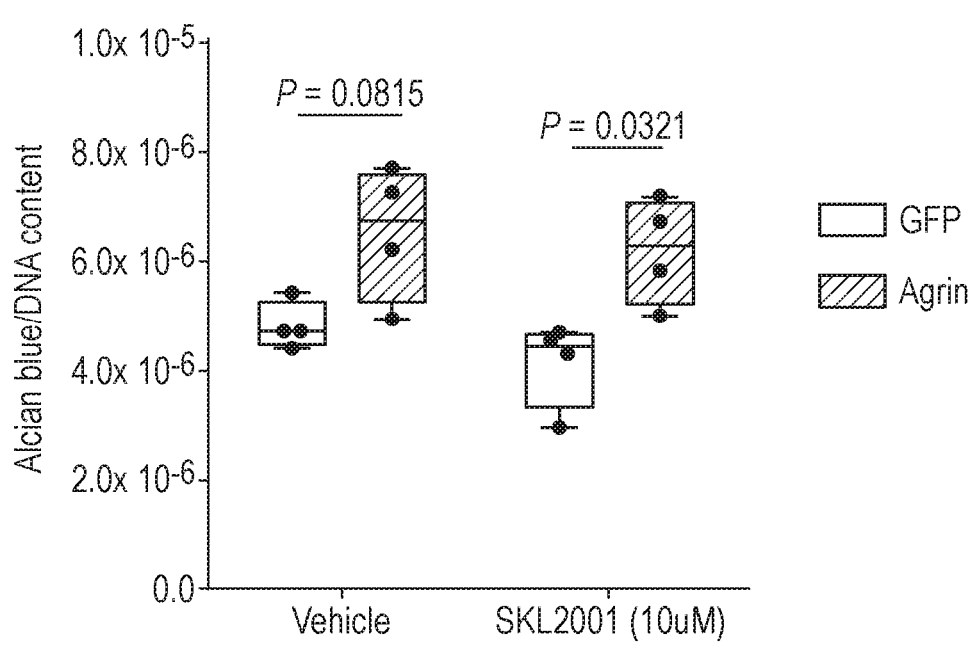

FIG. 10. Alcian blue staining and quantification of C28I/2 chondrocytes in micromass culture 4 days after transfection with Scrambled or AGRN siRNA with or without SKL2001 (n=4), two-way ANOVA P=0.0013.

Figure 11A:
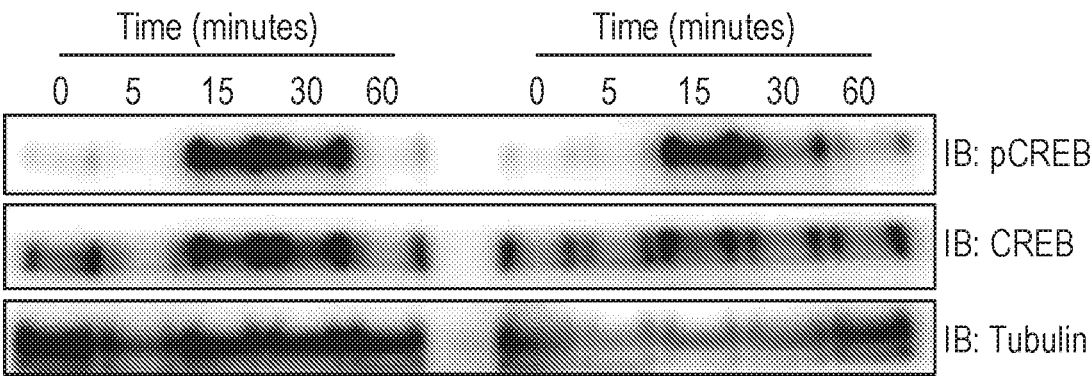
Figure 11B:
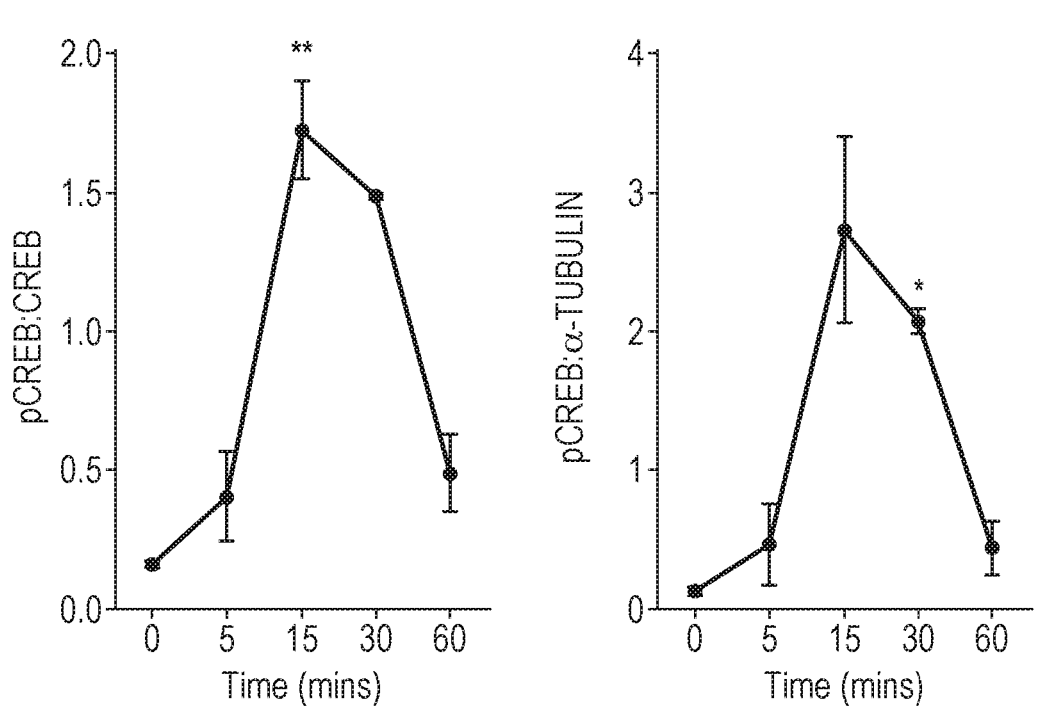

FIG. 11. (A) Temporal analysis by western blot of pCREB in C28/I2 cells treated with 100 ng/ml rAgrin normalized to (B) CREB and tubulin (one-way ANOVA followed by Dunnets multiple comparison test) (n=2).

FIG. 12. (A) Unoperated joint of a mouse stained with Safranin 0. (B) Untreated subchondral defect in mice 8 weeks post-surgery stained with toluidine blue. (C) MicroCT of Gdf5-Cre; Tom mice 8 weeks post-surgery.

Figure 13:
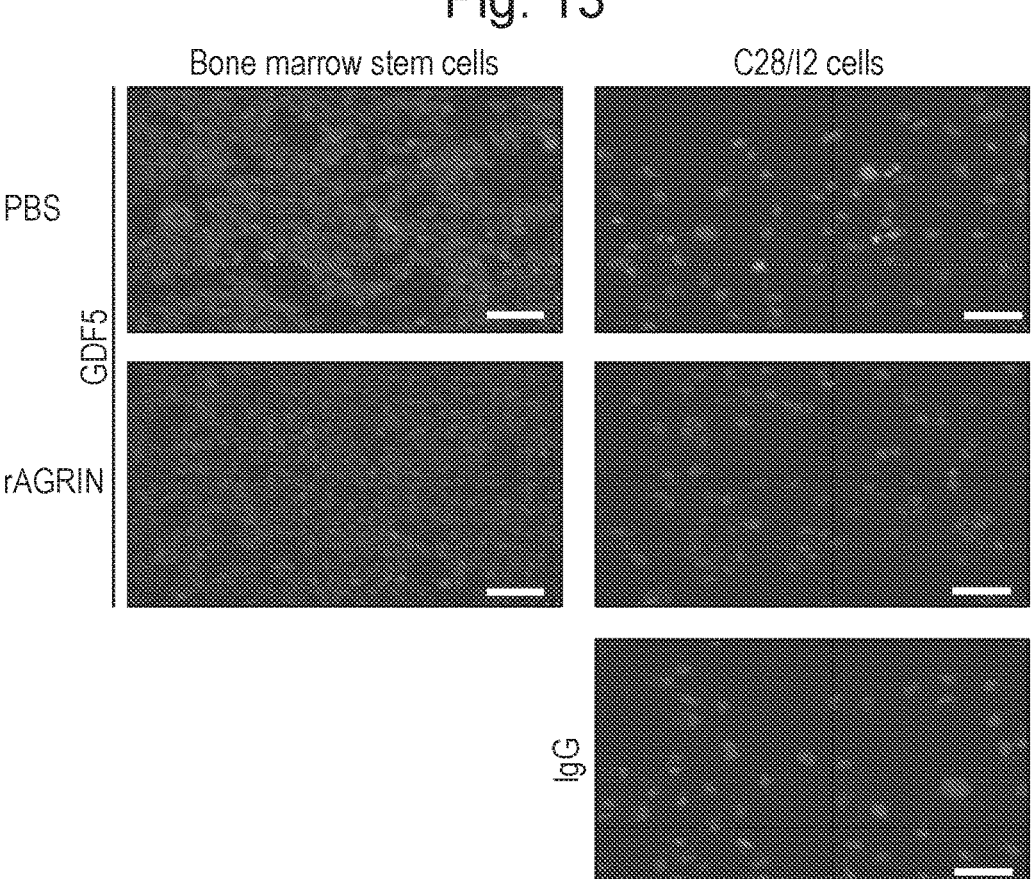

FIG. 13. Immunofluorescence for GDF5 in murine bone marrow derived stem cells treated with rAgrin (100 ng/ml) compared to C28/I2 chondrocytes as positive control; bars 50 μm.

Figure 14A:
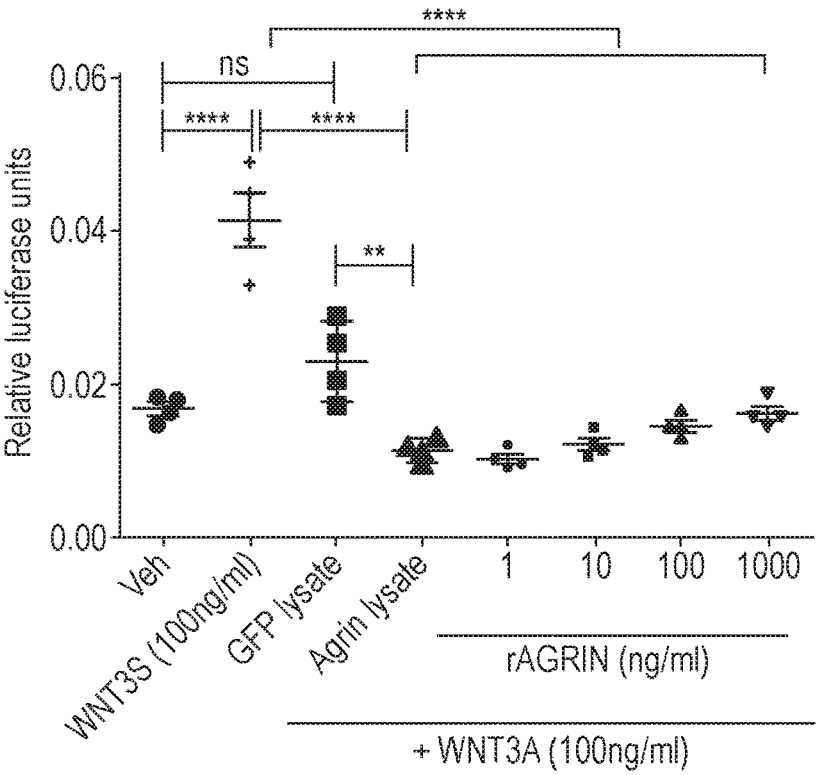
Figure 14B:
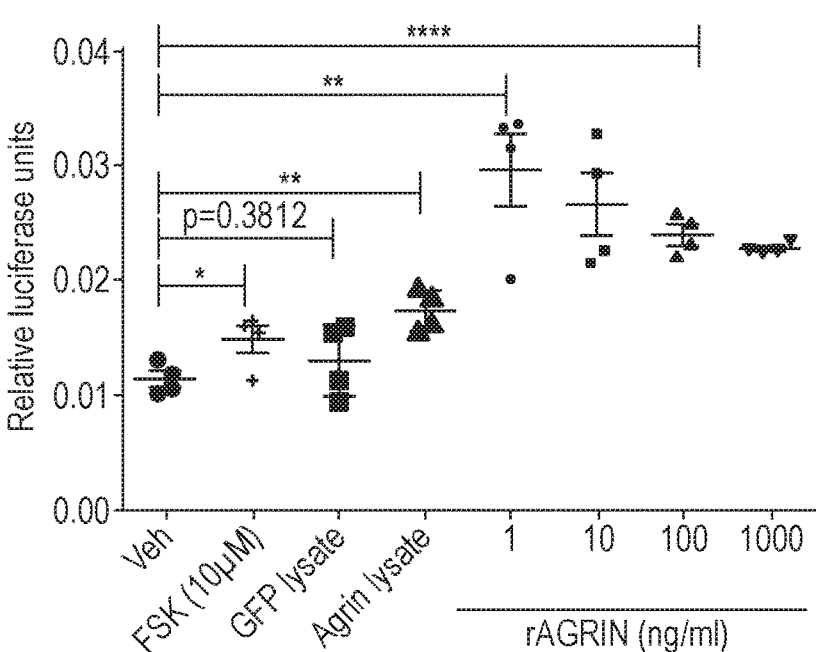

FIG. 14. (A) TOPFlash reporter assay of HEK293 cells cultured in the presence of COS7-AGRIN or COS7-GFP cell lysate (used at ratio equal to in vivo) and compared to increasing doses of recombinant Agrin (rAgrin) in the presence of WNT3A (n=4). (B) CREB reporter assay of HEK293 cells cultured in the presence of COS7-AGRIN or COS7-GFP cell lysate (used at ratio equal to in vivo) and compared to increasing doses of recombinant AGRIN (rAGRIN), forskolin was used as a positive control (n=4); (A&B)

one-way ANOVA, *=p<0.05, =p<0.01, *=p<0.001, ****=p<0.0001. (C) Immunofluorescence for Tomato in the defect of Gdf5:Tom transgenic mice 3 weeks after the generation of a joint surface defect filled with a collagen gel containing either rAGRIN (100 ng/ml) or PBS; bars 200 μm. Quantification of the number of Tom+ cells in (D) the synovial membrane and (E) repair mesenchyme in the defect site.

Figures 15, 16A, 16B:
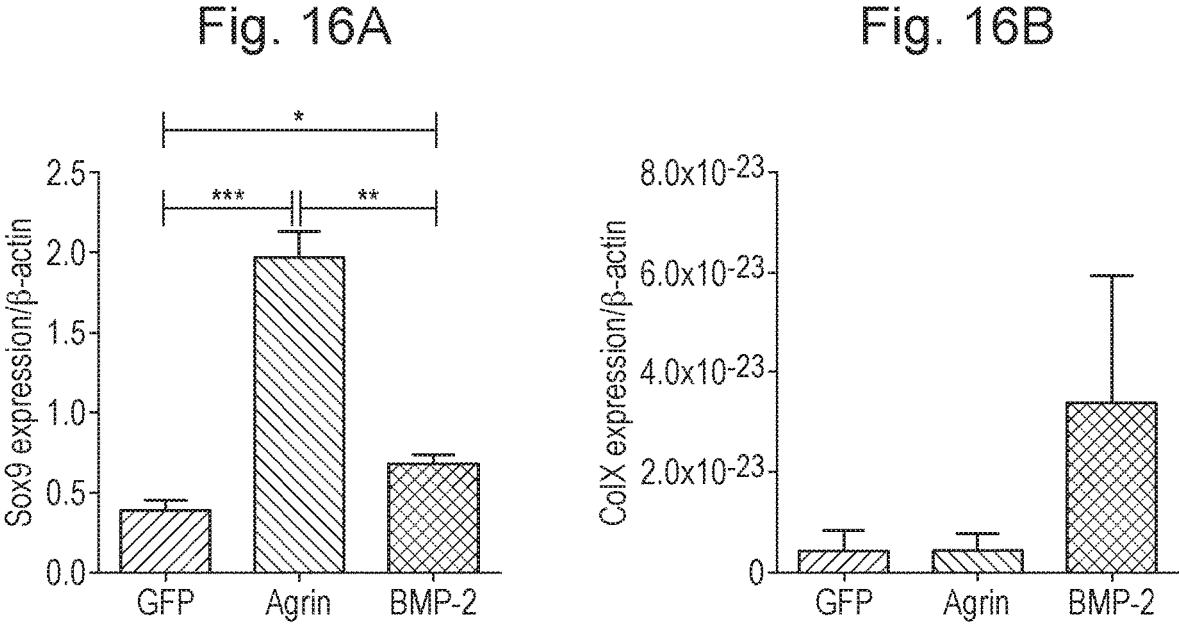
Figure 17A:
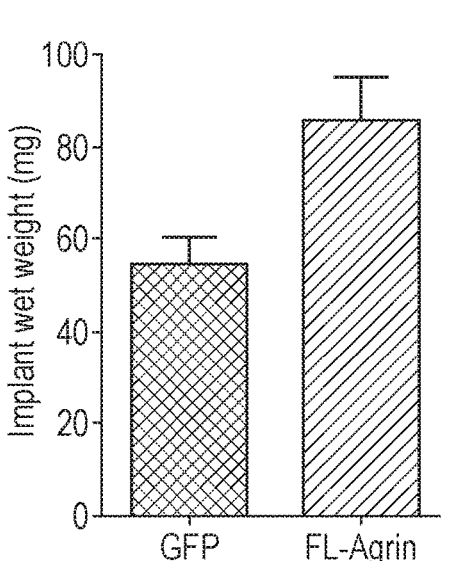
Figure 17B:
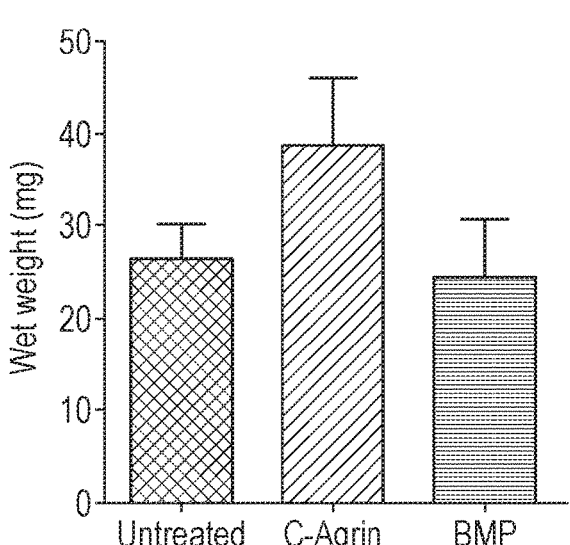
Figure 17C:
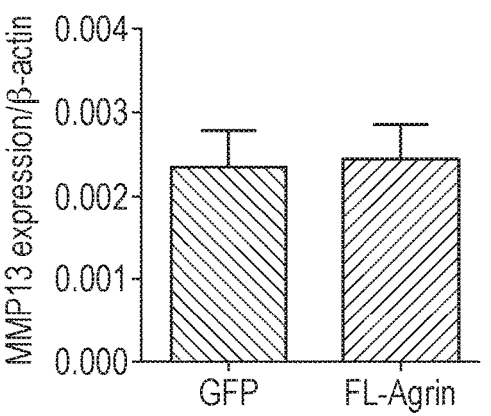
Figure 17D:
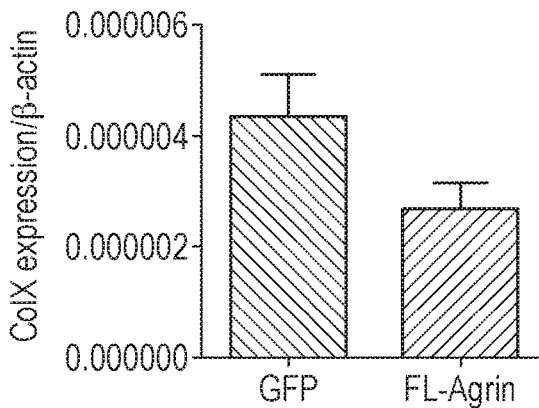

FIG. 15 shows that Both secreted and transmembrane full length rat Agrin plasmids increase the proteoglycan production and differentiation of C28/I2 cells in micromass culture. Where ss refers to secreted isoform (isoform 1) and TM refers to transmembrane isoform (isoform 2).

FIG. 16 shows that transfection with full length rat Agrin increases expression of SOX9 more potently than BMP2, but does not induce expression of Collagen type 10, conducted in bovine primary chondrocytes.

FIG. 17 shows that when bovine primary chondrocytes are implanted ectopically in vivo with growth-arrested COS7 cells expressing full length or C-terminal rat Agrin they produce larger cartilage nodules than BMP2. These cartilage explants do not express markers of hypertrophy (MMP13 or COLX).

FIG. 18 shows that human synovium derived stem cells cultured in vitro with growth-arrested COS7 cells expressing full length rat Agrin become larger and express articular cartilage markers SOX9, COL2A1 and Aggrecan.

Figure 19A:
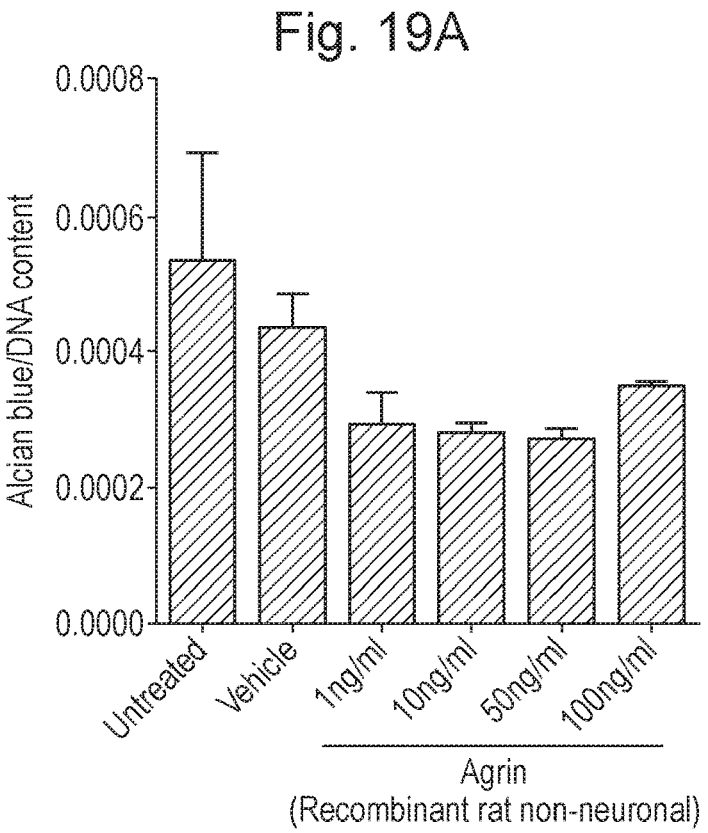
Figure 19B:
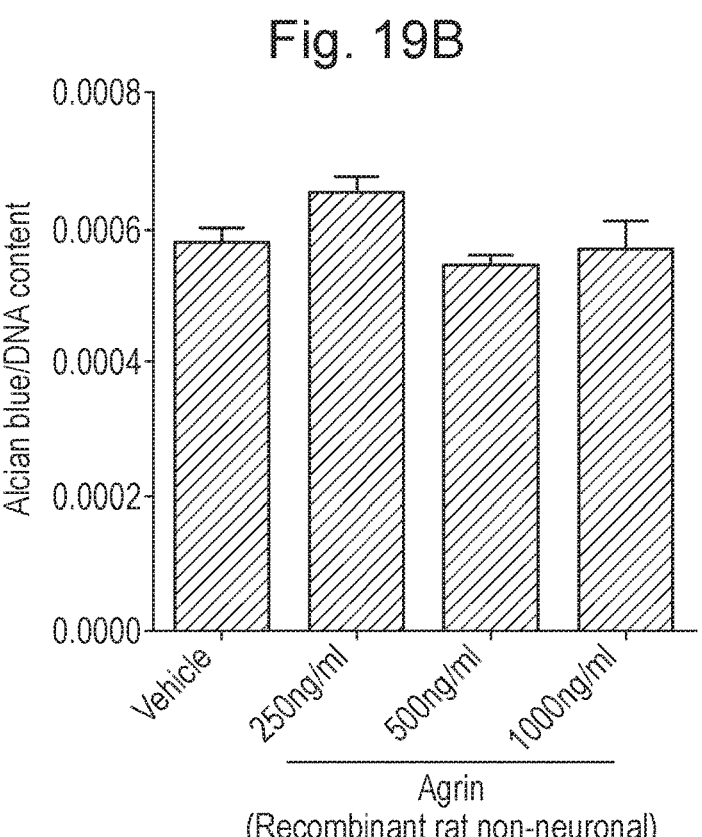
Figure 22A:
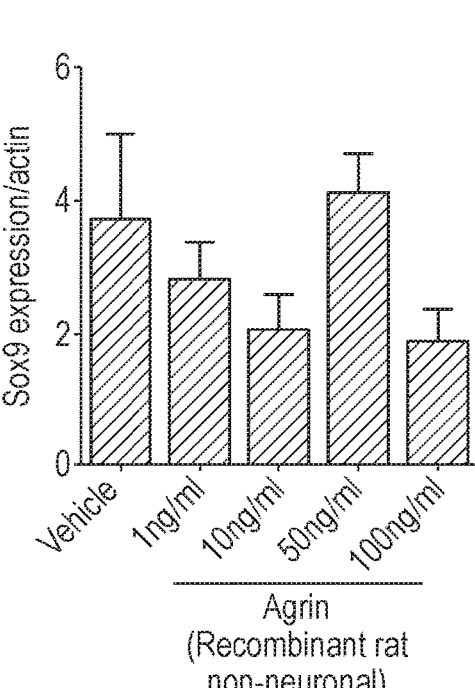
Figure 22B:
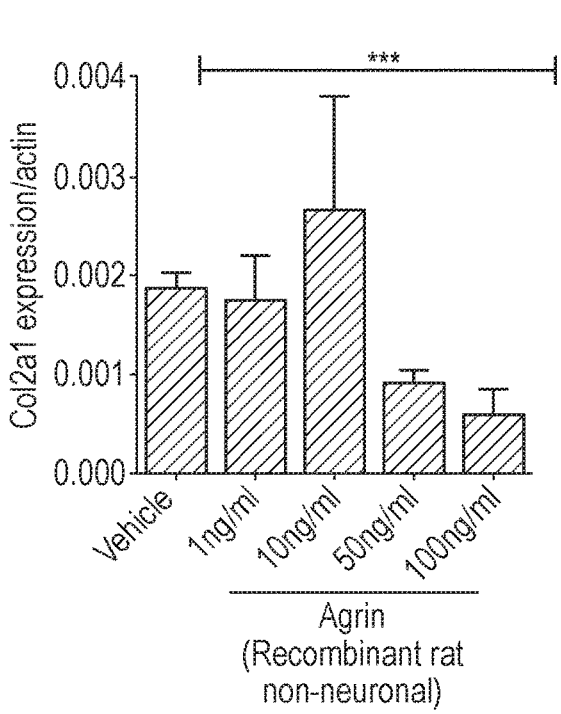
Figure 22C:
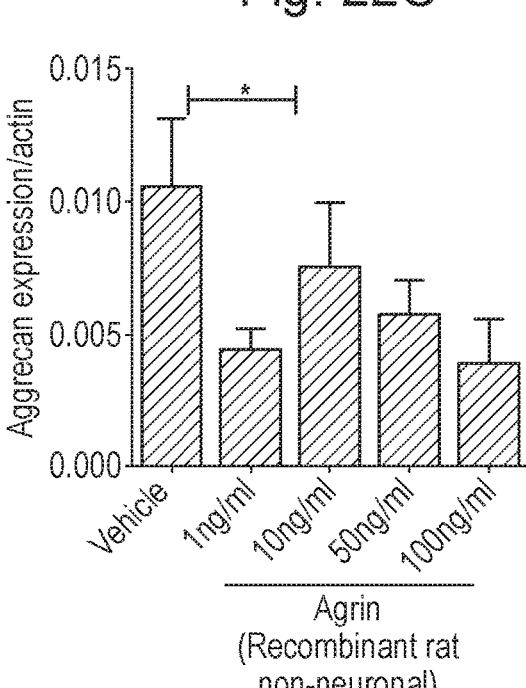
Figure 22D:
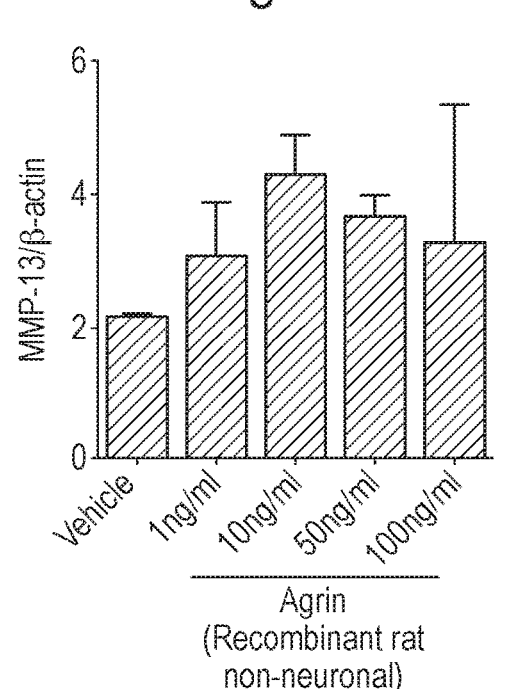

FIG. 19 shows that rat non-neuronal agrin from R&D could not induce increase in extracellular matrix formation in the human chondrocytic cell line C28/I2. C28/I2 cells were plated in micromass culture and treated for 4 days at low or high doses.

FIG. 20 shows that non-neuronal rat agrin (300 ng/ml) human chondrocytic cell line C28/I2. Cultured for 4 days in micromass in 10% serum. Recombinant agrin added for final 24 hrs. Chondrogenic markers were unchanged.

FIG. 21 shows that non-neuronal rat agrin (300 ng/ml) human chondrocytic cell line C28/I2. Cultured for 4 days in micromass in the absence of serum. Recombinant agrin added for final 24 hrs. Chondrogenic markers were unchanged.

FIG. 22 shows that rat non-neuronal agrin from R&D could not induce increase in SOX9, COL2A1, Aggrecan or lower MMP13 expression in the human chondrocytic cell line C28/I2. Cultured for 4 days in 10% serum.

Figure 23A:
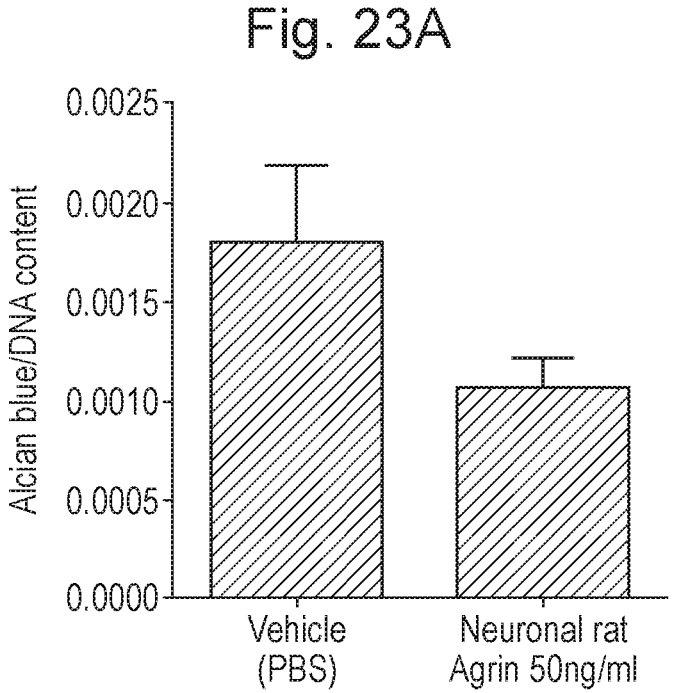
Figure 23B:
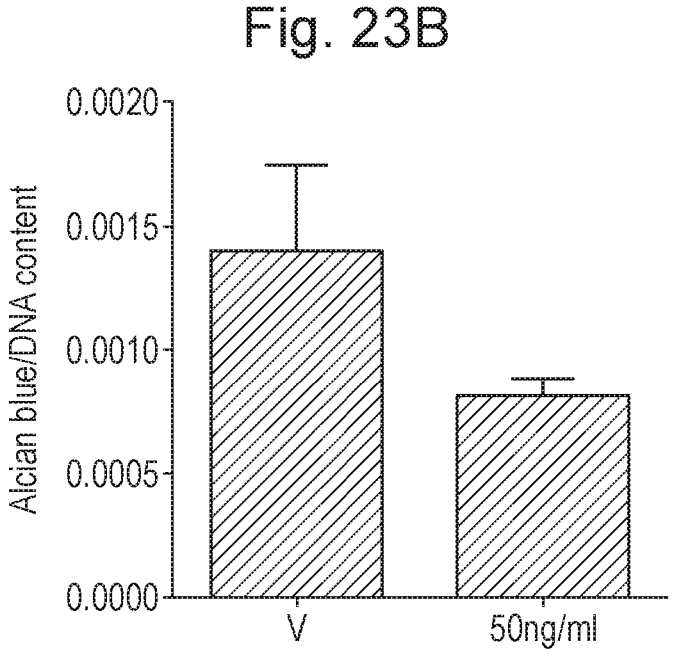
Figure 24B:
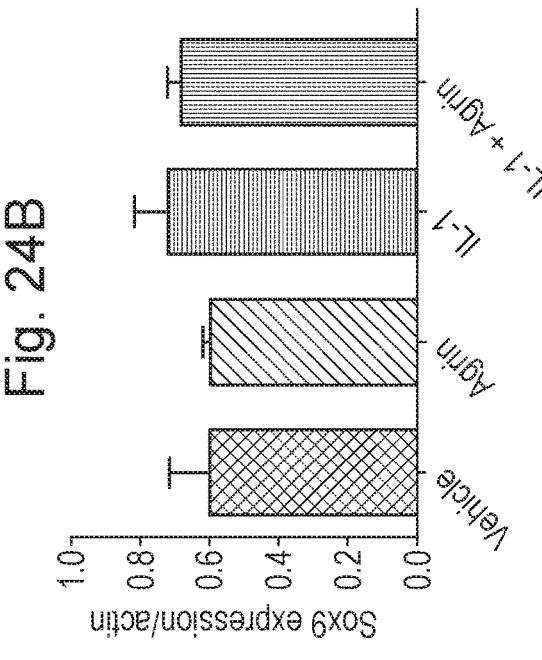
Figure 24D:
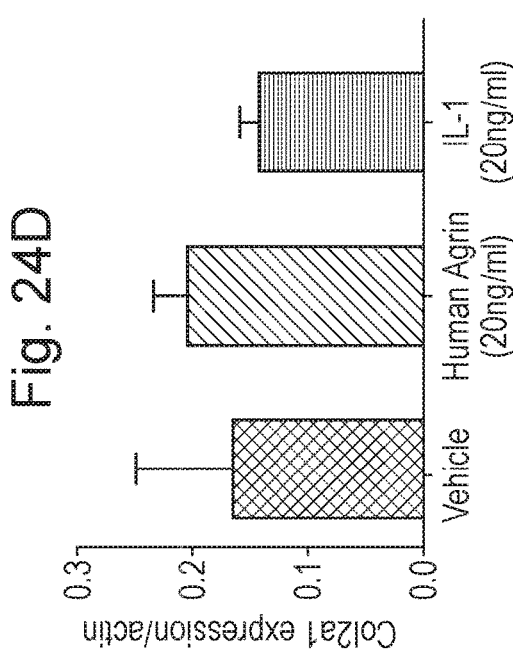
Figure 24A:
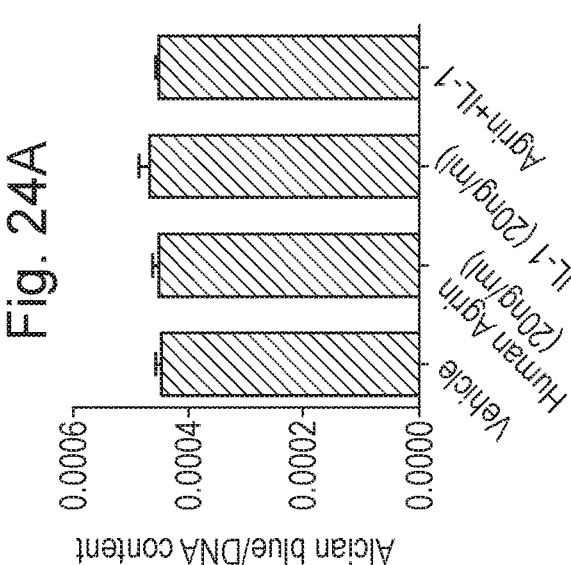
Figure 24C:
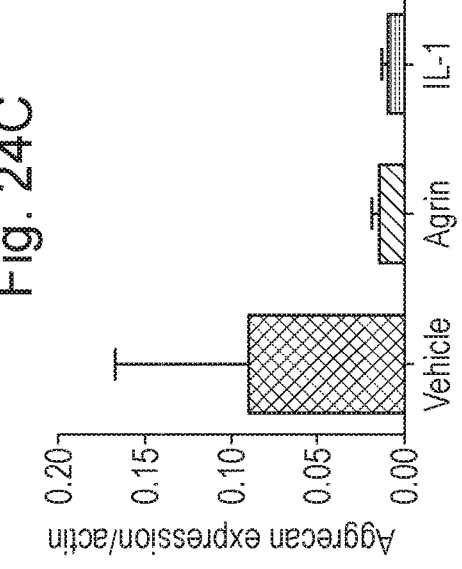
Figure 24E:
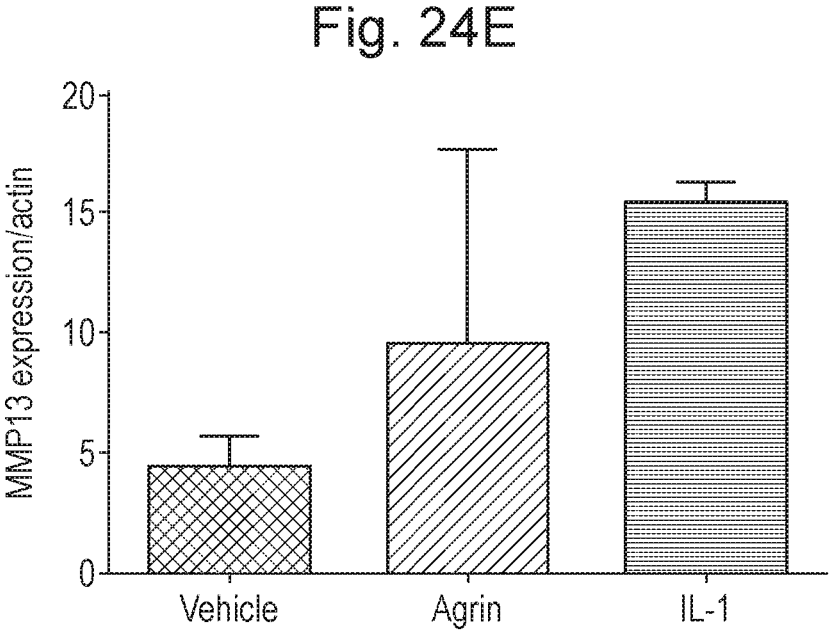

FIG. 23 shows that neuronal rat Agrin from R&D could not induce increase in extracellular matrix production in the human chondrocytic cell line C28/I2. If anything it reduced it, suggesting that this construct may compete with endogenous Agrin. (A) in the presence of 10% serum and (B) in the absence of serum, cultured for 4 days.

FIG. 24 shows that human non-neuronal Agrin from R&D could not induce changes in cartilage matrix and markers expression in the human chondrocytic cell line C2842. (A) Alcian blue, (B) SOX9 expression, (C) aggrecan expression, (D) Col2A1 expression and (E) MMP13 expression. Cells were cultured for 6 days in 10% serum.

Figure 25:
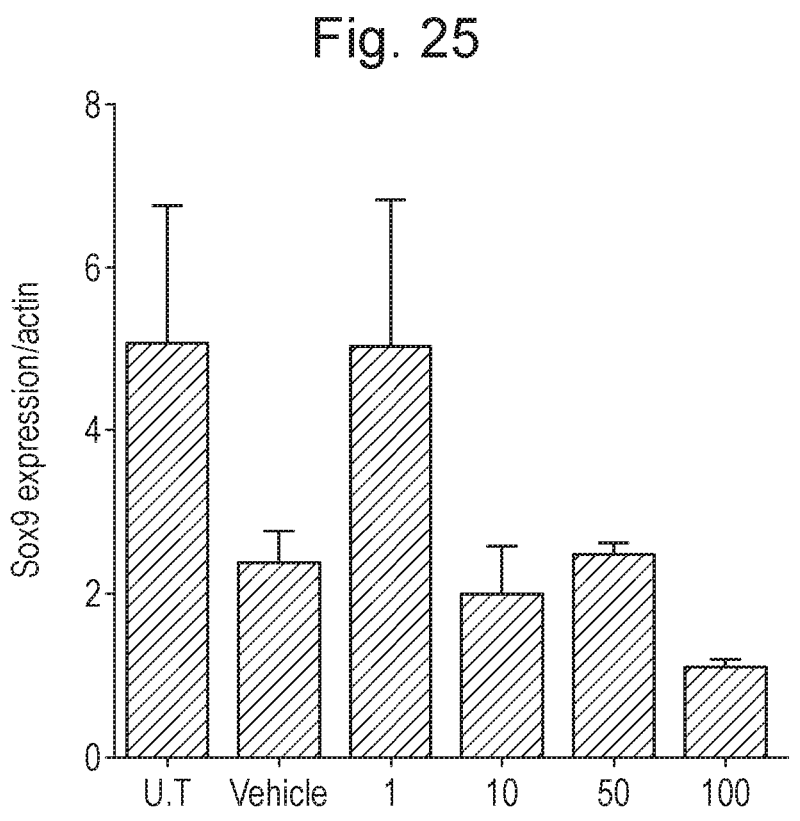
Figure 26A:
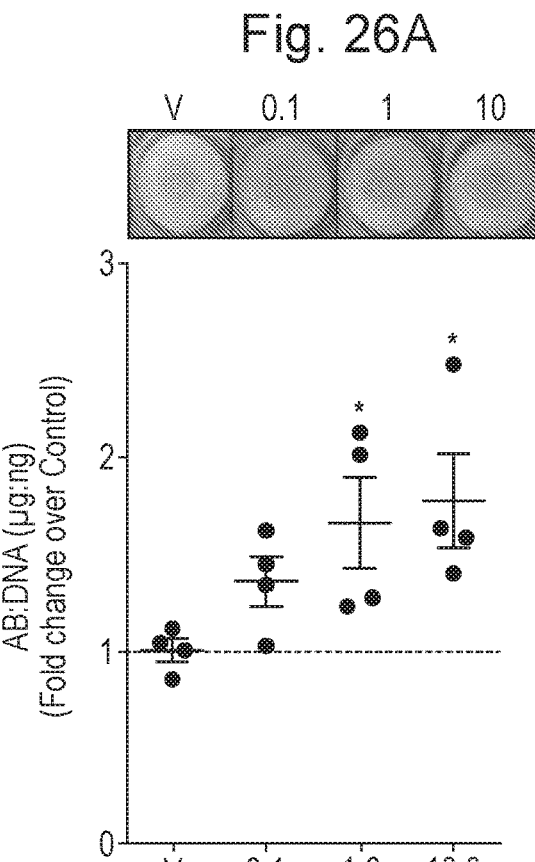
Figure 26B:
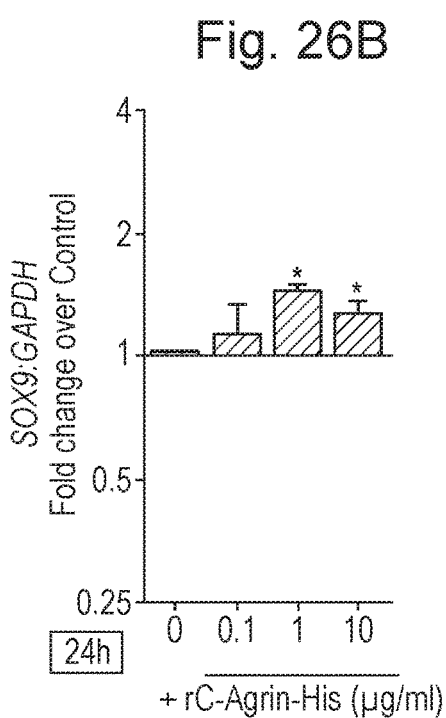
Figure 26C:
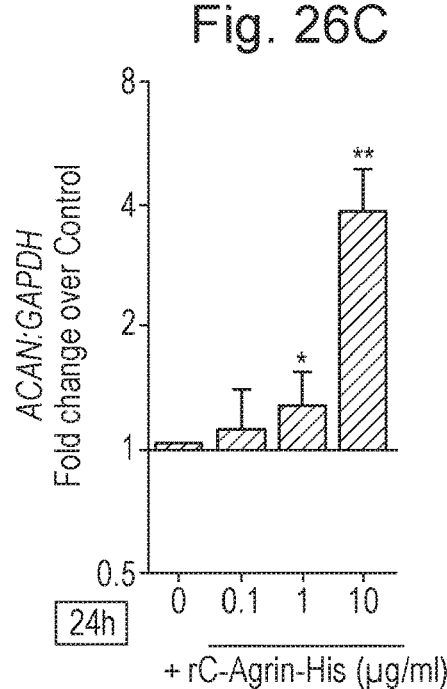
Figure 26D:
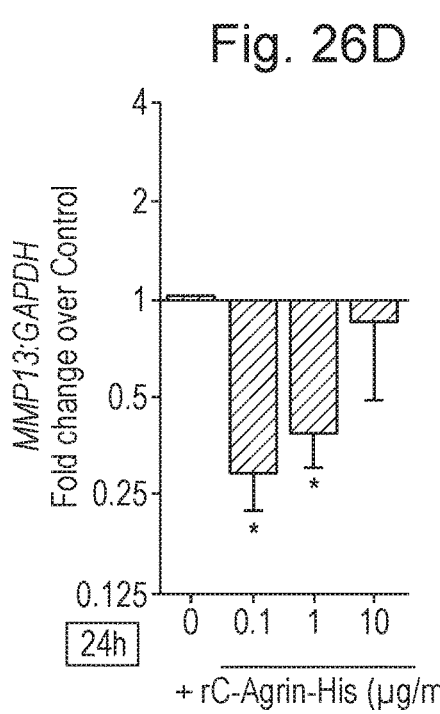
Figure 27A:
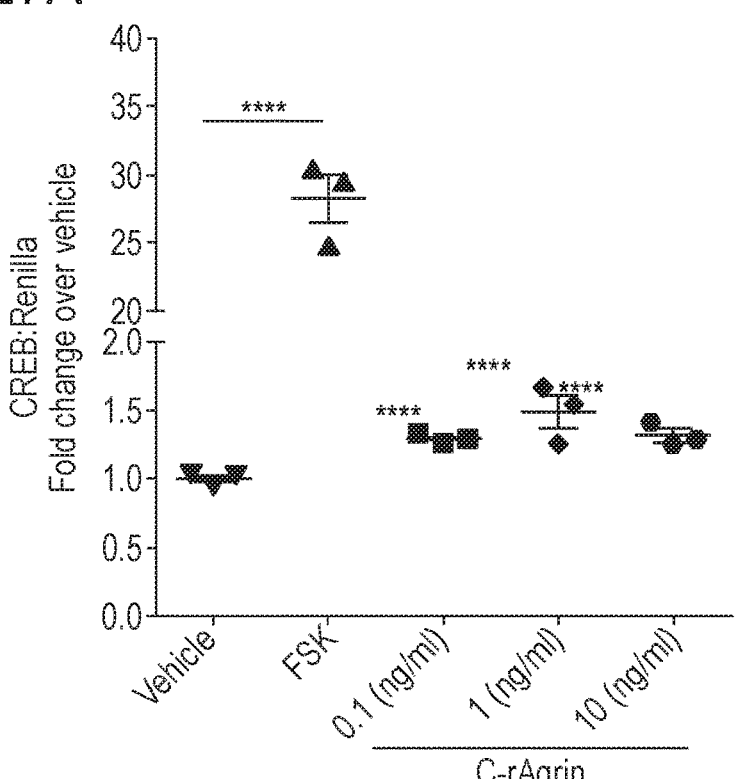
Figure 27B:
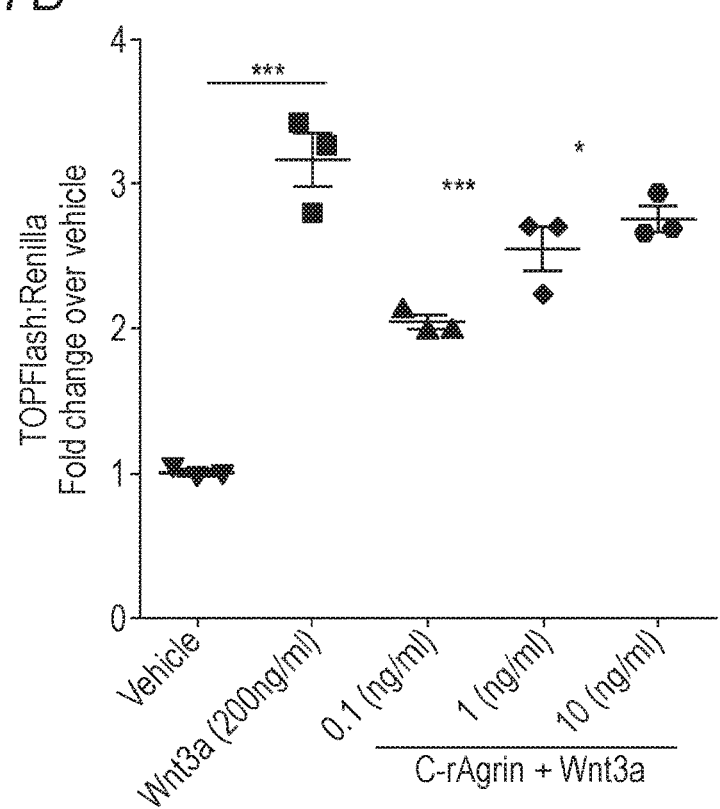
Figure 27C:
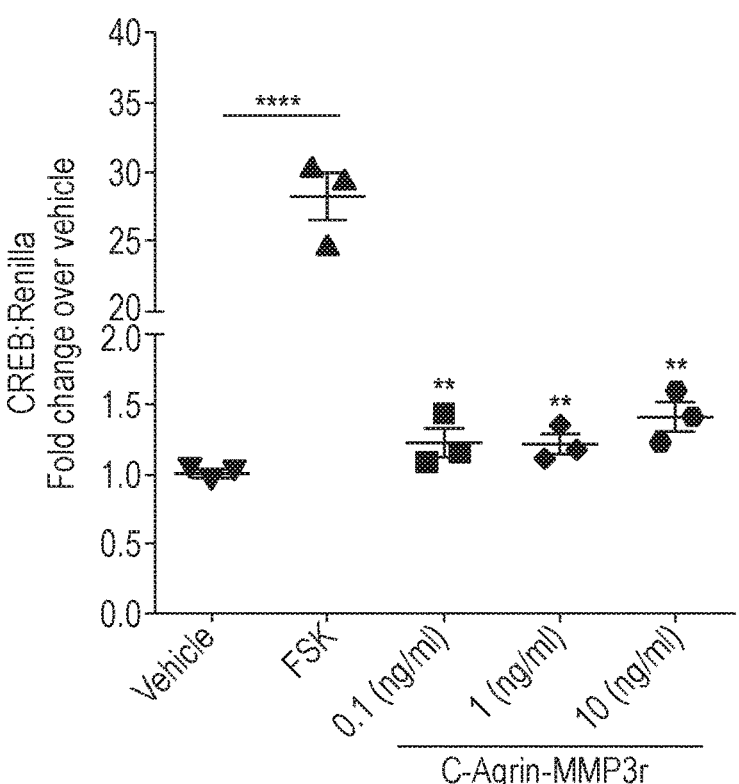
Figure 27D:
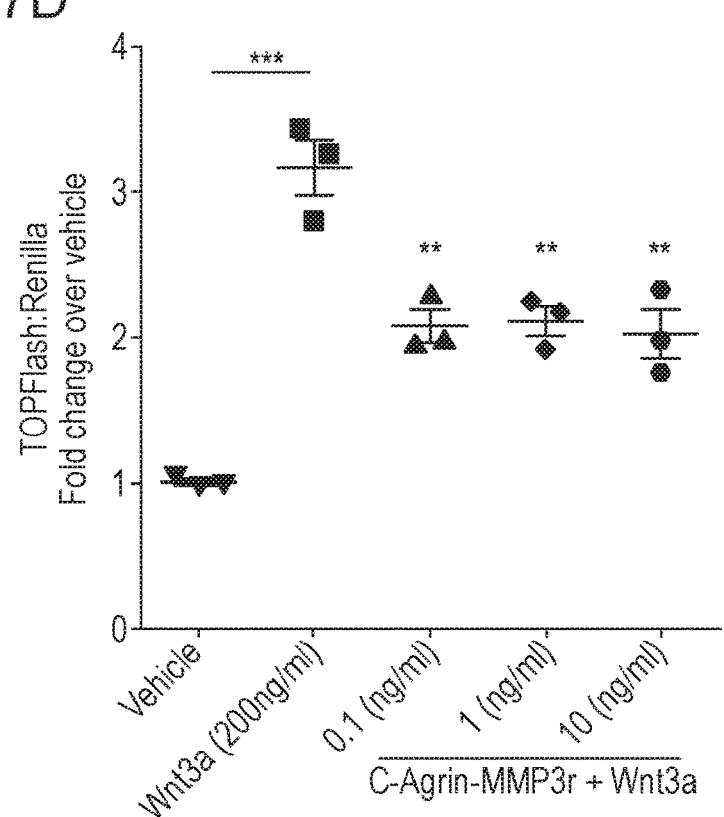

FIG. 25 shows that a dose response of human non-neuronal Agrin from R&D could not alter the expression of SOX9, cultured in serum 4 days.

FIG. 26 shows that a soluble polypeptide of the invention tested on C28/I2 cells for its chondrogenic capacity. Dose dependent upregulation of differentiation and proteoglycan content, SOX9 and Aggrecan expression was observed, and dose-dependent down-regulation of MMP13.

FIG. 27 shows that a soluble polypeptide of the invention, whether or not resistant to MMP-3 cleavage, tested on HEK293 cells for its WNT inhibition and CREB activation potency. Both soluble polypeptides of the invention, whether or not resistant to MMP-3 cleavage, inhibited WNT signaling and activated CREB.

Figure 28D:
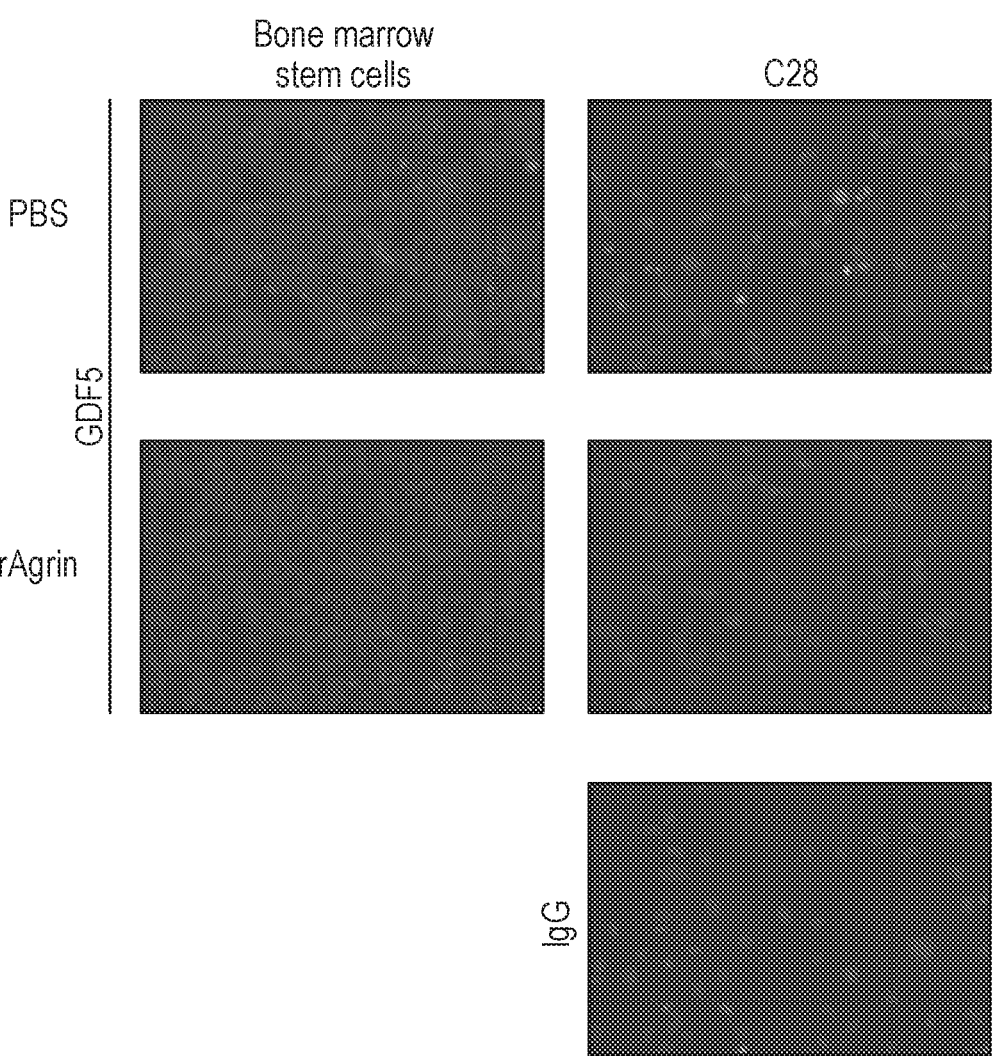

FIG. 28 shows that human synovium derived stem cells transfected with full-length human non-neuronal Agrin began expressing GDF5. A soluble polypeptide of the invention (100 ng/ml) was unable to induce the expression of GDF5 in murine derived bone marrow stem cells (GDF5-expressing C28/I2 are shown as positive control).

Figure 29A:
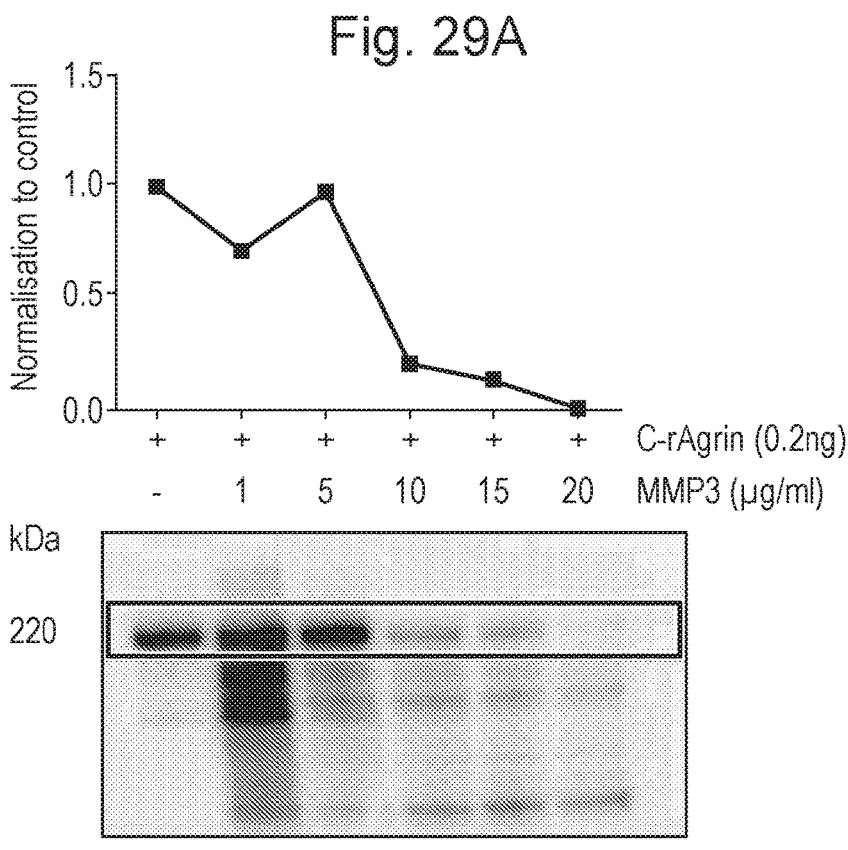
Figure 29B:
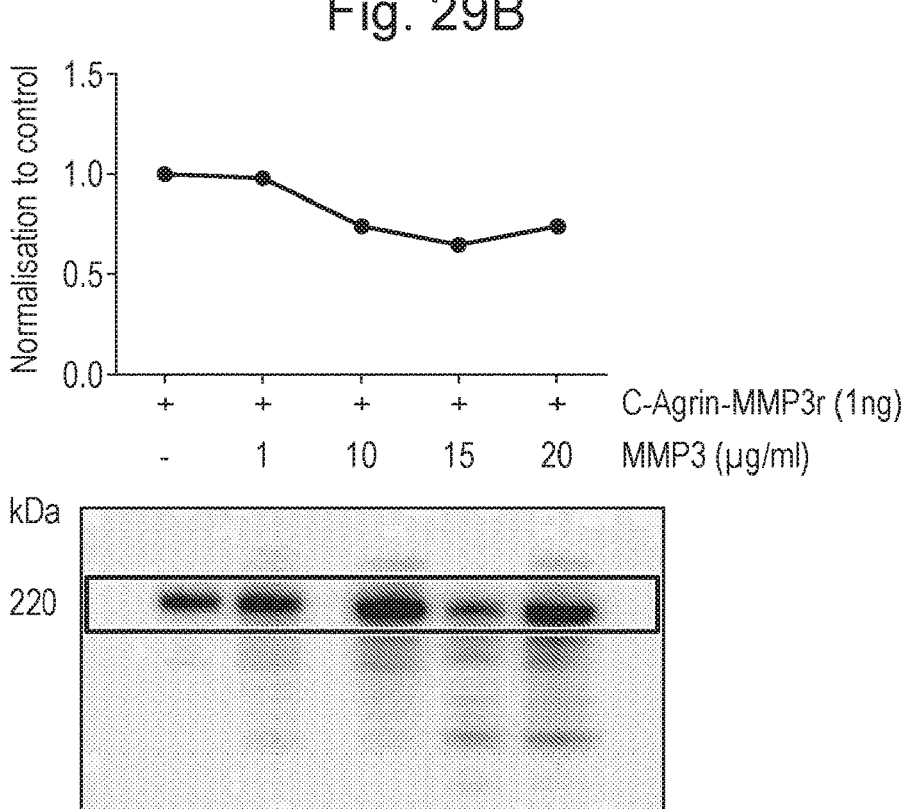

FIG. 29 shows that a soluble polypeptide of the invention, wherein at least one of amino acids corresponding to positions 1753, 1754, 1755, 1756, 1757 and 1758 of SEQ ID NO: 1 are deleted or substituted with another amino acid, is resistant to MMP3 degradation.

Figure 30:
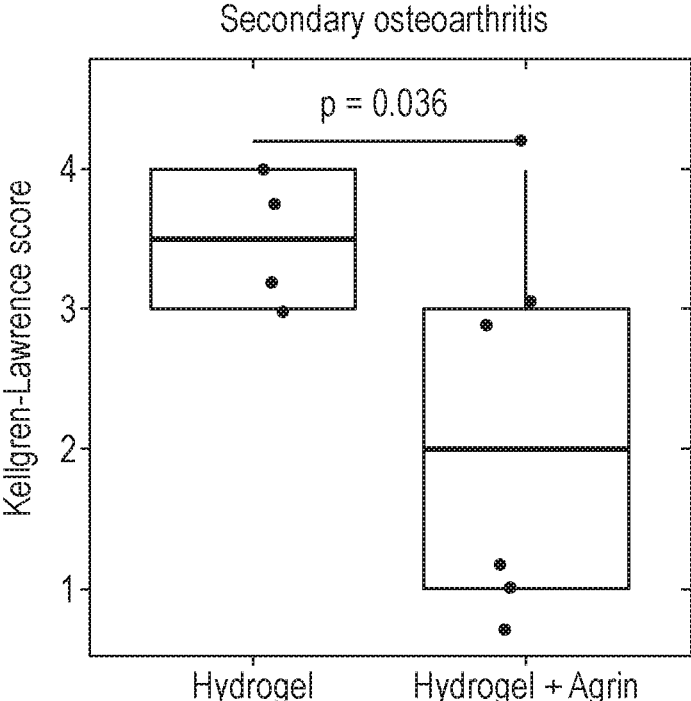

FIG. 30 shows that agrin implantation in full-thickness cartilage defects in sheep not only improves healing of the cartilage defect (see also FIG. 17) but also decreases the occurrence of post-traumatic osteoarthritis in other parts of the joint 6 months post-surgery.

Figure 31:
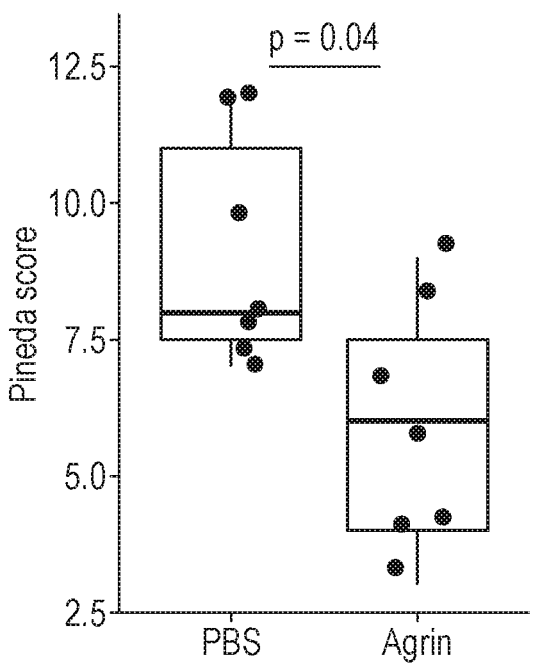

FIG. 31 shows that a soluble polypeptide of the invention improved osteochondral defects in mice 8 weeks post-surgery.

Figure 32A:
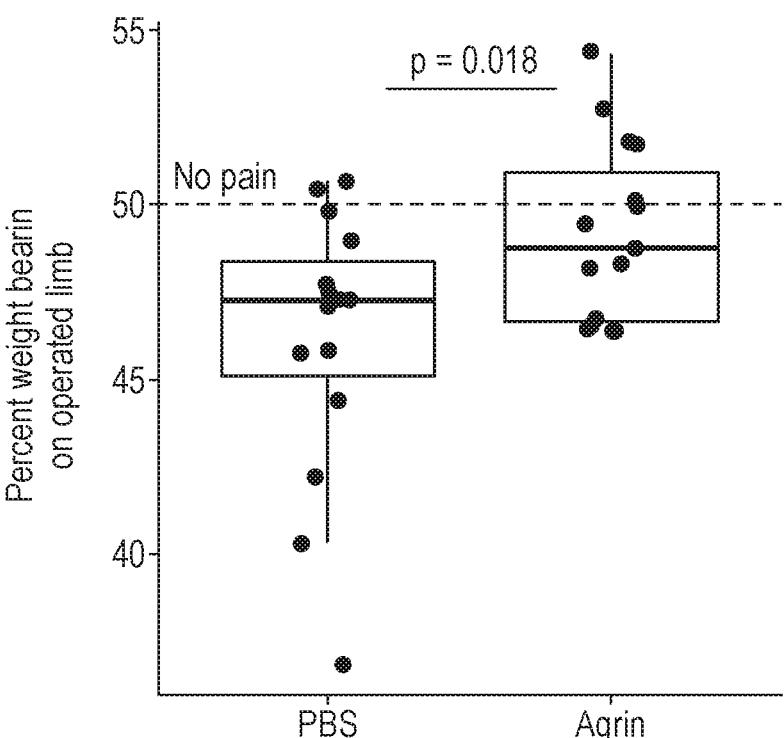
Figure 32B:
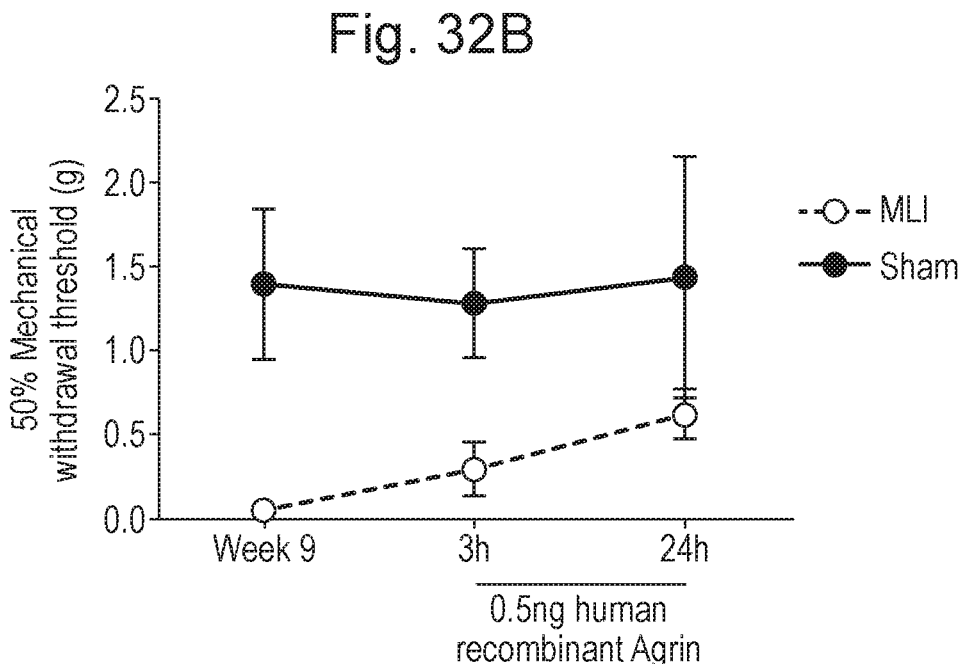

FIG. 32 shows that a soluble polypeptide of the invention results in post-surgical pain relief in a murine model of osteochondral defects when injected into the joint (5 days post injury induction)(A). A soluble polypeptide of the invention injected into the joint in mice with established osteoarthritis (OA) and OA-associated pain, relieves pain as quickly as 3 hrs post injection.

Figures 33, 34:
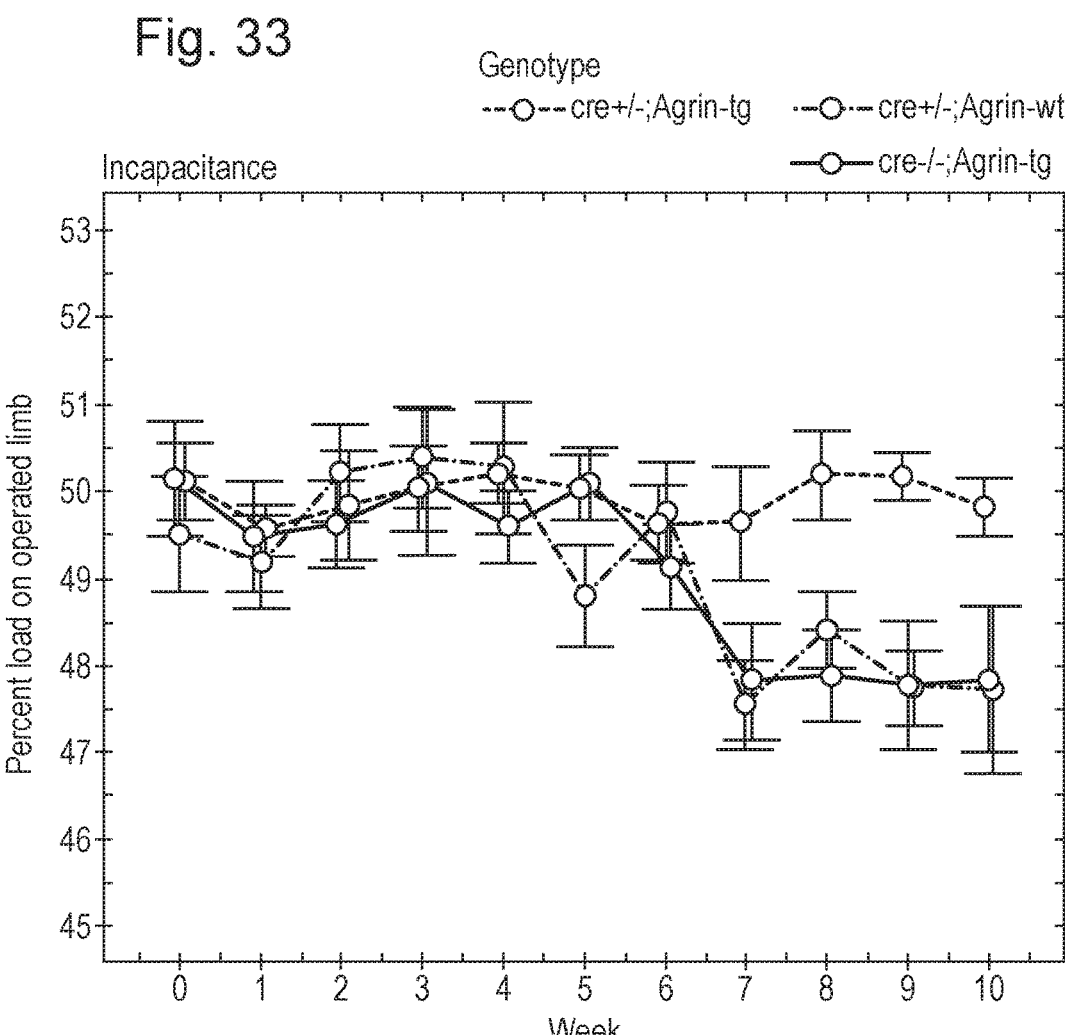

FIG. 33 shows that transgenic mice overexpressing full-length human Agrin do not experience pain in a murine model of osteoarthritis.

FIG. 34. 14 adult male C57BL/6 mice received an osteochondral defect in the lateral condyle of the right knee. In 7 mice the inventors filled the defect with a collagen gel containing 100 ng of recombinant Agrin and 7 mice received the collagen gel with some PBS. Pain (percent body weight on the operated limb) was measured at different time points and cartilage damage (Pineda score) was assessed at termination of the experiment (8 weeks). Mice in the control group developed pain early after the operation (3 days), but not mice receiving Agrin. Pain is not detected in later time points, therefore no late time-point pain was detected in either group in terms of difference in weight bearing between operated and unoperated limb.

Figure 35:
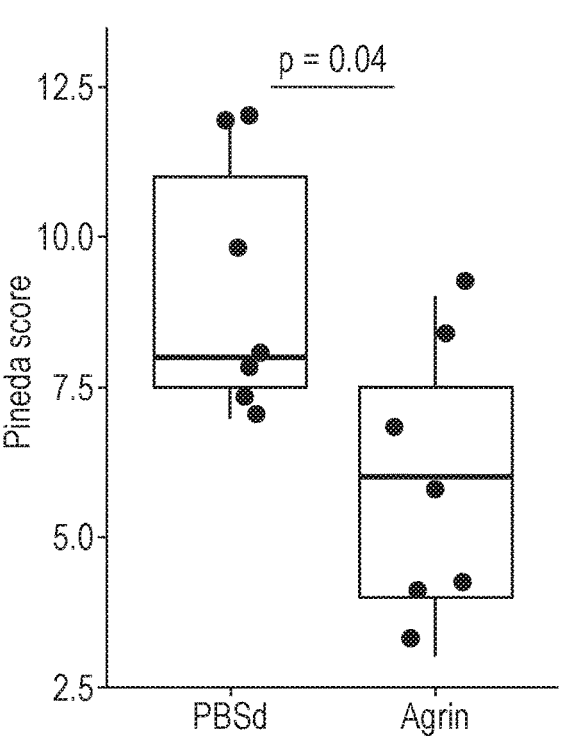

FIG. 35. 14 adult male C57BL/6 mice received an osteochondral defect in the lateral condyle of the right knee. In 7 mice the inventors filled the defect with a collagen gel containing 100 ng of recombinant Agrin and 7 mice received the collagen gel with some PBS Sections through the center of the defect were cut and stained with Safranin 0 and with Toluidine blue. The Pineda score was used to assess the degree of damage (the higher the score the more the damage.

Figure 36:
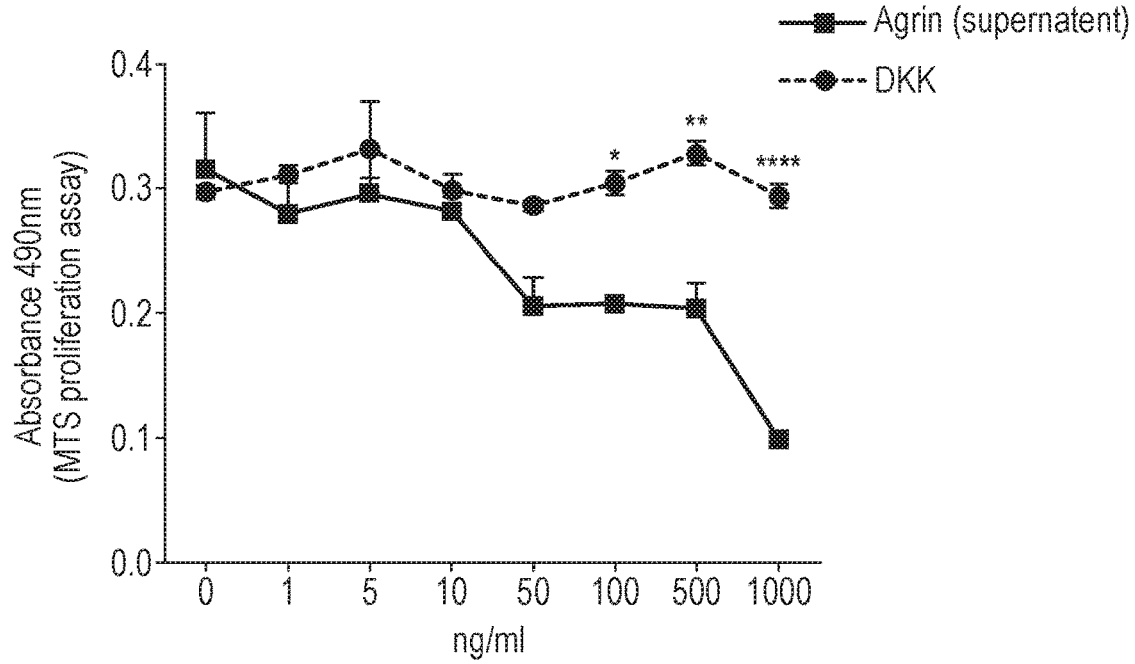

FIG. 36 shows that Agrin inhibits the growth of cancer cells (OVCR3 ovarian cancer cells) with mutations that hyperactivate the WNT signaling pathway, whilst the WNT inhibitor, DKK1, cannot inhibit the growth of OVCR3 cancer cells. MTS proliferation assay in which cells are treated with Agrin or DKK1 24 hours after seeding for a further 24 hours.

Figure 37A:
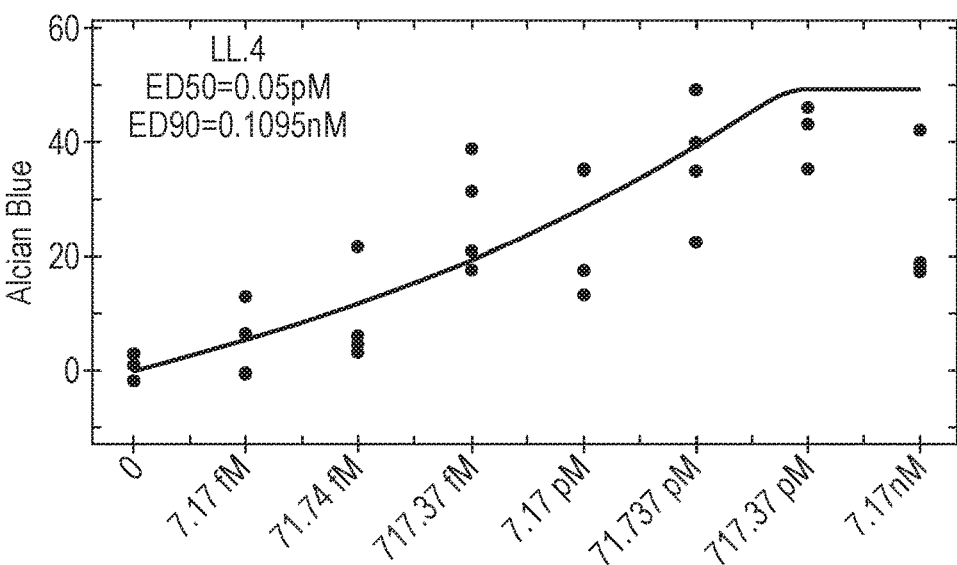
Figure 37B:
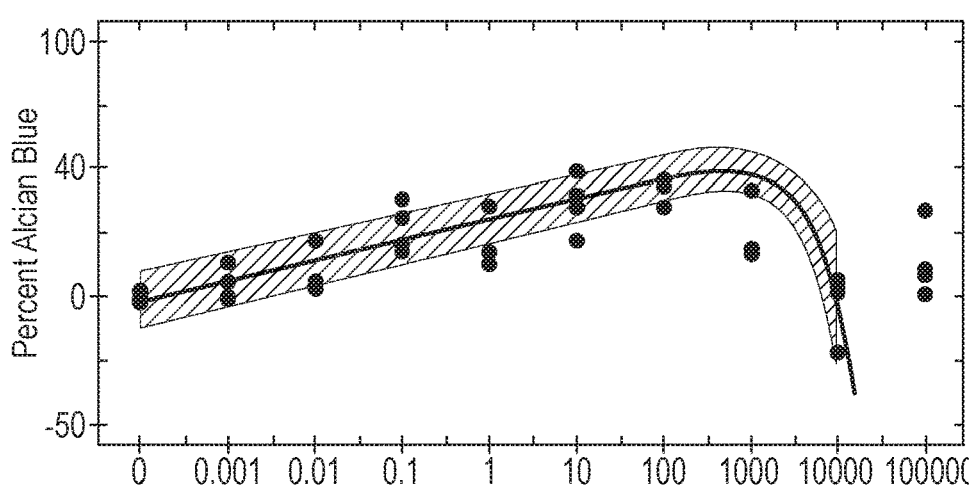
Figure 37C:
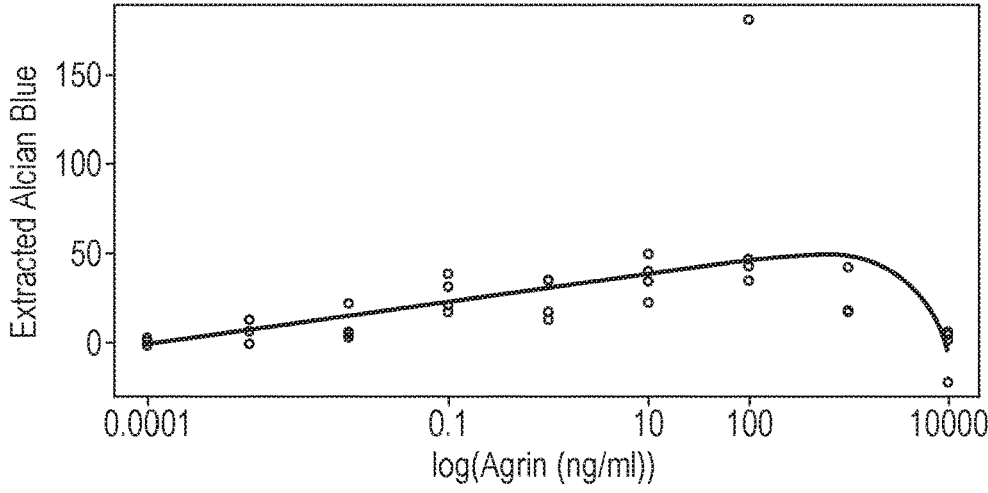
Figure 38A:
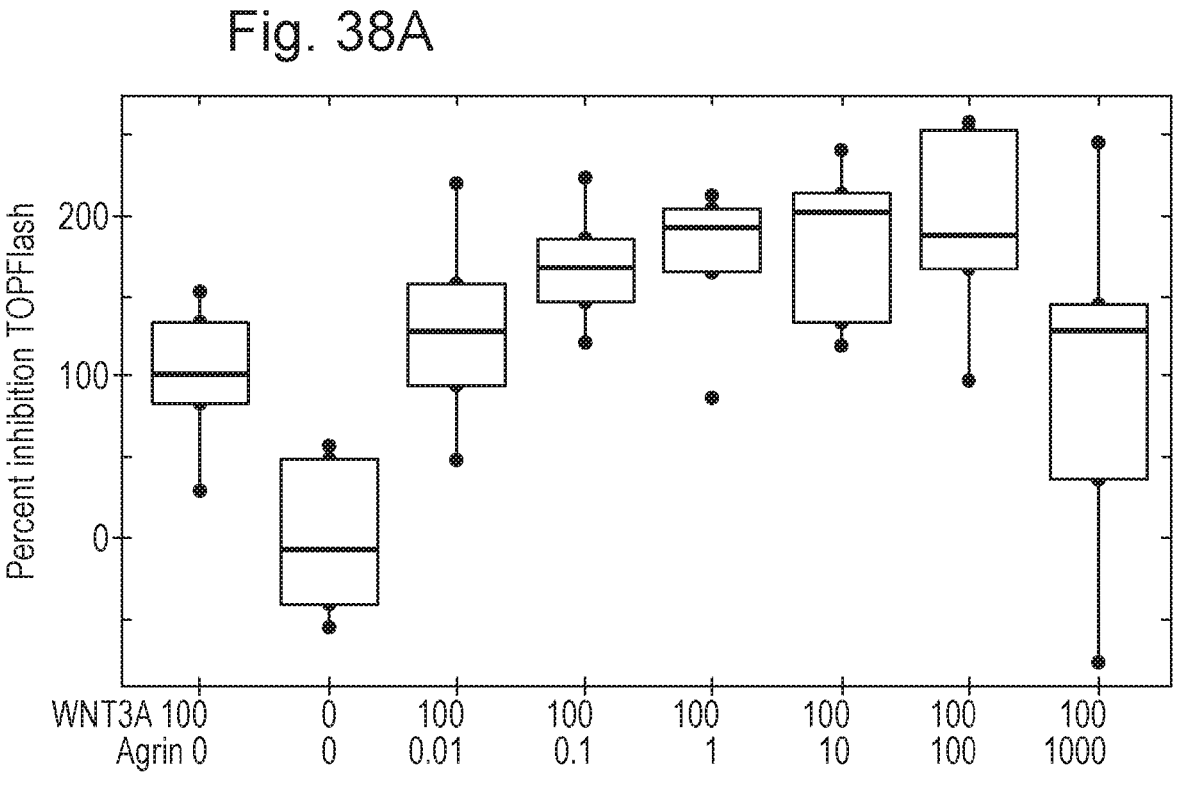
Figure 38B:
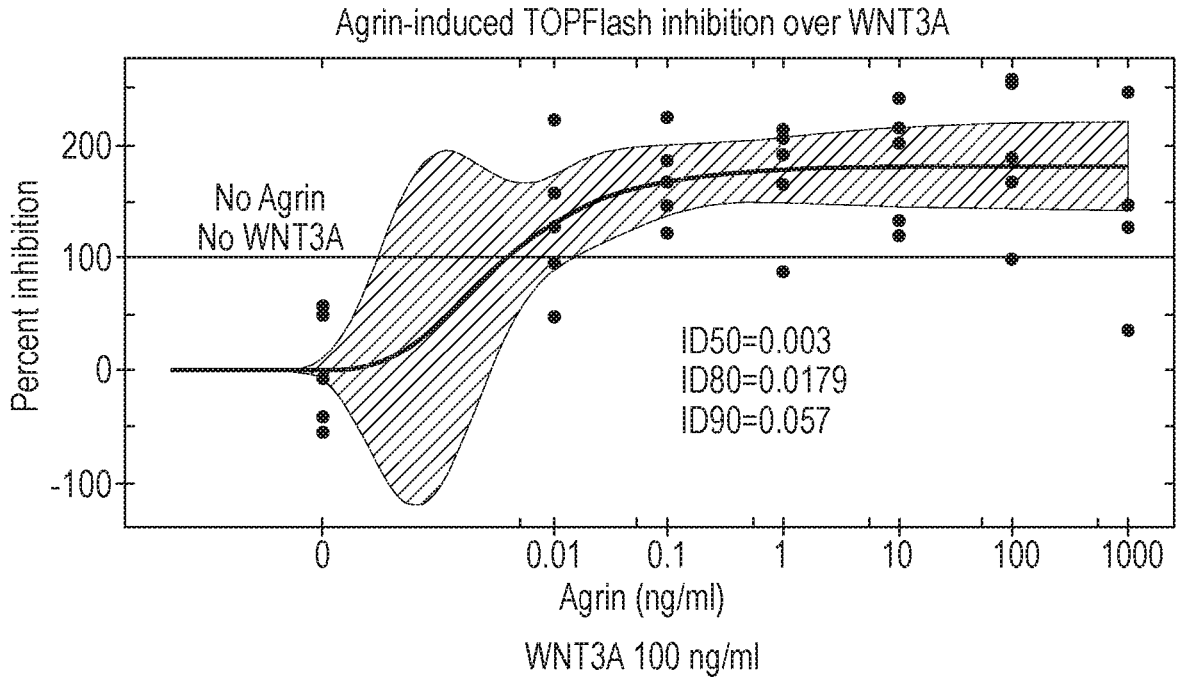
Figures 39A, 39B:
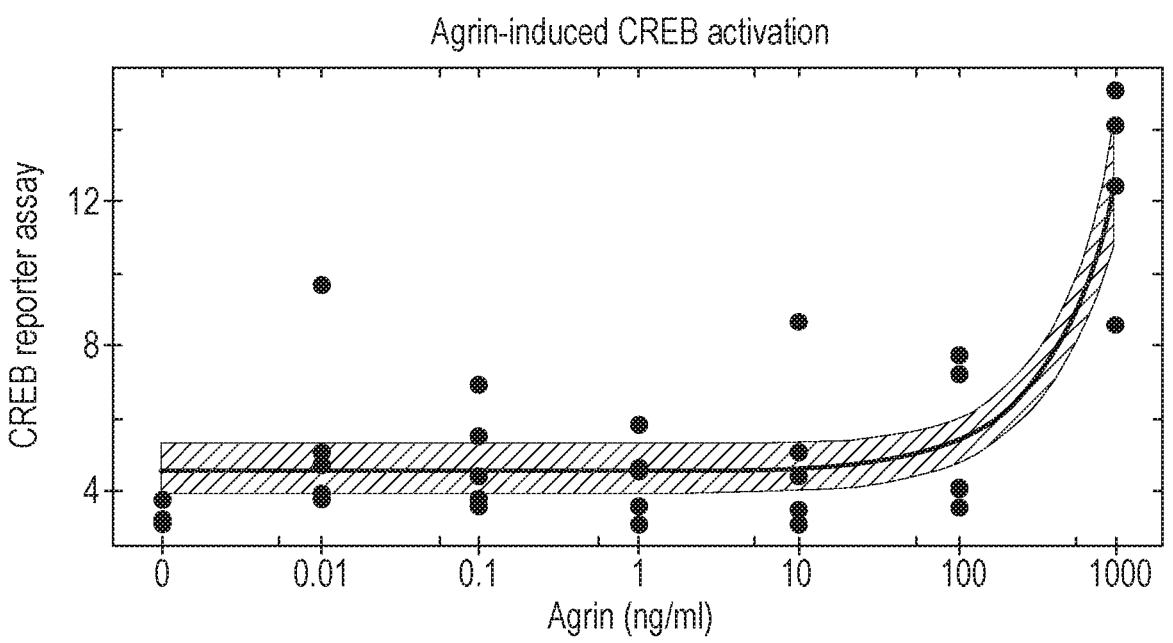

FIGS. 37-39 show in vitro dose response experiments showing effective pharmacological doses for chondrogenic effect (extracellular matrix production shown by alcian blue; inhibition of WNT signalling and activation of CREB signalling) of rAgrin (SEQ ID NO: 3).

FIG. 37 shows Chondrogenic potential or rAgrin. Chondrocytic cell line C28/I2 cells were cultured in micromass and treated with increasing concentration of tagged rAgrin. (A) rAgrin shown as pM, (B) rAgrin as ng/ml and (C) rAgrin shown as log(ng/ml). Estimated effective doses: ED50: 0.0074773 ng/ml=0.0538 pM, ED90:15.2689083 ng/ml=109.53 pM FIG. 38 shows inhibition of WNT signalling by rAgrin (SEQ ID NO: 3). Chondrocytic cell line C28/I2 cells were cultured in monolayer following transfection with the TOPFlashSuper8X WNT signalling reporter plasmid and normalising *Renilla* plasmid. Cells were treated with increasing concentrations of tagged rAgrin (SEQ ID NO: 3). (A) Data shown as relative luciferase units or (B) a percentage of inhibition of WNT signalling by rAgrin (ng/ml) (SEQ ID NO: 3). Estimated effective doses are shown in (B).

FIG. 39 shows activation of CREB signalling by rAgrin (SEQ ID NO: 3). Chondrocytic cell line C28/I2 cells were cultured in monolayer following transfection with the CREB reporter plasmid and normalising *Renilla* plasmid. Cells were treated with increasing concentrations of tagged rAgrin (SEQ ID NO: 3). (A) Data shown as relative luciferase units or (B) a percentage of CREB activation rAgrin (ng/ml) (SEQ ID NO: 3).

Figure 40:
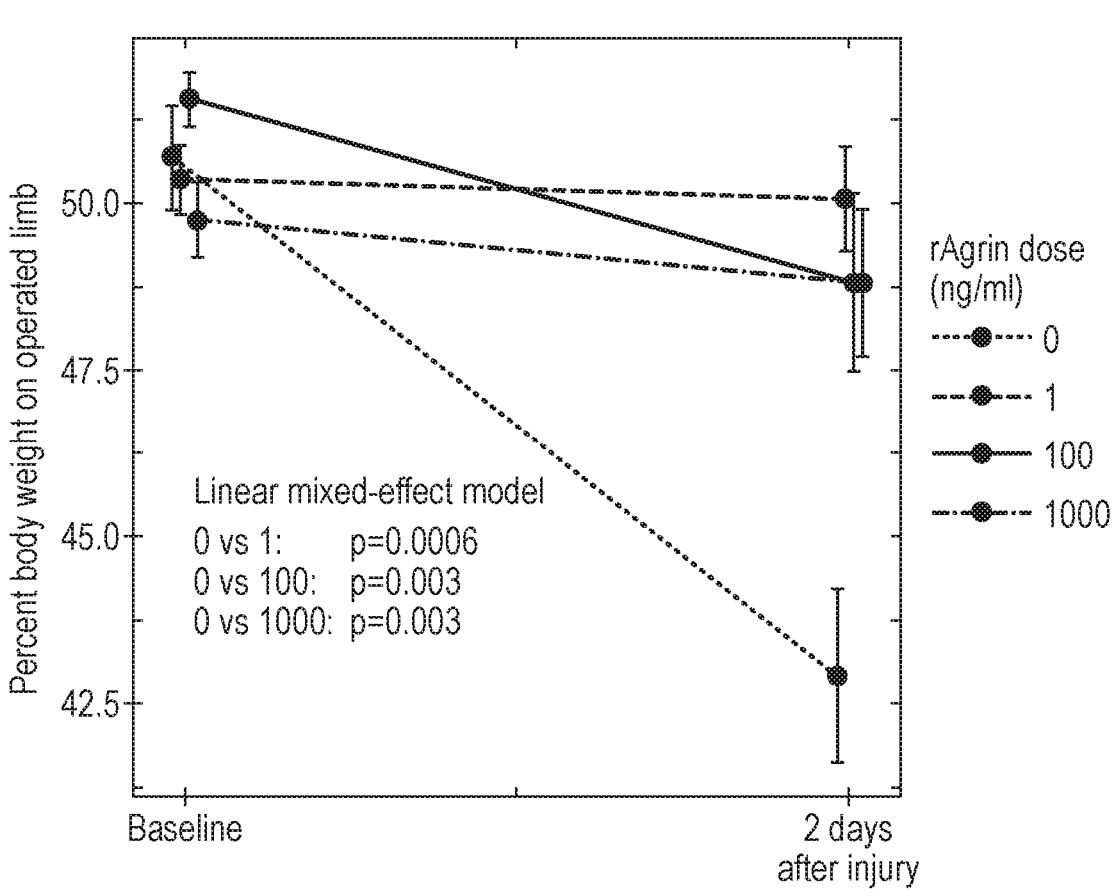
Figure 41A:
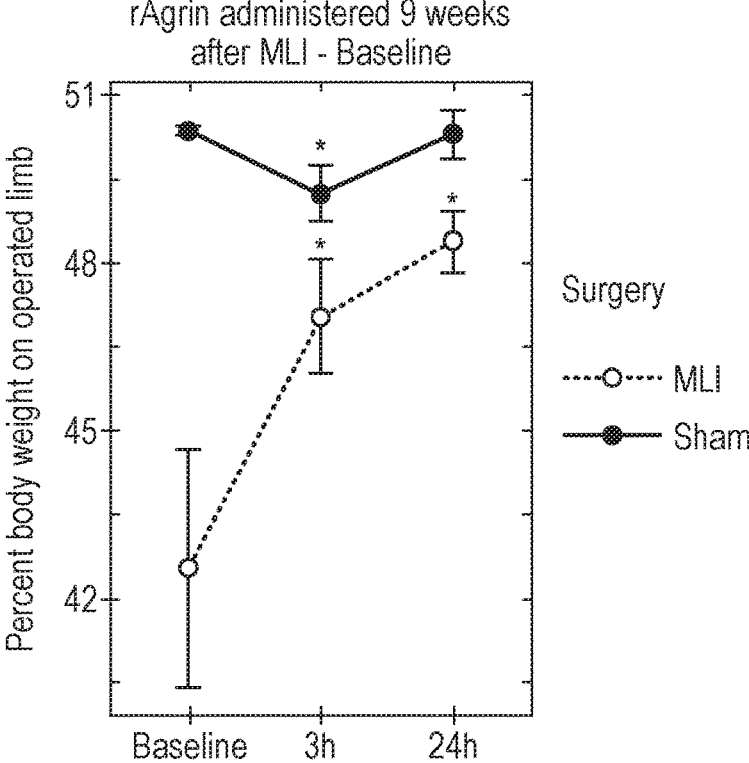
Figure 41B:
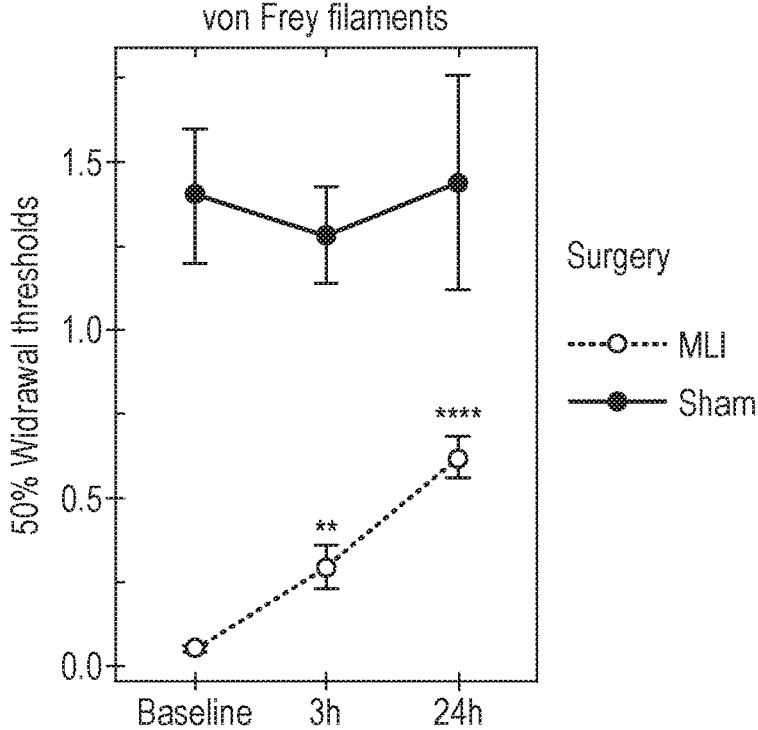

FIGS. 40-41 show the analgesic effects of rAgrin (SEQ ID NO: 3) in both acute (post-surgical) and chronic (established osteoarthritic) pain. The animal were injected intra-articularly in all cases—this is a novel, peripheral route, of administration. Previous studies show that neuronal agrin injected directly into the spinal cord of animals resulted in analgesia. Here the inventors show that non-neuronal rAgrin (SEQ ID NO: 3) acting as an analgesic when injected directly in the joint. This is novel route of administration but also suggests that rAgrin (SEQ ID NO: 3) could be a useful analgesic for other pain-associated indications, such as fibromyalgia, without the need for intra-spinal injections.

FIG. 40 shows that rAgrin (SEQ ID NO: 3) is analgesic in acute pain. Mice undergoing surgery to create a critical size osteochondral defect received 2 ul of 0, 1, 100 or 1000 ng/ml rAgrin (SEQ ID NO: 3). Pain was measured 2 days after surgery and is measured as weight bearing on the operated limbs vs unoperated (baseline 50%).

FIG. 41 shows that rAgrin (SEQ ID NO: 3) is analgesic in chronic pain. Osteoarthritis was surgically induced in adult mice. At the end of the study (9 weeks) the mice were determined to have established chronic pain, both in terms weight bearing capabilities (A) and of hyperalgesia (B). Mice were injected with 6 ul of 100 ng/ml of rAgrin (SEQ ID NO: 3) intra-articularly and their pain levels were measured at 3 and 24 hrs post injection. The treatment with 0.5 ng rAgrin (SEQ ID NO: 3) resulted in reduced hyperalgesia and restored weight bearing capabilities of these mice.

Figure 42:
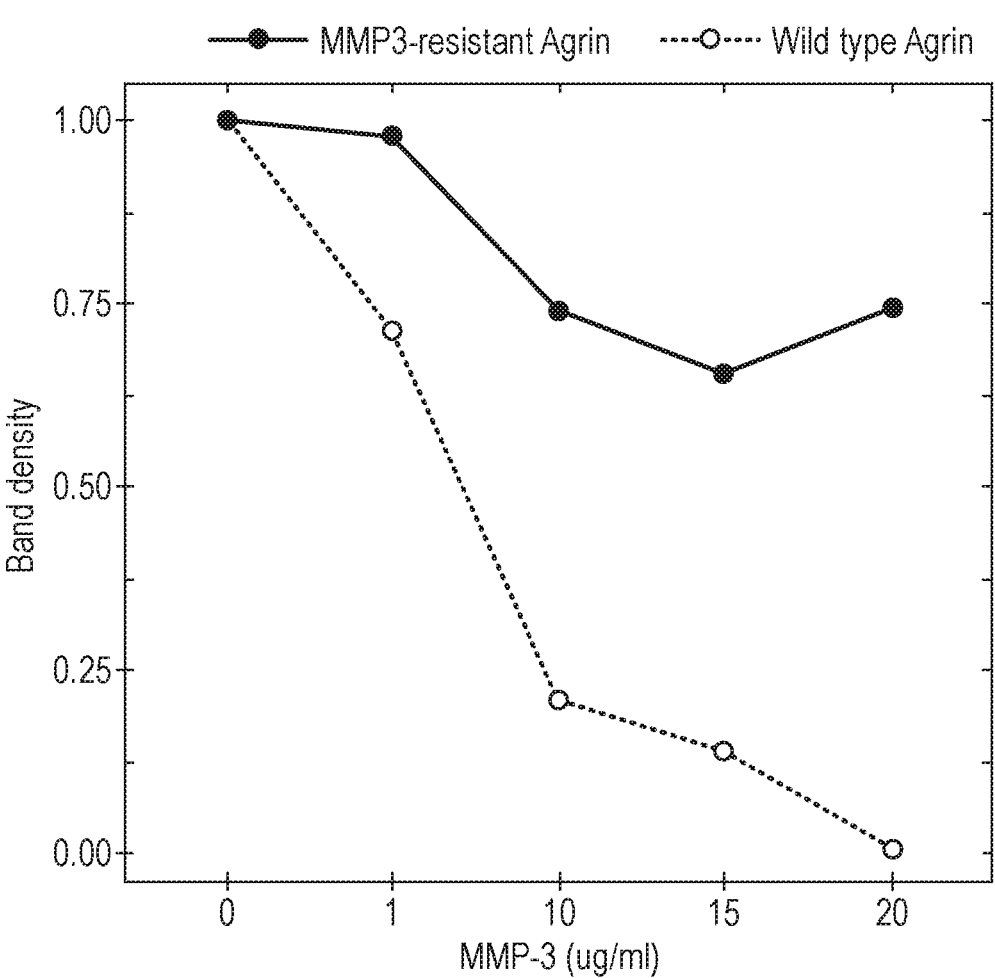
Figure 43A:
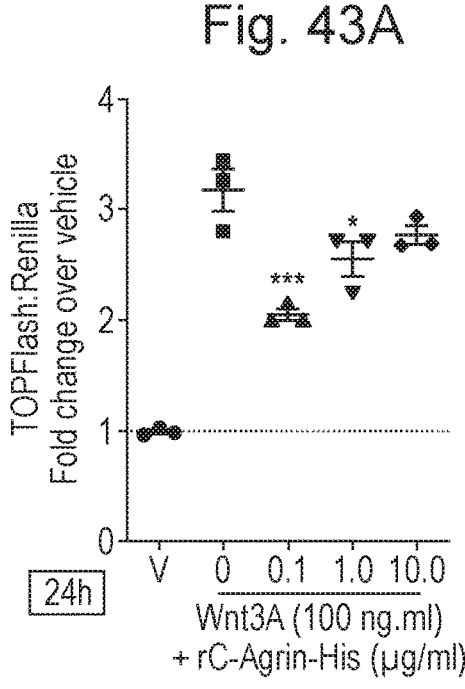
Figure 43B:
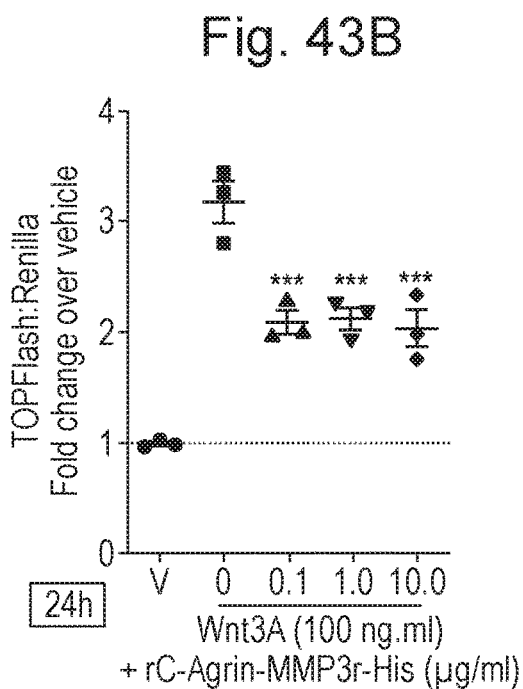
Figure 43C:
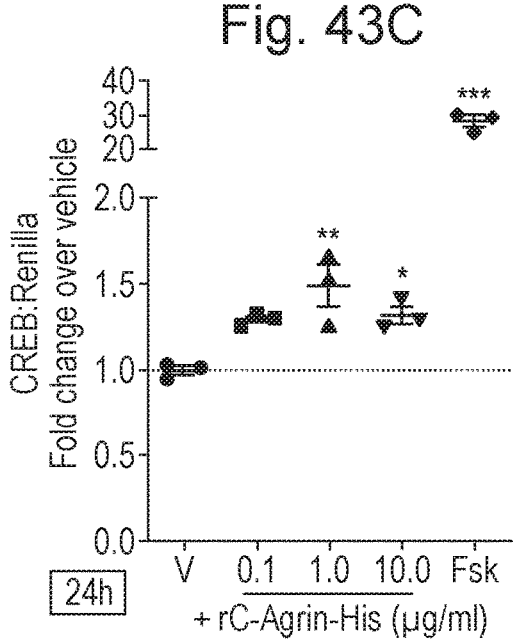
Figure 43D:
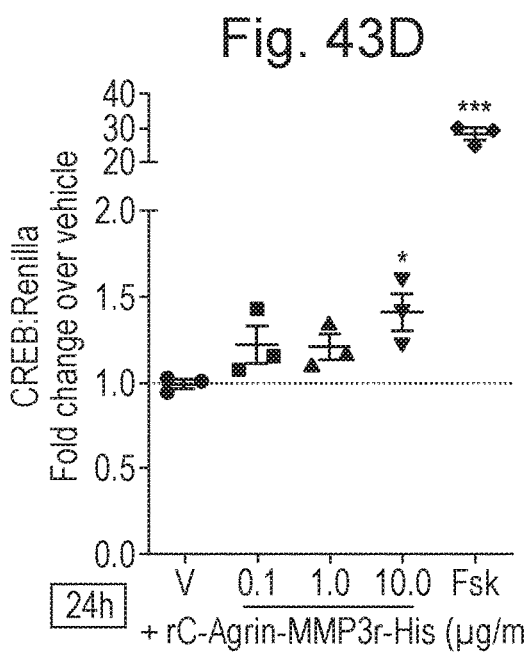

FIG. 42 shows that mutation of the MMP-3 cleavage site reduces degradation of Agrin (polypeptide defined by SEQ ID NO: 19) in the presence of increasing amounts of MMP3 for 24 hours.

FIG. 43 shows that MMP3 resistant Agrin (SEQ ID NO: 19) is as active as native rAgrin (SEQ ID NO: 3) in activating CREB and inhibiting WNT signalling. HEK293 cells were transfected with TOPFlashSuper8X (A and B) or CREB (C and D) reporter plasmids and co-transfected with *Renilla*. Cells were cultured in monolayer and treated with increasing doses of either rAgrin (A and C) or MMP3 resistant rAgrin (B and D)

BRIEF DESCRIPTION OF THE SEQUENCES

SEQ ID NO: 1 is a 2045 amino acid sequence corresponding to the complete, unspliced translation of the coding sequence of wildtype human agrin mRNA (which mRNA sequence is disclosed as GenBank Accession No. BAD52440.1).

SEQ ID NO: 2 is the amino acid sequence corresponding to amino acid residues 1244-1259 of SEQ ID NO: 1.

SEQ ID NO: 3 is the amino acid sequence corresponding to amino acid residues 1244-2045 of SEQ ID NO: 1.

SEQ ID NO: 4 is the amino acid sequence of a splice variant of human agrin corresponding to UniProt accession no. 000468-1.

SEQ ID NO: 5 is the amino acid sequence of a splice variant of human agrin corresponding to UniProt accession no. 000468-2.

SEQ ID NO: 6 is the amino acid sequence of a splice variant of human agrin corresponding to UniProt accession no. 000468-3.

SEQ ID NO: 7 is the amino acid sequence of a splice variant of human agrin corresponding to UniProt accession no. 000468-4.

SEQ ID NO: 8 is the amino acid sequence of a splice variant of human agrin corresponding to UniProt accession no. 000468-5.

SEQ ID NO: 9 is the amino acid sequence of a splice variant of human agrin corresponding to UniProt accession no. 000468-6.

SEQ ID NO: 10 is the amino acid sequence of a splice variant of human agrin corresponding to UniProt accession no. 000468-7.

SEQ ID NO: 11 is the amino acid sequence of a splice variant of human agrin corresponding to amino acid residues 1260-2045 of SEQ ID NO: 1.

SEQ ID NO: 12 is the amino acid sequence corresponding to the MMP3 recognition site in SEQ ID NO: 1.

SEQ ID NO: 13 is the polynucleotide sequence encoding the polypeptide sequence of SEQ ID NO: 3 and an enterokinase cleavage site, an alkaline phosphatase tag, a MYC tag and a His tag.

SEQ ID NO: 14 is the polypeptide sequence encoded by the polynucleotide sequence of SEQ ID NO: 13.

SEQ ID NO: 15 is the polynucleotide sequence encoding the polypeptide sequence of SEQ ID NO: 3.

SEQ ID NO: 16 is the polynucleotide sequence encoding the polypeptide sequence of SEQ ID NO: 3, further wherein the polypeptide sequence is MMP3 cleavage resistant, and an enterokinase cleavage site, an alkaline phosphatase tag, a MYC tag and a His tag.

SEQ ID NO: 17 is the polypeptide sequence encoded by the polynucleotide sequence of SEQ ID NO: 16.

SEQ ID NO: 18 is the polynucleotide sequence encoding the polypeptide sequence of SEQ ID NO: 3, further wherein the polypeptide sequence is MMP3 cleavage resistant.

SEQ ID NO: 19 is the polypeptide sequence encoded by the polynucleotide sequence of SEQ ID NO: 18.

DETAILED DESCRIPTION OF THE INVENTION

It is to be understood that different applications of the disclosed methods may be tailored to the specific needs in the art. It is also to be understood that the terminology used herein is for the purpose of describing particular embodiments of the invention only, and is not intended to be limiting.

In addition, as used in this specification and the appended claims, the singular forms "a", "an", and "the" include plural referents unless the content clearly dictates otherwise. Thus, for example, reference to "a polypeptide" includes "polypeptides", and the like.

A "polypeptide" is used herein in its broadest sense to refer to a compound of two or more subunit amino acids, amino acid analogs, or other peptidomimetics. The term "polypeptide" thus includes short peptide sequences and also longer polypeptides and proteins. As used herein, the term "amino acid" refers to either natural and/or unnatural or synthetic amino acids, including both D or L optical isomers, and amino acid analogs and peptidomimetics.

Unless otherwise specified, references herein to numerical positions of amino acids in a polypeptide are based on the positions of amino acids in the sequence of SEQ ID NO: 1, numbered from the N terminus to the C terminus.

The terms "patient", "subject" and "individual" are used interchangeably and typically refer to a human.

All publications, patents and patent applications cited herein, whether supra or infra, are hereby incorporated by reference in their entirety.

Polypeptide

The present inventors have determined that a polypeptide which is a fragment of a human agrin or a variant of a human agrin, and which comprises at least the amino acid sequence of SEQ ID NO: 2, has the ability to induce chondrocyte differentiation and/or chondrogenesis comparable to a wild-type human agrin, whilst having advantageous properties such as being more soluble and/or easier to manufacture than a full length agrin. The sequence of amino acids at positions 1244 to 1259 of SEQ ID NO: 1 directly corresponds to the amino acid sequence of SEQ ID NO: 2.

Human agrin is a heparan sulfate basal lamina glycol protein that is known to play a key role in the formation and the maintenance of the neuromuscular junction (NMJ) and directs key events in postsynaptic differentiation. Upon secretion, agrin is known to associate with the extracellular matrix and cell surfaces, which underlies the poor solubility of agrin. Agrin is particularly well-known for stabilising the clustering of acetylcholine receptors at the neuromuscular junction by binding to the LRP4 receptor. The present inventors have found that agrin is an orchestrator of repair morphogenesis at the joint surface by modulating multiple signaling pathways. Particularly, the inventors have demonstrated that agrin plays a role not only in differentiation of mature articular chondrocytes but also in chondrogenesis and may consequently mediate the repair of osteochondral defects. The soluble polypeptide of the invention retains the functional activity of human agrin, namely the ability to induce chondrocyte differentiation and/or chondrogenesis. In all of the assays described herein that are suitable for determining the functional activity of the soluble polypeptide of the invention, it is to be assumed that the soluble polypeptide of the invention is determined as "retaining" a particular functional activity of a human agrin when both the soluble polypeptide of the invention and the human agrin are subjected to the same assay for determining a particular functional activity.

Induction of chondrocyte differentiation by the soluble polypeptide of the invention relates to the differentiation of chondrocytes, particularly mature articular chondrocytes. Chondrocyte differentiation may be determined using any suitable method in the art, including in vivo and in vitro methods. For example, chondrocyte differentiation may be determined as having been induced if after being contacted by the soluble polypeptide of the invention said chondrocytes produce an increased amount of extracellular matrix proteins, such as those that form cartilage, and/or upregulate SOX9 (SRY-Box Transcription Factor 9) expression, relative to chondrocytes that have not been contacted with the soluble polypeptide of the invention. Cartilage production can be measured by any suitable assay in the art, although its production may particularly be determined by Alcian blue-positive extracellular matrix staining. SOX9 gene expression can be measured by any suitable assay in the art.

Induction of chondrogenesis by the soluble polypeptide of the invention relates to the differentiation of stem cells to form chondrocytes. Chondrogenesis may be determined using any suitable method in the art, including in vivo and in vitro methods. The stem cells induced by the soluble polypeptide of the invention may be mesenchymal stem cells (MSCs), and may particularly be MSCs that originate in the synovial membrane. The stem cells are preferably of GDF5 lineage, meaning that the stem cells previously expressed GDF5 during embryonic development and thereby giving rise to articular cartilage, menisci, and ligaments. It is well known in the art that the cells in the joint that form soft tissue such as articular cartilage, menisci, and ligaments are derived from GDF5 lineage cells. An assay for determining the differentiation of stem cells may, for example, determine whether the soluble polypeptide according to the invention when contacted with the soluble polypeptide of the invention:

a. induce MMP-13 or COL10A1 expression;
    b. induce SOX9 expression;
    c. induce COL2A1 expression;
    d. induce aggrecan expression; and/or
    e. induce cartilage production,
    relative to chondrocytes that have not been contacted with the soluble polypeptide of the invention.

The soluble polypeptide according the invention preferably, as compared to a human agrin, preferably the human agrin of SEQ ID NO: 1, retains:

a. an ability to promote differentiation of chondrocytes;
    b. an ability to induce chondrogenesis in mesenchymal stem cells;
    c. an ability to induce MMP-13 or COL10A1 expression;
    d. an ability to induce SOX9 expression;
    e. an ability to induce COL2A1 expression;
    f. an ability to induce aggrecan expression;
    g. an ability to induce cartilage production; and/or
    h. an ability to induce the differentiation of stem cells, preferably mesenchymal stem cells of synovial membrane origin, and more preferably mesenchymal stem cells of GDF5 lineage.

Induction of chondrocyte differentiation and/or chondrogenesis may also be determined by measuring the effects of these processes. The effects of chondrocyte differentiation and/or chondrogenesis may be determined by any suitable method in the art, particularly through utilisation of in vitro and in vivo models, although most preferably through utilisation of in vivo models. For example, chondrocyte differentiation and/or chondrogenesis induced by the soluble polypeptide of the invention, following injury in a subject or relative to baseline status in a subject, may:

i. improve osteochondral defects;
    ii. improve joint function;
    iii. improve weight bearing ability of a limb; and/or
    iv. reduce pain.

Exemplary effects of chondrocyte differentiation and/or chondrogenesis induced by the soluble polypeptide of the invention as set out above in i. to iv. may be determined by any suitable method in the art.

The soluble polypeptide of the invention comprises the amino acid sequence of SEQ ID NO: 2 and has the ability to induce chondrocyte differentiation and/or chondrogenesis, which polypeptide is a fragment of a human agrin or of a variant of a human agrin.

The human agrin of which the soluble polypeptide is a fragment may comprise:

the amino acid sequence of SEQ ID NO: 1 (the complete, unspliced translation of the coding sequence of wild-type human agrin mRNA);

the amino acid sequence of SEQ ID NO: 1 with an insert of up to 19 amino acids in one or more of the following location: (i) between positions 1250 and 1251; (ii) between positions 1751 and 1752; and (iii) between position 1884 and 1885; or the amino acid sequence of any one of the following splice variants of human agrin:

a. Isoform 1—SEQ ID NO: 4;
b. Isoform 2—SEQ ID NO: 5;
c. Isoform 3—SEQ ID NO: 6;
d. Isoform 4—SEQ ID NO: 7;
e. Isoform 5—SEQ ID NO: 8;
f. Isoform 6—SEQ ID NO: 9;
g. Isoform 7—SEQ ID NO: 10.

Alternatively, the soluble polypeptide may be a fragment of a variant of a human agrin. Said variant is typically has at least 60%, at least 65%, at least 70%, at least 75%, at least 80%, at least 85%, at least 90%, at least 95%, at least 97%, or at least 99% sequence identity with any one of SEQ ID NO: 1, 3, 4, 5, 6, 7, 8, 9 or 10.

The human agrin of which the soluble polypeptide of the invention is a fragment of may be any known human agrin sequence in the art. It is well understood that human agrin exists in a number of different isoforms, largely considered to be a consequence of the tissue in which the human agrin is expressed. Particularly, human agrin may exist in as a non-neuronal or neuronal isoform, depending on whether the human agrin is produced by non-neuronal cells or neuronal cells. The known isoforms of human agrin are defined by whether they comprise one or more insertions of one or more amino acids at three distinct splice sites within a human agrin polypeptide sequence that corresponds to the unspliced translated sequence of the complete coding sequence of the wildtype human agrin mRNA (GenBank accession no. of the coding sequence of the mRNA of the AGRN gene: AB191264). The unspliced translated sequence of the complete coding sequence mRNA of human agrin is defined by SEQ ID NO: 1 herein. The amino acid sequence of SEQ ID NO: 1 corresponds to the GenBank accession no. sequence of BAD52440. The three distinct splice sites within SEQ ID NO: 1 as known in the art exist between the amino acids at positions:

i. 1250 and 1251;
ii. 1751 and 1752; and
iii. 1884 and 1885.

The three distinct splice sites of i. to iii. Are known in the art as the 'x', 'y' and 'z' splice sites, respectively. The human agrin which the soluble polypeptide of the invention is a fragment of may comprise an insert of up to 19 amino acids between the amino acids corresponding to positions:

a. 1250 and 1251 of SEQ ID NO: 1; and/or
b. 1751 and 1752 of SEQ ID NO: 1; and/or
c. 1884 and 1885 of SEQ ID NO: 1.

The inserts of up to 19 amino acids may consist of any selection of one or more amino acids provided that the soluble polypeptide of the invention remains soluble and retains the ability to induce chondrocyte differentiation and/or chondrogenesis of the human agrin of SEQ ID NO: 1

The primary amino acid sequences of a number of human agrin isoforms have been defined in the art and are accessible via repositories such as UniProt. It is expected that the isoforms of human agrin are not limited to those whose primary amino acid sequences are known and therefore accessible via UniProt. In the any of soluble polypeptides of the invention described herein, it is not intended for sequence of human agrin which the soluble polypeptide of the invention is a fragment of to be limited to any one or more of the known human agrin isoform sequences, particularly in view of the expected functional redundancy in the insert sequences corresponding to the 'x', 'y' and 'z' splice sites.

Isoform 1 (UniProt accession no. 000468-1; SEQ ID NO: 4) includes a KSRK insertion at the 'y' site and a ELANEIPVPETLDSGALHS insertion at the 'z' site, and is otherwise identical to SEQ ID NO: 1.

Isoform 2 (UniProt accession no. 000468-2; SEQ ID NO: 5) lacks amino acids 1 to 104 and the sequence from amino acids 105-154 is substituted to MPXLAVARDTRQPA-GASLLV RGFMVPCNACLILLATATLG FAVLLFLNNY. The sequence of isoform 2 includes a KSRK insertion at the 'y' site and a ELANEIPVPETLDSGALHS insertion at the 'z' site, and is otherwise identical to SEQ ID NO: 1. Isoform 2 is unique among the known isoforms of human agrin in that, when expressed in a cell, it is not secreted. Rather, it exists as transmembrane protein.

Isoform 3 (UniProt accession no. 000468-3; SEQ ID NO: 6) includes a KSRK insertion at the 'y' site, and is otherwise identical to SEQ ID NO: 1.

Isoform 4 (UniProt accession no. 000468-4; SEQ ID NO: 7) includes a KSRK insertion at the 'y' site and a PETLDSGALHS insertion at the 'z' site, and is otherwise identical to SEQ ID NO: 1.

Isoform 5 (UniProt accession no. 000468-5; SEQ ID NO: 8) includes a KSRK insertion at the 'y' site and a ELANEIPV insertion at the 'z' site, and is otherwise identical to SEQ ID NO: 1.

Isoform 6 (UniProt accession no. 000468-6; SEQ ID NO: 9) is identical to SEQ ID NO: 1.

Isoform 7 (UniProt accession no. 000468-7; SEQ ID NO: 10) includes a ELANEIPVPETLDSGALHS insertion at the 'z' site, and is otherwise identical to SEQ ID NO: 1.

Functional redundancy is expected to exist among human agrin isoforms containing variable amino acid insertions at the 'x', 'y' and 'z' sites, therefore it is not intended to limit the sequence of human agrin which the soluble polypeptide of to any particular known isoform.

Neuronal human agrin will typically include amino acid insertions at the 'y' and 'z' splice sites. In some aspects of the invention, the sequence of human agrin which the soluble polypeptide of the invention is a fragment of may be neuronal or non-neuronal agrin. Preferably, the sequence of human agrin which the soluble polypeptide of the invention is non-neuronal agrin In some aspects of the invention, the sequence of human agrin which the soluble polypeptide of the invention is a fragment of may be defined by amino acid sequence of any one of the following splice variants of human agrin:

a. Isoform 1—SEQ ID NO: 4;
b. Isoform 2—SEQ ID NO: 5;
c. Isoform 3—SEQ ID NO: 6;
d. Isoform 4—SEQ ID NO: 7;
e. Isoform 5—SEQ ID NO: 8;
f. Isoform 6—SEQ ID NO: 9;
g. Isoform 7—SEQ ID NO: 10

The soluble polypeptide of the invention may be a fragment of a variant of a human agrin described herein. The variant may be an agrin from a non-human mammal or any other source. The variant will typically share the functional features of human agrin, such as the ability to induce chondrocyte differentiation and/or chondrogenesis, preferably comparable to the corresponding abilities of the human agrin of SEQ ID NO: 1. A variant agrin may be a human agrin sequence incorporating one or more amino acid modifications. The variant may share any percentage sequence identity greater than 55% with any human agrin described herein. The variant may have at least 60%, at least 65%, at least 70%, at least 75%, at least 80%, at least 85%, at least 90%, at least 95%, at least 97%, or at least 99% sequence identity with said any human agrin described herein, optionally wherein the human agrin is defined by SEQ ID NO: 1, 3, 4, 5, 6, 7, 8, 9 or 10.

The soluble polypeptide of the invention may comprise or consist of any amino acid sequence length provided that the sequence comprises SEQ ID NO: 2 and is soluble and has the ability to induce chondrocyte differentiation and/or chondrogenesis. The soluble polypeptide of the invention may particularly comprise or consist of up to 1000, 950, 900, 850 or 802 consecutive amino acids of the human agrin or variant of human agrin described herein. The soluble polypeptide of the invention may comprise or consist of a sequence of at least 200, at least 300, at least 400, at least 500, at least 600, at least 700, or at least 800, or at least 802 consecutive amino acids of SEQ ID NO: 1, and optionally may comprise or consist of the sequence of SEQ ID NO: 3.

The soluble polypeptide of the invention may comprise an insert of up to 19 amino acids in one or more of the following locations of SEQ ID NO: 1:
a. between positions 1250 and 1251;
b. between positions 1751 and 1752;
c. between positions 1884 and 1885.

In addition to a sequence of consecutive amino acids from a human agrin or a variant of a human agrin, a soluble polypeptide of the invention may include additional amino acids at the N- or C-terminus of said sequence of consecutive amino acids, provided the soluble polypeptide does not exceed a total of 810, 850, 900, 950 or 1000 amino acids in length. Said additional amino acids may impart one or more advantageous biochemical properties e.g. in relation to solubility, manufacture, purification, or delivery of the polypeptide. For example, the polypeptide may include an additional methionine (M) residue at the N terminus and/or a tag at the C terminus to assist with expression in and isolation from standard bacterial expression systems. Suitable tags include a histidine tag which may be joined directly to the C terminus of a polypeptide or joined indirectly by any suitable linker sequence, such as 3, 4 or 5 glycine residues. The histidine tag typically consists of six histidine residues, although it can be longer than this, typically up to 7, 8, 9, 10 or 20 amino acids or shorter, for example 5, 4, 3, 2 or 1 amino acids.

In any polypeptide disclosed herein, any one or more of the following modifications may also be made to improve physiochemical properties (e.g. stability), provided that the polypeptide remains soluble and retains the ability to induce chondrocyte differentiation and/or chondrogenesis, as compared to a soluble polypeptide having the unmodified sequence:
a) Replacement of the C terminal amino acid with the corresponding amide (may increase resistance to carboxypeptidases);
b) Replacement of the N terminal amino acid with the corresponding acylated amino acid (may increase resistance to aminopeptidases);
c) Replacement of one or more amino acids with the corresponding methylated amino acids (may improve proteolytic resistance);
d) Replacement of one or more amino acids with the corresponding amino acid in D-configuration (may improve proteolytic resistance).

In any of the soluble polypeptides of the invention described herein, the amino acid sequence may be modified by one, two, three, four, or five (that is upto five) additions, deletions or substitutions, provided that a polypeptide having the modified sequence remains soluble and retains the ability to induce chondrocyte differentiation and/or chondrogenesis, as compared to a soluble polypeptide having the unmodified sequence. By "the same" it is to be understood that the polypeptide of the modified sequence does not exhibit significantly reduced solubility or reduced ability to induce chondrocyte differentiation and/or chondrogenesis as compared to polypeptide of the unmodified sequence. Any comparison of solubility or ability to induce chondrocyte differentiation and/or chondrogenesis between sequences is to be conducted using the same assay.

Unless otherwise specified, modifications to a polypeptide sequence are preferably conservative amino acid substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table A1 below. Where amino acids have similar polarity, this can be determined by reference to the hydropathy scale for amino acid side chains in Table A2.

TABLE A1

| Chemical properties of amino acids | | | |
|---|---|---|---|
| Ala (A) | aliphatic, hydrophobic, neutral | Met (M) | hydrophobic, neutral |
| Cys (C) | polar, hydrophobic, neutral | Asn (N) | polar, hydrophilic, neutral |
| Asp (D) | polar, hydrophilic, charged (−) | Pro (P) | hydrophobic, neutral |
| Glu (E) | polar, hydrophilic, charged (−) | Gln (Q) | polar, hydrophilic, neutral |
| Phe (F) | aromatic, hydrophobic, neutral | Arg (R) | polar, hydrophilic, charged (+) |
| Gly (G) | aliphatic, neutral | Ser (S) | polar, hydrophilic, neutral |
| His (H) | aromatic, polar, hydrophilic, charged (+) | Thr (T) | polar, hydrophilic, neutral |
| Ile (I) | aliphatic, hydrophobic, neutral | Val (V) | aliphatic, hydrophobic, neutral |
| Lys (K) | polar, hydrophilic, charged(+) | Trp (W) | aromatic, hydrophobic, neutral |
| Leu (L) | aliphatic, hydrophobic, neutral | Tyr (Y) | aromatic, polar, hydrophobic |

TABLE A2

| Hydropathy scale | |
| --- | --- |
| Side Chain | Hydropathy |
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

The soluble polypeptide according the present invention may comprise a modification to its sequence in order to confer resistance to matrix metalloproteinases (MMP). Particularly, any MMP cleavage motif present in the amino acid sequence of the soluble polypeptide of the invention may be modified in order confer resistance to cleavage by MMP, provided that the polypeptide remains soluble and retains the ability to induce chondrocyte differentiation and/or chondrogenesis, as compared to a soluble polypeptide having the unmodified sequence. The soluble polypeptide of the invention may particularly be resistant to cleavage by MMP3. An MMP3 cleavage site is defined by the amino acid sequence PHTVLN. In any of the soluble polypeptides of the invention, wherein the soluble polypeptide contains a PHTVLN sequence, one or more amino acids within the PHTVLN sequence may be deleted or substituted in order to confer resistance to MMP3 cleavage. A PHTVLN sequence is contained within the amino acid sequence of human agrin as defined by SEQ ID NO: 1. Specifically, PHTVLN can be found at amino acids 1753 to 1758 of SEQ ID NO: 1. Thus, when the human agrin which the soluble polypeptide of the invention is a fragment of is SEQ ID NO: 1, at least one of the amino acids corresponding to positions 1753, 1754, 1755, 1756, 1757 and 1758 may be deleted or substituted with another amino acid in order to confer resistance to cleavage by MMP3. When the human agrin which the soluble polypeptide of the invention is a fragment of is SEQ ID NO: 1, at least two, at least three, at least four, at least five, or all of the amino acids corresponding to positions 1753, 1754, 1755, 1756, 1757 and 1758 may be deleted or substituted with another amino acid in order to confer resistance to cleavage by MMP3. When the human agrin which the soluble polypeptide of the invention is a fragment of is SEQ ID NO: 1, at least two, at least three, at least four, at least five, or all of the amino acids corresponding to positions 1753, 1754, 1755, 1756, 1757 and 1758 may be deleted or substituted with a glycine in order to confer resistance to cleavage by MMP3. When the human agrin which the soluble polypeptide of the invention is a fragment of is SEQ ID NO: 1, the amino acid at position 1754 may be substituted with a glycine, the amino acid at position 1755 may be substituted with a glycine, and the amino acid at position 1756 may be substituted with a glycine, thus the amino acid sequence at position 1753 to 1758 of SEQ ID NO: 1 may be substituted to PGGGLN.

A polypeptide as disclosed herein may be produced by any suitable means. For example, the polypeptide may be synthesised directly using standard techniques known in the art, such as Fmoc solid phase chemistry, Boc solid phase chemistry or by solution phase peptide synthesis. Alternatively, a polypeptide may be produced by transforming a cell, typically a bacterial cell, with a nucleic acid molecule or vector which encodes said polypeptide. The invention provides nucleic acid molecules and vectors which encode a polypeptide of the invention. The invention also provides a host cell, particularly a mammalian cell, comprising such a nucleic acid or vector.

A soluble polypeptide of the invention described herein may be obtainable by a method comprising transfection of mammalian cell line with a nucleic acid vector comprising a polynucleotide sequence encoding the soluble polypeptide of the invention. The mammalian cells may be any suitable cell line. Preferably the mammalian cells are Expi293 cells. The nucleic acid vector comprising a polynucleotide sequence encoding the soluble polypeptide of the invention may be any suitable nucleic acid vector. Preferably the nucleic acid vector is a lentivirus vector, and more preferably that the nucleic acid vector is a $3^{rd}$ generation lentivirus gene expression vector backbone. The polynucleotide sequence encoding the soluble polypeptide of the invention may be downstream of a CMV promoter, an IgG kappa signal peptide and followed by an enterokinase cleavage site, thermostable alkaline phosphatase, Myc and 10× His tags and finally by a stop codon. The nucleic acid vector comprising a polynucleotide sequence encoding the soluble polypeptide of the invention may be transiently transfected into the mammalian cells. Optionally, about three days post transfection, the soluble polypeptide of the invention is purified.

The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or substantially isolated form. By substantially isolated, it is meant that there may be substantial, but not total, isolation of the polypeptide from any surrounding medium. The polynucleotides may be mixed with carriers or diluents which will not interfere with their intended use and still be regarded as substantially isolated. A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences, for example in an expression vector. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

Polynucleotides can be synthesised according to methods well known in the art, as described by way of example in Sambrook et al (1989, Molecular Cloning—a laboratory manual; Cold Spring Harbor Press). The nucleic acid molecules of the present invention may be provided in the form of an expression cassette which includes control sequences operably linked to the inserted sequence, thus allowing for expression of the polypeptide of the invention in vivo. These expression cassettes, in turn, are typically provided within vectors (e.g., plasmids or recombinant viral vectors). Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

The invention also includes cells that have been modified to express a polypeptide of the invention. Such cells typically include prokaryotic cells such as bacterial cells, for example *E. coli*, or mammalian cells. Such cells may be cultured using routine methods to produce a polypeptide of the invention.

The polypeptide of the invention may be in a substantially isolated form. It may be mixed with carriers, preservatives, or diluents (discussed below) which will not interfere with the intended use, and/or with an adjuvant (also discussed below) and still be regarded as substantially isolated. It may also be in a substantially purified form, in which case it will generally comprise at least 90%, e.g. at least 95%, 98% or 99%, of the protein in the preparation.

Compositions

The present invention provides a composition comprising the soluble polypeptide of the invention and/or the polynucleotide encoding the soluble polypeptide of the invention, which comprises at least one pharmaceutically acceptable diluent, carrier or preservative.

The carrier may be any suitable carrier known to a person skilled in the art. Carrier proteins include keyhole limpet hemocyanin, serum proteins such as transferrin, bovine serum albumin, human serum albumin, thyroglobulin or ovalbumin, immunoglobulins, or hormones, such as insulin or palmitic acid. Alternatively, the carrier protein may be tetanus toxoid or diphtheria toxoid. Alternatively, the carrier may be a dextran such as sepharose. The carrier must be physiologically acceptable to humans and safe.

If the composition comprises an excipient, it must be 'pharmaceutically acceptable' in the sense of being compatible with the other ingredients of the composition and not deleterious to the recipient thereof. Auxiliary substances, such as wetting or emulsifying agents, pH buffering substances and the like, may be present in the excipient. These excipients and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

Formulation of a suitable composition can be carried out using standard pharmaceutical formulation chemistries and methodologies all of which are readily available to the reasonably skilled artisan. Such compositions may be prepared, packaged, or sold in a form suitable for bolus administration or for continuous administration. Injectable compositions may be prepared, packaged, or sold in unit dosage form, such as in ampoules or in multi-dose containers optionally containing a preservative. Compositions include, but are not limited to, suspensions, solutions, emulsions in oily or aqueous vehicles, pastes, and implantable sustained-release or biodegradable formulations. In one embodiment of a composition, the active ingredient is provided in dry (for e.g., a powder or granules) form for reconstitution with a suitable vehicle (e.g., sterile pyrogen-free water) prior to administration of the reconstituted composition. The composition may be prepared, packaged, or sold in the form of a sterile injectable aqueous or oily suspension or solution. This suspension or solution may be formulated according to the known art, and may comprise, in addition to the active ingredient, additional ingredients such as the adjuvants, excipients and auxiliary substances described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other compositions which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt. Alternatively, the active ingredients of the composition may be encapsulated, adsorbed to, or associated with, particulate carriers. Suitable particulate carriers include those derived from polymethyl methacrylate polymers, as well as PLG microparticles derived from poly(lactides) and poly (lactide-co-glycolides). See, e.g., Jeffery et al. (1993) Pharm. Res. Other particulate systems and polymers can also be used, for example, polymers such as polylysine, polyarginine, polyornithine, spermine, spermidine, as well as conjugates of these molecules.

Methods of Use

The soluble polypeptide, polynucleotide or composition of the invention may be used in a method of treating or preventing a disease or condition in a subject. The polypeptide or composition of the invention may be used in the manufacture of a medicament for use in a method of treating or preventing a disease or condition in a subject. The method comprises administering to the said subject the said polypeptide or the said composition. Administration may be of a therapeutically or prophylactically effective quantity of the said polypeptide or the said composition, to a subject in need thereof.

The disease or condition may be characterised at least in part by any one or more of:

a. pain;

b. osteochondral defects;

c. increased WNT signalling pathway activity, preferably wherein the increased WNT signalling pathway activity is evoked by, or at least partially evoked by, an activating mutation downstream of the WNT receptor within the WNT signalling pathway.

The disease or condition characterised by pain may be characterised by neuropathic and/or nociceptive pain, although most preferably nociceptive pain.

The disease or condition may be characterised by osteochondral defects, and particularly defects that would benefit from cartilage regeneration.

A disease or condition to be treated by the methods of the invention described herein may be determined as having increased WNT signalling pathway by any suitable method in the art. Examples of mutation candidates downstream of the WNT receptor that may evoke an activation of the WNT pathway, thereby increasing WNT signalling pathway activity, are:

i. mutations in exon 3 of beta catenin which render beta catenin resistant to degradation;

ii. loss of function mutations or deletion of Adenomatous poliposis coli (APC);

iii. loss of function of Axin1 or Axin2;

iv. increased expression of TCF1, TCF4 or LEF1 transcription factors.

Diseases and conditions characterised by a.-c. are well known in the art. Particularly, the disease or condition may be a disease characterised by chondral and/or osteochondral defects; diseases characterised by cartilage destruction following a form of inflammatory arthritis such rheumatoid arthritis or psoriatic arthritis; diseases or conditions characterised by an injury to the cartilage, meniscus, patella, ligament or tendon; osteoarthritis; diseases characterised by neuropathic pain such as multiple sclerosis, nerve root compression (e.g. carpal tunnel syndrome, sciatic) or following trauma or amputation; cancer, particularly wherein the cancer is ovarian, bowel and/or breast cancer. Preferably, the disease or condition may be a disease characterised by chondral and or osteochondral defects. The disease or condition may be osteoarthritis.

The soluble polypeptide, polynucleotide or composition of the invention may be used in a method of inducing stem cells. The stem cells may be mesenchymal stem cells, and are most preferably mesenchymal stem cells of GDF5 lineage.

The method comprises contacting the stem cells with the polypeptide, polynucleotide or composition of the invention. The induction of stem cells may be determined by any suitable method in the art. Particularly, the induction of stem cells may be determined by assaying for one or more of:

a. increased MMP-13 or COL10A 1 expression;

b. increased SOX9 expression;

c. increased COL2A1 expression;

d. increased aggrecan expression; and/or e. increased cartilage production, relative to stem cells prior to contacting with the soluble polypeptide, polynucleotide or composition of the invention.

The method of inducing stem cells in accordance with the present invention preferably results in the differentiation of the stem cells along a chondrocyte lineage. Markers of chondrocyte lineage are well known in the art. Particularly, chondrocytes are known to express one or more of:

a. MMP-13;

b. COL10A1;

c. SOX9;

d. COL2A1;

e. aggrecan, and/or produce cartilage.

The soluble polypeptide may be administered to a subject at any suitable dose. The suitable dose may depend on the severity of the disease or condition in an individual. The suitable dose may depend on the route of administration of the soluble polypeptide, wherein exemplary administration routes are described further herein. The skilled person would understand that a range of doses of the soluble polypeptide of the invention may be suitable for administration and treatment of a disease or condition described herein. Preferably, the concentration of the dose of soluble polypeptide of the invention administered to the individual may be at least about 7.17 fM and no greater than about 717 nM. The dose may more preferably be at least about 71.7 fM and no greater than about 71.7 nM, or yet more preferably be at least about 717 fM and no greater than about 7.17 nM. The soluble polypeptide of the invention is advantageously efficacious at particularly low dosages, as described further in the Examples herein.

The soluble polypeptide, polynucleotide or composition of the invention may be delivered to a subject by any suitable route. The route of delivery may be determined by the particularly disease or condition to be treated. Preferable routes of treatment administration for particular disease types are well known in the art. The soluble polypeptide, polynucleotide or composition of the invention may, for example, be delivered to a subject by intra-articular and/or systemic delivery. For mono- or olygoarticular disease, intraarticular delivery may be most preferable. For chronic pain, nociplastic pain, or polyarticular disease, systemic delivery may be most preferable. The soluble polypeptide, polynucleotide or composition of the invention may be delivered by injection. For example, in mono- or olygoarticular disease, a collagen gel comprising the soluble polypeptide of the invention at a suitable dose may be administered to a subject by intraarticular injection, as described further in the Examples herein.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

EXAMPLE

As described herein, it was surprisingly found that a fragment of human agrin comprising the amino acid sequence of SEQ ID NO: 2 is capable of inducing chondrocyte differentiation and/or chondrogenesis, whilst being soluble and therefore easy to produce and easy to purify, thereby providing an polypeptide that is suitable for use in treating osteochondral defects, pain and cancer. In the Example below, the efficacy of recombinant fragments of human agrin comprising the amino acid sequence of SEQ ID NO: 2 (i.e. a soluble polypeptide of the invention) is compared against full length human agrin, of neuronal and non-neuronal origin, and polypeptide sequence corresponding to amino acids 1260-2045 of SEQ ID NO: 1 (R&D Systems, product no. 6624-AG). The soluble polypeptide of the invention is shown to retail all of the desirable characteristics of full length agrin, whilst being soluble, easy to produce and easy to purify.

Materials and Methods

Study Design

The overall scope of this controlled laboratory study was to assess the effect of agrin in the regeneration of osteochondral defects and its mechanism of action. Human primary cells were obtained from patients undergoing joint replacement as described below according to ethics approval REC N. 07/Q0605/29. Cell lines were acquired commercially. Treatments, for each experiment, are detailed in the figure legends. Sample size of in vitro and in vivo experiments was determined by power calculations based on previous similar experiments to ensure a power of at least 0.8 in detecting an effect size of 0.5.

In Vivo Studies

Preliminary Efficacy Study in FIG. 5.

Wild type, 10 week old male C57BL/6 mice (4 animals per group, 4 joints analysed) were subjected to the generation of osteochondral defects as described below and the defect was filled immediately with either a collagen gel containing GFP (crude cell extract from transduced COS7 cells) or a collagen gel containing full length agrin (crude cell extract from transduced COS7 cells). The animals were killed 8 weeks after surgery.

Efficacy Study in FIG. 7.

Female Gdf5-Cre; Tom reporter mice (age 10 week old, 8 mice per group) were subjected to the generation of bilateral osteochondral defects. The defects were filled immediately with either a collagen gel containing GFP (crude cell extract from transduced COS7 cells) or a collagen gel containing full length agrin (crude cell extract from transduced COS7 cells). Three mice per group were killed 3 weeks after surgery and 5 mice per treatment group were killed after 8 weeks. One joint from the control group at 8 week time point was excluded from analysis because of an accidental cortical fracture during surgery.

Confirmation of Recruitment of Gdf5-Tom+ Cells Using Recombinant Agrin (FIG. 14).

Eight Gdf5-Cre;Tom mice (2 females and 6 males; 3 males and 1 female per treatment group) were subjected to the generation of bilateral osteochondral defects. The defects were filled immediately with either a collagen gel or a collagen gel containing 100 ng/ml of recombinant C-terminal agrin (rAGRIN). Animals were killed after 3 weeks and one joint per animal was processed for analysis.

Efficacy Study in Sheep (FIG. 8).

Twelve female sheep aged 2.9 years±0.41 (SD) were subjected to the generation of an osteochondral defect. The defects were filled immediately with either a collagen gel containing GFP (crude cell extract from transduced COS7 cells) or a collagen gel containing full length agrin (crude cell extract from transduced COS7 cells). In the GFP group 2 animals were excluded from the histological analysis, one because of osteomyelitis and one because of a subchondral cyst. All animals were killed 6 months after surgery.

In all animal studies, neither the operator nor the assessors were aware of the treatment. To minimize the risk that fights within individual cages skewed biased the results, treatment was randomized in each cage in the experiment with wild type mice. All sheep were kept in the same flock. The treatment table and the outcome tables were kept in separate databases until the outcomes had been recorded and only merged at the time of statistical analysis. Conditions to stop collection of data and humane endpoints for mice included weight loss>15% or evidence of excoriating dermatitis for more than 1 week or of ulcerative dermatitis for any length but were never met. No mouse, therefore, was killed early or excluded from analysis. Three sheep developed large subchondral cysts as a complication of surgery, which were detected radiographically and were excluded from further analysis.

Cells, Cell Lines and Expression Vectors

Adult human articular cartilage and synovial membrane were obtained following informed consent from patients who underwent joint replacement for knee OA after obtaining informed consent (5 men and 3 women, with a mean±SD age of 68±7 years). All procedures were approved by the East London and The City Research Ethics Committee 3 (ethics approval REC N. 07/Q0605/29).

Articular chondrocytes and synovial membrane mesenchymal stem cells were isolated and expanded as previously described. Bovine chondrocytes were isolated from the metatarsal joints of 18-month-old bovine, obtained within 6 hrs of death from a local abattoir, as previously described, chondrocytes from three joints were pooled. C28/I2 chondrocytes were a kind gift from Dr Mary Goldring (HSS Research Institute, Hospital for Special Surgery, New York, New York). COS-7 cells were a kind gift from Dr Michael Ferns (UC Davis Health system, USA). HEK293 cells were purchased from ATCC.

All cells were cultured in complete medium (DMEM/F-12, containing 10% FBS and 1% antibiotic antimycotic solution) (Thermo Fisher Scientific). COS-7 feeders producing Agrin or GFP or TGF-β were obtained as previously described. Transfections were performed using JetPrime (Polyplus) according to the manufacturer's instructions.

With all cells, chondrogenesis was assessed in micromass culture as previously described. Extracellular matrix deposition was quantified by staining with Alcian Blue 8 GS (Merck) at pH 0.2 followed by extraction in 8 M guanidine HCl (Thermo Fisher Scientific) and spectrophotometric quantitation at a wavelength of 630 nm. DNA was quantified using the Sybr Green method according to manufacturer's instruction (Origene).

The Rat Agrin plasmid was a kind gift from Dr Michael Ferns (UC Davis Health system, USA). The Lrp4 plasmid was a kind gift of Dr Lin Mei (Medical College of Georgia, Augusta, USA). TGF-β plasmid was a kind gift from Dr. Gerhard Gross. The caLEF1 and the caCTNNB1 plasmids were a kind gift from Dr. Caries Gasson-Massuet.

siRNA oligonucleotide sequences can be found in Table 1. A Stealth RNAi negative control duplex of low guanine-cytosine (GC) content (Invitrogen) was used as a negative control for AGRN siRNA.

TABLE 1

| Treatment group | Age | Exclusion |
| --- | --- | --- |
| COS7-GFP | 2.6 | |
| COS7-GFP | 2.5 | |
| COS7-GFP | 3.3 | |
| COS7-GFP | 3.6 | Osteomyelitis in the forelimb, CT analysis only |
| COS7-GFP | 2.6 | Cyst, CT analysis only |
| COS7-GFP | 2.8 | |
| COS7-AGRIN | 3.4 | |
| COS7-AGRIN | 2.5 | |
| COS7-AGRIN | 2.5 | |
| COS7-AGRIN | 2.8 | |
| COS7-AGRIN | 3.3 | |
| COS7-AGRIN | 3.2 | |

Generation of Agrin-Expressing COST Cells and Agrin-Containing Collagen Gel

The full-length coding sequence of human agrin (Gen-Bank Accession No. AB191264) was cloned into the BamHI and Kpn1 site of the pLNTSFFV. The agrin sequence was synthesized in 3 parts by Gene-Art (Life Technologies). The 5' fragment was ligated into the BamHI/XhoI sites of the vector. The 3' fragment was the ligated into this plasmid at the XhoI and Kpn1 sites. Finally, the Xho1 fragment comprising the central portion of the gene was ligated into the XhoI site of the vector to give the complete cDNA. Lenti-viruses were packaged in HEK 293T cells using standard procedures. The agrin lentivirus (or GFP lentivirus as control) was used to transduce COS7 cells, which were then cloned by limiting dilution. After three passages, the clone with the highest expression of agrin as determined by immunofluorescence was selected and used for further studies.

To generate collagen gel containing agrin (or GFP as control), agrin or GFP-overexpressing COS7 cells were washed twice in ice-cold PBS, detached mechanically with a cell scraper, resuspended in PBS, pelleted at 10000 g for 20 minutes and resuspended in an equal volume of PBS. The samples were subjected to 5 cycles of freeze-thawing alternating between liquid nitrogen and a 37° C. water bath and finally diluted 1:1 in a 5 mg/ml solution of ice-cold type I rat tail collagen at pH 7.5 (Corning-354249) prepared according to the manufacturer's instruction. The preparation was kept on ice to prevent polymerization until injected.

Generation of Recombinant Agrin

Recombinant human non-neuronal C-terminal Agrin (rAGRIN) was generated as follows. The C-terminal portion of Agrin (AA 1244-2045 from GeneBank accession number BAD52440) was cloned by PCR from the backbone of the full-length human non-neuronal Agrin adenovirus and sub-cloned into a 3 rd generation lentivirus gene expression vector backbone downstream of the CMV promoter, an IgG kappa signal peptide and followed by an enterokinase cleavage site, thermostable alkaline phosphatase, Myc and 10× His tags and finally by a stop codon. The lentivirus backbone was transiently transfected into Expi293 cells (Thermo Fisher Scientific) using the Expi293 Expression System (Thermo Fisher Scientific) as per manufacturer's instructions. At day 3 post transfection, cell-free supernatant was collected and recombinant Agrin was recovered using His SpinTrap columns (GE Healthcare), according to manufacturer's instructions.

Animals and Animal Procedures

All animal procedures were subjected to local ethical approval and Home Office Licensing. Mouse experiments were regulated by PPL no. 70/7986 and 60/4528, sheep experiments by PPL no.70/7740. C57BL/6 mice were purchased from Charles River UK. Gdf5-Cre;Tom mice were generated by crossing Gdf5-Cre transgenics (Tg(Gdf5-Cre-ALPP)1Kng) (Kind gift of Dr D. Kingsley, Stanford, CA, USA) with Cre-inducible tdTomato (Tom) reporter mice (B6.Cg-Gt(ROSA) 26Sortm14(CAG-tdTomato)Hze/J) (Jackson Laboratories). Gdf5-Cre;Tom mice were on a mixed FVB/C57BL/6 background. All mice were maintained in isolator cages or standard housing in groups of 3-5 and fed ad libitum.

Murine Model of Osteochondral Defect Repair

Mice were anesthetized with isofluorane. The knees were shaved and disinfected with 70% ethanol. The skin was cut with fine scissors and separated from the underlying tissue by blunt dissection. The femur was placed so that the shaft was perfectly vertical, with the knee flexed at 90°. A 25G needle (Terumo Agani G25, cannula 0.5 mm, length 25 mm, bevel 11°) was placed on the lateral condyle in correspondence of the intersection of a vertical line tangent to the lateral margin of the patella and a horizontal line tangent to the inferior margin of the patella. By applying gentle pressure and rotation, the needle was driven through the joint capsule, the cartilage, and the bone, while aiming for the center of the femoral shaft. As soon as the bevel of the needle was completely buried, the G25 needle was retracted and replaced with a G21 needle (Terumo Agani, G21, cannula 0.8 mm, length 50 mm, bevel 11°). The G21 needle was again gently rotated and advanced until its bevel was completely hidden. The G21 was retracted while still turning to extract the bone debris and leaving a cavity. If there was any bleeding, this was blotted with sterile gauze. Liquid collagen type I gel containing the lysate of COS7 cells overexpressing full-length human agrin (crude extract from transduced COS7 cells) accession No. AB191264) or recombinant C-terminal agrin as indicated, or GFP (crude extract from transduced COS7 cells) or PBS as indicated, was injected using a pulled glass pipette tip with a diameter of approximately 10 μm mounted at the end of a regular 2 μl pipette tip until the defect was full. After waiting approximately 20 seconds to allow the gel to set, the joint capsule was closed with a single suture with Vycril 6-0 and the skin was closed with an interrupted suture (Ethilon 5-0 a-traumatic needle). After recovery mice, fed ad libitum in individually filtered cages (3-5 mice per cage). For wildtype mice, treatments were randomized within each cage. The animals were monitored post-operatively for signs of suffering and local infection. The operator and the scorers were blind to the treatment.

At the stated time points mice were killed, the joint dissected and processed for histology. Sagittal sections through the center of the defect were identified as the first section that, starting from the lateral side, intersected the lateral margin of the patellar bone. Such sections were stained with Safranin O and scored using the Pineda score.

Where full length crude-extract agrin is used, 2 ul of a 1 ng/ml solution=14.34 fmol=0.01434 pmol is injected into the peripheral tissues of the mice. Where recombinant human agrin according to the invention is used, the inventors injected at a concentration of 1.14 pmol (2 ul of a 717 pM).

TABLE 4

| C-terminal human rAgrin protein | Molecular weight | 1 ng | 1 ng/ml |
|---|---|---|---|
| Tagged | 139.999 kDa | 0.00717 pmol | 7.17 pM |
| Untagged | 85.650 kDa | 0.01181 pmol | 11.81 pM |

Ovine Model of Osteochondral Defect Repair

Adult [aged 2.9 years±0.41 (SD); individual ages can be found in Table 1] female sheep were anesthetized with isoflurane. Following a sterile preparation of the skin, the joint was opened using a lateral para-patella approach. An 8 mm diameter, 5 mm deep osteochondral defect was created using a hand drill. The defect was lavaged to remove debris. Defects were filled with liquid collagen type I gel containing the lysate of COS7 cells overexpressing full length human agrin or GFP as control. After waiting about 20 seconds to allow the gel to set, the capsule was closed using 3M Monocryl in an interrupted mattress pattern. The skin was closed with 2M Vicryl. Sheep were recovered and then housed for two weeks post-surgery indoors in pens. Carprofen was administered at a dose of 4 mg/kg at the time of surgery then 4 mg/kg once a day for three days post-surgery. After this time, sheep were kept in one flock in a field to allow free and natural movement. At 6 months post-surgery sheep were killed, the knees processed for μCT and subsequently processed for histology. Mid-defect sections were stained and scored as described above.

For μCT analysis, sheep knee joints were scanned using a Nikon XT H 225 ST CT scanner. Reconstruction was done using CT Pro V2.2 Nikon software (Nikon Metrology UK Ltd) and the images were saved as a tif series. These were then viewed using Dataviewer v1.5 software (Bruker, Kontich). To allow subsequent analysis the data was then resaved as a transaxial (x,y) dataset. This new dataset was then opened in CTAn (v1.13) (Bruker, Kontich). Before analysis was carried out the true pixel value from the Nikon scan was manually added using the image properties option, as the calibration was not automatically saved. A region of interest was drawn to define the defect area in each joint, from which the defect volume was determined. The person analyzing the μCT data was blinded to the study groups.

Histology and Immunostainings

All samples were fixed in 4% paraformaldehyde at 4° C. overnight, decalcified in 10% EDTA in PBS for 2 weeks at 4° C. (Gdf5-Cre;Tom) or in 33% Formic Acid for 24 hrs and then washed for 24 hrs in water at room temperate (wild-type), dehydrated in an ethanol series, embedded in paraffin and 5 μm sections were obtained. Safranin O staining (pH 4.2) or toluidine blue (pH 4.5) was performed according to standard protocols.

Immunofluorescence and immunohistochemical, staining was carried out as previously described. For antigen retrieval on paraffin sections pepsin digestion was performed. Where phosphatase treatment was carried out, sections were incubated with Lambda phosphatase for 2 hrs at 37° C. according to manufacturer's instructions (CST). Antibodies and dilutions used are provided in Table 2. Tissue staining was carried out using an overnight incubation of the primary antibody at 4° C., immunocytochemistry was performed following 1 hr incubation at room temperature. Sections were counterstained with hematoxylin or with 4',6-diamidino-2-phenylindole (DAPI) (Life Technologies). Slides were mounted in Mowiol (EMD Millipore, Darmstadt), and images were acquired with a fluorescence microscope (BX61; Olympus) using a Uplan-Fluor 40× NA 0.85 objective lens, a Zeiss 710 META Laser-Scanning Confocal Microscope (Carl Zeiss Ltd), or a Zeiss Axioscan Z1 slide scanner (Carl Zeiss Ltd). Images were acquired by using an F-View II Soft Imaging Solutions (SIS) camera and Cell P software (Olympus), or using ZEN software (Carl Zeiss Ltd). Image contrast was modified with Photoshop 7.0 for best graphic rendering, equally for all treatments.

Histomorphometry

Histomorphometry was performed with ImageJ software (NIH). The number of cells positive for phospho-CREB (pCREB) was calculated as follows. Images of immunohistochemistry counterstained with hematoxylin were opened in ImageJ. All cells (positive and negative) were selected using the color threshold tool (Image>Adjust>Color threshold). The tool was set on the RGB color space and all three (red, blue and green) channels were passed, ensuring that the blue channel (hematoxylin positive cells) was passed with the upper limit on the peak of the histogram. The passed component of the image was sampled and pasted on a new image. Such image contained all cells, positive (brown) and negative (blue) and no background. This image was converted to 8 bit and thresholded in such a way to maximize separation of adjacent cells while still selecting every cell. A further deconvolution of overlapping cells was obtained using the watershed tool (Process>binary>watershed). Total cells were then counted with the Analyze Particles tool (Analyze>Analyze Particles). Care was taken to optimize the size of the particles to count so to exclude specks that did not reach the minimum size of a cell. In this case the inventors used 100 px~infinity. The positive cells were counted in the same way except that during colour thresholding, the upper limit of the blue channel was placed immediately to the left of the blue histogram, so that all blue cells were thresholded out and the resulting image only contained brown cells. The counts were expressed as (positive/total cells)×100.

The number of cells positive for Tomato in immunohistochemistry could not be quantified in the same way because the cytoplasmic staining of neighboring cells could not always reliably be deconvoluted. Therefore, the area occupied by brown (immunohistochemistry) or blue (hematoxylin) staining was considered as proportional to the positive and negative cells. Image processing for this analysis was similar to that described above for phospho-CREB staining, with the following differences. First, after color thresholding, the second round of thresholding was performed so to include the entire histogram of the 8-bit images so not to alter the area occupied by any positive staining in the 8-bit images. Second, instead of the particle count, the inventors used the "total area" of the results from "Analyze Particles" as (total area total cells/total area positive cells)×100.

Western Blotting

Cells were washed in ice-cold PBS and lysed in ice-cold RIPA Buffer in the presence of protease and phosphatase inhibitors (Sigma) for 20 mins on ice. Protein concentrations were determined by bicinchoninic acid protein assay (Pierce). Samples were prepared for SDS-PAGE on 10% (wt/vol) Bis-Tris NuPAGE gels (Invitrogen) and transferred

TABLE 2

| Antibodies | Species | Code | Supplier | Western Blotting | Immunofluorescence |
|---|---|---|---|---|---|
| AGRIN | Rabbit | H300 | Santa Cruz Biotechnology | | 1:100 |
| CREB | Rabbit | 9197 | Cell Signaling | 1:1000 | 1:800 |
| pCREB | Rabbit | 9198 | Cell signaling | 1:1000 | 1:800 |
| GDF5 | Rabbit | 93855 | Abcam | | 1:1000 |
| IgG | Rabbit | 37415 | Abcam | | 1:100-1:800 |
| AlexaFluro555 | Goat | 150078 | ThermoFisher | | 1:300 |
| α-TUBULIN | Mouse | T5168 | Sigma | 1:5000 | |
| COL2A1 | Rabbit | Ab21291 | Abcam | | 1:100 |
| Tomato | Goat | Ab0081 | Sicgen | | 1:100 |
| Tomato | Rabbit | 600-401-379 | Rockland | | 1:600 | to nitrocellulose membrane. Blots were blocked in 5% BSA in 0.1% TBS-Tween) and incubated with primary antibodies at the concentrations stated in supplementary table I overnight at 4° C. After three washes in 0.1% TBST, blots were incubated for one hour at room temperature with HRP-conjugated secondary IgG (Dako). After further three washes, protein bands were visualized by chemiluminescence (Luminata Forte; Merk Millipore) using FluorChem E imaging system (Protein Simple). Measurements of band densitometry and quantification of protein expression was conducted using ImageJ (NIH). Phospho protein expression was normalized to total protein levels and to $\alpha$-TUBULIN (endogenous loading control).

Reporter Assays

Subconfluent cells were co-transfected with SUPER8XTOPFlash TCF/LEF-firefly luciferase reporter vector (Addgene) and CMV-*Renilla* luciferase vector (in a ratio 1:100). 24 hrs after transfection, the medium was replaced and the cells were treated for 24 hrs as specified. Luciferase activity was measured using the Dual Luciferase Reporter Assay System (Promega) in a TD-20/20 Luminometer (Turner Designs). Firefly luciferase activity was normalized by *Renilla* luciferase activity and expressed as relative luciferase units. See Table 3 for all reagents.

TABLE 3

| Recombinant | Concentration | Resuspended in | Code | Supplier |
|---|---|---|---|---|
| IL-1β | 20 ng/ml | 0.1% BSA in PBS | 201-LB | R&D systems |
| TNF-α | 20 ng/ml | 0.1% BSA in PBS | 210-TA | R&D systems |
| WNT3A | 50-200 ng/ml | 0.1% BSA in PBS | 5036-WN | R&D systems |
| Wnt-9A | 200 ng/ml | 0.1% BSA in PBS | 8148-WN | R&D systems |
| SKL2001 | 10 uM | DMSO | 681667 | Calbiochem |
| BIO | 10 uM | DMSO | 3194 | Tocris |
| MeBIO | 10 uM | DMSO | 3873 | Tocris |
| Forskolin | 10 uM | DMSO | F6886 | Sigma |
| 666-15 | 1 uM | DMSO | 5661 | Tocris |
| KN92 | 10 uM | DMSO | 4130 | Tocris |
| KN93 | 10 uM | DMSO | 1278 | Tocris |
| AIP | 5 uM | DMSO | 5959 | R&D systems |

Gene Expression Analysis

RNA extraction was performed using Trizol (Invitrogen) according to the manufacturer's instruction. Reverse transcription and real-time PCR were performed as previously described. Primers and amplicon length are listed in table S4. Microarray data from previously published datasets were accessed through the Gene Expression Omnibus database at NIH (GEO accession GSE75181). Briefly, normalized data were downloaded from GEO as an expression dataset; the samples of interest (IL-1β-treated and control) were selected and gene expression was compared by fitting a linear model independently for each probe, with group as the y variable, using 'lmfit' ('limma' R package). The linear fit for each comparison was subsequently modified using the empirical Bayes ('eBayes') approach. For each comparison, $\log_2$ fold-change (log FC), P value, and adjusted P value (false discovery rate, FDR for multiple comparisons) was output. Individual samples expression data for Agrin were extracted from the expression dataset and the statistics obtained from the statistics output and used to build the graph. To facilitate the reproduction of the data, an R script is supplied in supplementary materials to obtain the raw data, select the samples of interest, perform the statistical analysis and generate the graph. Pre-processed, normalized data for individual genes were obtained using the GEO2R functionality.

Statistical Analysis

Means of parametric data were compared with a student's t test or with ANOVA followed by Tukey HSD post hoc test for multiple comparisons. When necessary, log or square root transformation was applied to correct skewed distributions in order to satisfy the assumptions of parametric tests. Non-parametric data were analyzed with the Mann-Whitney U test or, for multiple comparisons, the Kruskal Wallis test followed by the Dunn test. Dose response curves and repeated measures were assessed by two-way ANOVA and, if different treatments were applied, ANCOVA followed by Tukey HSD for multiple comparisons. Statistical analysis was performed using either R or GraphPad Prism software. Data shown as box and whisker blot. Box extends from the 25th to 75th percentiles. Line represents the median. P values<0.05 were considered significant.

Chondrocyte & Stem Cell Differentiation and Cartilage Extracellular Matrix Production Assay The human chondrocytic cell line, C28/I2, were cultured in micromass at a density of 2.0×107 cells/mL in complete medium (DMEM Glutamax, 10% Fetal Bovine Serum and 1% antibiotics/antimycotics), and micromass cultures were obtained by pipetting 15 µl drops of cell suspension into each well of a 24 well plate. The cells were allowed to attach for 3 h and then 1 ml of medium was added (in the presence or absence of serum, as stated; in the presence of the stated recombinant protein). Micromasses were cultured for 3-7 days (as stated), changing the medium every 48 h. Micromasses were harvested for RT-PCR gene expression analysis or fixed and whole-mount stained with Alcian blue. Extracellular matrix deposition was quantified by staining with Alcian Blue 8GS at pH 0.2 followed by extraction in 8M guanidine HCl and spectrophotometric quantitation at a wavelength of 630 nm. DNA was quantified using the Sybr Green method according to manufacturer's instruction (Origene).

Synovium Derived Stem Cell Chondrogenesis Assays

COS7 cells were transfected with GFP, full-length human Agrin or BMP plasmids and growth arrested to act as a protein delivery system. COS7 cells were mixed at a ratio of 1:10 with human synovium derived MSCs and pelleted. Pellets were cultured for 14 days in the medium containing 10% serum (changed every 3-4 days). Pellets were weighed and RNA was extracted to perform RT-PCR.

Wnt and CREB Signaling Reporter Assays

Reporter assays conducted using the luciferase WNT reporter (TOPFlash plasmid) or CREB reporters. HEK293 cells were co-transfected with the reporter plasmid (TOPFlash or CREB) and *Renilla* and cultured in monolayer for 24 hrs before being stimulated with recombinant Agrin in the presence of positive controls (WNT3A for TOPFlash) or alongside Forskolin (CREB activator) for a further 24 hrs. Luciferase activity was measure and normalized for *Renilla* (transfection control plasmid).

Results

AGRIN is Upregulated in Injured Cartilage and Induces Chondrogenesis in MSCs

Figure 9A:
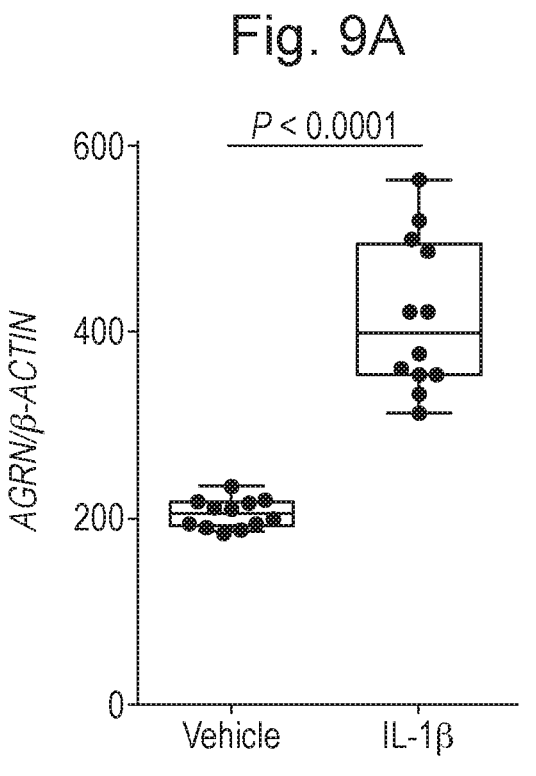

In the context of screening for genes upregulated after acute cartilage injury, the inventors discovered that agrin was upregulated at the mRNA and protein level twenty-four hours after mechanical injury to human articular cartilage explants ex vivo (FIG. 1, A to C). AGRN mRNA was also upregulated in C28/I2 human chondrocytes by treatment with IL-1β (FIG. 1D) and TNF-α (FIG. 1E), two inflammatory cytokines released by injured cartilage. Agrin upregulation in adult primary human articular chondrocytes after IL-1β treatment was confirmed as assessed by mining a publicly accessible gene expression dataset (FIG. 9A). Compared to green fluorescent protein (GFP), used hereafter as transfection control, agrin overexpression in human adult synovial membrane-derived mesenchymal stem cells (SM-MSCs) resulted in their differentiation into cartilage as assessed by increased production of cartilage-specific Alcian blue-positive extracellular matrix and upregulation of the cartilage master transcription factor SOX9 mRNA (FIGS. 1, F and G). Together, these data show that agrin is upregulated in injured cartilage and induces chondrogenic differentiation in SM-MSCs that normally reside in the joint.

Figure 2A:
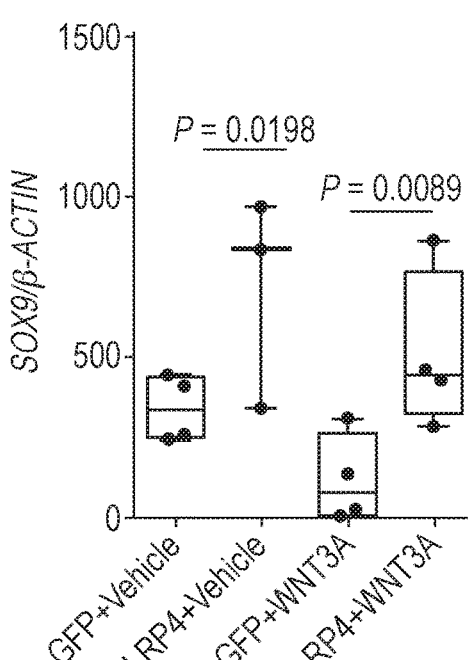
FIG. 2 shows that Agrin/LRP4 signaling activates chondrogenesis by inhibiting WNT signalling. (A-C) RT-PCR for SOX9 of primary bovine chondrocytes transfected with (A and C) LRP4 or (B) AGRIN and treated with (A-B) recombinant WNT3A or (C) co-transfected with AGRN siRNA (n=3, lined bars; n=4, square bars)); (A) SOX9 levels were compared using a generalized linear model followed by pairwise comparison within each WNT3A treatment (Tukey correction), GFP+Vehicle vs LRP4+vehicle P=0.0198, GFP+WNT3A vs LRP4+WNT3A P=0.0089. (B) Square root transformed SOX9 levels were compared using a generalized linear model followed by pairwise comparison within each WNT3A treatment (Tukey correction), AGRIN+ Vehicle vs GFP+Vehicle P<0.0001, AGRIN+WNT3A vs GFP+WNT3A P=0.0278; (C) t-test, GFP+Scrambled vs LRP4+Scrambled P=0.0157, LRP4+Scrambled vs LRP4+ AGRN siRNA P=0.0107. (D) TOPFlash reporter assay in COS7 cells transduced with AGRIN or GFP and treated with recombinant WNT3A (100 ng/ml) (n=4); t-test GFP vehicle vs GFP WNT3A P=0.0001, GFP WNT3A vs AGRIN WNT3A P=0.0005. (E) TOPFlash reporter assay in HEK293 cells transfected with AGRIN or GFP and treated with recombinant WNT9A (200 ng/ml) (n=3); one way ANOVA with Tukey GFP+Vehicle vs GFP+WNT9A P=0.0015, GFP+WNT9A vs AGRIN+WNT9A p<0.0001. (F) TOPFlash reporter assay of COS7 cells stably expressing AGRIN or GFP and transfected with either Empty plasmid or LRP4 plasmid and treated with increasing doses of recombinant WNT3A (n=4; two-way ANOVA—Tukey HSD. AGRIN vs GFP P<0.0001; AGRIN+LRP4 vs Agrin P=0.027. (G) Alcian blue staining and quantification of C28I/2 chondrocytes in micromass culture 4 days after transfection with AGRIN or GFP with or without caLEF-1 (n=4) two-way ANOVA P=0.0088; bars 0.5 mm.
Figure 2B:
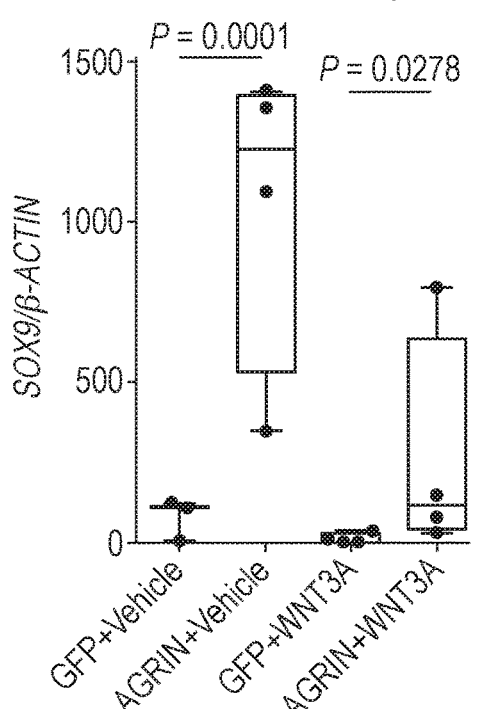
Figure 2C:
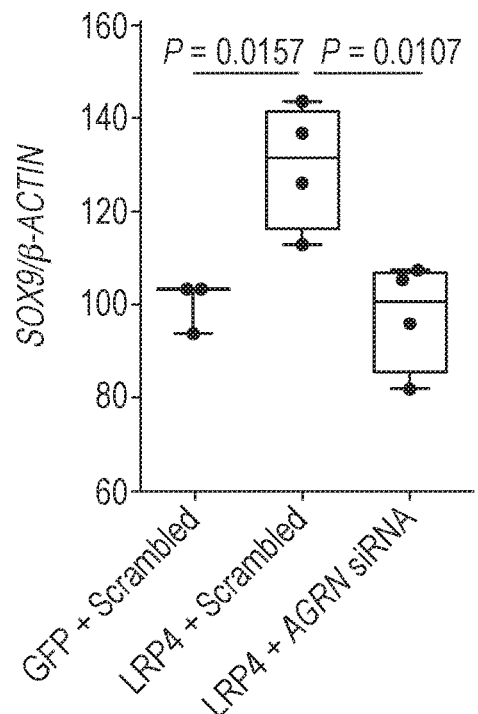
Figure 2D:
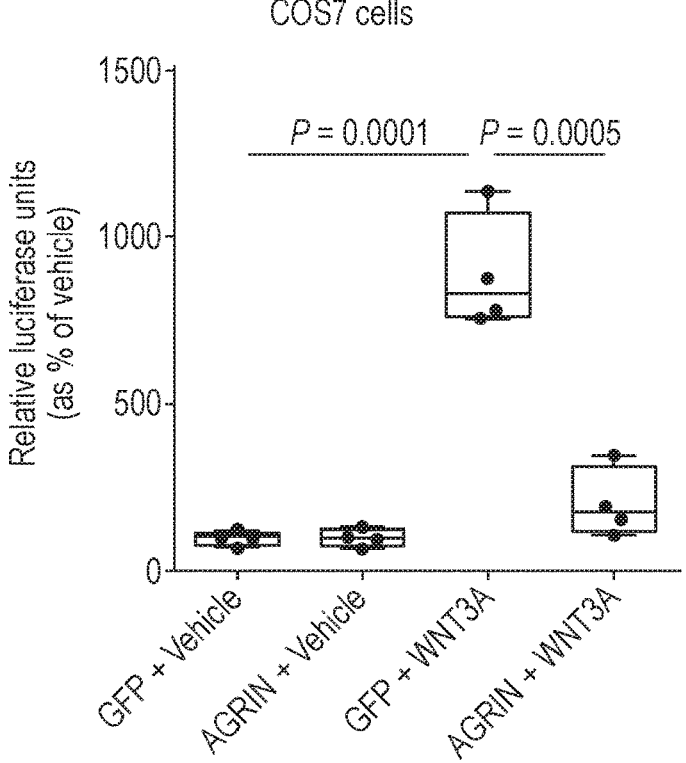
Figure 2E:
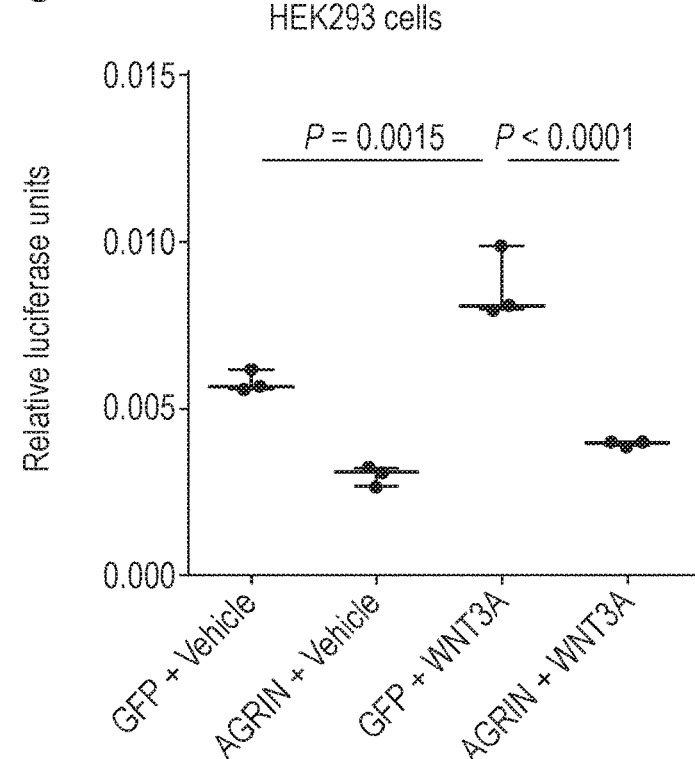
Figure 9B:
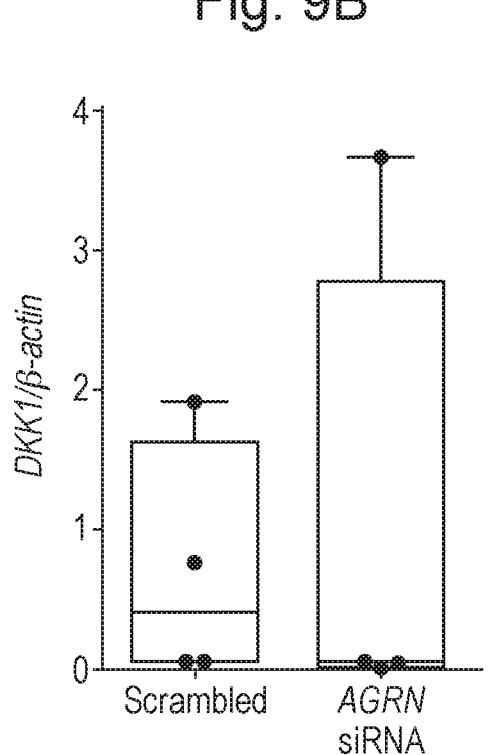

Agrin Induces Chondrogenesis by Suppressing WNT Signaling Downstream of β-Catenin Next, the inventors investigated the molecular pathway underlying the chondrogenic effect of agrin. The agrin receptor LDL receptor related protein 4 (LRP4) mediates chondrocytic differentiation in the murine chondrocytic cell line ATDC5 by inhibiting canonical WNT signaling. The inventors found that overexpression of either LRP4 (FIG. 2A) or agrin itself (FIG. 2B), both in the absence and presence of WNT3A, in primary bovine chondrocytes upregulated SOX9 mRNA. LRP4 is known to bind to and mediate the function of WNT inhibitory molecules such as DKK1 and SOST; therefore, the inventors investigated whether agrin is required for the chondrogenic function of LRP4. Silencing AGRN in C28I/2 chondrocytes prevented the SOX9 upregulation induced by LRP4 overexpression (FIG. 2C). These data indicate that agrin is necessary for the chondrogenic effects of LRP4. Agrin silencing did not alter expression of DKK1 mRNA (FIG. 9B). SOST is not expressed in articular chondrocytes and was not detected by PCR.

Figure 2F:
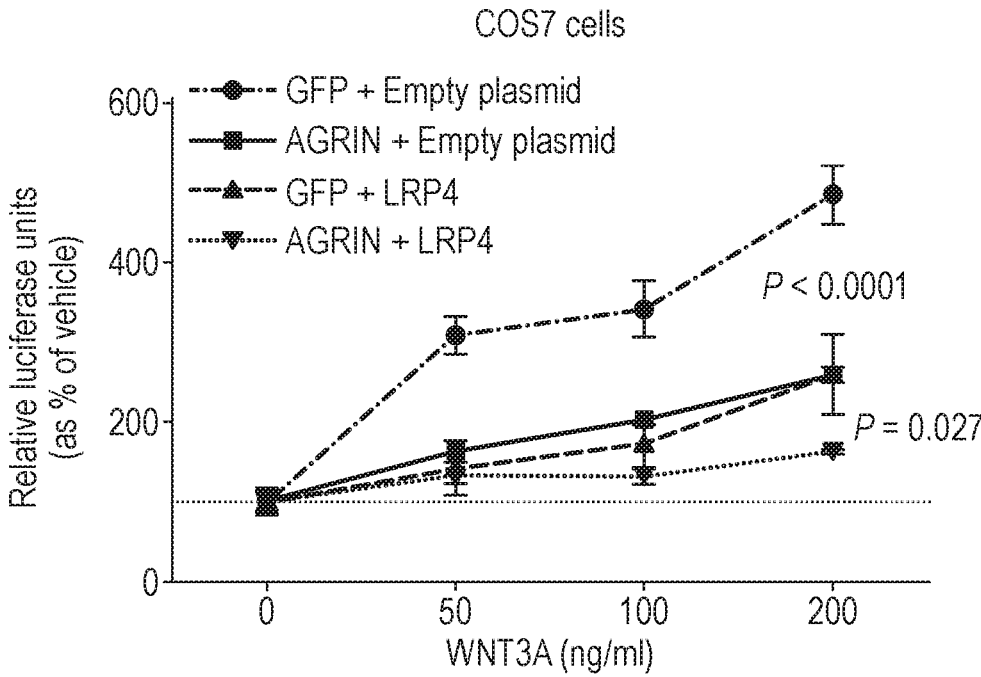
Figure 2G:
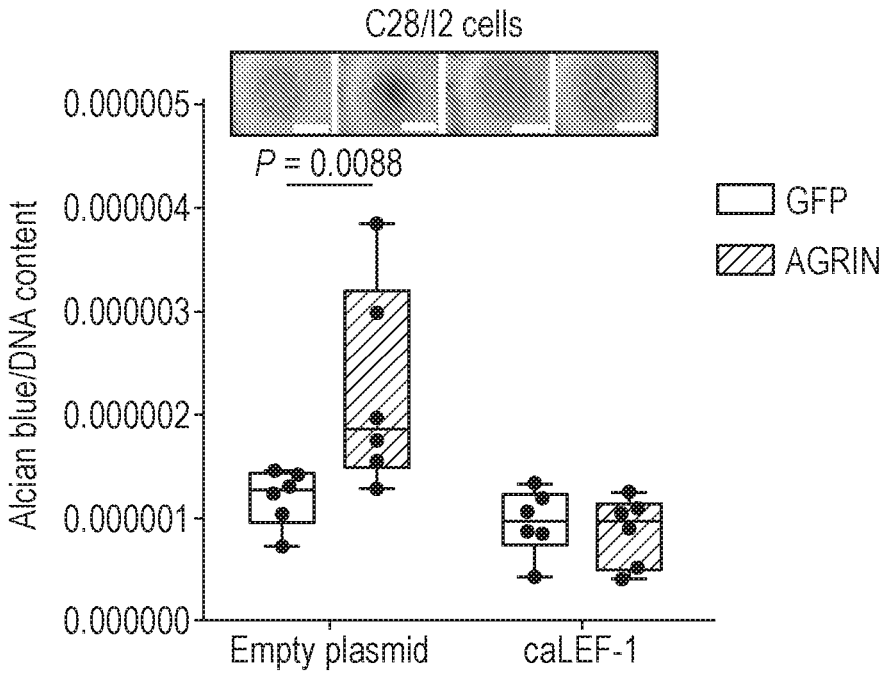

Canonical WNT signaling is known to suppress chondrogenesis. Agrin overexpression blocked the capacity of WNT3A and WNT9A to activate the WNT/β-catenin-dependent reporter assay TOPFlash (FIGS. 2, D and E). Overexpression of either LRP4 or agrin suppressed TOPFlash activation in a WNT3A dose-response curve and co-overexpression of LRP4 and agrin was further inhibited TOPFlash activation (FIG. 2F). Moreover, agrin failed to induce extracellular matrix formation in C28/I2 chondrocytes in which activation of canonical WNT signaling was achieved directly in the nucleus by overexpressing a constitutively active form of LEF1 (caLEF1) composed of the trans activation domain of VP16 and the DNA-binding domain of LEF1 (FIG. 2G). Therefore, the capacity of agrin to suppress canonical WNT signaling is essential to its chondrogenic effect. Taken together, these data indicate that agrin induces chondrogenesis by suppressing canonical WNT signaling.

Figure 3A:
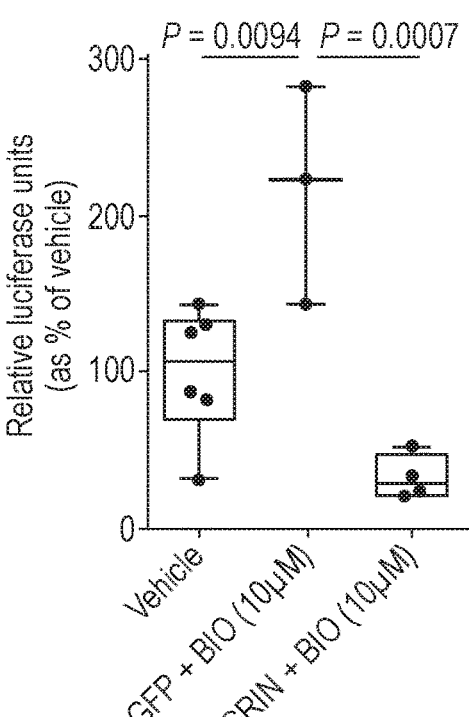
FIG. 3 shows that Agrin inhibits canonical WNT signaling downstream of β-catenin and activates CREB-dependent transcription. (A) TOPFlash reporter assay in COS7 cells transduced with AGRIN or GFP treated with BIO, (GFP+ Vehicle, n=6, GFP+BIO n=3, Agrin+BIO n=4), (B) SKL2001, (GFP+Vehicle n=8, GFP+SKL2001 n=4, AGRIN+SKL2001 n=3), (C) transfected with caCTNNB1 (Δex3) (n=4) or (D) constitutively active LEF-1 (n=4); (A to D) one way ANOVA followed by Tukey's HSD post-hoc. (A) Vehicle vs GFP+BIO P=0.0094, GFP+BIO vs AGRIN+ BIO P=0.0007, (B) Vehicle vs GFP+SKL2001 P=0.0028, GFP+SKL2001 vs AGRIN+SKL2001 P=0.0053, (C) GFP+ Empty plasmid vs AGRIN+Empty plasmid P<0.0001, GFP+ caCTNNB1 vs AGRIN+caCTNNB1 P=0.0292, (D) GFP+ Empty plasmid vs GFP+caLEF1 P<0.0001. (E) Immunostaining for CREB or phosphorylated CREB (pCREB) in C28/I2 cells 24 hr after transfection with AGRIN or GFP (DAPI counterstain). Quantification in (F and G) (n=3); (G) t-test P=0.0256. (H) C28/I2 chondrocytes were cultured for 3 days in micromass, transfected as indicated, and CREB phosphorylation (p-CREB) was assessed by western blotting (n=3); two-way ANOVA GFP vs AGRIN P=0.0055, AGRIN vs GFP+caLEF1 P=0.008, AGRIN vs AGRIN+caLEF1 P=0.0035. (I) CREB reporter assay in COS7 cells transfected with AGRIN (n=4) or GFP (n=3); t-test P=0.0462. (J) Immunostaining for CREB and phosphorylated CREB (pCREB) in C28/I2 cells 24 hr after transfection with Scrambled or AGRN siRNA and quantification in (K and L) (n=3) P=0.0021.
Figure 3B:
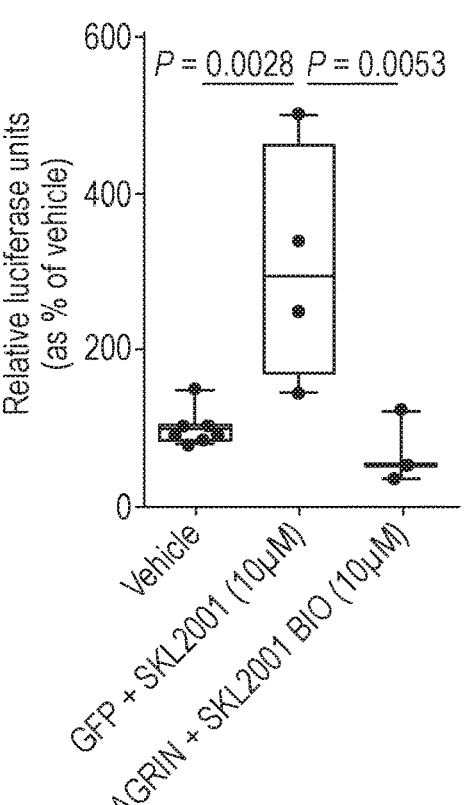
Figure 3C:
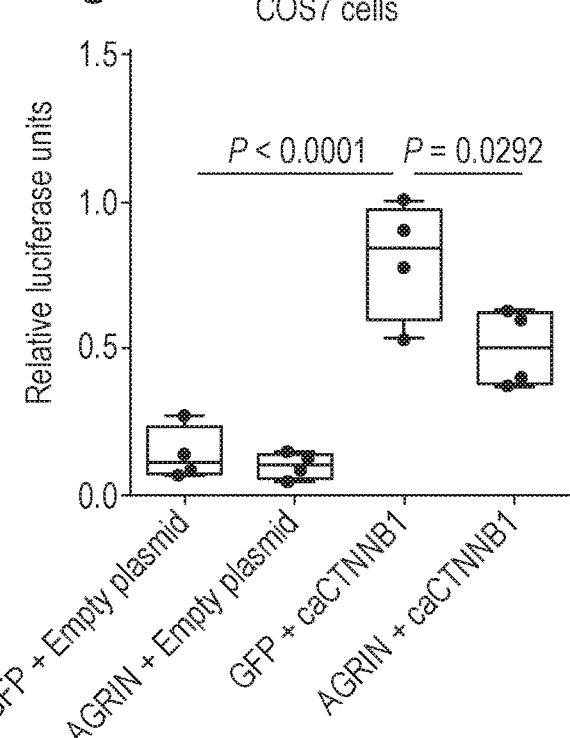
Figure 3D:
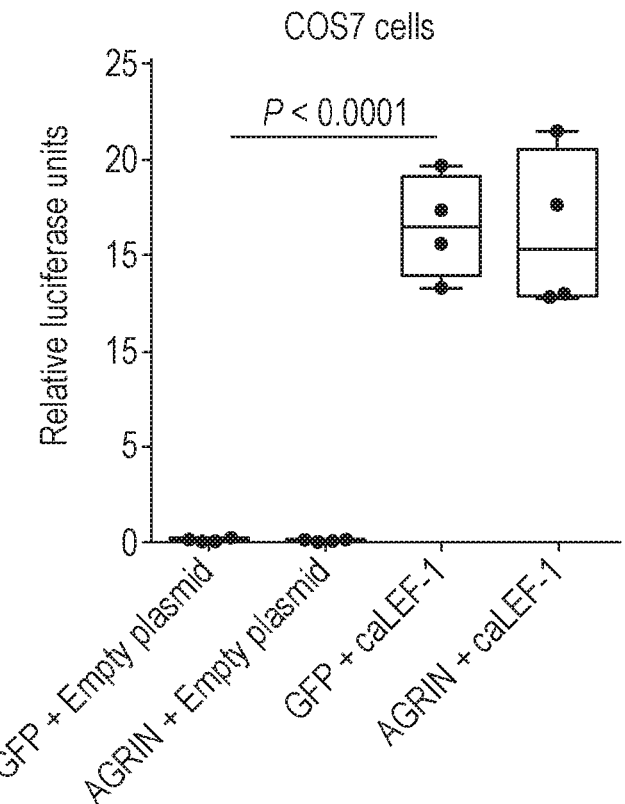
Figure 3E:
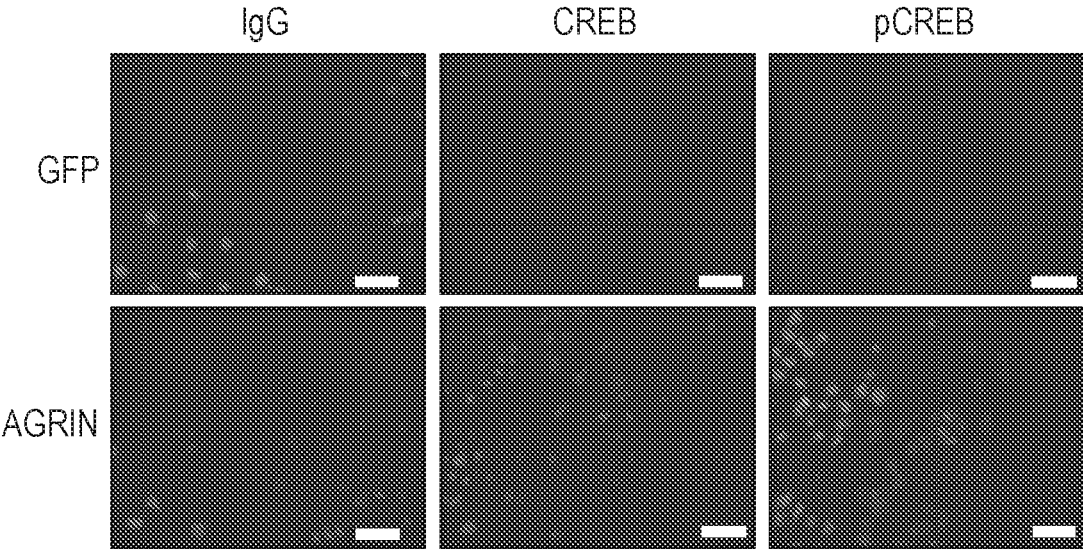
Figure 3F:
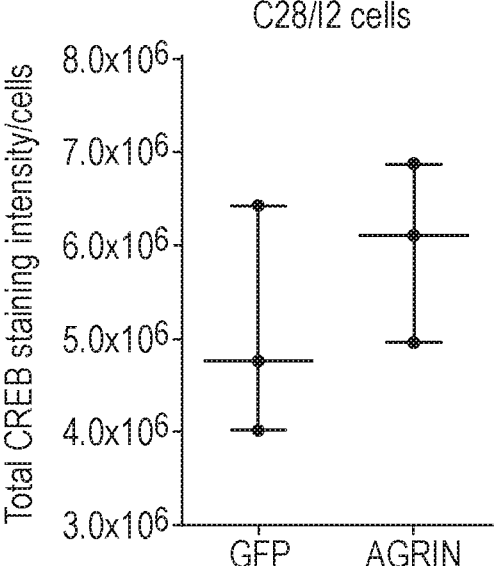
Figure 3G:
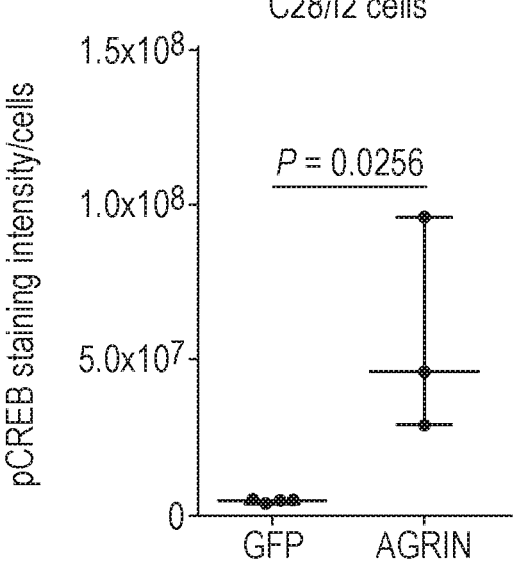
Figure 3I:
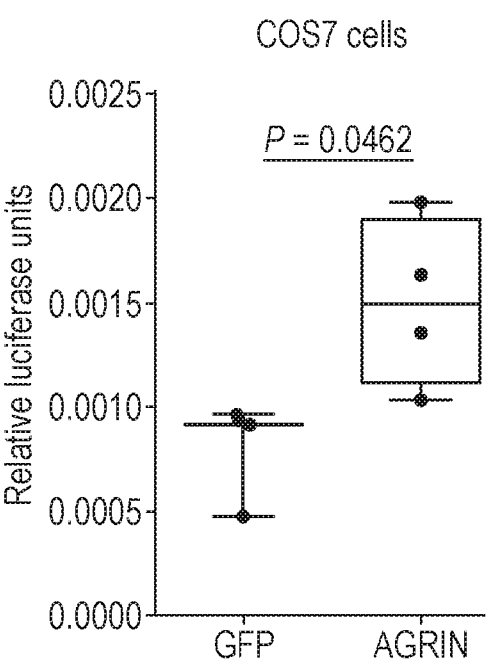
Figure 3J:
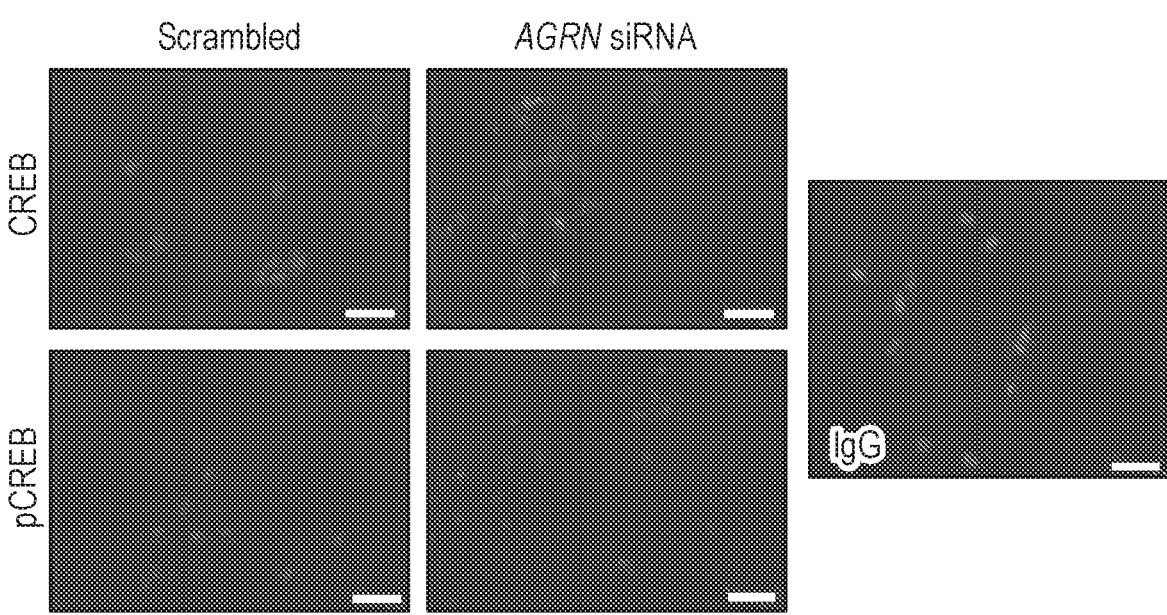
Figure 3K:
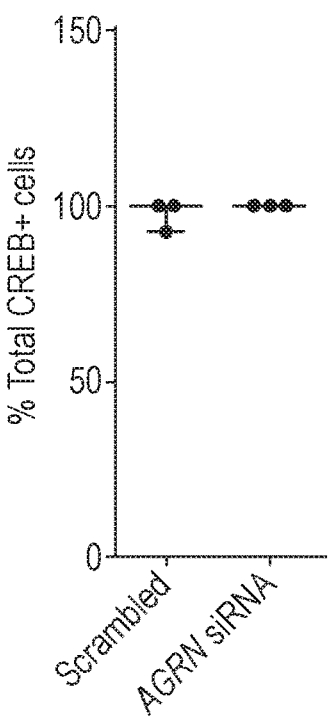
Figure 3L:
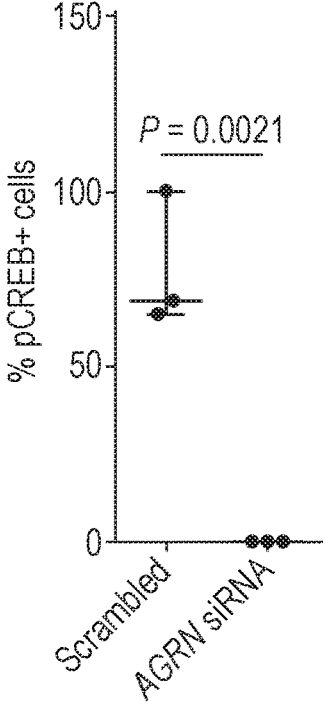

To test at what level in the signaling cascade agrin inhibits WNTs, the inventors activated WNT signaling in COS7 cells using either the GSK-3β inhibitor BIO or the inhibitor of AXIN/GSK3-β interaction SKL2001. Disruption of the β-catenin destruction complex with either compound resulted in ligand/receptor-independent activation of the TOPFlash reporter assay; however, agrin overexpression was still able to inhibit such activation (FIGS. 3, A and B), thereby demonstrating that the capacity of agrin to inhibit canonical WNT signaling resides downstream of the β-catenin destruction complex. Similarly, agrin inhibited the activation of the TOPFlash reporter assay induced by overexpression of constitutively active β-catenin KTNNB1 (Aex3), caCTNNB11 (FIG. 3C). In keeping with the notion that agrin acts downstream of the β-CATENIN destruction complex, agrin enhanced extracellular matrix production in C28/I2 chondrocytes even in the presence of SKL2001 (FIG. 9). However, when COS7 cells were transfected with caLEF1, Agrin was unable to prevent activation of the TOPFlash reporter (FIG. 3D). Taken together, these data suggest that agrin suppresses canonical WNT signaling downstream of β-catenin.

Agrin Activates CREB Signaling

Figure 4A:
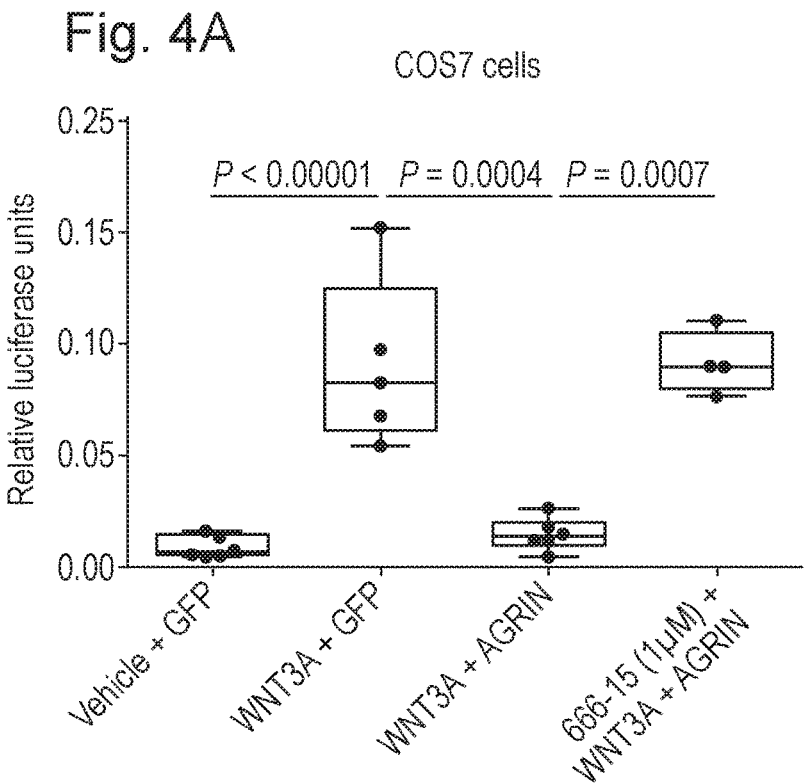
FIG. 4 shows that Agrin requires CREB for its capacity to suppress WNT signaling and induce chondrogenesis. (A) TOPFlash reporter assay in COS7 cells transfected with Agrin or GFP 24 hours after treatment with WNT3A in the presence or the absence of the CREB inhibitor 666-15 (n=4). (B and C) TOPFlash reporter assay in COS7 cells transfected with Agrin or GFP 24 hrs after WNT3A (200 ng/ml) treatment in the presence or in the absence of (B) the CaMKII inhibitor KN93 or its inactive control KN92 or (C) the CAMKII inhibitor AIP; (A to C) two-way ANOVA Tukey's HSD post-hoc, (A) Vehicle+GFP vs WNT3a+GFP P<0.00001, WNT3a+GFP vs WNT3a+AGRIN P=0.0004, WNT3a+AGRIN vs 666-15+WNT3a+AGRIN P=0.0007; (B) KN92+GFP vs KN92+WNT3A+GFP P<0.00001, KN92+WNT3A+GFP vs KN92+WNT3A+AGRIN P=0.0001, KN92+WNT3A+AGRIN vs KN93+WNT3A+ AGRIN P=0.0046, KN92+GFP vs KN93+WNT3A+AGRIN P=0.0025, (C) Vehicle+GFP vs WNT3A+GFP P<0.0001, Vehicle+GFP vs AIP+WNT3A+AGRIN P<0.0001, WNT3A+GFP vs WNT3A+AGRIN P<0.0001, WNT3A+ AGRIN vs AIP+WNT3A+AGRIN P=0.0019. (D) TOPFlash reporter assay in COS7 cells transfected with either Agrin or GFP treated with WNT3A (200 ng/ml) and/or Forskolin (10 μM); Kruskal-Wallace, overall P=0.0168. Multiple comparison was carried out using a Dunn test, P values obtained with the Benjamini-Hochberg correction Vehicle vs WNT3A P=0.0280, WNT3Avs WNT3A+AGRIN P=0.0451, Vehicle vs Forskolin+WNT3A+GFP. (A to D n=4). (E) Representative images of Alcian blue staining of C28/I2 chondrocytes in micromass culture transfected with either empty plasmid or Agrin and LRP4 in the presence or the absence of the CREB inhibitor 666-15; bars 0.5 mm (F to H) Glycosaminoglycans quantification from the experiment in E (n=4); log transformed values, one way ANOVA, Tukey t-test, (F) Empty plasmid vs LRP4 P=0.0032, LRP4 vs LRP4+666-15 P=0.0002, (G) Empty plasmid vs AGRIN P=0.0023, AGRIN vs AGRIN+666-15 P<0.0001, (H) Empty plasmid vs LRP4+ AGRIN P=0.0094, AGRIN+LRP4 vs AGRIN+LRP4+666-15 P=0.0027.
Figure 4B:
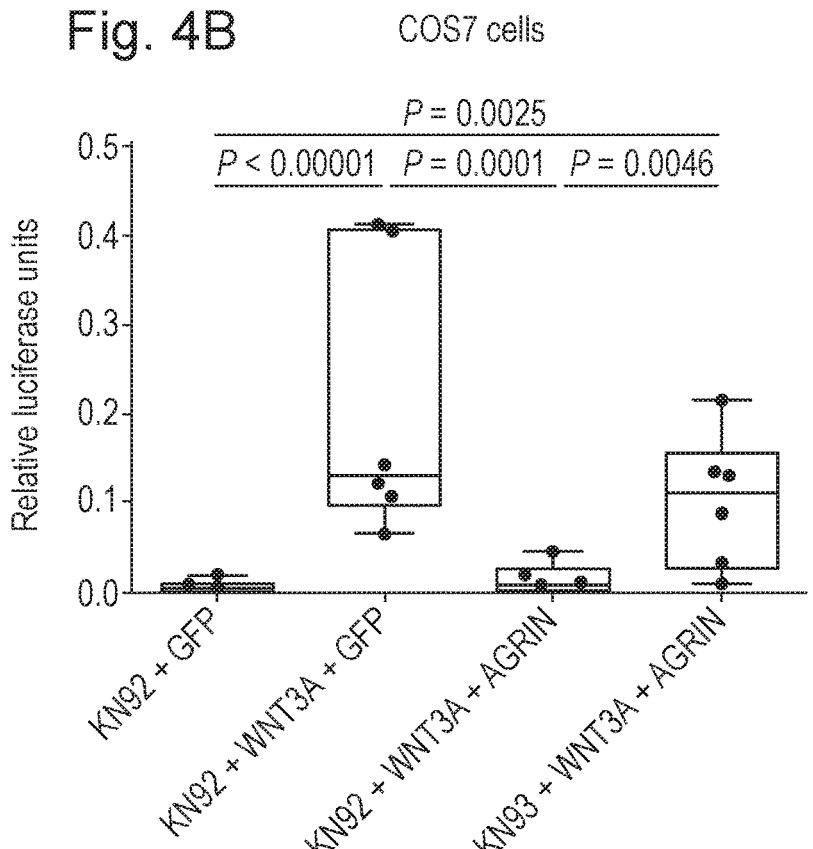
Figures 4C, 4D:
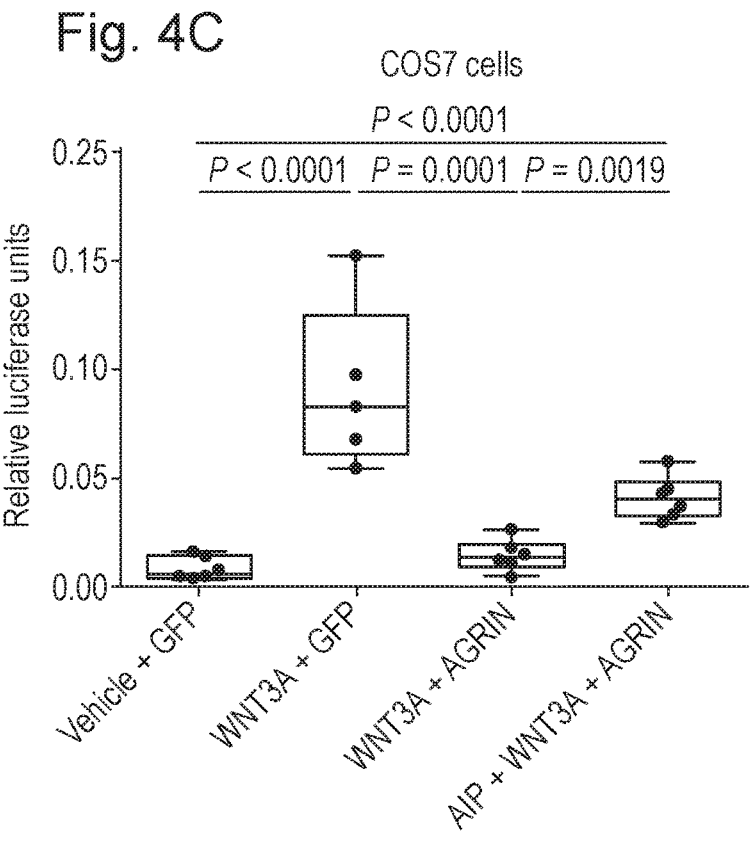
Figure 4E:
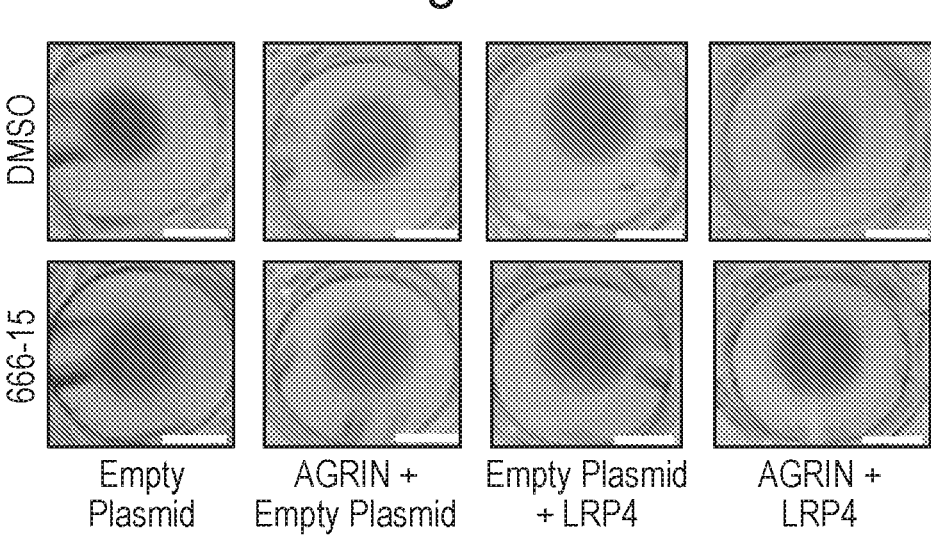
Figure 4F:
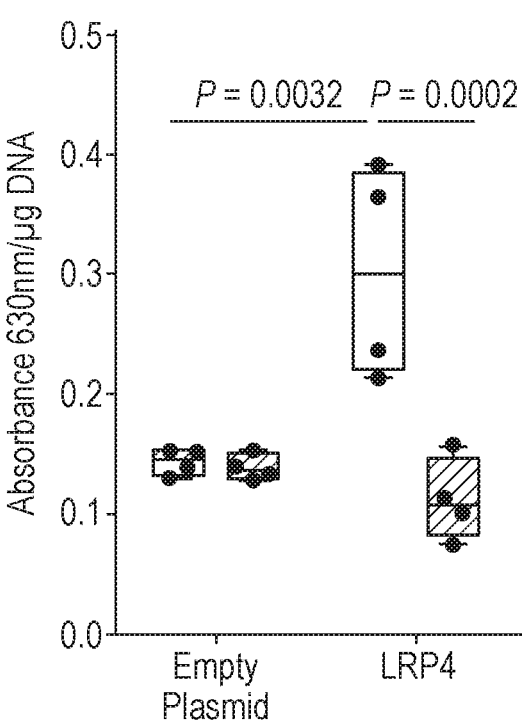
Figure 4G:
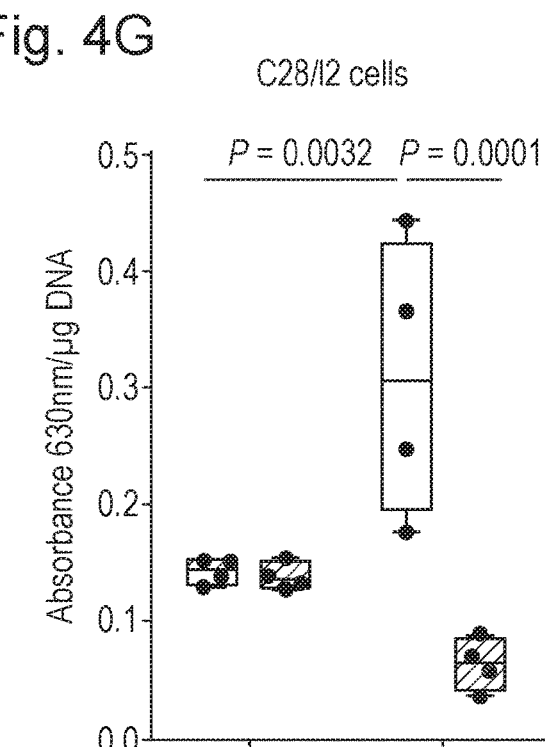
Figure 4H:
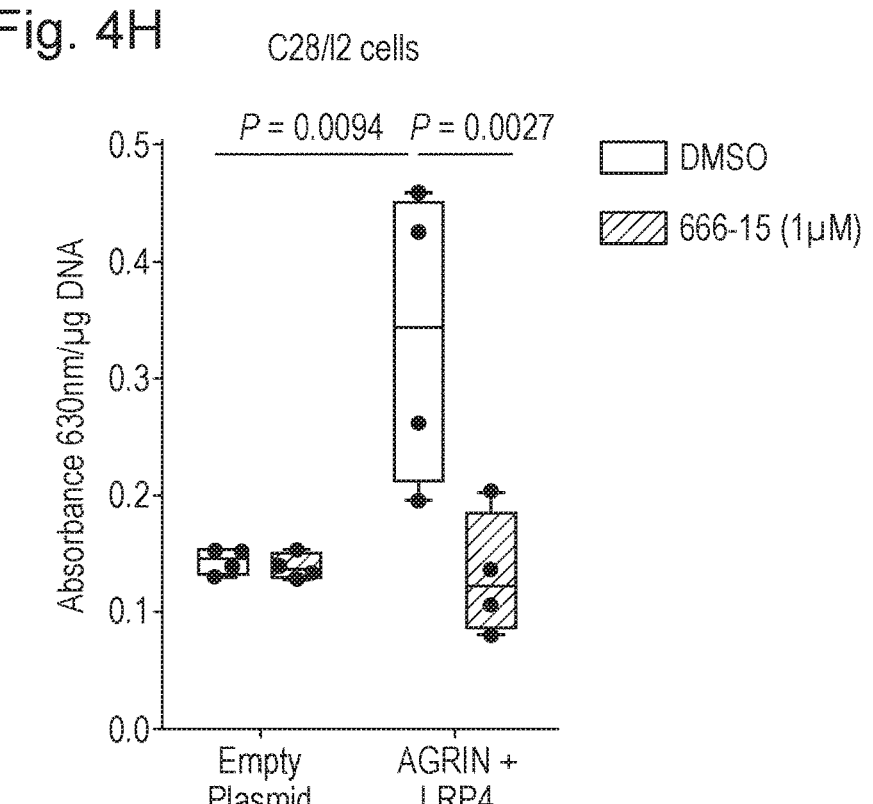

Agrin was previously reported to activate the Calcium/CaMKII/CREB signaling pathway in neurons. The inventors therefore hypothesized that agrin might be blocking canonical WNT signaling downstream of β-catenin by activating the CaMKII/CREB pathway. Agrin transfection or exogenous recombinant agrin resulted in phosphorylation and consequent activation of CREB (pCREB) in C28/I2 chondrocytes (FIG. 3, E to H and FIG. 11) and activation of a CREB reporter assay (FIG. 31). Conversely, silencing endogenous AGRN in C28/I2 cells using siRNA resulted in a decrease in the number of phosphorylated CREB-positive cells, while total CREB-positive cells remained unchanged (FIG. 3, J to L). In the presence of the CREB inhibitor 666-15, agrin failed to suppress the capacity of WNT3A to activate the TOPFlash reporter assay (FIG. 4A), suggesting that the capacity of agrin to inhibit WNT signaling is mediated by CREB. Confirming the epistasis of CaMKII in the CREB activation cascade, the CaMKII inhibitors KN93 and AIP negated the capacity of agrin to suppress the activation of the TOPFlash reporter assay induced by WNT3A when compared to KN92 (inactive control) or vehicle control respectively (FIGS. 4B and C). Several signaling pathways converge onto the CREB pathway with distinct, context-dependent transcriptional and biological outcomes. Therefore, the inventors investigated whether the capacity to suppress canonical WNT signaling is specific to agrin or is a general effect of CREB activation. Forskolin, an activator of adenyl cyclase and CREB agonist, failed to inhibit activation of the TOPFlash reporter assay after WNT3A treatment (FIG. 4D). Therefore, CREB activation is required but not per se sufficient for the capacity of agrin to suppress WNT signaling. The inventors next tested whether agrin-induced CREB activation is essential for its chondrogenic capacity. In keeping with this hypothesis, agrin or LRP4 lost the capacity to enhance extracellular matrix formation in C28I/2 chondrocytes in the presence of the CREB inhibitor 666-15 (FIG. 4E to H). Taken together, these data demonstrate that agrin activates the CaMKII/CREB cascade and that these events are essential for its capacity to inhibit WNT signaling and to induce cartilage formation.

Figure 5A:
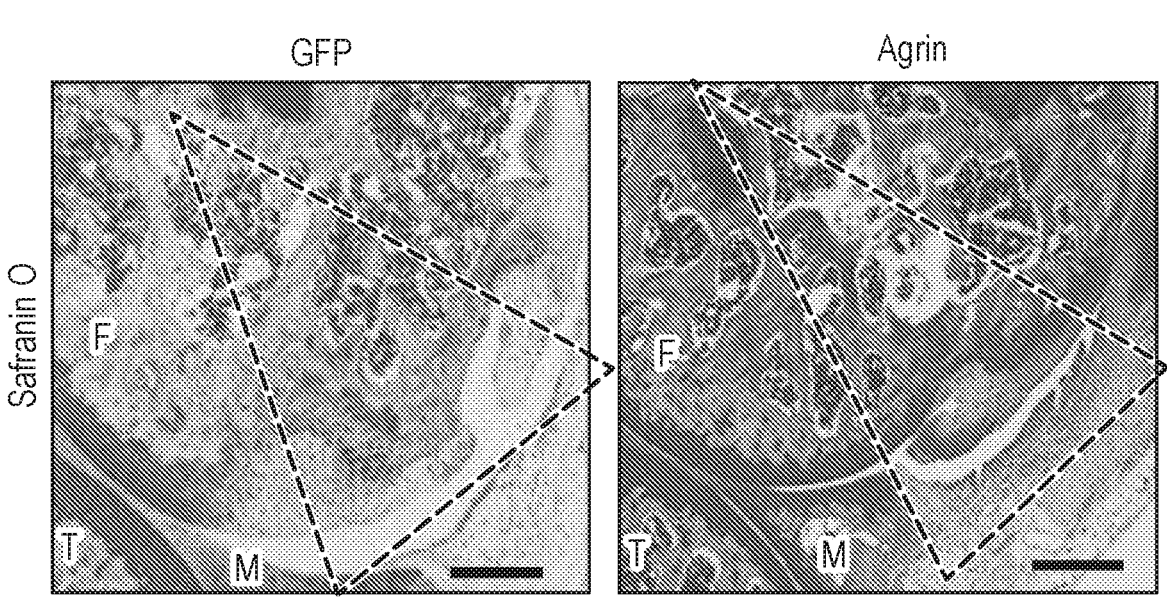
Figures 5B, 5C:
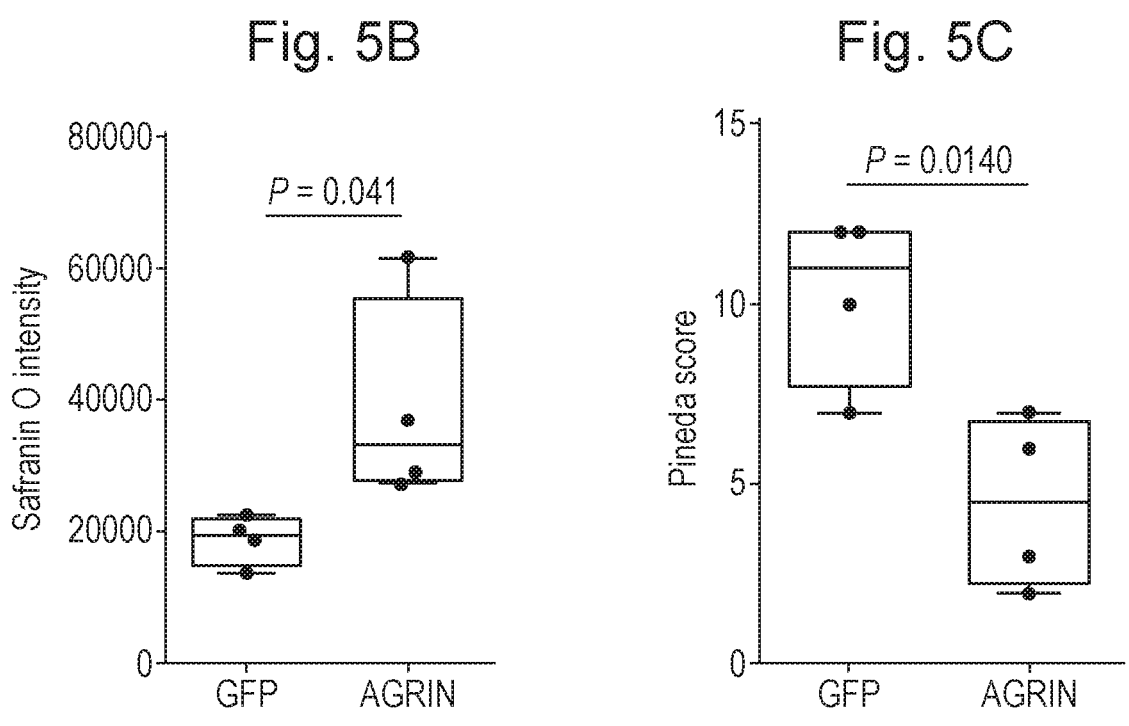
Figure 5D:
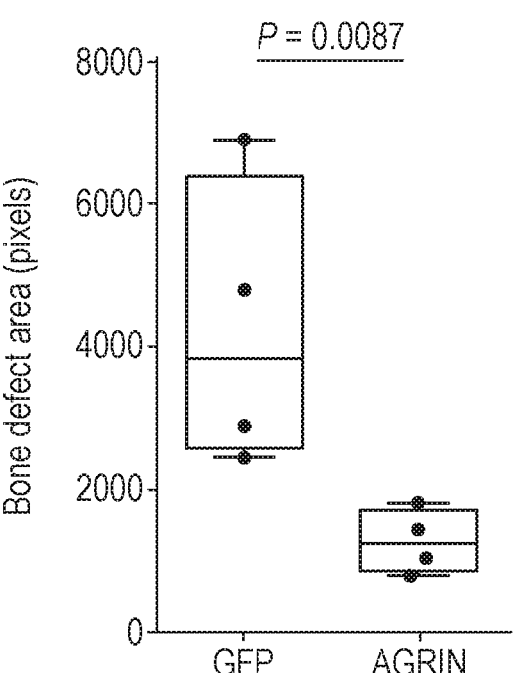
Figure 5E:
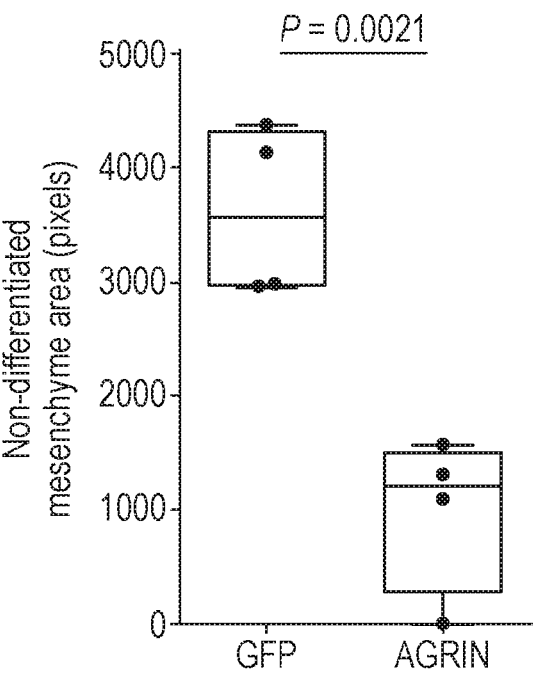
Figure 12A:
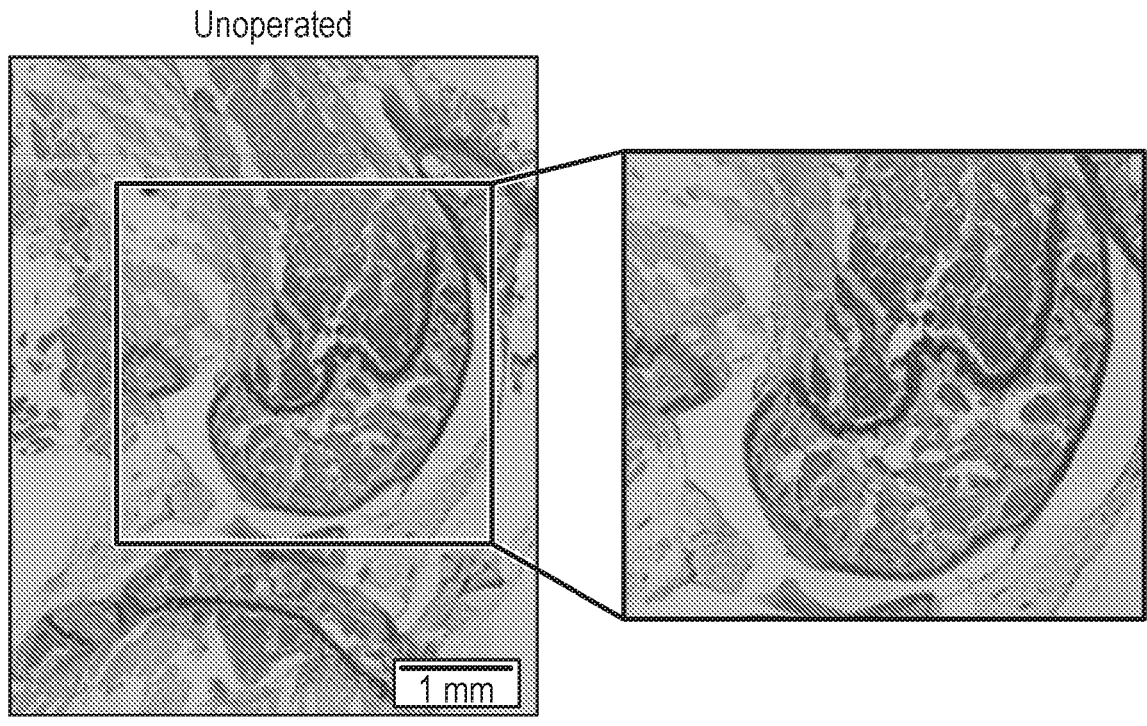
Figure 12B:
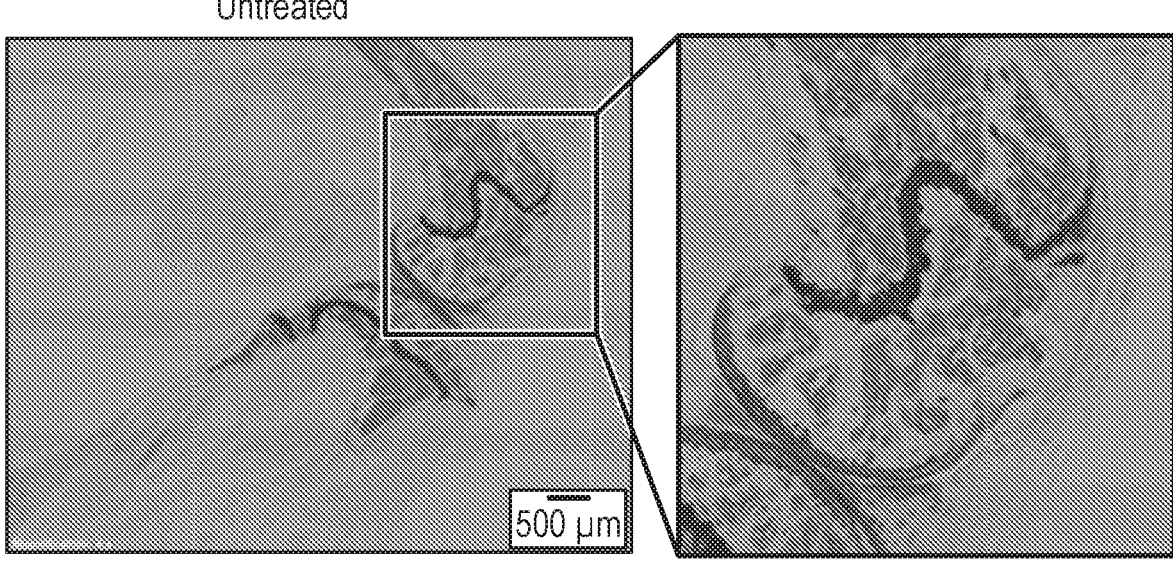
Figure 12C:
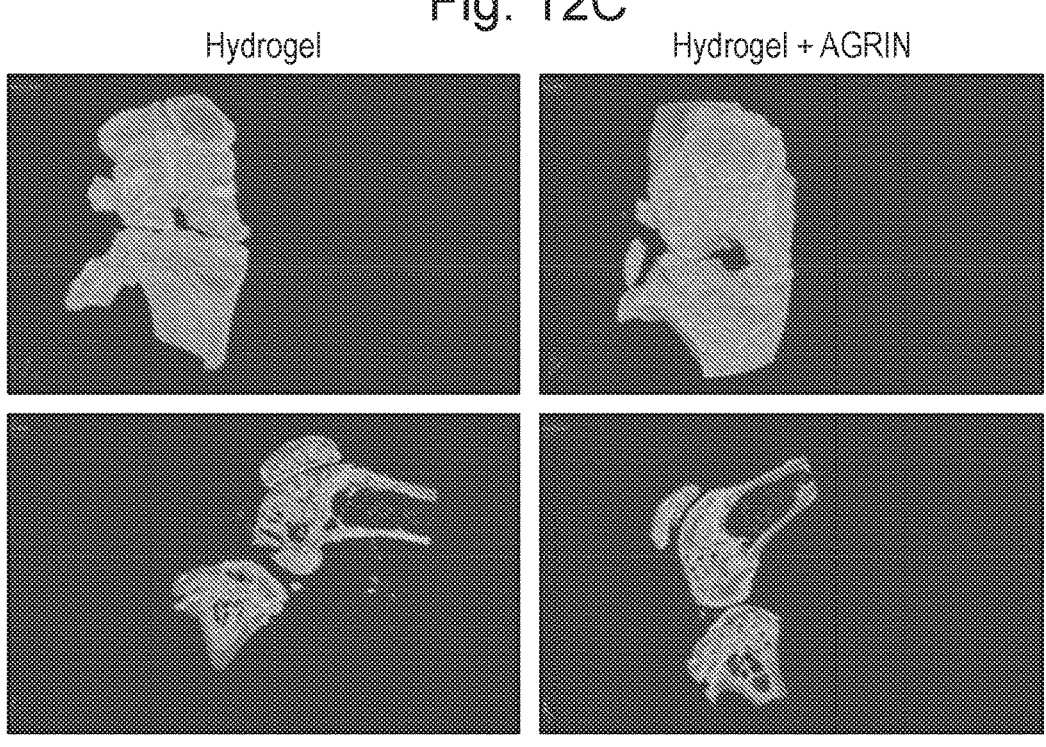

Agrin Supports the Repair of Critical Size Osteochondral Joint Surface Defects in Mice To test if exogenous agrin is sufficient to improve the outcome of joint surface repair in vivo, the inventors generated cylindrical osteochondral defects in the lateral femoral condyle of adult mice. Defects were 0.78±0.042 mm wide and 1.79±0.056 mm deep (mean±SD) and extended into the subchondral spongiosa. Without treatment, such defects result in partial healing of the bone, but not of the articular cartilage or the subchondral plate, after 8 weeks (FIG. 12A-B). A type I collagen gel containing either human full-length agrin or GFP as control was injected into the joint surface defect immediately after it was generated. Eight weeks after surgery, the cartilage layer regenerated significantly better in the agrin group (FIG. 5A) both in terms of glycosaminoglycan content (P=0.04141) (FIG. 5B) and Pineda injury score (P=0.04083) (FIG. 5C). The size of the residual bone defect was also reduced in the agrin group (FIG. 5D), however no evidence of ectopic bone formation was observed by μCT (FIG. 12C). Whereas in the agrin group most of the repair tissue was composed of either bone or cartilage, in the GFP group there was a larger amount of non-differentiated fibroblast-like mesenchyme (FIG. 5E).

Agrin Induces GDF5 Upregulation in a CREB-Dependent Manner

Figures 6A, 6B:
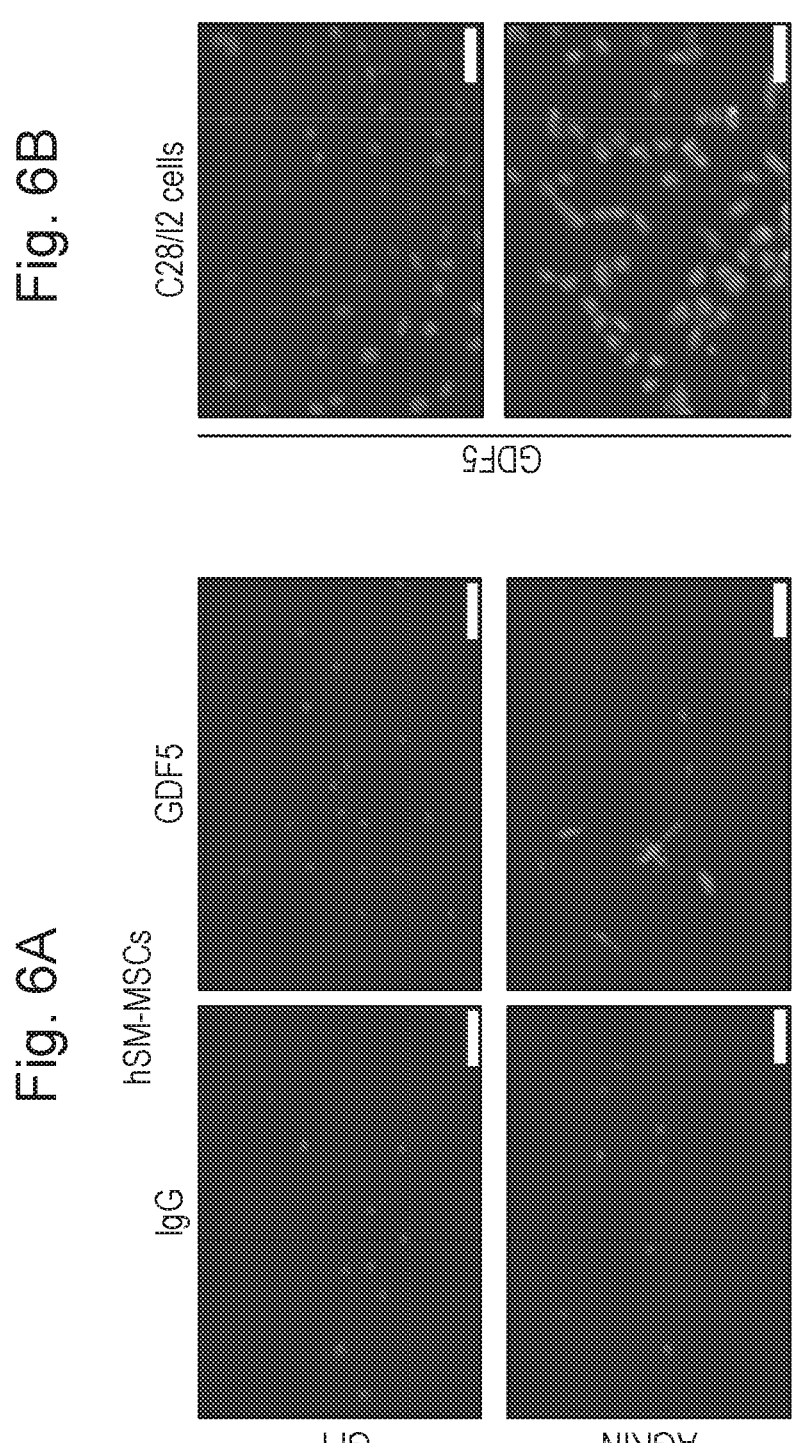
Figure 6G:
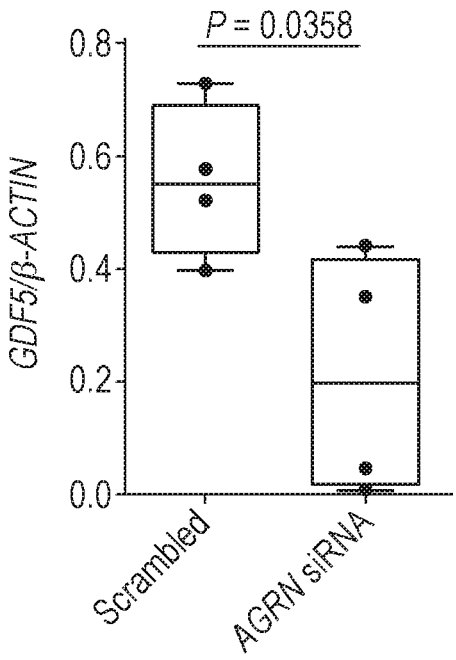
Figure 6H:
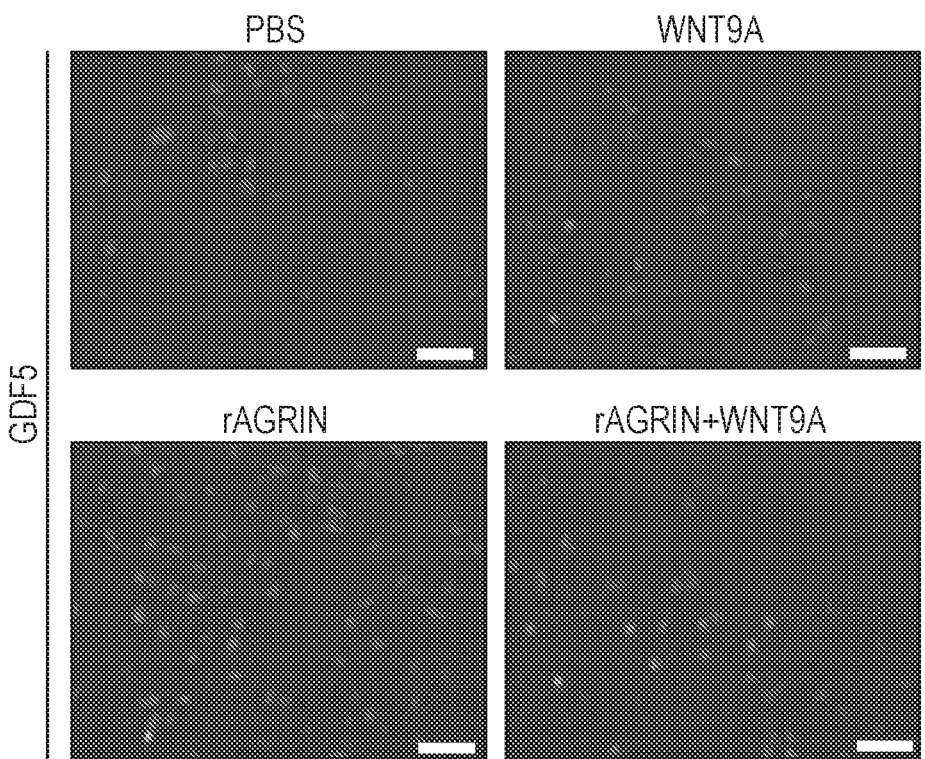

The inventors previously reported that the cells that contribute to the repair of cartilage defects derive from a lineage of progenitor cells that, during skeletal development, express the joint interzone marker GDF5. During skeletal development, WNT9A induces the expression of GDF5 in the mesenchymal cells residing in the portion of the skeletal elements that will give rise to the articular cartilage, menisci, and ligaments, and that are resistant to endochondral bone formation. In adulthood, joint-specific progenitor cells derived from the GDF5 lineage persist within the synovial membrane and are the main contributors to the regeneration of cartilage defects, which, when small in size, repair spontaneously. Unstimulated human SM-MSCs did not express detectable GDF5, however, 24 hr after agrin transfection, many of the cells highly expressed GDF5 (FIG. 6A). In addition, agrin transfection induced GDF5 upregulation in C28/I2 human chondrocytes at protein (FIG. 6B-C) and mRNA levels (FIG. 6D). Conversely, silencing of endogenous AGRN using siRNA in C28/I2 cells resulted in a reduction of GDF5 expression at protein (FIGS. 6 E and F) and mRNA levels (FIG. 6G). This loss of GDF5 was rescued with the addition of exogenous rAgrin (FIGS. 6E and F). Strikingly, agrin was unable to induce GDF5 expression in bone marrow-derived MSCs (FIG. 13). This suggests that the capacity of agrin to induce GDF5 is restricted to cells of the GDF5-derived lineage, such as chondrocytes and synovial membrane-derived MSCs.

During embryonic development, WNT9A is sufficient to induce GDF5 expression in the joint interzones. Agrin and WNT9A alone or in combination induced GDF5 protein expression (FIG. 6H to I) and activated the CREB reporter assay (FIG. 6J). Interestingly, agrin and WNT9A in combination induced activation of the CREB reporter assay more than agrin or WNT9A alone. The CREB inhibitor 666-15 negated the capacity of agrin to induce GDF5 mRNA upregulation in C28/I2 cells (FIG. 6K), suggesting that the capacity of agrin to upregulate GDF5 is CREB-dependent. Finally, overexpression of constitutively active LEF1, but not WNT3A, also negated agrin-induced GDF5 upregulation (FIG. 6L to M). This does not necessarily mean that suppression of WNT signaling drives activation of GDF5, because caLEF1 overexpression also suppressed the capacity of agrin to induce CREB phosphorylation. Taken together, these results indicate that agrin activates GDF5 expression and prompts chondrogenesis through activation of CREB-dependent transcription and suppression of canonical WNT signaling.

Figure 7A:
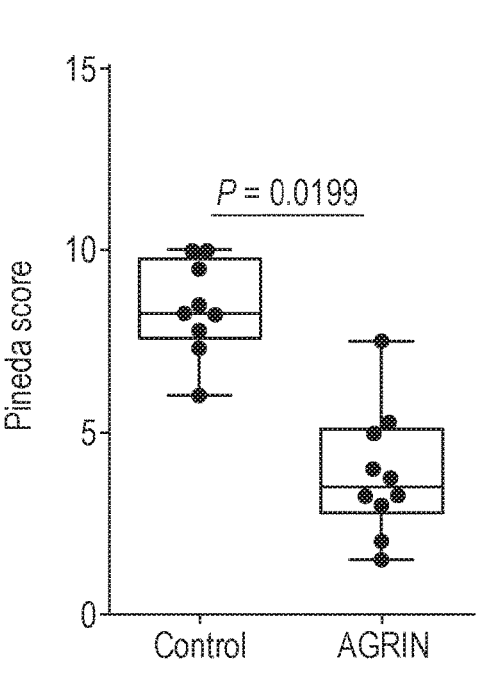
Figure 7B:
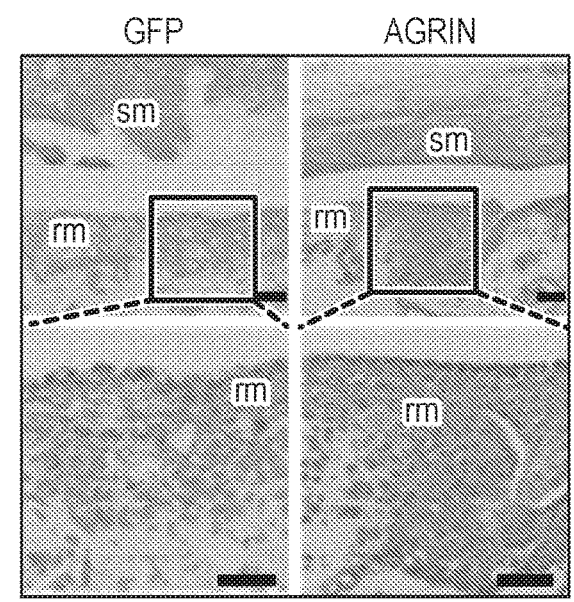
Figure 7C:
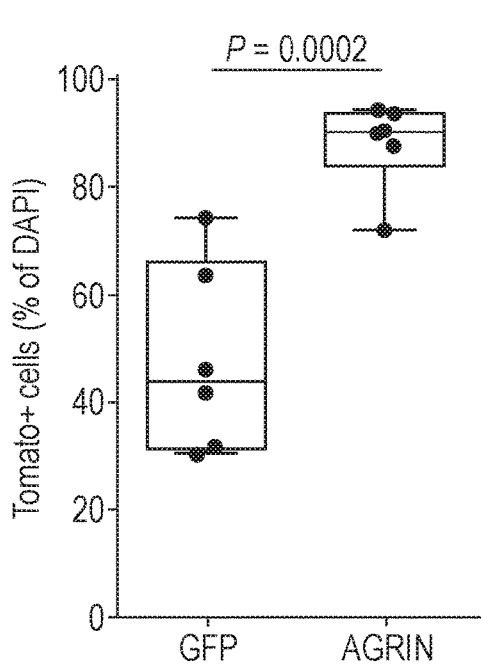
Figure 7D:
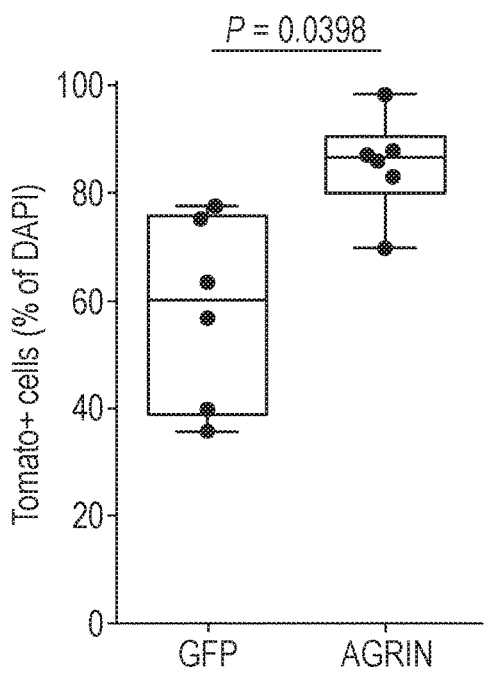
Figure 7E:
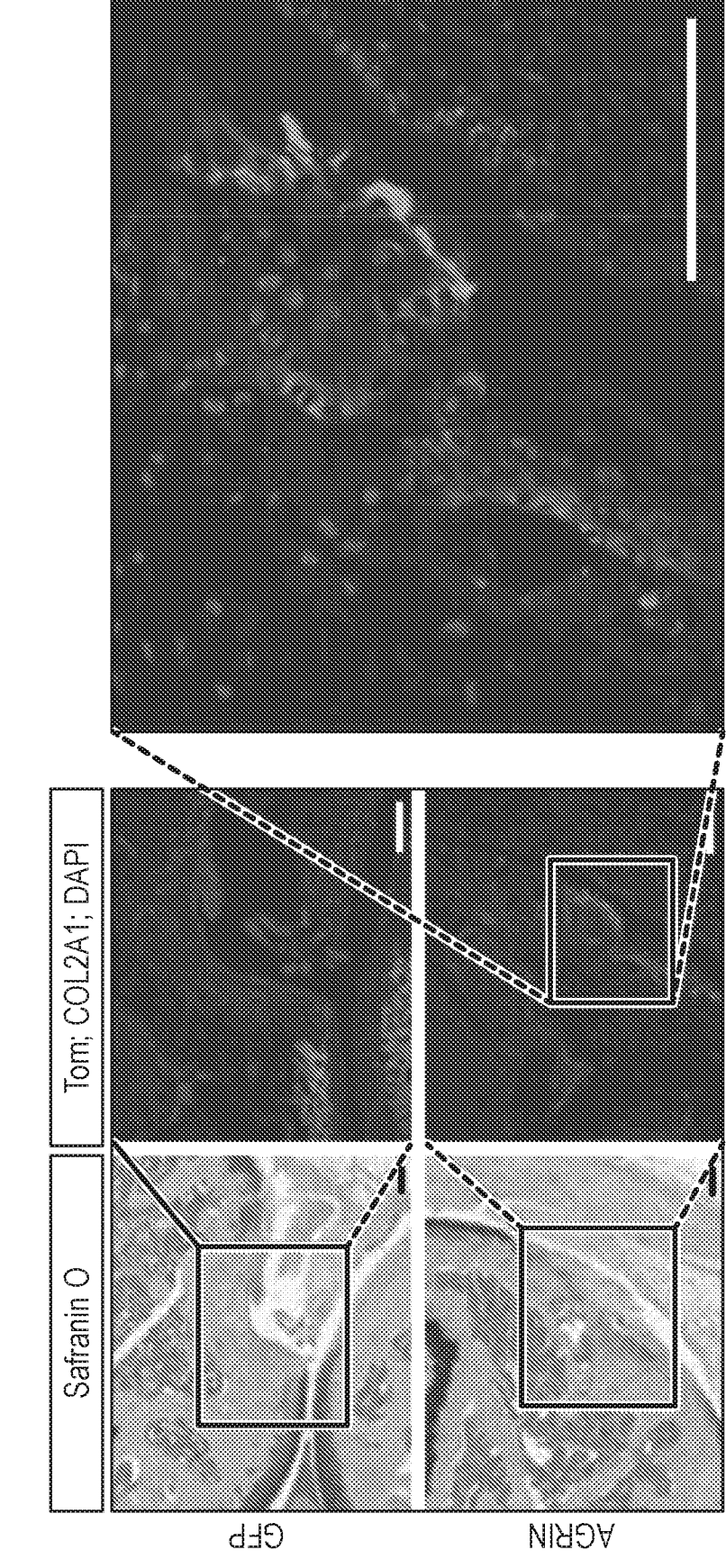

Agrin Induces Local Accumulation of Gdf5-Lineage Joint Stem Cells and Phosphorylation of CREB In Vivo To study whether the Gdf5-lineage of joint-specific MSCs contribute to agrin induced joint surface repair, the inventors used transgenic mice harboring a tdTomato (Tom) cassette preceded by a LoxP-flanked stop cassette within the ROSA26 locus and Cre recombinase under the control of the Gdf5 responsive elements active during embryonic development. In these Gdf5-Cre;Tom reporter mice, the progeny of cells that at any point during embryonic development have expressed Gdf5 will express Tom, regardless of whether they still express Gdf5. Similar to the inventors' findings in wild type mice, agrin enhanced joint surface regeneration in Gdf5-Cre;Tom reporter mice (FIG. 7A). Three weeks after surgery there was a marked increase in the number of Tom+ cells within the superficial portion of the repair tissue as well as in the synovial membrane of the mice that received agrin compared to controls (FIG. 7B to D). Co-immunofluorescence staining for Tom and collagen type II at eight weeks after injury revealed the presence of Tom+ chondrocytes embedded in a collagen type II-containing matrix along the joint surface of the repair tissue (FIG. 7E).

Figure 7F:
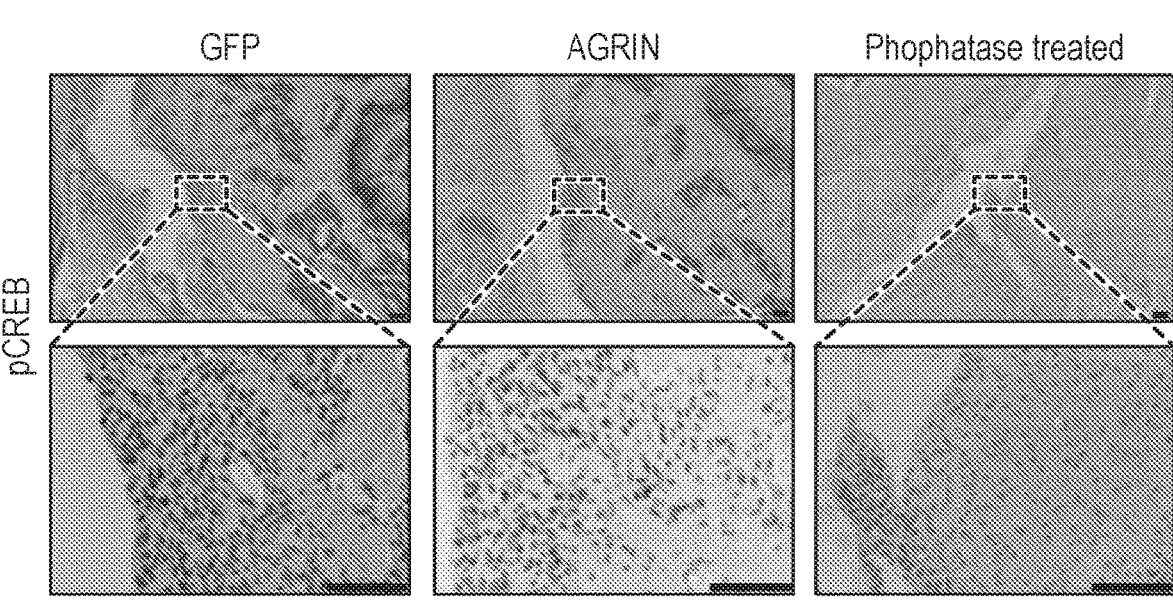

In keeping with inventors' in vitro data, three weeks after surgery the inventors detected a higher percentage of cells positive for pCREB within the repair tissue of agrin-treated animals (FIGS. 7F and G). Dose response experiments using recombinant agrin revealed that concentrations between 1 and 1000 ng/ml suppressed WNT signaling and activated CREB signaling to a similar extent as COS7-AGRIN cell lysates (FIGS. 14A and B). An injection of a collagen gel containing 100 ng/ml rAGRIN into osteochondral defects also led to increased Tom+ cells in the repair mesenchyme three weeks after surgery compared to PBS control (FIG. 14, C to E), as observed with the COS7-AGRIN cell lysates.

Intra-Articular Agrin Delivery Improves Long-Term Repair of Critical Size Osteochondral Defects and Improves Joint Function in Sheep Finally, the inventors tested whether agrin could also support long-term cartilage repair in a large animal model. A critical-size osteochondral defect (8 mm diameter and 5 mm deep) was generated in the weight-bearing region of the medial femoral condyle of adult sheep. The defect was filled with a type I collagen gel containing either human full-length agrin or GFP as control. At 6 months post-surgery, μCT analysis revealed that bone repair was better in the agrin than the control group, as noted by reduced defect volume (FIGS. 8A and B). The Pineda injury score revealed superior healing of the defect in the agrin group (FIGS. 8C and D). Sheep that received the agrin-containing gel spent more time playing and less time resting throughout the study (FIGS. 8E and F), suggesting that the improved repair was associated with improved function.

DISCUSSION

Figure 7G:
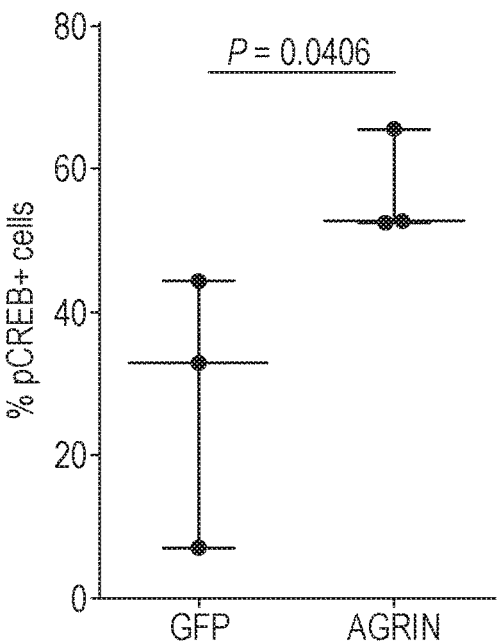

The inventors demonstrated that joint surface injury triggers expression of agrin, which in turn recruits chondrogenic GDF5 lineage joint-resident progenitor cells to the repair mesenchyme and enables the morphogenesis of joint surface. In critical size defects, which do not heal spontaneously, exogenous agrin induced GDF5 expression in joint-resident MSCs and triggered their chondrocytic differentiation by inhibiting WNT signaling downstream of in a CREB-dependent manner (FIG. 7G). Tissue patterning requires temporal and spatial coordination of cell migration, proliferation and differentiation. The WNT, BMP and CREB-dependent signaling pathways are key players in the patterning and morphogenesis of synovial joints during embryonic development. Whereas the modulation of these pathways individually failed to result in morphogenesis—for instance, BMP2 is chondrogenic but leads to ectopic cartilage and bone formation—exogenous agrin resulted in harmonious postnatal repair morphogenesis.

During embryonic development WNT9A is sufficient but not required to induce joint formation whereas GDF5 is required (at least for some joints) but not sufficient, because disruption of Gdf5 in mice is not associated with joint fusion. It was previously thought that the GDF5 lineage of progenitor cells was established early in development and that cells later migrated to the joint interzones, thereby contributing to the formation of the articular cartilage and ligaments. This concept was challenged by subsequent lineage-tracking experiments using an inducible system allowing genetic labeling of Gdf5-positive cells at different stages of development. Such experiments demonstrated a continuous recruitment of Gdf5-lineage cells to the joint interzones throughout development. Cells entering the Gdf5 lineage at different developmental stages contributed to different tissue structures within the joints. This new paradigm is in keeping with the inventors' data showing recruitment of Gdf5-lineage cells to the site of injury induced by agrin even in adulthood. Agrin failed to induce GDF5 in bone marrow-derived MSCs, thereby suggesting that its function is specific to GDF5-lineage cells. This may explain why agrin, as opposed to other chondrogenic molecules such as BMPs and TGF-β, did not induce ectopic cartilage or bone formation.

Although both WNT9A and agrin induced GDF5 upregulation, the former is an activator of the canonical WNT signaling and inhibits chondrogenesis whereas the latter is an inhibitor of canonical WNT signaling and promotes chondrogenesis. WNT9A enhanced the capacity of agrin in activating CREB in HEK293 cells. The presence of a cAMP response element (CRE) in the GDF5 promoter suggests that CREB is a critical element for the capacity of agrin to upregulate GDF5.

Agrin inhibited canonical WNT signaling downstream of β-catenin. Such mechanism is independent of the ligands moiety and the WNT receptor repertoire and therefore overrides all other upstream regulation including activating mutations of β-catenin which result in cancer. This property of agrin may open therapeutic opportunities for its use in other conditions such as osteoarthritis and cancer, in which downregulation of canonical WNT signaling is desirable without incurring compensatory mechanisms. Notably, WNT inhibition is currently being tested as a treatment for osteoarthritis.

The capacity of agrin to induce long-term cartilage regeneration after a single administration makes it an excellent candidate for clinical use. One problem in clinical translation is manufacturing. In its fully glycosylated state, agrin is a large, poorly soluble molecule of ~500-600 kD which is difficult to purify to clinical grade in a biologically active form. The inventors have shown that a purified C-terminal deletion mutant of only ~95 kD is sufficient to induce chondrogenesis in vitro at least as potently as the full-length molecule, but the efficacy of such deletion needs to be confirmed in vivo, since the N-terminus contains domains responsible for binding to the extracellular matrix. Such domains, and the capacity of agrin to bind to the extracellular matrix, may be responsible for its remarkable long-term efficacy.

No ectopic cartilage was observed after intraarticular delivery despite the chondrogenic capacity of agrin. This is in contrast with the abundant ectopic cartilage and bone formation observed after delivery of TGF-β or BMP2. In addition, the chondrogenic and anabolic capacity of agrin could be detected consistently even in the presence of 10% fetal bovine serum, which overrides the anabolic capacity of TGF-β and BMPs. The capacity of agrin to preserve the architecture of the native tissue is distinct and of important translational relevance. The inventors anticipate that the optimization of delivery will be key for the clinical translation in cartilage repair strategies.

In summary, the inventors have surprisingly found that a fragment of human agrin comprising the amino acid sequence of SEQ ID NO: 2 is capable of inducing chondrocyte differentiation and/or chondrogenesis, whilst being soluble and therefore easy to produce and easy to purify, thereby providing an polypeptide that is suitable for use in treating osteochondral defects, pain and cancer. In the Example below, the efficacy of recombinant fragments of human agrin comprising the amino acid sequence of SEQ ID NO: 2 (i.e. a soluble polypeptide of the invention) is compared against full length human agrin, of neuronal and non-neuronal origin, and polypeptide sequence corresponding to amino acids 1260-2045 of SEQ ID NO: 1 (R&D Systems, product no. 6624-AG). The soluble polypeptide of the invention is shown to retail all of the desirable characteristics of full length agrin, whilst being soluble, easy to produce and easy to purify.

SEQUENCES

SEQ ID NO: 1

```
MAGRSHPGPLRPLLPLLVVAACVLPGAGGTCPERALERREEEANVVLIGTVEEILNVDPVQHTYSCKVRVWRYLK
GKDLVARESLLDGGNKVVISGFGDPLICDNQVSTGDTRIFFVNPAPPYLWPAHKNELMLNSSLMRITLRNLEEVE
FCVEDKPGTHFTPVPPTPPDACRGMLCGFGAVCEPNAEGPGRASCVCKKSPCPSVVAPVCGSDASTYSNECELQR
AQCSQQRRIRLLSRGPCGSRDPCSNVTCSFGSTCARSADGLTASCLCPATCRGAPEGTVCGSDGADYPGECQLLR
RACARQENVFKKFDGPCDPCQGALPDPSRSCRVNPRTRRPEMLLRPESCPARQAPVCGDDGVTYENDCVMGRSGA
ARGLLLQKVRSGQCQGRDQCPEPCRFNAVCLSRRGRPRCSCDRVTCDGAYRPVCAQDGRTYDSDCWRQQAECRQQ
RAIPSKHQGPCDQAPSPCLGVQCAFGATCAVKNGQAACECLQACSSLYDPVCGSDGVTYGSACELEATACTLGRE
IQVARKGPCDRCGQCRFGALCEAETGRCVCPSECVALAQPVCGSDGHTYPSECMLHVHACTHQISLHVASAGPCE
TCGDAVCAFGAVCSAGQCVCPRCEHPPPGPVCGSDGVTYGSACELREAACLQQTQIEEARAGPCEQAECGSGGSG
SGEDGDCEQELCRQRGGIWDEDSEDGPCVCDFSCQSVPGSPVCGSDGVTYSTECELKKARCESQRGLYVAAQGAC
RGPTFAPLPPVAPLICAQTPYGCCQDNITAARGVGLAGCPSACQCNPHGSYGGTCDPATGQCSCRPGVGGLRCDR
CEPGFWNFRGIVTDGRSGCTPCSCDPQGAVRDDCEQMTGLCSCKPGVAGPKCGQCPDGRALGPAGCEADASAPAT
CAEMRCEFGARCVEESGSAHCVCPMLTCPEANATKVCGSDGVTYGNECQLKTIACRQGLQISIQSLGPCQEAVAP
STHPTSASVTVTTPGLLLSQALPAPPGALPLAPSSTAHSQTTPPPSSRPRTTASVPRTTVWPVLTVPPTAPSPAP
SLVASAFGESGSTDGSSDEELSGDQEASGGGSGGLEPLEGSSVATPGPPVERASCYNSALGCCSDGKTPSLDAEG
SNCPATKVFQGVLELEGVEGQELFYTPEMADPKSELFGETARSIESTLDDLFRNSDVKKDFRSVRLRDLGPGKSV
RAIVDVHFDPTTAFRAPDVARALLRQIQVSRRRSLGVRRPLQEHVRFMDFDWFPAFITGATSGAIAAGATARATT
ASRLPSSAVTPRAPHPSHTSQPVAKTTAAPTTRRPPTTAPSRVPGRRPPAPQQPPKPCDSQPCFHGGTCQDWALG
GGFTCSCPAGRGGAVCEKVLGAPVPAFEGRSFLAPPTLRAYHTLRLALEFRALEPQGLLLYNGNARGKDFLALAL
LDGRVQLRFDTGSGPAVLTSAVPVEPGQWHRLELSRHWRRGTLSVDGETPVLGESPSGTDGLNLDTDLFVGGVPE
DQAAVALERTFVGAGLRGCIRLLDVNNQRLELGIGPGAATRGSGVGECGDHPCLPNPCHGGAPCQNLEAGRFHCQ
CPPGRVGPTCADEKSPCQPNPCHGAAPCRVLPEGGAQCECPLGREGTFCQTASGQDGSGPFLADENGFSHLELRG
LHTFARDLGEKMALEVVFLARGPSGLLLYNGQKTDGKGDFVSLALRDRRLEFRYDLGKGAAVIRSREPVTLGAWT
RVSLERNGRKGALRVGDGPRVLGESPVPHTVLNLKEPLYVGGAPDFSKLARAAAVSSGEDGAIQLVSLGGRQLLT
PEHVLRQVDVTSFAGHPCTRASGHPCLNGASCVPREAAYVCLCPGGFSGPHCEKGLVEKSAGDVDTLAFDGRTFV
```

-continued

SEQUENCES

EYLNAVTESEKALQSNHFELSLRTEATQGLVLWSGKATERADYVALAIVDGHLQLSYNLGSQPVVLRSTVPVNTN
RWLRVVAHREQREGSLQVGNEAPVTGSSPLGATQLDTDGALWLGGLPELPVGPALPKAYGTGFVGCLRDVVVGRH
PLHLLEDAVTKPELRPCPTP

SEQ ID NO: 2

HVRFMDFDWFPAFITG

SEQ ID NO: 3

HVRFMDFDWFPAFITGATSGAIAAGATARATTASRLPSSAVTPRAPHPSHTSQPVAKTTAAPTTRRPPTTAPSRV
PGRRPPAPQQPPKPCDSQPCFHGGTCQDWALGGGFTCSCPAGRGGAVCEKVLGAPVPAFEGRSFLAFPTLRAYHT
LRLALEFRALEPQGLLLYNGNARGKDFLALALLDGRVQLRFDTGSGPAVLTSAVPVEPGQWHRLELSRHWRRGTL
SVDGETPVLGESPSGTDGLNLDTDLFVGGVPEDQAAVALERTFVGAGLRGCIRLLDVNNQRLELGIGPGAATRGS
GVGECGDHPCLPNPCHGGAPCQNLEAGRFHCQCPPGRVGPTCADEKSPCQPNPCHGAAPCRVLPEGGAQCECPLG
REGTFCQTASGQDGSGPFLADENGFSHLELRGLHTFARDLGEKMALEVVFLARGPSGLLLYNGQKTDGKGDFVSL
ALRDRRLEFRYDLGKGAAVIRSREPVTLGAWTRVSLERNGRKGALRVGDGPRVLGESPVPHTVLNLKEPLYVGGA
PDFSKLARAAAVSSGFDGAIQLVSLGGRQLLTPEHVLRQVDVTSFAGHPCTRASGHPCLNGASCVPREAAYVCLC
PGGFSGPHCEKGLVEKSAGDVDTLAFDGRTFVEYLNAVTESEKALQSNHFELSLRTEATQGLVLWSGKATERADY
VALAIVDGHLQLSYNLGSQPVVLRSTVPVNTNRWLRVVAHREQREGSLQVGNEAPVTGSSPLGATQLDTDGALWL
GGLPELPVGPALPKAYGTGFVGCLRDVVVGRHPLHLLEDAVTKPELRPCPTP

SEQ ID NO: 4

MAGRSHPGPLRPLLPLLVVAACVLPGAGGTCPERALERREEEANVVLIGTVEEILNVDPVQHTYSCKVRVWRYLK
GKDLVARESLLDGGNKVVISGFGDPLICDNQVSTGDTRIFFVNPAPPYLWPAHKNELMLNSSLMRITLRNLEEVE
FCVEDKPGTHFTPVPPTPPDACRGMLCGFGAVCEPNAEGPGRASCVCKKSPCPSVVAPVCGSDASTYSNECELQR
AQCSQQRRIRLLSRGPCGSRDPCSNVTCSFGSTCARSADGLTASCLCPATCRGAPEGTVCGSDGADYPGECQLLR
RACARQENVFKKFDGPCDPCQGALPDPSRSCRVNPRTRRPEMLLRPESCPARQAPVCGDDGVTYENDCVMGRSGA
ARGLLLQKVRSGQCQGRDQCPEPCRFNAVCLSRRGRPRCSCDRVTCDGAYRPVCAQDGRTYDSDCWRQQAECRQQ
RAIPSKHQGPCDQAPSPCLGVQCAFGATCAVKNGQAACECLQACSSLYDPVCGSDGVTYGSACELEATACTLGRE
IQVARKGPCDRCGQCRFGALCEAETGRCVCPSECVALAQPVCGSDGHTYPSECMLHVHACTHQISLHVASAGPCE
TCGDAVCAFGAVCSAGQCVCPRCEHPPPGPVCGSDGVTYGSACELREAACLQQTQIEEARAGPCEQAECGSGGSG
SGEDGDCEQELCRQRGGIWDEDSEDGPCVCDFSCQSVPGSPVCGSDGVTYSTECELKKARCESQRGLYVAAQGAC
RGPTFAPLPPVAPLHCAQTPYGCCQDNITAARGVGLAGCPSACQCNPHGSYGGTCDPATGQCSCRPGVGGLRCDR
CEPGFWNFRGIVTDGRSGCTPCSCDPQGAVRDDCEQMTGLCSCKPGVAGPKCGQCPDGRALGPAGCEADASAPAT
CAEMRCEFGARCVEESGSAHCVCPMLTCPEANATKVCGSDGVTYGNECQLKTIACRQGLQISIQSLGPCQEAVAP
STHPTSASVTVTTPGLLLSQALPAPPGALPLAPSSTAHSQTTPPPSSRPRTTASVPRTTVWPVLTVPPTAPSPAP
SLVASAFGESGSTDGSSDEELSGDQEASGGGSGGLEPLEGSSVATPGPPVERASCYNSALGCCSDGKTPSLDAEG
SNCPATKVFQGVLELEGVEGQELFYTPEMADPKSELFGETARSIESTLDDLFRNSDVKKDFRSVRLRDLGPGKSV
RAIVDVHFDPTTAFRAPDVARALLRQIQVSRRRSLGVRRPLQEHVRFMDFDWFPAFITGATSGAIAAGATARATT
ASRLPSSAVTPRAPHPSHTSQPVAKTTAAPTTRRPPTTAPSRVPGRRPPAPQQPPKPCDSQPCFHGGTCQDWALG
GGFTCSCPAGRGGAVCEKVLGAPVPAFEGRSFLAFPTLRAYHTLRLALEFRALEPQGLLLYNGNARGKDFLALAL
LDGRVQLRFDTGSGPAVLTSAVPVEPGQWHRLELSRHWRRGTLSVDGETPVLGESPSGTDGLNLDTDLFVGGVPE
DQAAVALERTFVGAGLRGCIRLLDVNNQRLELGIGPGAATRGSVGECGDHPCLPNPCHGGAPCQNLEAGRFHCQ
CPPGRVGPTCADEKSPCQPNPCHGAAPCRVLPEGGAQCECPLGREGTFCQTASGQDGSGPFLADFNGFSHLELRG
LHTFARDLGEKMALEVVFLARGPSGLLLYNGQKTDGKGDFVSLALRDRRLEFRYDLGKGAAVIRSREPVTLGAWT
RVSLERNGRKGALRVGDGPRVLGESPKSRKVPHTVLNLKEPLYVGGAPDFSKLARAAAVSSGFDGAIQLVSLGGR
QLLTPEHVLRQVDVTSFAGHPCTRASGHPCLNGASCVPREAAYVCLCPGGFSGPHCEKGLVEKSAGDVDTLAFDG
RTFVEYLNAVTESELANEIPVPETLDSGALHSEKALQSNHFELSLRTEATQGLVLWSGKATERADYVALAIVDGH
LQLSYNLGSQPVVLRSTVPVNTNRWLRVVAHREQREGSLQVGNEAPVTGSSPLGATQLDTDGALWLGGLPELPVG
PALPKAYGTGFVGCLRDVVVGRHPLHLLEDAVTKPELRPCPTP

SEQ ID NO: 5

MPXLAVARDTRQPAGASLLVRGFMVPCNACLILLATATLGFAVLLFLNNYDKPGTHFTPVPPTPPDACRGMLCGF
GAVCEPNAEGPGRASCVCKKSPCPSVVAPVCGSDASTYSNECELQRAQCSQQRRIRLLSRGPCGSRDPCSNVTCS
FGSTCARSADGLTASCLCPATCRGAPEGTVCGSDGADYPGECQLLRRACARQENVFKKFDGPCDPCQGALPDPSR
SCRVNPRTRRPEMLLRPESCPARQAPVCGDDGVTYENDCVMGRSGAARGLLLQKVRSGQCQGRDQCPEPCRFNAV
CLSRRGRPRCSCDRVTCDGAYRPVCAQDGRTYDSDCWRQQAECRQQRAIPSKHQGPCDQAPSPCLGVQCAFGATC
AVKNGQAACECLQACSSLYDPVCGSDGVTYGSACELEATACTLGREIQVARKGPCDRCGQCRFGALCEAETGRCV
CPSECVALAQPVCGSDGHTYPSECMLHVHACTHQISLHVASAGPCETCGDAVCAFGAVCSAGQCVCPRCEHPPPG
PVCGSDGVTYGSACELREAACLQQTQIEEARAGPCEQAECGSGGSGSGEDGDCEQELCRQRGGIWDEDSEDGPCV
CDFSCQSVPGSPVCGSDGVTYSTECELKKARCESQRGLYVAAQGACRGPTFAPLPPVAPLHCAQTPYGCCQDNIT
AARGVGLAGCPSACQCNPHGSYGGTCDPATGQCSCRPGVGGLRCDRCEPGFWNFRGIVTDGRSGCTPCSCDPQGA
VRDDCEQMTGLCSCKPGVAGPKCGQCPDGRALGPAGCEADASAPATCAEMRCEFGARCVEESGSAHCVCPMLTCP
EANATKVCGSDGVTYGNECQLKTIACRQGLQISIQSLGPCQEAVAPSTHPTSASVTVTTPGLLLSQALPAPPGAL
PLAPSSTAHSQTTPPPSSRPRTTASVPRTTVWPVLTVPPTAPSPAPSLVASAFGESGSTDGSSDEELSGDQEASG
GGSGGLEPLEGSSVATPGPPVERASCYNSALGCCSDGKTPSLDAEGSNCPATKVFQGVLELEGVEGQELFYTPEM
ADPKSELFGETARSIESTLDDLFRNSDVKKDFRSVRLRDLGPGKSVRAIVDVHFDPTTAFRAPDVARALLRQIQV
SRRRSLGVRRPLQEHVRFMDFDWFPAFITGATSGAIAAGATARATTASRLPSSAVTPRAPHPSHTSQPVAKTTAA
PTTRRPPTTAPSRVPGRRPPAPQQPPKPCDSQPCFHGGTCQDWALGGGFTCSCPAGRGGAVCEKVLGAPVPAFEG
RSFLAFPTLRAYHTLRLALEFRALEPQGLLLYNGNARGKDFLALALLDGRVQLRFDTGSGPAVLTSAVPVEPGQW
HRLELSRHWRRGTLSVDGETPVLGESPSGTDGLNLDTDLFVGGVPEDQAAVALERTFVGAGLRGCIRLLDVNNQR
LELGIGPGAATRGSVGECGDHPCLPNPCHGGAPCQNLEAGRFHCQCPPGRVGPTCADEKSPCQPNPCHGAAPCR
VLPEGGAQCECPLGREGTFCQTASGQDGSGPFLADFNGFSHLELRGLHTFARDLGEKMALEVVFLARGPSGLLLY
NGQKTDGKGDFVSLALRDRRLEFRYDLGKGAAVIRSREPVTLGAWTRVSLERNGRKGALRVGDGPRVLGESPKSR
KVPHTVLNLKEPLYVGGAPDFSKLARAAAVSSGFDGAIQLVSLGGRQLLTPEHVLRQVDVTSFAGHPCTRASGHP

SEQUENCES

CLNGASCVPREAAYVCLCPGGFSGPHCEKGLVEKSAGDVDTLAFDGRTEVEYLNAVTESELANEIPVPETLDSGA
LHSEKALQSNHFELSLRTEATQGLVLWSGKATERADYVALAIVDGHLQLSYNLGSQPVVLRSTVPVNTNRWLRVV
AHREQREGSLQVGNEAPVTGSSPLGATQLDTDGALWLGGLPELPVGPALPKAYGTGFVGCLRDVVVGRHPLHLLE
DAVTKPELRPCPTP

SEQ ID NO: 6
MAGRSHPGPLRPLLPLLVVAACVLPGAGGTCPERALERREEEANVVLIGTVEEILNVDPVQHTYSCKVRVWRYLK
GKDLVARESLLDGGNKVVISGFGDPLICDNQVSTGDTRIFFVNPAPPYLWPAHKNELMLNSSLMRITLRNLEEVE
FCVEDKPGTHFTPVPPTPPDACRGMLCGFGAVCEPNAEGPGRASCVCKKSPCPSVVAPVCGSDASTYSNECELQR
AQCSQQRRIRLLSRGPCGSRDPCSNVTCSFGSTCARSADGLTASCLCPATCRGAPEGTVCGSDGADYPGECQLLR
RACARQENVFKKFDGPCDPCQGALPDPSRSCRVNPRTRRPEMLLRPESCPARQAPVCGDDGVTYENDCVMGRSGA
ARGLLLQKVRSGQCQGRDQCPEPCRFNAVCLSRRGRPRCSCDRVTCDGAYRPVCAQDGRTYDSDCWRQQAECRQQ
RAIPSKHQGPCDQAPSPCLGVQCAFGATCAVKNGQAACECLQACSSLYDPVCGSDGVTYGSACELEATACTLGRE
IQVARKGPCDRCGQCRFGALCEAETGRCVCPSECVALAQPVCGSDGHTYPSECMLHVHACTHQISLHVASAGPCE
TCGDAVCAFGAVCSAGQCVCPRCEHPPPGPVCGSDGVTYGSACELREAACLQQTQIEEARAGPCEQAECGSGGSG
SGEDGDCEQELCRQRGGIWDEDSEDGPCVCDFSCQSVPGSPVCGSDGVTYSTECELKKARCESQRGLYVAAQGAC
RGPTFAPLPPVAPLHCAQTPYGCCQDNITAARGVGLAGCPSACQCNPHGSYGGTCDPATGQCSCRPGVGGLRCDR
CEPGFWNFRGIVTDGRSGCTPCSCDPQGAVRDDCEQMTGLCSCKPGVAGPKCGQCPDGRALGPAGCEADASAPAT
CAEMRCEFGARCVEESGSAHCVCPMLTCPEANATKVCGSDGVTYGNECQLKTIACRQGLQISIQSLGPCQEAVAP
STHPTSASVTVTTPGLLLSQALPAPPGALPLAPSSTAHSQTTPPPSSRPRTTASVPRTTVWPVLTVPPTAPSPAP
SLVASAFGESGSTDGSSDEELSGDQEASGGGSGGLEPLEGSSVATPGPPVERASCYNSALGCCSDGKTPSLDAEG
SNCPATKVFQGVLELEGVEGQELFYTPEMADPKSELFGETARSIESTLDDLFRNSDVKKDFRSVRLRDLGPGKSV
RAIVDVHFDPTTAFRAPDVARALLRQIQVSRRRSLGVRRPLQEHVREMDFDWFPAFITGATSGAIAAGATARATT
ASRLPSSAVTPRAPHPSHTSQPVAKTTAAPTTRRPPTTAPSRVPGRRPPAPQQPPKPCDSQPCFHGGTCQDWALG
GGFTCSCPAGRGGAVCEKVLGAPVPAFEGRSFLAFPTLRAYHTLRLALEFRALEPQGLLLYNGNARGKDFLALAL
LDGRVQLRFDTGSGPAVLTSAVPVEPGQWHRLELSRHWRRGTLSVDGETPVLGESPSGTDGLNLDTDLFVGGVPE
DQAAVALERTFVGAGLRGCIRLLDVNNQRLELGIGPGAATRGSGVGECGDHPCLPNPCHGGAPCQNLEAGRFHCQ
CPPGRVGPTCADEKSPCQPNPCHGAAPCRVLPEGGAQCECPLPNPCHGGAPCQNLEAGRFHCQ
LHTFARDLGEKMALEVVFLARGPSGLLLYNGQKTDGKGDFVSLALRDRRLEFRYDLGKGAAVIRSREPVTLGAWT
RVSLERNGRKGALRVGDGPRVLGESPKSRKVPHTVLNLKEPLYVGGAPDFSKLARAAAVSSGFDGAIQLVSLGGR
QLLTPEHVLRQVDVTSFAGHPCTRASGHPCLNGASCVPREAAYVCLCPGGFSGPHCEKGLVEKSAGDVDTLAFDG
RTFVEYLNAVTESEKALQSNHFELSLRTEATQGLVLWSGKATERADYVALAIVDGHLQLSYNLGSQPVVLRSTVP
VNTNRWLRVVAHREQREGSLQVGNEAPVTG
SSPLGATQLDTDGALWLGGLPELPVGPALPKAYGTGFVGCLRDVVVGRHPLHLLEDAVTKPELRPCPTP

SEQ ID NO: 7
MAGRSHPGPLRPLLPLLVVAACVLPGAGGTCPERALERREEEANVVLIGTVEEILNVDPVQHTYSCKVRVWRYLK
GKDLVARESLLDGGNKVVISGFGDPLICDNQVSTGDTRIFFVNPAPPYLWPAHKNELMLNSSLMRITLRNLEEVE
FCVEDKPGTHFTPVPPTPPDACRGMLCGFGAVCEPNAEGPGRASCVCKKSPCPSVVAPVCGSDASTYSNECELQR
AQCSQQRRIRLLSRGPCGSRDPCSNVTCSFGSTCARSADGLTASCLCPATCRGAPEGTVCGSDGADYPGECQLLR
RACARQENVFKKFDGPCDPCQGALPDPSRSCRVNPRTRRPEMLLRPESCPARQAPVCGDDGVTYENDCVMGRSGA
ARGLLLQKVRSGQCQGRDQCPEPCRFNAVCLSRRGRPRCSCDRVTCDGAYRPVCAQDGRTYDSDCWRQQAECRQQ
RAIPSKHQGPCDQAPSPCLGVQCAFGATCAVKNGQAACECLQACSSLYDPVCGSDGVTYGSACELEATACTLGRE
IQVARKGPCDRCGQCRFGALCEAETGRCVCPSECVALAQPVCGSDGHTYPSECMLHVHACTHQISLHVASAGPCE
TCGDAVCAFGAVCSAGQCVCPRCEHPPPGPVCGSDGVTYGSACELREAACLQQTQIEEARAGPCEQAECGSGGSG
SGEDGDCEQELCRQRGGIWDEDSEDGPCVCDFSCQSVPGSPVCGSDGVTYSTECELKKARCESQRGLYVAAQGAC
RGPTFAPLPPVAPLHCAQTPYGCCQDNITAARGVGLAGCPSACQCNPHGSYGGTCDPATGQCSCRPGVGGLRCDR
CEPGFWNFRGIVTDGRSGCTPCSCDPQGAVRDDCEQMTGLCSCKPGVAGPKCGQCPDGRALGPAGCEADASAPAT
CAEMRCEFGARCVEESGSAHCVCPMLTCPEANATKVCGSDGVTYGNECQLKTIACRQGLQISIQSLGPCQEAVAP
STHPTSASVTVTTPGLLLSQALPAPPGALPLAPSSTAHSQTTPPPSSRPRTTASVPRTTVWPVLTVPPTAPSPAP
SLVASAFGESGSTDGSSDEELSGDQEASGGGSGGLEPLEGSSVATPGPPVERASCYNSALGCCSDGKTPSLDAEG
SNCPATKVFQGVLELEGVEGQELFYTPEMADPKSELFGETARSIESTLDDLFRNSDVKKDFRSVRLRDLGPGKSV
RAIVDVHFDPTTAFRAPDVARALLRQIQVSRRRSLGVRRPLQEHVREMDFDWFPAFITGATSGAIAAGATARATT
ASRLPSSAVTPRAPHPSHTSQPVAKTTAAPTTRRPPTTAPSRVPGRRPPAPQQPPKPCDSQPCFHGGTCQDWALG
GGFTCSCPAGRGGAVCEKVLGAPVPAFEGRSFLAFPTLRAYHTLRLALEFRALEPQGLLLYNGNARGKDFLALAL
LDGRVQLRFDTGSGPAVLTSAVPVEPGQWHRLELSRHWRRGTLSVDGETPVLGESPSGTDGLNLDTDLFVGGVPE
DQAAVALERTFVGAGLRGCIRLLDVNNQRLELGIGPGAATRGSGVGECGDHPCLPNPCHGGAPCQNLEAGRFHCQ
CPPGRVGPTCADEKSPCQPNPCHGAAPCRVLPEGGAQCECPLGREGTFCQTASGQDGSGPFLADENGFSHLELRG
LHTFARDLGEKMALEVVFLARGPSGLLLYNGQKTDGKGDFVSLALRDRRLEFRYDLGKGAAVIRSREPVTLGAWT
RVSLERNGRKGALRVGDGPRVLGESPKSRKVPHTVLNLKEPLYVGGAPDFSKLARAAAVSSGFDGAIQLVSLGGR
QLLTPEHVLRQVDVTSFAGHPCTRASGHPCLNGASCVPREAAYVCLCPGGFSGPHCEKGLVEKSAGDVDTLAFDG
RTFVEYLNAVTESPETLDSGALHSEKALQSNHFELSLRTEATQGLVLWSGKATERADYVALAIVDGHLQLSYNLG
SQPVVLRSTVPVNTNRWLRVVAHREQREGSLQVGNEAPVTGSSPLGATQLDTDGALWLGGLPELPVGPALPKAYG
TGFVGCLRDVVVGRHPLHLLEDAVTKPELRPCPTP

SEQ ID NO: 8
MAGRSHPGPLRPLLPLLVVAACVLPGAGGTCPERALERREEEANVVLIGTVEEILNVDPVQHTYSCKVRVWRYLK
GKDLVARESLLDGGNKVVISGFGDPLICDNQVSTGDTRIFFVNPAPPYLWPAHKNELMLNSSLMRITLRNLEEVE
FCVEDKPGTHFTPVPPTPPDACRGMLCGFGAVCEPNAEGPGRASCVCKKSPCPSVVAPVCGSDASTYSNECELQR
AQCSQQRRIRLLSRGPCGSRDPCSNVTCSFGSTCARSADGLTASCLCPATCRGAPEGTVCGSDGADYPGECQLLR
RACARQENVFKKFDGPCDPCQGALPDPSRSCRVNPRTRRPEMLLRPESCPARQAPVCGDDGVTYENDCVMGRSGA
ARGLLLQKVRSGQCQGRDQCPEPCRFNAVCLSRRGRPRCSCDRVTCDGAYRPVCAQDGRTYDSDCWRQQAECRQQ
RAIPSKHQGPCDQAPSPCLGVQCAFGATCAVKNGQAACECLQACSSLYDPVCGSDGVTYGSACELEATACTLGRE
IQVARKGPCDRCGQCRFGALCEAETGRCVCPSECVALAQPVCGSDGHTYPSECMLHVHACTHQISLHVASAGPCE
TCGDAVCAFGAVCSAGQCVCPRCEHPPPGPVCGSDGVTYGSACELREAACLQQTQIEEARAGPCEQAECGSGGSG
SGEDGDCEQELCRQRGGIWDEDSEDGPCVCDFSCQSVPGSPVCGSDGVTYSTECELKKARCESQRGLYVAAQGAC
RGPTFAPLPPVAPLICAQTPYGCCQDNITAARGVGLAGCPSACQCNPHGSYGGTCDPATGQCSCRPGVGGLRCDR

SEQUENCES

CEPGFWNFRGIVTDGRSGCTPCSCDPQGAVRDDCEQMTGLCSCKPGVAGPKCGQCPDGRALGPAGCEADASAPAT
CAEMRCEFGARCVEESGSAHCVCPMLTCPEANATKVCGSDGVTYGNECQLKTIACRQGLQISIQSLGPCQEAVAP
STHPTSASVTVTTPGLLLSQALPAPPGALPLAPSSTAHSVPRTTASVPRTTVWPVLTVPPTAPSPAP
SLVASAFGESGSTDGSSDEELSGDQEASGGGSGGLEPLEGSSVATPGPPVERASCYNSALGCCSDGKTPSLDAEG
SNCPATKVFQGVLELEGVEGQELFYTPEMADPKSELFGETARSIESTLDDLFRNSDVKKDFRSVRLRDLGPGKSV
RAIVDVHFDPTTAFRAPDVARALLRQIQVSRRRSLGVRRPLQEHVRFMDFDWFPAFITGATSGAIAAGATARATT
ASRLPSSAVTPRAPHPSHTSQPVAKTTAAPTTRRPPTTAPSRVPGRRPPAPQQPPKPCDSQPCFHGGTCQDWALG
GGFTCSCPAGRGGAVCEKVLGAPVPAFEGRSFLAFPTLRAYHTLRLALEFRALEPQGLLLYNGNARGKDFLALAL
LDGRVQLRFDTGSGPAVLTSAVPVEPGQWHRLELSRHWRRGTLSVDGETPVLGESPSGTDGLNLDTDLFVGGVPE
DQAAVALERTFVGAGLRGCIRLLDVNNQRLELGIGPGAATRGSGVGECGDHPCLPNPCHGGAPCQNLEAGRFHCQ
CPPGRVGPTCADEKSPCQPNPCHGAAPCRVLPEGGAQCECPLGREGTFCQTASGQDGSGPFLADFNGFSHLELRG
LHTFARDLGEKMALEVVFLARGPSGLLLYNGQKTDGKGDFVSLALRDRRLEFRYDLGKGAAVIRSREPVTLGAWT
RVSLERNGRKGALRVGDGPRVLGESPKSRKVPHTVLNLKEPLYVGGAPDFSKLARAAAVSSGFDGAIQLVSLGGR
QLLTPEHVLRQVDVTSFAGHPCTRASGHPCLNGASCVPREAAYVCLCPGGFSGPHCEKGLVEKSAGDVDTLAFDG
RTFVEYLNAVTESELANEIPVEKALQSNHFELSLRTEATQGLVLWSGKATERADYVALAIVDGHLQLSYNLGSQP
VVLRSTVPVNTNRWLRVVAHREQREGSLQVGNEAPVTGSSPLGATQLDTDGALWLGGLPELPVGPALPKAYGTGF
VGCLRDVVVGRHPLHLLEDAVTKPELRPCPTP

SEQ ID NO: 9
MAGRSHPGPLRPLLPLLVVAACVLPGAGGTCPERALERREEEANVVLIGTVEEILNVDPVQHTYSCKVRVWRYLK
GKDLVARESLLDGGNKVVISGFGDPLICDNQVSTGDTRIFFVNPAPPYLWPAHKNELMLNSSLMRITLRNLEEVE
FCVEDKPGTHFTPVPPTPPDACRGMLCGFGAVCEPNAEGPGRASCVCKKSPCPSVVAPVCGSDASTYSNECELQR
AQCSQQRRIRLLSRGPCGSRDPCSNVTCSFGSTCARSADGLTASCLCPATCRGAPEGTVCGSDGADYPGECQLLR
RACARQENVFKKFDGPCDPCQGALPDPSRSCRVNPRTRRPEMLLRPESCPARQAPVCGDDGVTYENDCVMGRSGA
ARGLLLQKVRSGQCQGRDQCPEPCRFNAVCLSRRGRPRCSCDRVTCDGAYRPVCAQDGRTYDSDCWRQQAECRQQ
RAIPSKHQGPCDQAPSPCLGVQCAFGATCAVKNGQAACECLQACSSLYDPVCGSDGVTYGSACELEATACTLGRE
IQVARKGPCDRCGQCRFGALCEAETGRCVCPSECVALAQPVCGSDGHTYPSECMLHVHACTHQISLHVASAGPCE
TCGDAVCAFGAVCSAGQCVCPRCEHPPPGPVCGSDGVTYGSACELREAACLQQTQIEEARAGPCEQAECGSGGSG
SGEDGDCEQELCRQRGGIWDEDSEDGPCVCDFSCQSVPGSPVCGSDGVTYSTECELKKARCESQRGLYVAAQGAC
RGPTFAPLPPVAPLHCAQTPYGCCQDNITAARGVGLAGCPSACQCNPHGSYGGTCDPATGQCSCRPGVGGLRCDR
CEPGFWNFRGIVTDGRSGCTPCSCDPQGAVRDDCEQMTGLCSCKPGVAGPKCGQCPDGRALGPAGCEADASAPAT
CAEMRCEFGARCVEESGSAHCVCPMLTCPEANATKVCGSDGVTYGNECQLKTIACRQGLQISIQSLGPCQEAVAP
STHPTSASVTVTTPGLLLSQALPAPPGALPLAPSSTAHSQTTPPPSSRPRITASVPRTTVWPVLTVPPTAPSPAP
SLVASAFGESGSTDGSSDEELSGDQEASGGGSGGLEPLEGSSVATPGPPVERASCYNSALGCCSDGKTPSLDAEG
SNCPATKVFQGVLELEGVEGQELFYTPEMADPKSELFGETARSIESTLDDLFRNSDVKKDFRSVRLRDLGPGKSV
RAIVDVHFDPTTAFRAPDVARALLRQIQVSRRRSLGVRRPLQEHVRFMDFDWFPAFITGATSGAIAAGATARATT
ASRLPSSAVTPRAPHPSHTSQPVAKTTAAPTTRRPPTTAPSRVPGRRPPAPQQPPKPCDSQPCFHGGTCQDWALG
GGFTCSCPAGRGGAVCEKVLGAPVPAFEGRSFLAFPTLRAYHTLRLALEFRALEPQGLLLYNGNARGKDFLALAL
LDGRVQLRFDTGSGPAVLTSAVPVEPGQWHRLELSRHWRRGTLSVDGETPVLGESPSGTDGLNLDTDLFVGGVPE
DQAAVALERTFVGAGLRGCIRLLDVNNQRLELGIGPGAATRGSGVGECGDHPCLPNPCHGGAPCQNLEAGRFHCQ
CPPGRVGPTCADEKSPCQPNPCHGAAPCRVLPEGGAQCECPLGREGTFCQTASGQDGSGPFLADFNGFSHLELRG
LHTFARDLGEKMALEVVFLARGPSGLLLYNGQKTDGKGDFVSLALRDRRLEFRYDLGKGAAVIRSREPVTLGAWT
RVSLERNGRKGALRVGDGPRVLGESPVPHTVLNLKEPLYVGGAPDFSKLARAAAVSSGFDGAIQLVSLGGRQLLT
PEHVLRQVDVTSFAGHPCTRASGHPCLNGASCVPREAAYVCLCPGGFSGPHCEKGLVEKSAGDVDTLAFDGRTFV
EYLNAVTESEKALQSNHFELSLRTEATQGLVLWSGKATERADYVALAIVDGHLQLSYNLGSQPVVLRSTVPVNIN
RWLRVVAHREQREGSLQVGNEAPVTGSSPLGATQLDTDGALWLGGLPELPVGPALPKAYGTGFVGCLRDVVVGRH
PLHLLEDAVTKPELRPCPTP

SEQ ID NO: 10
MAGRSHPGPLRPLLPLLVVAACVLPGAGGTCPERALERREEEANVVLIGTVEEILNVDPVQHTYSCKVRVWRYLK
GKDLVARESLLDGGNKVVISGFGDPLICDNQVSTGDTRIFFVNPAPPYLWPAHKNELMLNSSLMRITLRNLEEVE
FCVEDKPGTHFTPVPPTPPDACRGMLCGFGAVCEPNAEGPGRASCVCKKSPCPSVVAPVCGSDASTYSNECELQR
AQCSQQRRIRLLSRGPCGSRDPCSNVTCSFGSTCARSADGLTASCLCPATCRGAPEGTVCGSDGADYPGECQLLR
RACARQENVFKKFDGPCDPCQGALPDPSRSCRVNPRTRRPEMLLRPESCPARQAPVCGDDGVTYENDCVMGRSGA
ARGLLLQKVRSGQCQGRDQCPEPCRFNAVCLSRRGRPRCSCDRVTCDGAYRPVCAQDGRTYDSDCWRQQAECRQQ
RAIPSKHQGPCDQAPSPCLGVQCAFGATCAVKNGQAACECLQACSSLYDPVCGSDGVTYGSACELEATACTLGRE
IQVARKGPCDRCGQCRFGALCEAETGRCVCPSECVALAQPVCGSDGHTYPSECMLHVHACTHQISLHVASAGPCE
TCGDAVCAFGAVCSAGQCVCPRCEHPPPGPVCGSDGVTYGSACELREAACLQQTQIEEARAGPCEQAECGSGGSG
SGEDGDCEQELCRQRGGIWDEDSEDGPCVCDFSCQSVPGSPVCGSDGVTYSTECELKKARCESQRGLYVAAQGAC
RGPTFAPLPPVAPLHCAQTPYGCCQDNITAARGVGLAGCPSACQCNPHGSYGGTCDPATGQCSCRPGVGGLRCDR
CEPGFWNFRGIVTDGRSGCTPCSCDPQGAVRDDCEQMTGLCSCKPGVAGPKCGQCPDGRALGPAGCEADASAPAT
CAEMRCEFGARCVEESGSAHCVCPMLTCPEANATKVCGSDGVTYGNECQLKTIACRQGLQISIQSLGPCQEAVAP
STHPTSASVTVTTPGLLLSQALPAPPGALPLAPSSTAHSQTTPPPSSRPRTTASVPRTTVWPVLTVPPTAPSPAP
SLVASAFGESGSTDGSSDEELSGDQEASGGGSGGLEPLEGSSVATPGPPVERASCYNSALGCCSDGKTPSLDAEG
SNCPATKVFQGVLELEGVEGQELFYTPEMADPKSELFGETARSIESTLDDLFRNSDVKKDFRSVRLRDLGPGKSV
RAIVDVHFDPTTAFRAPDVARALLRQIQVSRRRSLGVRRPLQEHVRFMDFDWFPAFITGATSGAIAAGATARATT
ASRLPSSAVTPRAPHPSHTSQPVAKTTAAPTTRRPPTTAPSRVPGRRPPAPQQPPKPCDSQPCFHGGTCQDWALG
GGFTCSCPAGRGGAVCEKVLGAPVPAFEGRSFLAFPTLRAYHTLRLALEFRALEPQGLLLYNGNARGKDFLALAL
LDGRVQLRFDTGSGPAVLTSAVPVEPGQWHRLELSRHWRRGTLSVDGETPVLGESPSGTDGLNLDTDLFVGGVPE
DQAAVALERTFVGAGLRGCIRLLDVNNQRLELGIGPGAATRGSGVGECGDHPCLPNPCHGGAPCQNLEAGRFHCQ
CPPGRVGPTCADEKSPCQPNPCHGAAPCRVLPEGGAQCECPLGREGTFCQTASGQDGSGPFLADENGFSHLELRG
LHTFARDLGEKMALEVVFLARGPSGLLLYNGQKTDGKGDFVSLALRDRRLEFRYDLGKGAAVIRSREPVTLGAWT
RVSLERNGRKGALRVGDGPRVLGESPVPHTVLNLKEPLYVGGAPDFSKLARAAAVSSGFDGAIQLVSLGGRQLLT
PEHVLRQVDVTSFAGHPCTRASGHPCLNGASCVPREAAYVCLCPGGFSGPHCEKGLVEKSAGDVDTLAFDGRTFV
EYLNAVTESELANEIPVPETLDSGALHSEKALQSNHFELSLRTEATQGLVLWSGKATERADYVALAIVDGHLQLS
YNLGSQPVVLRSTVPVNTNRWLRVVAHREQREGSLQVGNEAPVTGSSPLGATQLDTDGALWLGGLPELPVGPALP
KAYGTGFVGCLRDVVVGRHPLHLLEDAVTKPELRPCPTP

-continued

SEQUENCES

SEQ ID NO: 11
ATSGAIAAGATARATTASRLPSSAVTPRAPHPSHTSQPVAKTTAAPTTRRPPTTAPSRVPGRRPPAPQQPPKPCD
SQPCFHGGTCQDWALGGGFTCSCPAGRGGAVCEKVLGAPVPAFEGRSFLAFPTLRAYHTLRLALEFRALEPQGLL
LYNGNARGKDFLALALLDGRVQLRFDTGSGPAVLTSAVPVEPGQWHRLELSRHWRRGTLSVDGETPVLGESPSGT
DGLNLDTDLFVGGVPEDQAAVALERTFVGAGLRGCIRLLDVNNQRLELGIGPGAATRGSGVGECGDHPCLPNPCH
GGAPCQNLEAGRFHCQCPPGRVGPTCADEKSPCQPNPCHGAAPCRVLPEGGAQCECPLGREGTFCQTASGQDGSG
PFLADENGFSHLELRGLHTFARDLGEKMALEVVFLARGPSGLLLYNGQKTDGKGDFVSLALRDRRLEFRYDLGKG
AAVIRSREPVTLGAWTRVSLERNGRKGALRVGDGPRVLGESPVPHTVLNLKEPLYVGGAPDFSKLARAAAVSSGF
DGAIQLVSLGGRQLLTPEHVLRQVDVTSFAGHPCTRASGHPCLNGASCVPREAAYVCLCPGGFSGPHCEKGLVEK
SAGDVDTLAFDGRTFVEYLNAVTESEKALQSNHFELSLRTEATQGLVLWSGKATERADYVALAIVDGHLQLSYNL
GSQPVVLRSTVPVNTNRWLRVVAHREQREGSLQVGNEAPVTGSSPLGATQLDTDGALWLGGLPELPVGPALPKAY
GTGFVGCLRDVVVGRHPLHLLEDAVTKPELRPCPTP

SEQ ID NO: 12
PHTVLN

SEQ ID NO: 13
CACGTGCGATTTATGGACTTTGACTGGTTTCCTGCGTTTATCACGGGGGCCACGTCAGGAGCCATTGCTGCGGGA
GCCACGGCCAGAGCCACCACTGCATCGCGCCTGCCGTCCTCTGCTGTGACCCTCGGGCCCCGCACCCCAGTCAC
ACAAGCCAGCCCGTTGCCAAGACCACGGCAGCCCCCACCACACGTCGGCCCCCCACCACTGCCCCCAGCCGTGTG
CCCGGACGTCGGCCCCCGGCCCCCCAGCAGCCTCCAAAGCCCTGTGACTCACAGCCCTGCTTCCACGGGGGGACC
TGCCAGGACTGGGCATTGGGCGGGGGCTTCACCTGCAGCTGCCCGGCAGGCAGGGGAGGCGCCGTCTGTGAGAAG
GTGCTTGGCGCCCCTGTGCCGGCCTTCGAGGGCCGCTCCTTCCTGGCCTTCCCCACTCTCCGCGCCTACCACACG
CTGCGCCTGGCACTGGAATTCCGGGCGCTGGAGCCTCAGGGGCTGCTGCTGTACAATGGCAACGCCCGGGGCAAG
GACTTCCTGGCATTGGCGCTGCTAGATGGCCGCGTGCAGCTCAGGTTTGACACAGGTTCGGGGCCGGCGGTGCTG
ACCAGTGCCGTGCCGGTAGAGCCGGGCCAGTGGCACCGCCTGGAGCTGTCCCGGCACTGGCGCCGGGGCACCCTC
TCGGTGGATGGTGAGACCCCTGTTCTGGGCGAGAGTCCCAGTGGCACCGACGGCCTCAACCTGGACACAGACCTC
TTTGTGGGCGGCGTACCCGAGGACCAGGCTGCCGTGGCGCTGGAGCGGACCTTCGTGGGCGCCGGCCTGAGGGGG
TGCATCCGTTTGCTGGACGTCAACAACCAGCGCCTGGAGCTTGGCATTGGGCCGGGGGCTGCCACCCGAGGCTCT
GGCGTGGGCGAGTGCGGGGACCACCCCTGCCTGCCCAACCCCTGCCATGGCGGGGCCCCATGCCAGAACCTGGAG
GCTGGAAGGTTCCATTGCCAGTGCCCGCCCGGCCGCGTCGGACCAAGGTGTGCCGATGAGAAGAGCCCCTGCCAG
CCCAACCCCTGCCATGGGGCGGCGCCCTGCCGTGTGCTGCCCGAGGGTGGTGCTCAGTGCGAGTGCCCCCTGGGG
CGTGAGGGCACCTTCTGCCAGACAGCCTCGGGGCAGGACGGCTCTGGGCCCTTCCTGGCTGACTTCAACGGCTTC
TCCCACCTGGAGCTGAGAGGCCTGCACACCTTTGCACGGGACCTGGGGGAGAAGATGGCGCTGGAGGTCGTGTTC
CTGGCACGAGGCCCCAGCGGCCTCCTGCTCTACAACGGGCAGAAGACGGACGGCAAGGGGGACTTCGTGTCGCTG
GCACTGCGGGACCGCCGCCTGGAGTTCCGCTACGACCTGGGCAAGGGGGCAGCGGTCATCAGGAGCAGGGAGCCA
GTCACCCTGGGAGCCTGGACCAGGGTCTCACTGGAGCGAAACGGCCGCAAGGGTGCCCTGCGTGTGGGCGACGGC
CCCCGTGTGTTGGGGGAGTCCCCGGTTCCGCACACCGTCCTCAACCTGAAGGAGCCGCTCTACGTAGGGGGCGCT
CCCGACTTCAGCAAGCTGGCCCGTGCTGCTGCCGTGTCCTCTGGCTTCGACGGTGCCATCCAGCTGGTCTCCCTC
GGAGGCCGCCAGCTGCTGACCCCGGAGCACGTGCTGCGGCAGGTGGACGTCACGTCCTTTGCAGGTCACCCCTGC
ACCCGGGCCTCAGGCCACCCCTGCCTCAATGGGGCCTCCTGCGTCCCGAGGGAGGCTGCCTATGTGTGCCTGTGT
CCCGGGGGATTCTCAGGACCGCACTGCGAGAAGGGGCTGGTGGAGAAGTCAGCGGGGGACGTGGATACCTTGGCC
TTTGACGGGCGGACCTTTGTCGAGTACCTCAACGCTGTGACCGAGAGCGAGAAGGCACTGCAGAGCAACCACTTT
GAACTGAGCCTGCGCACTGAGGCCACGCAGGGGCTGGTGCTCTGGAGTGGCAAGGCCACAGAGCGGGCAGACTAT
GTGGCACTGGCCATTGTGGACGGGCACCTGCAACTGAGCTACAACCTGGGCTCCCAGCCCGTGGTGCTGCGTTCC
ACCGTGCCCGTCAACACCAACCGCTGGTTGCGGGTCGTGGCACATAGGGAGCAGAGGGAAGGTTCCCTGCAGGTG
GGCAATGAGGCCCCTGTGACCGGCTCCTCCCCGCTGGGCGCCACGCAGCTGGACACTGATGGAGCCCTGTGGCTT
GGGGGCCTGCCGGAGCTGCCCGTGGGCCCAGCACTGCCCAAGGCCTACGGCACAGGCTTTGTGGGCTGCTTGCGG
GACGTGGTGGTGGGGCCGGCACCCGCTGCACCTGCTGGAGGACGCCGTCACCAAGCCAGAGCTGCGGCCCTGCCCC
ACCCCAGACGATGACGACAAGATCATCCCAGTTGAGGAGGAGAACCCGGACTTCTGGAACCGCGAGGCAGCCGAG
GCCCTGGGTGCCGCCAAGAAGCTGCAGCCTGCACAGACAGCCGCCAAGAACCTCATCATCTTCCTGGGCGATGGG
ATGGGGGTGTCTACGGTGACAGCTGCCAGGATCCTAAAAGGGCAGAAGAAGGACAAACTGGGGCCTGAGATACCC
CTGGCCATGGACCGCTTCCCATATGTGGCTCTGTCCAAGACATACAATGTAGACAAACATGTGCCAGACAGTGGA
GCCACAGCCACGGCCTACCTGTGCGGGGTCAAGGGCAACTTCCAGACCATTGGCTTGAGTGCAGCCGCCCGCTTT
AACCAGTGCAACACGACACGCGGCAACGAGGTCATCTCCGTGATGAATCGGGCCAAGAAAGCAGGGAAGTCAGTG
GGAGTGGTAACCACCACACGAGTGCAGCACGCCTCGCCAGCCGGCACCTACGCCCACACGGTCCTCCTTACAGTGG
TACTCGGACGCCGACGTGCCTGCCTCGGCCCGCCAGGAGGGGTGCCAGGACATCGCTACGCAGCTCATCTCCAAC
ATGGACATTGACGTGATCCTAGGTGGAGGCCGAAAGTACATGTTTCGCATGGGAACCCCAGACCCTGAGTACCCA
GATGACTACAGCCAAGGTGGGACCAGGCTGGACGGGAAGAATCTGGTGCAGGAATGGCTGGCGAAGCGCCAGGGT
GCCCGGTATGTGTGGAACCGCACTGAGCTCATGCAGGCTTCCTGGACCCGTCTGTGACCCATCTCATGGGTCTC
TTTGAGCCTGGAGACATGAAATACGAGATCCACCGAGCTCCACACTGGACCCCTCCCTGATGGAGATGACAGAG
GCTGCCCTGCGCCTGCTGAGCAGGAACCCCCGCGGCTTCTTCCTCTTCGTGGAGGGTGGTCGCATCGACCATGGT
CATCATGAAAGCAGGGCTTACCGGGCACTGACTGAGACGATCATGTTCGACGACGCCATTGAGAGGGCGGGCCAG
CTCACCAGCGAGGAGGACACGCTGAGCCTCGTCACTGCCGACCACTCCCACGTCTTCTCCTTCGGAGGCTACCCC
CTGCGAGGGAGCTCCATCTTCGGGCTGGCCCCTGGCAAGGCCCGGGACCTACGCGGTCCTCCTATAC
GGAAACGGTCCAGGCTATGTGCTCAAGGACGGCGCCCGGCCGGATGTTACCGAGAGCGAGAGCGGGAGCCCCGAG
TATCGGCAGCAGTCAGCAGTGCCCCTGGACGAAGAGACCCACGCAGGCGAGGACGTGGCGGTGTTCGCGCGCGGC
CCGCAGGCGCACCTGGTTCACGGCGTGCAGGAGCAGACCTTCATAGCGCACGTCATGGCCTTCGCCGCCTGCCTG
GAGCCCTACACCGCCTGCGACCTGGCGCCCCCGCCGGCACCACCGACGCCGCGCACCCGGGTGAACAAAAACTC
ATCTCAGAAGAGGATCTGCATCACCATCACCATCAC

SEQ ID NO: 14
HVRFMDFDWFPAFITGATSGAIAAGATARATTASRLPSSAVTPRAPHPSHTSQPVAKTTAAPTTRRPPTTAPSRV
PGRRPPAPQQPPKPCDSQPCFHGGTCQDWALGGGFTCSCPAGRGGAVCEKVLGAPVPAFEGRSFLAFPTLRAYHT
LRLALEFRALEPQGLLLYNGNARGKDFLALALLDGRVQLRFDTGSGPAVLTSAVPVEPGQWHRLELSRHWRRGTL
SVDGETPVLGESPSGTDGLNLDTDLFVGGVPEDQAAVALERTFVGAGLRGCIRLLDVNNQRLELGIGPGAATRGS

SEQUENCES

GVGECGDHPCLPNPCHGGAPCQNLEAGRFHCQCPPGRVGPTCADEKSPCQPNPCHGAAPCRVLPEGGAQCECPLG
REGTFCQTASGQDSGPFLADFNGFSHLELRGLHTFARDLGEKMALEVVFLARGPSGLLLYNGQKTDGKGDFVSL
ALRDRRLEFRYDLGKGAAVIRSREPVTLGAWTRVSLERNGRKGALRVGDGPRVLGESPVPHTVLNLKEPLYVGGA
PDFSKLARAAAVSSGFDGAIQLVSLGGRQLLTPEHVLRQVDVTSFAGHPCTRASGHPCLNGASCVPREAAYVCLC
PGGFSGPHCEKGLVEKSAGDVDTLAFDGRTFVEYLNAVTESEKALQSNHFELSLRTEATQGLVLWSGKATERADY
VALAIVDGHLQLSYNLGSQPVVLRSTVPVNTNRWLRVVAHREQREGSLQVGNEAPVTGSSPLGATQLDTDGALWL
GGLPELPVGPALPKAYGTGFVGCLRDVVVGRHPLHLLEDAVTKPELRPCPTPDDDDKIIPVEEENPDFWNREAAE
ALGAAKKLQPAQTAAKNLIIFLGDGMGVSTVTAARILKGQKKDKLGPEIPLAMDRFPYVALSKTYNVDKHVPDSG
ATATAYLCGVKGNFQTIGLSAAARFNQCNTTRGNEVISVMNRAKKAGKSVGVVTTTRVQHASPAGTYAHTVNRNW
YSDADVPASARQEGCQDIATQLISNMDIDVILGGGRKYMFRMGTPDPEYPDDYSQGGTRLDGKNLVQEWLAKRQG
ARYVWNRTELMQASLDPSVTHLMGLFEPGDMKYEIHRDSTLDPSLMEMTEAALRLLSRNPRGFFLFVEGGRIDHG
HHESRAYRALTETIMFDDAIERAGQLTSEEDTLSLVTADHSHVFSFGGYPLRGSSIFGLAPGKARDRKAYTVLLY
GNGPGYVLKDGARPDVTESESGSPEYRQQSAVPLDEETHAGEDVAVFARGPQAHLVHGVQEQTFIAHVMAFAACL
EPYTACDLAPPAGTTDAAHPGEQKLISEEDLHHHHHH

SEQ ID NO: 15
CACGTGCGATTTATGGACTTTGACTGGTTTCCTGCGTTTATCACGGGGGCCACGTCAGGAGCCATTGCTGCGGGA
GCCACGGCCAGAGCCACCACTGCATCGCGCCTGCCGTCCTCTGCTGTGACCCCTCGGGCCCCGCACCCCAGTCAC
ACAAGCCAGCCCGTTGCCAAGACCACGGCAGCCCCCACCACACGTCGGCCCCCCACCACTGCCCCCAGCCGTGTG
CCCGGACGTCGGCCCCCGGCCCCCCAGCAGCCTCCAAAGCCCTGTGACTCACAGCCCTGCTTCCACGGGGGGACC
TGCCAGGACTGGGCATTGGGCGGGGGCTTCACCTGCAGCTGCCCGGCAGGCAGGGGAGGCGCCGTCTGTGAGAAG
GTGCTTGGCGCCCCTGTGCCGGCCTTCGAGGGCCGCTCCTTCCTGGCCTTCCCCACTCTCCGCGCCTACCACACG
CTGCGCCTGGCACTGGAATTCCGGGCGCTGGAGCCTCAGGGGCTGCTGCTGTACAATGGCAACGCCCGGGGCAAG
GACTTCCTGGCATTGGCGCTGCTAGATGGCCGCGTGCAGCTCAGGTTTGACACAGGTTCGGGGCCGGCGGTGCTG
ACCAGTGCCGTGCCGGTAGAGCCGGGCCAGTGGCACCGCCTGGAGCTGTCCCGGCACTGGCGCCGGGGCACCCTC
TCGGTGGATGGTGAGACCCCTGTTCTGGGCGAGAGTCCCAGTGGCACCGACGGCCTCAACCTGGACACAGACCTC
TTTGTGGGCGGCGTACCCGAGGACCAGGCTGCCGTGGCGCTGGAGCGGACCTTCGTGGGCGCCGGCCTGAGGGGG
TGCATCCGTTTGCTGGACGTCAACAACCAGCGCCTGGAGCTTGGCATTGGGCCGGGGGCTGCCACCCGAGGCTCT
GGCGTGGGCGAGTGCGGGGACCACCCCTGCCTGCCCAACCCCTGCCATGGCGGGGCCCCATGCCAGAACCTGGAG
GCTGGAAGGTTCCATTGCCAGTGCCCGCCCGGCCGCGTCGGACCAACCTGTGCCGATGAGAAGAGCCCCTGCCAG
CCCAACCCCTGCCATGGGGCGGCGCCCTGCCGTGTGCTGCCCGAGGGTGGTGCTCAGTGCGAGTGCCCCCTGGGG
CGTGAGGGCACCTTCTGCCAGACAGCCTCGGGGCAGGACGGCTCTGGGCCCTTCTGGCTGACTTCAACGGCTTC
TCCCACCTGGAGCTGAGGGGCCTGCACACCTTTGCACGGGACCTGGGGGAGAAGATGGCGCTGGAGGTCGTGTTC
CTGGCACGAGGCCCCAGCGGCCTCCTGCTCTACAACGGGCAGAAGACGGACGGCAAGGGGGACTTCGTGTCGCTG
GCACTGCGGGACCGCCGCCTGGAGTTCCGCTACGACCTGGGCAAGGGGGCAGCGGTCATCAGGAGCAGGGAGCCA
GTCACCCTGGGAGCCTGGACCAGGGTCTCACTGGAGCGAAACGGCCGCAAGGGTGCCCTGCGTGTGGGCGACGGC
CCCGTGTGTTGGGGGAGTCCCCGGTTCCGCACACCGTCCTCAACCTGAAGGAGCCGCTCTACGTAGGGGGCGCT
CCCGACTTCAGCAAGCTGGCCCGTGCTGCTGCCGTGTCCTCTGGCTTCGACGGTGCCATCCAGCTGGTCTCCCTC
GGAGGCCGCCAGCTGCTGACCCCGGAGCACGTGCTGCGGCAGGTGGACGTCACGTCCTTTGCAGGTCACCCCTGC
ACCCGGGCCTCAGGCCACCCCTGCCTCAATGGGGCCTCCTGCGTCCCGAGGGAGGCTGCCTATGTGTGCCTGTGT
CCCGGGGGATTCTCAGGACCGCACTGCGAGAAGGGGCTGGTGGAGAAGTCAGCGGGGGACGTGGATACCTTGGCC
TTTGACGGGCGGACCTTTGTCGAGTACCTCAACGCTGTGACCGAGAGCGAGAAGGCACTGCAGAGCAACCACTTT
GAACTGAGCCTGCGCACTGAGGCCACGCAGGGGCTGGTGCTCTGGAGTGGCAAGGCCACGGAGCGGGCAGACTAT
GTGGCACTGGCCATTGTGGACGGGCACCTGCAACTGAGCTACAACCTGGGCTCCCAGCCCGTGGTGCTGCGTTCC
ACCGTGCCCGTCAACACCAACCGCTGGTTGCGGGTCGTGGCACATAGGGAGCAGAGGGAAGGTTCCCTGCAGGTG
GGCAATGAGGCCCCTGTGACCGGCTCCTCCCCGCTGGGCGCCACGCAGCTGGACACTGATGGAGCCCTGTGGCTT
GGGGGCCTGCCGGAGCTGCCCGTGGGCCCAGCACTGCCCAAGGCCTACGGCACAGGCTTTGTGGGCTGCTTGCGG
GACGTGGTGGTGGGCCGGCACCCGCTGCACCTGCTGGAGGACGCCGTCACCAAGCCAGAGCTGCGGCCCTGCCCC
ACCCCA

SEQ ID NO: 16
CACGTGCGATTTATGGACTTTGACTGGTTTCCTGCGTTTATCACGGGGGCCACGTCAGGAGCCATTGCTGCGGGA
GCCACGGCCAGAGCCACCACTGCATCGCGCCTGCCGTCCTCTGCTGTGACCCCTCGGGCCCCGCACCCCAGTCAC
ACAAGCCAGCCCGTTGCCAAGACCACGGCAGCCCCCACCACACGTCGGCCCCCCACCACTGCCCCCAGCCGTGTG
CCCGGACGTCGGCCCCCGGCCCCCCAGCAGCCTCCAAAGCCCTGTGACTCACAGCCCTGCTTCCACGGGGGGACC
TGCCAGGACTGGGCATTGGGCGGGGGCTTCACCTGCAGCTGCCCGGCAGGCAGGGGAGGCGCCGTCTGTGAGAAG
GTGCTTGGCGCCCCTGTGCCGGCCTTCGAGGGCCGCTCCTTCCTGGCCTTCCCCACTCTCCGCGCCTACCACACG
CTGCGCCTGGCACTGGAATTCCGGGCGCTGGAGCCTCAGGGGCTGCTGCTGTACAATGGCAACGCCCGGGGCAAG
GACTTCCTGGCATTGGCGCTGCTAGATGGCCGCGTGCAGCTCAGGTTTGACACAGGTTCGGGGCCGGCGGTGCTG
ACCAGTGCCGTGCCGGTAGAGCCGGGCCAGTGGCACCGCCTGGAGCTGTCCCGGCACTGGCGCCGGGGCACCCTC
TCGGTGGATGGTGAGACCCCTGTTCTGGGCGAGAGTCCCAGTGGCACCGACGGCCTCAACCTGGACACAGACCTC
TTTGTGGGCGGCGTACCCGAGGACCAGGCTGCCGTGGCGCTGGAGCGGACCTTCGTGGGCGCCGGCCTGAGGGGG
TGCATCCGTTTGCTGGACGTCAACAACCAGCGCCTGGAGCTTGGCATTGGGCCGGGGGCTGCCACCCGAGGCTCT
GGCGTGGGCGAGTGCGGGGACCACCCCTGCCTGCCCAACCCCTGCCATGGCGGGGCCCCATGCCAGAACCTGGAG
GCTGGAAGGTTCCATTGCCAGTGCCCGCCCGGCCGCGTCGGACCAACCTGTGCCGATGAGAAGAGCCCCTGCCAG
CCCAACCCCTGCCATGGGGCGGCGCCCTGCCGTGTGCTGCCCGAGGGTGGTGCTCAGTGCGAGTGCCCCCTGGGG
CGTGAGGGCACCTTCTGCCAGACAGCCTCGGGGCAGGACGGCTCTGGGCCCTTCTGGCTGACTTCAACGGCTTC
TCCCACCTGGAGCTGAGGGGCCTGCACACCTTTGCACGGGACCTGGGGGAGAAGATGGCGCTGGAGGTCGTGTTC
CTGGCACGAGGCCCCAGCGGCCTCCTGCTCTACAACGGGCAGAAGACGGACGGCAAGGGGGACTTCGTGTCGCTG
GCACTGCGGGACCGCCGCCTGGAGTTCCGCTACGACCTGGGCAAGGGGGCAGCGGTCATCAGGAGCAGGGAGCCA
GTCACCCTGGGAGCCTGGACCAGGGTCTCACTGGAGCGAAACGGCCGCAAGGGTGCCCTGCGTGTGGGCGACGGC
CCCGTGTGTTGGGGGAGTCCCCGGTTCCGGAGGGGGGGGCTCAACCTGAAGGAGCCGCTCTACGTAGGGGGCGCT
CCCGACTTCAGCAAGCTGGCCCGTGCTGCTGCCGTGTCCTCTGGCTTCGACGGTGCCATCCAGCTGGTCTCCCTC
GGAGGCCGCCAGCTGCTGACCCCGGAGCACGTGCTGCGGCAGGTGGACGTCACGTCCTTTGCAGGTCACCCCTGC
ACCCGGGCCTCAGGCCACCCCTGCCTCAATGGGGCCTCCTGCGTCCCGAGGGAGGCTGCCTATGTGTGCCTGTGT
CCCGGGGGATTCTCAGGACCGCACTGCGAGAAGGGGCTGGTGGAGAAGTCAGCGGGGGACGTGGATACCTTGGCC
TTTGACGGGCGGACCTTTGTCGAGTACCTCAACGCTGTGACCGAGAGCGAGAAGGCACTGCAGAGCAACCACTTT

| SEQUENCES |
| --- |

```
GAACTGAGCCTGCGCACTGAGGCCACGCAGGGGCTGGTGCTCTGGAGTGGCAAGGCCACGGAGCGGGCAGACTAT
GTGGCACTGGCCATTGTGGACGGGCACCTGCAACTGAGCTACAACCTGGGCTCCCAGCCCGTGGTGCTGCGTTCC
ACCGTGCCCGTCAACACCAACCGCTGGTTGCGGGTCGTGGCACATAGGGAGCAGAGGGAAGGTTCCCTGCAGGTG
GGCAATGAGGCCCCTGTGACCGGCTCCTCCCCGCTGGGCGCCACGCAGCTGGACACTGATGGAGCCCTGTGGCTT
GGGGGCCTGCCGGAGCTGCCCGTGGGCCCAGCACTGCCCAAGGCCTACGGCACAGGCTTTGTGGGCTGCTTGCGG
GACGTGGTGGTGGGCCGGCACCCGCTGCACCTGCTGGAGGACGCCGTCACCAAGCCAGAGCTGCGGCCCTGCCCC
ACCCCAGACGATGACGACAAGATCATCCCAGTTGAGGAGGAGAACCCGGACTTCTGGAACCGCGAGGCAGCCGAG
GCCCTGGGTGCCGCCAAGAAGCTGCAGCCTGCACAGACAGCCGCCAAGAACCTCATCATCTTCCTGGGCGATGGG
ATGGGGGTGTCTACGGTGACAGCTGCCAGGATCCTAAAAGGGCAGAAGAAGGACAAACTGGGGCCTGAGATACCC
CTGGCCATGGACCGCTTCCCATATGTGGCTCTGTCCAAGACATACAATGTAGACAAACATGTGCCAGACAGTGGA
GCCACAGCCACGGCCTACCTGTGCGGGGTCAAGGGCAACTTCCAGACCATTGGCTTGAGTGCAGCCGCCCGCTTT
AACCAGTGCAACACGACACGCGGCAACGAGGTCATCTCCGTGATGAATCGGGCCAAGAAAGCAGGGAAGTCAGTG
GGAGTGGTAACCACCACGAGTGCAGCACGCCTCGCCAGCCGGCACCTACGCCCACACGGTGAACCGCAACTGG
TACTCGGACGCCGACGTGCCTGCCTCGGCCCGCCAGGAGGGGTGCCAGGACATCGCTACGCAGCTCATCTCCAAC
ATGGACATTGACGTGATCCTAGGTGGAGGCCGAAAGTACATGTTTCGCATGGGAACCCCAGACCCTGAGTACCCA
GATGACTACAGCCAAGGTGGGACCAGGCTGGACGGGAAGAATCTGGTGCAGGAATGGCTGGCGAAGCGCCAGGGT
GCCCGGTATGTGTGGAACCGCACTGAGCTCATGCAGGCTTCCCTGGACCCGTCTGTGACCCATCTCATGGGTCTC
TTTGAGCCTGGAGACATGAAATACGAGATCCACCGAGACTCCACACTGGACCCCTCCCTGATGGAGATGACAGAG
GCTGCCCTGCGCCTGCTGAGCAGGAACCCCGCGGCTTCTTCCTCTTCGTGGAGGGTGGTCGCATCGACCATGGT
CATCATGAAAGCAGGGCTTACCGGGCACTGACTGAGACGATCATGTTCGACGATGCCATTGAGAGGGCGGGCCAG
CTCACCAGCGAGGAGGACACGCTGAGCCTCGTCACTGCCGACCACTCCCACGTCTTCTCCTTCGGAGGCTACCCC
CTGCGAGGGAGCTCCATCTTCGGGCTGGCCCCTGGCAAGGCCCGGGACAGGAAGGCCTACACGGTCCTCCTATAC
GGAAACGGTCCAGGCTATGTGCTCAAGGACGGCGCCCGGCCGGATGTTACCGAGAGCGAGAGCGGGAGCCCCGAG
TATCGGCAGCAGTCAGCAGTGCCCCTGGACGAAGAGACCCACGCAGGCGAGGACGTGGCGGTGTTCGCCCGCGGC
CCGCAGGCGCACCTGGTTCACGGCGTGCAGGAGCAGACCTTCATAGCGCACGTCATGGCCTTCGCCGCCTGCCTG
GAGCCCTACACCGCCTGCGACCTGGCGCCCCCGCCGGCCACCACCGACGCCGCGCACCCGGGTGAACAAAAACTC
ATCTCAGAAGAGGATCTGCACCACCACCATCACCATCATCACCACCAC
```

SEQ ID NO: 17

```
HVRFMDFDWFPAFITGATSGAIAAGATARATTASRLPSSAVTPRAPHPSHTSQPVAKTTAAPTTRRPPTTAPSRV
PGRRPPAPQQPPKPCDSQPCFHGGTCQDWALGGGFTCSCPAGRGGAVCEKVLGAPVPAFEGRSFLAFPTLRAYHT
LRLALEFRALEPQGLLLYNGNARGKDFLALALLDGRVQLRFDTGSGPAVLTSAVPVEPGQWHRLELSRHWRRGTL
SVDGETPVLGESPSGTDGLNLDTDLFVGGVPEDQAAVALERTFVGAGLRGCIRLLDVNNQRLELGIGPGAATRGS
GVGECGDHPCLPNPCHGGAPCQNLEAGRFHCQCPPGRVGPTCADEKSPCQPNPCHGAAPCRVLPEGGAQCECPLG
REGTFCQTASGQDSGPFLADFNGFSHLELRGLHTFARDLGEKMALEVVFLARGPSGLLLYNGQKTDGKGDFVSL
ALRDRRLEFRYDLGKGAAVIRSREPVTLGAWTRVSLERNGRKGALRVGDGPRVLGESPVPGGGLNLKEPLYVGGA
PDFSKLARAAAVSSGFDGAIQLVSLGGRQLLTPEHVLRQVDVTSFAGHPCTRASGHPCLNGASCVPREAAYVCLC
PGGFSGPHCEKGLVEKSAGDVDTLAFDGRTFVEYLNAVTESEKALQSNHFELSLRTEATQGLVLWSGKATERADY
VALAIVDGHLQLSYNLGSQPVVLRSTVPVNTNRWLRVVAHREQREGSLQVGNEAPVTGSSPLGATQLDTDGALWL
GGLPELPVGPALPKAYGTGFVGCLRDVVVGRHPLHLLEDAVTKPELRPCPTPDDDDKIIPVEEENPDFWNREAAE
ALGAAKKLQPAQTAAKNLIIFLGDGMGVSTVTAARILKGQKKDKLGPEIPLAMDRFPYVALSKTYNVDKHVPDSG
ATATAYLCGVKGNFQTIGLSAAARFNQCNTTRGNEVISVMNRAKKAGKSVGVVTTTRVQHASPAGTYAHTVNRNW
YSDADVPASARQEGCQDIATQLISNMDIDVILGGGRKYMFRMGTPDPEYPDDYSQGGTRLDGKNLVQEWLAKRQG
ARYVWNRTELMQASLDPSVTHLMGLFEPGDMKYEIHRDSTLDPSLMEMTEAALRLLSRNPRGFFLFVEGGRIDHG
HHESRAYRALTETIMFDDAIERAGQLTSEEDTLSLVTADHSHVFSFGGYPLRGSSIFGLAPGKARDRKAYTVLLY
GNGPGYVLKDGARPDVTESESGSPEYRQQSAVPLDEETHAGEDVAVFARGPQAHLVHGVQEQTFIAHVMAFAACL
EPYTACDLAPPAGTTDAAHPGEQKLISEEDLHHHHHHHHHH
```

SEQ ID NO: 18

```
CACGTGCGATTTATGGACTTTGACTGGTTTCCTGCGTTTATCACGGGGGCCACGTCAGGAGCCATTGCTGCGGGA
GCCACGGCCAGAGCCACCACTGCATCGCGCCTGCCGTCCTCTGCTGTGACCCCTCGGGCCCCGCACCCCAGTCAC
ACAAGCCAGCCCGTTGCCAAGACCACGGCAGCCCCCACCACACGTCGGCCCCCCACCACTGCCCCCAGCCGTGTG
CCCGGACGTCGGCCCCCGGCCCCCCAGCAGCCTCCAAAGCCCTGTGACTCACAGCCCTGCTTCCACGGGGGGACC
TGCCAGGACTGGGCATTGGGCGGGGGCTTCACCTGCAGCTGCCCGGCAGGCAGGGGAGGCGCCGTCTGTGAGAAG
GTGCTTGGCGCCCCTGTGCCGGCCTTCGAGGGCCGCTCCTTCCTGGCCTTCCCCACTCTCCGCGCCTACCACACG
CTGCGCCTGGCACTGGAATTCCGGGCGCTGGAGCCTCAGGGGCTGCTGCTGTACAATGGCAACGCCCGGGGCAAG
GACTTCCTGGCATTGGCGCTGCTAGATGGCCGCGTGCAGCTCAGGTTTGACACAGGTTCGGGGCCGGCGGTGCTG
ACCAGTGCCGTGCCGGTAGAGCCGGGCCAGTGGCACCGCCTGGAGCTGTCCCGGCACTGGCGCCGGGGCACCCTC
TCGGTGGATGGTGAGACCCCTGTTCTGGGCGAGAGTCCCAGTGGCACCGACGGCCTCAACCTGGACACAGACCTC
TTTGTGGGCGGCGTACCCGAGGACCAGGCTGCCGTGGCGCTGGAGCGGACCTTCGTGGGCGCCGGCCTGAGGGGG
TGCATCCGTTTGCTGGACGTCAACAACCAGCGCCTGGAGCTTGGCATTGGCCCGGGGCTGCCACCCGAGGCTCT
GGCGTGGGCGAGTGCGGGGACCACCCCTGCCTGCCCAACCCCTGCCATGGCGGGGCCCCATGCCAGAACCTGGAG
GCTGGAAGGTTCCATTGCCAGTGCCCGCCCGGCCGCGTCGGACCAACCTGTGCCGATGAGAAGAGCCCCTGCCAG
CCCAACCCCTGCCATGGGGCGGCGCCCTGCCGTGTGCTGCCCGAGGGTGGTGCTCAGTGCGAGTGCCCCCTGGGG
CGTGAGGGCACCTTCTGCCAGACAGCCTCGGGGCAGGACGGCTCTGGGCCCTTCCTGGCTGACTTCAACGGCTTC
TCCCACCTGGAGCTGAGGGGCCTGCACACCTTTGCACGGGACCTGGGGGAGAAGATGGCGCTGGAGGTCGTGTTC
CTGGCACGAGGCCCCAGCGGCCTCCTGCTCTACAACGGGCAGAAGACGGACGGCAAGGGGGACTTCGTGTCGCTG
GCACTGCGGGACCGCCGCCTGGAGTTCCGCTACGACCTGGGCAAGGGGGCAGCGGTCATCAGGAGCAGGGAGCCA
GTCACCCTGGGAGCCTGGACCAGGGTCTCACTGGAGCGAAACGGCCGCAAGGGTGCCCTGCGTGTGGGCGACGGC
CCCCGTGTGTTGGGGGAGTCCCCGGTTCCGGGGGGGGGGCTCAACCTGAAGGAGCCGCTCTACGTAGGGGGCGCT
CCCGACTTCAGCAAGCTGGCCCGTGCTGCCGTGTGCTCTGGCTTCGACGGTGCCATCCAGCTGGTCTCCCTC
GGAGGCCGCCAGCTGCTGACCCCGGAGCACGTGCTGCGGCAGGTGGACGTCACGTCCTTTGCAGGTCACCCCTGC
ACCCGGGCCTCAGGCCACCCCTGCCTCAATGGGGCCTCCTGCGTCCCGAGGGAGGCTGCCTATGTGTGCCTGTGT
CCCGGGGGGATTCTCAGGACCGCACTGCGAGAAGGGGCTGGTGGAGAGTCAGCGGGGGACGTGGATACCTTGGCC
TTTGACGGGCGGACCTTTGTCGAGTACCTCAACGCTGTGACCGAGAGCGAGAAGGCACTGCAGAGCAACCACTTT
GAACTGAGCCTGCGCACTGAGGCCACGCAGGGGCTGGTGCTCTGGAGTGGCAAGGCCACGGAGCGGGCAGACTAT
GTGGCACTGGCCATTGTGGACGGGCACCTGCAACTGAGCTACAACCTGGGCTCCCAGCCCGTGGTGCTGCGTTCC
```

-continued

---

SEQUENCES

---

```
ACCGTGCCCGTCAACACCAACCGCTGGTTGCGGGTCGTGGCACATAGGGAGCAGAGGGAAGGTTCCCTGCAGGTG
GGCAATGAGGCCCCTGTGACCGGCTCCTCCCCGCTGGGCGCCACGCAGCTGGACACTGATGGAGCCCTGTGGCTT
GGGGGCCTGCCGGAGCTGCCCGTGGGCCCAGCACTGCCCAAGGCCTACGGCACAGGCTTTGTGGGCTGCTTGCGG
GACGTGGTGGTGGGCCGGCACCCGCTGCACCTGCTGGAGGACGCCGTCACCAAGCCAGAGCTGCGGCCCTGCCCC
ACCCCA
```

SEQ ID NO: 19

```
HVRFMDFDWFPAFITGATSGAIAAGATARATTASRLPSSAVTPRAPHPSHTSQPVAKTTAAPTTRRPPTTAPSRV
PGRRPPAPQQPPKPCDSQPCFHGGTCQDWALGGGFTCSCPAGRGGAVCEKVLGAPVPAFEGRSFLAFPTLRAYHT
LRLALEFRALEPQGLLLYNGNARGKDFLALALLDGRVQLRFDTGSGPAVLTSAVPVEPGQWHRLELSRHWRRGTL
SVDGETPVLGESPSGTDGLNLDTDLFVGGVPEDQAAVALERTFVGAGLRGCIRLLDVNNQRLELGIGPGAATRGS
GVGECGDHPCLPNPCHGGAPCQNLEAGRFHCQCPPGRVGPTCADEKSPCQPNPCHGAAPCRVLPEGGAQCECPLG
REGTFCQTASGQDGSGPFLADFNGFSHLELRGLHTFARDLGEKMALEVVFLARGPSGLLLYNGQKTDGKGDFVSL
ALRDRRLEFRYDLGKGAAVIRSREPVTLGAWTRVSLERNGRKGALRVGDGPRVLGESPVPGGGLNLKEPLYVGGA
PDFSKLARAAAVSSGFDGAIQLVSLGGRQLLTPEHVLRQVDVTSFAGHPCTRASGHPCLNGASCVPREAAYVCLC
PGGFSGPHCEKGLVEKSAGDVDTLAFDGRTFVEYLNAVTESEKALQSNHFELSLRTEATQGLVLWSGKATERADY
VALAIVDGHLQLSYNLGSQPVVLRSTVPVNTNRWLRVVAHREQREGSLQVGNEAPVTGSSPLGATQLDTDGALWL
GGLPELPVGPALPKAYGTGFVGCLRDVVVGRHPLHLLEDAVTKPELRPCPTP
```

---

SEQUENCE LISTING

---

```
<160> NUMBER OF SEQ ID NOS: 19

<210> SEQ ID NO 1
<211> LENGTH: 2045
<212> TYPE: PRT
<213> ORGANISM: Artificial Sequence
<220> FEATURE:
<223> OTHER INFORMATION: Wild type human agrin define by GenBank
      Accession No. BAD52440.1

<400> SEQUENCE: 1

Met Ala Gly Arg Ser His Pro Gly Pro Leu Arg Pro Leu Leu Pro Leu
1               5                   10                  15

Leu Val Val Ala Ala Cys Val Leu Pro Gly Ala Gly Gly Thr Cys Pro
            20                  25                  30

Glu Arg Ala Leu Glu Arg Arg Glu Glu Glu Ala Asn Val Val Leu Thr
        35                  40                  45

Gly Thr Val Glu Glu Ile Leu Asn Val Asp Pro Val Gln His Thr Tyr
    50                  55                  60

Ser Cys Lys Val Arg Val Trp Arg Tyr Leu Lys Gly Lys Asp Leu Val
65                  70                  75                  80

Ala Arg Glu Ser Leu Leu Asp Gly Gly Asn Lys Val Val Ile Ser Gly
            85                  90                  95

Phe Gly Asp Pro Leu Ile Cys Asp Asn Gln Val Ser Thr Gly Asp Thr
            100                 105                 110

Arg Ile Phe Phe Val Asn Pro Ala Pro Pro Tyr Leu Trp Pro Ala His
        115                 120                 125

Lys Asn Glu Leu Met Leu Asn Ser Ser Leu Met Arg Ile Thr Leu Arg
    130                 135                 140

Asn Leu Glu Glu Val Glu Phe Cys Val Glu Asp Lys Pro Gly Thr His
145                 150                 155                 160

Phe Thr Pro Val Pro Pro Thr Pro Pro Asp Ala Cys Arg Gly Met Leu
                165                 170                 175

Cys Gly Phe Gly Ala Val Cys Glu Pro Asn Ala Glu Gly Pro Gly Arg
            180                 185                 190

Ala Ser Cys Val Cys Lys Lys Ser Pro Cys Pro Ser Val Val Ala Pro
        195                 200                 205

Val Cys Gly Ser Asp Ala Ser Thr Tyr Ser Asn Glu Cys Glu Leu Gln
```

-continued

```
            210               215               220

Arg Ala Gln Cys Ser Gln Gln Arg Arg Ile Arg Leu Leu Ser Arg Gly
225               230               235               240

Pro Cys Gly Ser Arg Asp Pro Cys Ser Asn Val Thr Cys Ser Phe Gly
                  245               250               255

Ser Thr Cys Ala Arg Ser Ala Asp Gly Leu Thr Ala Ser Cys Leu Cys
              260               265               270

Pro Ala Thr Cys Arg Gly Ala Pro Glu Gly Thr Val Cys Gly Ser Asp
              275               280               285

Gly Ala Asp Tyr Pro Gly Glu Cys Gln Leu Leu Arg Arg Ala Cys Ala
          290               295               300

Arg Gln Glu Asn Val Phe Lys Lys Phe Asp Gly Pro Cys Asp Pro Cys
305               310               315               320

Gln Gly Ala Leu Pro Asp Pro Ser Arg Ser Cys Arg Val Asn Pro Arg
                  325               330               335

Thr Arg Arg Pro Glu Met Leu Leu Arg Pro Glu Ser Cys Pro Ala Arg
              340               345               350

Gln Ala Pro Val Cys Gly Asp Asp Gly Val Thr Tyr Glu Asn Asp Cys
              355               360               365

Val Met Gly Arg Ser Gly Ala Ala Arg Gly Leu Leu Leu Gln Lys Val
          370               375               380

Arg Ser Gly Gln Cys Gln Gly Arg Asp Gln Cys Pro Glu Pro Cys Arg
385               390               395               400

Phe Asn Ala Val Cys Leu Ser Arg Arg Gly Arg Pro Arg Cys Ser Cys
                  405               410               415

Asp Arg Val Thr Cys Asp Gly Ala Tyr Arg Pro Val Cys Ala Gln Asp
              420               425               430

Gly Arg Thr Tyr Asp Ser Asp Cys Trp Arg Gln Gln Ala Glu Cys Arg
              435               440               445

Gln Gln Arg Ala Ile Pro Ser Lys His Gln Gly Pro Cys Asp Gln Ala
          450               455               460

Pro Ser Pro Cys Leu Gly Val Gln Cys Ala Phe Gly Ala Thr Cys Ala
465               470               475               480

Val Lys Asn Gly Gln Ala Ala Cys Glu Cys Leu Gln Ala Cys Ser Ser
                  485               490               495

Leu Tyr Asp Pro Val Cys Gly Ser Asp Gly Val Thr Tyr Gly Ser Ala
              500               505               510

Cys Glu Leu Glu Ala Thr Ala Cys Thr Leu Gly Arg Glu Ile Gln Val
              515               520               525

Ala Arg Lys Gly Pro Cys Asp Arg Cys Gly Gln Cys Arg Phe Gly Ala
          530               535               540

Leu Cys Glu Ala Glu Thr Gly Arg Cys Val Cys Pro Ser Glu Cys Val
545               550               555               560

Ala Leu Ala Gln Pro Val Cys Gly Ser Asp Gly His Thr Tyr Pro Ser
                  565               570               575

Glu Cys Met Leu His Val His Ala Cys Thr His Gln Ile Ser Leu His
              580               585               590

Val Ala Ser Ala Gly Pro Cys Glu Thr Cys Gly Asp Ala Val Cys Ala
              595               600               605

Phe Gly Ala Val Cys Ser Ala Gly Gln Cys Val Cys Pro Arg Cys Glu
          610               615               620

His Pro Pro Pro Gly Pro Val Cys Gly Ser Asp Gly Val Thr Tyr Gly
625               630               635               640
```

-continued

```
Ser Ala Cys Glu Leu Arg Glu Ala Ala Cys Leu Gln Gln Thr Gln Ile
            645                 650                 655

Glu Glu Ala Arg Ala Gly Pro Cys Glu Gln Ala Glu Cys Gly Ser Gly
            660                 665                 670

Gly Ser Gly Ser Gly Glu Asp Gly Asp Cys Glu Gln Glu Leu Cys Arg
            675                 680                 685

Gln Arg Gly Gly Ile Trp Asp Glu Asp Ser Glu Asp Gly Pro Cys Val
        690                 695                 700

Cys Asp Phe Ser Cys Gln Ser Val Pro Gly Ser Pro Val Cys Gly Ser
705                 710                 715                 720

Asp Gly Val Thr Tyr Ser Thr Glu Cys Glu Leu Lys Lys Ala Arg Cys
                725                 730                 735

Glu Ser Gln Arg Gly Leu Tyr Val Ala Ala Gln Gly Ala Cys Arg Gly
            740                 745                 750

Pro Thr Phe Ala Pro Leu Pro Pro Val Ala Pro Leu His Cys Ala Gln
            755                 760                 765

Thr Pro Tyr Gly Cys Cys Gln Asp Asn Ile Thr Ala Ala Arg Gly Val
        770                 775                 780

Gly Leu Ala Gly Cys Pro Ser Ala Cys Gln Cys Asn Pro His Gly Ser
785                 790                 795                 800

Tyr Gly Gly Thr Cys Asp Pro Ala Thr Gly Gln Cys Ser Cys Arg Pro
                805                 810                 815

Gly Val Gly Gly Leu Arg Cys Asp Arg Cys Glu Pro Gly Phe Trp Asn
            820                 825                 830

Phe Arg Gly Ile Val Thr Asp Gly Arg Ser Gly Cys Thr Pro Cys Ser
            835                 840                 845

Cys Asp Pro Gln Gly Ala Val Arg Asp Asp Cys Glu Gln Met Thr Gly
        850                 855                 860

Leu Cys Ser Cys Lys Pro Gly Val Ala Gly Pro Lys Cys Gly Gln Cys
865                 870                 875                 880

Pro Asp Gly Arg Ala Leu Gly Pro Ala Gly Cys Glu Ala Asp Ala Ser
            885                 890                 895

Ala Pro Ala Thr Cys Ala Glu Met Arg Cys Glu Phe Gly Ala Arg Cys
            900                 905                 910

Val Glu Glu Ser Gly Ser Ala His Cys Val Cys Pro Met Leu Thr Cys
            915                 920                 925

Pro Glu Ala Asn Ala Thr Lys Val Cys Gly Ser Asp Gly Val Thr Tyr
        930                 935                 940

Gly Asn Glu Cys Gln Leu Lys Thr Ile Ala Cys Arg Gln Gly Leu Gln
945                 950                 955                 960

Ile Ser Ile Gln Ser Leu Gly Pro Cys Gln Glu Ala Val Ala Pro Ser
                965                 970                 975

Thr His Pro Thr Ser Ala Ser Val Thr Val Thr Thr Pro Gly Leu Leu
            980                 985                 990

Leu Ser Gln Ala Leu Pro Ala Pro  Pro Gly Ala Leu Pro  Leu Ala Pro
        995                 1000                 1005

Ser Ser  Thr Ala His Ser Gln  Thr Thr Pro Pro Pro  Ser Ser Arg
    1010                 1015                 1020

Pro Arg  Thr Thr Ala Ser Val  Pro Arg Thr Thr Val  Trp Pro Val
    1025                 1030                 1035

Leu Thr  Val Pro Pro Thr Ala  Pro Ser Pro Ala Pro  Ser Leu Val
    1040                 1045                 1050
```

```
Ala Ser  Ala Phe Gly Glu Ser  Gly Ser Thr Asp Gly  Ser Ser Asp
    1055              1060              1065

Glu Glu  Leu Ser Gly Asp Gln  Glu Ala Ser Gly Gly  Gly Ser Gly
    1070              1075              1080

Gly Leu  Glu Pro Leu Glu Gly  Ser Ser Val Ala Thr  Pro Gly Pro
    1085              1090              1095

Pro Val  Glu Arg Ala Ser Cys  Tyr Asn Ser Ala Leu  Gly Cys Cys
    1100              1105              1110

Ser Asp  Gly Lys Thr Pro Ser  Leu Asp Ala Glu Gly  Ser Asn Cys
    1115              1120              1125

Pro Ala  Thr Lys Val Phe Gln  Gly Val Leu Glu Leu  Glu Gly Val
    1130              1135              1140

Glu Gly  Gln Glu Leu Phe Tyr  Thr Pro Glu Met Ala  Asp Pro Lys
    1145              1150              1155

Ser Glu  Leu Phe Gly Glu Thr  Ala Arg Ser Ile Glu  Ser Thr Leu
    1160              1165              1170

Asp Asp  Leu Phe Arg Asn Ser  Asp Val Lys Lys Asp  Phe Arg Ser
    1175              1180              1185

Val Arg  Leu Arg Asp Leu Gly  Pro Gly Lys Ser Val  Arg Ala Ile
    1190              1195              1200

Val Asp  Val His Phe Asp Pro  Thr Thr Ala Phe Arg  Ala Pro Asp
    1205              1210              1215

Val Ala  Arg Ala Leu Leu Arg  Gln Ile Gln Val Ser  Arg Arg Arg
    1220              1225              1230

Ser Leu  Gly Val Arg Arg Pro  Leu Gln Glu His Val  Arg Phe Met
    1235              1240              1245

Asp Phe  Asp Trp Phe Pro Ala  Phe Ile Thr Gly Ala  Thr Ser Gly
    1250              1255              1260

Ala Ile  Ala Ala Gly Ala Thr  Ala Arg Ala Thr Thr  Ala Ser Arg
    1265              1270              1275

Leu Pro  Ser Ser Ala Val Thr  Pro Arg Ala Pro His  Pro Ser His
    1280              1285              1290

Thr Ser  Gln Pro Val Ala Lys  Thr Thr Ala Ala Pro  Thr Thr Arg
    1295              1300              1305

Arg Pro  Pro Thr Thr Ala Pro  Ser Arg Val Pro Gly  Arg Arg Pro
    1310              1315              1320

Pro Ala  Pro Gln Gln Pro Pro  Lys Pro Cys Asp Ser  Gln Pro Cys
    1325              1330              1335

Phe His  Gly Gly Thr Cys Gln  Asp Trp Ala Leu Gly  Gly Gly Phe
    1340              1345              1350

Thr Cys  Ser Cys Pro Ala Gly  Arg Gly Gly Ala Val  Cys Glu Lys
    1355              1360              1365

Val Leu  Gly Ala Pro Val Pro  Ala Phe Glu Gly Arg  Ser Phe Leu
    1370              1375              1380

Ala Phe  Pro Thr Leu Arg Ala  Tyr His Thr Leu Arg  Leu Ala Leu
    1385              1390              1395

Glu Phe  Arg Ala Leu Glu Pro  Gln Gly Leu Leu Leu  Tyr Asn Gly
    1400              1405              1410

Asn Ala  Arg Gly Lys Asp Phe  Leu Ala Leu Ala Leu  Leu Asp Gly
    1415              1420              1425

Arg Val  Gln Leu Arg Phe Asp  Thr Gly Ser Gly Pro  Ala Val Leu
    1430              1435              1440

Thr Ser  Ala Val Pro Val Glu  Pro Gly Gln Trp His  Arg Leu Glu
```

-continued

```
            1445                    1450                    1455

Leu Ser  Arg His Trp Arg Arg  Gly Thr Leu Ser Val  Asp Gly Glu
    1460                 1465                    1470

Thr Pro  Val Leu Gly Glu Ser  Pro Ser Gly Thr Asp  Gly Leu Asn
    1475                 1480                    1485

Leu Asp  Thr Asp Leu Phe Val  Gly Gly Val Pro Glu  Asp Gln Ala
    1490                 1495                    1500

Ala Val  Ala Leu Glu Arg Thr  Phe Val Gly Ala Gly  Leu Arg Gly
    1505                 1510                    1515

Cys Ile  Arg Leu Leu Asp Val  Asn Asn Gln Arg Leu  Glu Leu Gly
    1520                 1525                    1530

Ile Gly  Pro Gly Ala Ala Thr  Arg Gly Ser Gly Val  Gly Glu Cys
    1535                 1540                    1545

Gly Asp  His Pro Cys Leu Pro  Asn Pro Cys His Gly  Gly Ala Pro
    1550                 1555                    1560

Cys Gln  Asn Leu Glu Ala Gly  Arg Phe His Cys Gln  Cys Pro Pro
    1565                 1570                    1575

Gly Arg  Val Gly Pro Thr Cys  Ala Asp Glu Lys Ser  Pro Cys Gln
    1580                 1585                    1590

Pro Asn  Pro Cys His Gly Ala  Ala Pro Cys Arg Val  Leu Pro Glu
    1595                 1600                    1605

Gly Gly  Ala Gln Cys Glu Cys  Pro Leu Gly Arg Glu  Gly Thr Phe
    1610                 1615                    1620

Cys Gln  Thr Ala Ser Gly Gln  Asp Gly Ser Gly Pro  Phe Leu Ala
    1625                 1630                    1635

Asp Phe  Asn Gly Phe Ser His  Leu Glu Leu Arg Gly  Leu His Thr
    1640                 1645                    1650

Phe Ala  Arg Asp Leu Gly Glu  Lys Met Ala Leu Glu  Val Val Phe
    1655                 1660                    1665

Leu Ala  Arg Gly Pro Ser Gly  Leu Leu Leu Tyr Asn  Gly Gln Lys
    1670                 1675                    1680

Thr Asp  Gly Lys Gly Asp Phe  Val Ser Leu Ala Leu  Arg Asp Arg
    1685                 1690                    1695

Arg Leu  Glu Phe Arg Tyr Asp  Leu Gly Lys Gly Ala  Ala Val Ile
    1700                 1705                    1710

Arg Ser  Arg Glu Pro Val Thr  Leu Gly Ala Trp Thr  Arg Val Ser
    1715                 1720                    1725

Leu Glu  Arg Asn Gly Arg Lys  Gly Ala Leu Arg Val  Gly Asp Gly
    1730                 1735                    1740

Pro Arg  Val Leu Gly Glu Ser  Pro Val Pro His Thr  Val Leu Asn
    1745                 1750                    1755

Leu Lys  Glu Pro Leu Tyr Val  Gly Gly Ala Pro Asp  Phe Ser Lys
    1760                 1765                    1770

Leu Ala  Arg Ala Ala Ala Val  Ser Ser Gly Phe Asp  Gly Ala Ile
    1775                 1780                    1785

Gln Leu  Val Ser Leu Gly Gly  Arg Gln Leu Leu Thr  Pro Glu His
    1790                 1795                    1800

Val Leu  Arg Gln Val Asp Val  Thr Ser Phe Ala Gly  His Pro Cys
    1805                 1810                    1815

Thr Arg  Ala Ser Gly His Pro  Cys Leu Asn Gly Ala  Ser Cys Val
    1820                 1825                    1830

Pro Arg  Glu Ala Ala Tyr Val  Cys Leu Cys Pro Gly  Gly Phe Ser
    1835                 1840                    1845
```

-continued

```
Gly Pro  His Cys Glu Lys Gly  Leu Val Glu Lys Ser  Ala Gly Asp
    1850                1855             1860

Val Asp  Thr Leu Ala Phe Asp  Gly Arg Thr Phe Val  Glu Tyr Leu
    1865                1870             1875

Asn Ala  Val Thr Glu Ser Glu  Lys Ala Leu Gln Ser  Asn His Phe
    1880                1885             1890

Glu Leu  Ser Leu Arg Thr Glu  Ala Thr Gln Gly Leu  Val Leu Trp
    1895                1900             1905

Ser Gly  Lys Ala Thr Glu Arg  Ala Asp Tyr Val Ala  Leu Ala Ile
    1910                1915             1920

Val Asp  Gly His Leu Gln Leu  Ser Tyr Asn Leu Gly  Ser Gln Pro
    1925                1930             1935

Val Val  Leu Arg Ser Thr Val  Pro Val Asn Thr Asn  Arg Trp Leu
    1940                1945             1950

Arg Val  Val Ala His Arg Glu  Gln Arg Glu Gly Ser  Leu Gln Val
    1955                1960             1965

Gly Asn  Glu Ala Pro Val Thr  Gly Ser Ser Pro Leu  Gly Ala Thr
    1970                1975             1980

Gln Leu  Asp Thr Asp Gly Ala  Leu Trp Leu Gly Gly  Leu Pro Glu
    1985                1990             1995

Leu Pro  Val Gly Pro Ala Leu  Pro Lys Ala Tyr Gly  Thr Gly Phe
    2000                2005             2010

Val Gly  Cys Leu Arg Asp Val  Val Val Gly Arg His  Pro Leu His
    2015                2020             2025

Leu Leu  Glu Asp Ala Val Thr  Lys Pro Glu Leu Arg  Pro Cys Pro
    2030                2035             2040

Thr Pro
    2045

<210> SEQ ID NO 2
<211> LENGTH: 16
<212> TYPE: PRT
<213> ORGANISM: Artificial Sequence
<220> FEATURE:
<223> OTHER INFORMATION: Amino acid residues 1244-1259 of wild type
      human agrin

<400> SEQUENCE: 2

His Val Arg Phe Met Asp Phe Asp Trp Phe Pro Ala Phe Ile Thr Gly
1               5                   10                  15

<210> SEQ ID NO 3
<211> LENGTH: 802
<212> TYPE: PRT
<213> ORGANISM: Artificial Sequence
<220> FEATURE:
<223> OTHER INFORMATION: Amino acid residues 1244-2045 of wild type
      human agrin

<400> SEQUENCE: 3

His Val Arg Phe Met Asp Phe Asp Trp Phe Pro Ala Phe Ile Thr Gly
1               5                   10                  15

Ala Thr Ser Gly Ala Ile Ala Ala Gly Ala Thr Ala Arg Ala Thr Thr
            20                  25                  30

Ala Ser Arg Leu Pro Ser Ser Ala Val Thr Pro Arg Ala Pro His Pro
        35                  40                  45

Ser His Thr Ser Gln Pro Val Ala Lys Thr Thr Ala Ala Pro Thr Thr
    50                  55                  60
```

```
Arg Arg Pro Pro Thr Thr Ala Pro Ser Arg Val Pro Gly Arg Arg Pro
65              70              75              80

Pro Ala Pro Gln Gln Pro Pro Lys Pro Cys Asp Ser Gln Pro Cys Phe
                85          90                  95

His Gly Gly Thr Cys Gln Asp Trp Ala Leu Gly Gly Gly Phe Thr Cys
            100             105             110

Ser Cys Pro Ala Gly Arg Gly Gly Ala Val Cys Glu Lys Val Leu Gly
        115             120             125

Ala Pro Val Pro Ala Phe Glu Gly Arg Ser Phe Leu Ala Phe Pro Thr
    130             135             140

Leu Arg Ala Tyr His Thr Leu Arg Leu Ala Leu Glu Phe Arg Ala Leu
145             150             155             160

Glu Pro Gln Gly Leu Leu Leu Tyr Asn Gly Asn Ala Arg Gly Lys Asp
            165             170             175

Phe Leu Ala Leu Ala Leu Leu Asp Gly Arg Val Gln Leu Arg Phe Asp
            180             185             190

Thr Gly Ser Gly Pro Ala Val Leu Thr Ser Ala Val Pro Val Glu Pro
            195             200             205

Gly Gln Trp His Arg Leu Glu Leu Ser Arg His Trp Arg Arg Gly Thr
    210             215             220

Leu Ser Val Asp Gly Glu Thr Pro Val Leu Gly Glu Ser Pro Ser Gly
225             230             235             240

Thr Asp Gly Leu Asn Leu Asp Thr Asp Leu Phe Val Gly Gly Val Pro
            245             250             255

Glu Asp Gln Ala Ala Val Ala Leu Glu Arg Thr Phe Val Gly Ala Gly
            260             265             270

Leu Arg Gly Cys Ile Arg Leu Leu Asp Val Asn Asn Gln Arg Leu Glu
            275             280             285

Leu Gly Ile Gly Pro Gly Ala Ala Thr Arg Gly Ser Gly Val Gly Glu
    290             295             300

Cys Gly Asp His Pro Cys Leu Pro Asn Pro Cys His Gly Gly Ala Pro
305             310             315             320

Cys Gln Asn Leu Glu Ala Gly Arg Phe His Cys Gln Cys Pro Pro Gly
            325             330             335

Arg Val Gly Pro Thr Cys Ala Asp Glu Lys Ser Pro Cys Gln Pro Asn
            340             345             350

Pro Cys His Gly Ala Ala Pro Cys Arg Val Leu Pro Glu Gly Gly Ala
        355             360             365

Gln Cys Glu Cys Pro Leu Gly Arg Glu Gly Thr Phe Cys Gln Thr Ala
    370             375             380

Ser Gly Gln Asp Gly Ser Gly Pro Phe Leu Ala Asp Phe Asn Gly Phe
385             390             395             400

Ser His Leu Glu Leu Arg Gly Leu His Thr Phe Ala Arg Asp Leu Gly
            405             410             415

Glu Lys Met Ala Leu Glu Val Val Phe Leu Ala Arg Gly Pro Ser Gly
            420             425             430

Leu Leu Leu Tyr Asn Gly Gln Lys Thr Asp Gly Lys Gly Asp Phe Val
        435             440             445

Ser Leu Ala Leu Arg Asp Arg Arg Leu Glu Phe Arg Tyr Asp Leu Gly
    450             455             460

Lys Gly Ala Ala Val Ile Arg Ser Arg Glu Pro Val Thr Leu Gly Ala
465             470             475             480
```

-continued

```
Trp Thr Arg Val Ser Leu Glu Arg Asn Gly Arg Lys Gly Ala Leu Arg
                485                 490                 495

Val Gly Asp Gly Pro Arg Val Leu Gly Glu Ser Pro Val Pro His Thr
            500                 505                 510

Val Leu Asn Leu Lys Glu Pro Leu Tyr Val Gly Gly Ala Pro Asp Phe
            515                 520                 525

Ser Lys Leu Ala Arg Ala Ala Ala Val Ser Ser Gly Phe Asp Gly Ala
    530                 535                 540

Ile Gln Leu Val Ser Leu Gly Gly Arg Gln Leu Leu Thr Pro Glu His
545                 550                 555                 560

Val Leu Arg Gln Val Asp Val Thr Ser Phe Ala Gly His Pro Cys Thr
                565                 570                 575

Arg Ala Ser Gly His Pro Cys Leu Asn Gly Ala Ser Cys Val Pro Arg
            580                 585                 590

Glu Ala Ala Tyr Val Cys Leu Cys Pro Gly Gly Phe Ser Gly Pro His
            595                 600                 605

Cys Glu Lys Gly Leu Val Glu Lys Ser Ala Gly Asp Val Asp Thr Leu
    610                 615                 620

Ala Phe Asp Gly Arg Thr Phe Val Glu Tyr Leu Asn Ala Val Thr Glu
625                 630                 635                 640

Ser Glu Lys Ala Leu Gln Ser Asn His Phe Glu Leu Ser Leu Arg Thr
                645                 650                 655

Glu Ala Thr Gln Gly Leu Val Leu Trp Ser Gly Lys Ala Thr Glu Arg
                660                 665                 670

Ala Asp Tyr Val Ala Leu Ala Ile Val Asp Gly His Leu Gln Leu Ser
            675                 680                 685

Tyr Asn Leu Gly Ser Gln Pro Val Val Leu Arg Ser Thr Val Pro Val
        690                 695                 700

Asn Thr Asn Arg Trp Leu Arg Val Val Ala His Arg Glu Gln Arg Glu
705                 710                 715                 720

Gly Ser Leu Gln Val Gly Asn Glu Ala Pro Val Thr Gly Ser Ser Pro
                725                 730                 735

Leu Gly Ala Thr Gln Leu Asp Thr Asp Gly Ala Leu Trp Leu Gly Gly
            740                 745                 750

Leu Pro Glu Leu Pro Val Gly Pro Ala Leu Pro Lys Ala Tyr Gly Thr
            755                 760                 765

Gly Phe Val Gly Cys Leu Arg Asp Val Val Val Gly Arg His Pro Leu
    770                 775                 780

His Leu Leu Glu Asp Ala Val Thr Lys Pro Glu Leu Arg Pro Cys Pro
785                 790                 795                 800

Thr Pro
```

<210> SEQ ID NO 4
<211> LENGTH: 2068
<212> TYPE: PRT
<213> ORGANISM: Artificial Sequence
<220> FEATURE:
<223> OTHER INFORMATION: Polypeptide sequence corresponding to splice
      variant of human agrin corresponding to UniProt accession no.
      O00468-1

<400> SEQUENCE: 4

```
Met Ala Gly Arg Ser His Pro Gly Pro Leu Arg Pro Leu Leu Pro Leu
1               5                   10                  15

Leu Val Val Ala Ala Cys Val Leu Pro Gly Ala Gly Gly Thr Cys Pro
            20                  25                  30
```

```
Glu Arg Ala Leu Glu Arg Arg Glu Glu Glu Ala Asn Val Val Leu Thr
        35              40                  45

Gly Thr Val Glu Glu Ile Leu Asn Val Asp Pro Val Gln His Thr Tyr
    50                  55                  60

Ser Cys Lys Val Arg Val Trp Arg Tyr Leu Lys Gly Lys Asp Leu Val
65                  70                  75                  80

Ala Arg Glu Ser Leu Leu Asp Gly Gly Asn Lys Val Val Ile Ser Gly
            85                  90                  95

Phe Gly Asp Pro Leu Ile Cys Asp Asn Gln Val Ser Thr Gly Asp Thr
            100                 105                 110

Arg Ile Phe Phe Val Asn Pro Ala Pro Pro Tyr Leu Trp Pro Ala His
            115                 120                 125

Lys Asn Glu Leu Met Leu Asn Ser Ser Leu Met Arg Ile Thr Leu Arg
    130                 135                 140

Asn Leu Glu Glu Val Glu Phe Cys Val Glu Asp Lys Pro Gly Thr His
145                 150                 155                 160

Phe Thr Pro Val Pro Pro Thr Pro Pro Asp Ala Cys Arg Gly Met Leu
            165                 170                 175

Cys Gly Phe Gly Ala Val Cys Glu Pro Asn Ala Glu Gly Pro Gly Arg
            180                 185                 190

Ala Ser Cys Val Cys Lys Lys Ser Pro Cys Pro Ser Val Val Ala Pro
            195                 200                 205

Val Cys Gly Ser Asp Ala Ser Thr Tyr Ser Asn Glu Cys Glu Leu Gln
    210                 215                 220

Arg Ala Gln Cys Ser Gln Gln Arg Arg Ile Arg Leu Leu Ser Arg Gly
225                 230                 235                 240

Pro Cys Gly Ser Arg Asp Pro Cys Ser Asn Val Thr Cys Ser Phe Gly
            245                 250                 255

Ser Thr Cys Ala Arg Ser Ala Asp Gly Leu Thr Ala Ser Cys Leu Cys
            260                 265                 270

Pro Ala Thr Cys Arg Gly Ala Pro Glu Gly Thr Val Cys Gly Ser Asp
            275                 280                 285

Gly Ala Asp Tyr Pro Gly Glu Cys Gln Leu Leu Arg Arg Ala Cys Ala
    290                 295                 300

Arg Gln Glu Asn Val Phe Lys Lys Phe Asp Gly Pro Cys Asp Pro Cys
305                 310                 315                 320

Gln Gly Ala Leu Pro Asp Pro Ser Arg Ser Cys Arg Val Asn Pro Arg
            325                 330                 335

Thr Arg Arg Pro Glu Met Leu Leu Arg Pro Glu Ser Cys Pro Ala Arg
            340                 345                 350

Gln Ala Pro Val Cys Gly Asp Asp Gly Val Thr Tyr Glu Asn Asp Cys
            355                 360                 365

Val Met Gly Arg Ser Gly Ala Ala Arg Gly Leu Leu Leu Gln Lys Val
    370                 375                 380

Arg Ser Gly Gln Cys Gln Gly Arg Asp Gln Cys Pro Glu Pro Cys Arg
385                 390                 395                 400

Phe Asn Ala Val Cys Leu Ser Arg Arg Gly Arg Pro Arg Cys Ser Cys
            405                 410                 415

Asp Arg Val Thr Cys Asp Gly Ala Tyr Arg Pro Val Cys Ala Gln Asp
            420                 425                 430

Gly Arg Thr Tyr Asp Ser Asp Cys Trp Arg Gln Gln Ala Glu Cys Arg
    435                 440                 445
```

-continued

```
Gln Gln Arg Ala Ile Pro Ser Lys His Gln Gly Pro Cys Asp Gln Ala
    450                 455             460

Pro Ser Pro Cys Leu Gly Val Gln Cys Ala Phe Gly Ala Thr Cys Ala
465                 470             475                 480

Val Lys Asn Gly Gln Ala Ala Cys Glu Cys Leu Gln Ala Cys Ser Ser
                485             490             495

Leu Tyr Asp Pro Val Cys Gly Ser Asp Gly Val Thr Tyr Gly Ser Ala
            500             505             510

Cys Glu Leu Glu Ala Thr Ala Cys Thr Leu Gly Arg Glu Ile Gln Val
        515             520             525

Ala Arg Lys Gly Pro Cys Asp Arg Cys Gly Gln Cys Arg Phe Gly Ala
    530             535             540

Leu Cys Glu Ala Glu Thr Gly Arg Cys Val Cys Pro Ser Glu Cys Val
545             550             555             560

Ala Leu Ala Gln Pro Val Cys Gly Ser Asp Gly His Thr Tyr Pro Ser
            565             570             575

Glu Cys Met Leu His Val His Ala Cys Thr His Gln Ile Ser Leu His
        580             585             590

Val Ala Ser Ala Gly Pro Cys Glu Thr Cys Gly Asp Ala Val Cys Ala
    595             600             605

Phe Gly Ala Val Cys Ser Ala Gly Gln Cys Val Cys Pro Arg Cys Glu
    610             615             620

His Pro Pro Pro Gly Pro Val Cys Gly Ser Asp Gly Val Thr Tyr Gly
625             630             635             640

Ser Ala Cys Glu Leu Arg Glu Ala Ala Cys Leu Gln Gln Thr Gln Ile
            645             650             655

Glu Glu Ala Arg Ala Gly Pro Cys Glu Gln Ala Glu Cys Gly Ser Gly
            660             665             670

Gly Ser Gly Ser Gly Glu Asp Gly Asp Cys Glu Gln Glu Leu Cys Arg
    675             680             685

Gln Arg Gly Gly Ile Trp Asp Glu Asp Ser Glu Asp Gly Pro Cys Val
    690             695             700

Cys Asp Phe Ser Cys Gln Ser Val Pro Gly Ser Pro Val Cys Gly Ser
705             710             715             720

Asp Gly Val Thr Tyr Ser Thr Glu Cys Glu Leu Lys Lys Ala Arg Cys
            725             730             735

Glu Ser Gln Arg Gly Leu Tyr Val Ala Ala Gln Gly Ala Cys Arg Gly
        740             745             750

Pro Thr Phe Ala Pro Leu Pro Pro Val Ala Pro Leu His Cys Ala Gln
        755             760             765

Thr Pro Tyr Gly Cys Cys Gln Asp Asn Ile Thr Ala Ala Arg Gly Val
    770             775             780

Gly Leu Ala Gly Cys Pro Ser Ala Cys Gln Cys Asn Pro His Gly Ser
785             790             795             800

Tyr Gly Gly Thr Cys Asp Pro Ala Thr Gly Gln Cys Ser Cys Arg Pro
            805             810             815

Gly Val Gly Gly Leu Arg Cys Asp Arg Cys Glu Pro Gly Phe Trp Asn
            820             825             830

Phe Arg Gly Ile Val Thr Asp Gly Arg Ser Gly Cys Thr Pro Cys Ser
        835             840             845

Cys Asp Pro Gln Gly Ala Val Arg Asp Asp Cys Glu Gln Met Thr Gly
850             855             860

Leu Cys Ser Cys Lys Pro Gly Val Ala Gly Pro Lys Cys Gly Gln Cys
```

```
865                 870                 875                 880

Pro Asp Gly Arg Ala Leu Gly Pro Ala Gly Cys Glu Ala Asp Ala Ser
                885                 890                 895

Ala Pro Ala Thr Cys Ala Glu Met Arg Cys Glu Phe Gly Ala Arg Cys
                900                 905                 910

Val Glu Glu Ser Gly Ser Ala His Cys Val Cys Pro Met Leu Thr Cys
                915                 920                 925

Pro Glu Ala Asn Ala Thr Lys Val Cys Gly Ser Asp Gly Val Thr Tyr
930                 935                 940

Gly Asn Glu Cys Gln Leu Lys Thr Ile Ala Cys Arg Gln Gly Leu Gln
945                 950                 955                 960

Ile Ser Ile Gln Ser Leu Gly Pro Cys Gln Glu Ala Val Ala Pro Ser
                965                 970                 975

Thr His Pro Thr Ser Ala Ser Val Thr Val Thr Thr Pro Gly Leu Leu
                980                 985                 990

Leu Ser Gln Ala Leu Pro Ala Pro  Pro Gly Ala Leu Pro  Leu Ala Pro
                995                 1000                1005

Ser Ser  Thr Ala His Ser Gln  Thr Thr Pro Pro Pro  Ser Ser Arg
    1010                1015                1020

Pro Arg  Thr Thr Ala Ser Val  Pro Arg Thr Thr Val  Trp Pro Val
    1025                1030                1035

Leu Thr  Val Pro Pro Thr Ala  Pro Ser Pro Ala Pro  Ser Leu Val
    1040                1045                1050

Ala Ser  Ala Phe Gly Glu Ser  Gly Ser Thr Asp Gly  Ser Ser Asp
    1055                1060                1065

Glu Glu  Leu Ser Gly Asp Gln  Glu Ala Ser Gly Gly  Gly Ser Gly
    1070                1075                1080

Gly Leu  Glu Pro Leu Glu Gly  Ser Ser Val Ala Thr  Pro Gly Pro
    1085                1090                1095

Pro Val  Glu Arg Ala Ser Cys  Tyr Asn Ser Ala Leu  Gly Cys Cys
    1100                1105                1110

Ser Asp  Gly Lys Thr Pro Ser  Leu Asp Ala Glu Gly  Ser Asn Cys
    1115                1120                1125

Pro Ala  Thr Lys Val Phe Gln  Gly Val Leu Glu Leu  Glu Gly Val
    1130                1135                1140

Glu Gly  Gln Glu Leu Phe Tyr  Thr Pro Glu Met Ala  Asp Pro Lys
    1145                1150                1155

Ser Glu  Leu Phe Gly Glu Thr  Ala Arg Ser Ile Glu  Ser Thr Leu
    1160                1165                1170

Asp Asp  Leu Phe Arg Asn Ser  Asp Val Lys Lys Asp  Phe Arg Ser
    1175                1180                1185

Val Arg  Leu Arg Asp Leu Gly  Pro Gly Lys Ser Val  Arg Ala Ile
    1190                1195                1200

Val Asp  Val His Phe Asp Pro  Thr Thr Ala Phe Arg  Ala Pro Asp
    1205                1210                1215

Val Ala  Arg Ala Leu Leu Arg  Gln Ile Gln Val Ser  Arg Arg Arg
    1220                1225                1230

Ser Leu  Gly Val Arg Arg Pro  Leu Gln Glu His Val  Arg Phe Met
    1235                1240                1245

Asp Phe  Asp Trp Phe Pro Ala  Phe Ile Thr Gly Ala  Thr Ser Gly
    1250                1255                1260

Ala Ile  Ala Ala Gly Ala Thr  Ala Arg Ala Thr Thr  Ala Ser Arg
    1265                1270                1275
```

-continued

Leu Pro Ser Ser Ala Val Thr Pro Arg Ala Pro His Pro Ser His
    1280            1285            1290

Thr Ser Gln Pro Val Ala Lys Thr Thr Ala Ala Pro Thr Thr Arg
    1295            1300            1305

Arg Pro Pro Thr Thr Ala Pro Ser Arg Val Pro Gly Arg Arg Pro
    1310            1315            1320

Pro Ala Pro Gln Gln Pro Pro Lys Pro Cys Asp Ser Gln Pro Cys
    1325            1330            1335

Phe His Gly Gly Thr Cys Gln Asp Trp Ala Leu Gly Gly Gly Phe
    1340            1345            1350

Thr Cys Ser Cys Pro Ala Gly Arg Gly Gly Ala Val Cys Glu Lys
    1355            1360            1365

Val Leu Gly Ala Pro Val Pro Ala Phe Glu Gly Arg Ser Phe Leu
    1370            1375            1380

Ala Phe Pro Thr Leu Arg Ala Tyr His Thr Leu Arg Leu Ala Leu
    1385            1390            1395

Glu Phe Arg Ala Leu Glu Pro Gln Gly Leu Leu Leu Tyr Asn Gly
    1400            1405            1410

Asn Ala Arg Gly Lys Asp Phe Leu Ala Leu Ala Leu Leu Asp Gly
    1415            1420            1425

Arg Val Gln Leu Arg Phe Asp Thr Gly Ser Gly Pro Ala Val Leu
    1430            1435            1440

Thr Ser Ala Val Pro Val Glu Pro Gly Gln Trp His Arg Leu Glu
    1445            1450            1455

Leu Ser Arg His Trp Arg Arg Gly Thr Leu Ser Val Asp Gly Glu
    1460            1465            1470

Thr Pro Val Leu Gly Glu Ser Pro Ser Gly Thr Asp Gly Leu Asn
    1475            1480            1485

Leu Asp Thr Asp Leu Phe Val Gly Gly Val Pro Glu Asp Gln Ala
    1490            1495            1500

Ala Val Ala Leu Glu Arg Thr Phe Val Gly Ala Gly Leu Arg Gly
    1505            1510            1515

Cys Ile Arg Leu Leu Asp Val Asn Asn Gln Arg Leu Glu Leu Gly
    1520            1525            1530

Ile Gly Pro Gly Ala Ala Thr Arg Gly Ser Gly Val Gly Glu Cys
    1535            1540            1545

Gly Asp His Pro Cys Leu Pro Asn Pro Cys His Gly Gly Ala Pro
    1550            1555            1560

Cys Gln Asn Leu Glu Ala Gly Arg Phe His Cys Gln Cys Pro Pro
    1565            1570            1575

Gly Arg Val Gly Pro Thr Cys Ala Asp Glu Lys Ser Pro Cys Gln
    1580            1585            1590

Pro Asn Pro Cys His Gly Ala Ala Pro Cys Arg Val Leu Pro Glu
    1595            1600            1605

Gly Gly Ala Gln Cys Glu Cys Pro Leu Gly Arg Glu Gly Thr Phe
    1610            1615            1620

Cys Gln Thr Ala Ser Gly Gln Asp Gly Ser Gly Pro Phe Leu Ala
    1625            1630            1635

Asp Phe Asn Gly Phe Ser His Leu Glu Leu Arg Gly Leu His Thr
    1640            1645            1650

Phe Ala Arg Asp Leu Gly Glu Lys Met Ala Leu Glu Val Val Phe
    1655            1660            1665

-continued

```
Leu Ala  Arg Gly Pro Ser Gly  Leu Leu Leu Tyr Asn  Gly Gln Lys
    1670             1675             1680

Thr Asp  Gly Lys Gly Asp Phe  Val Ser Leu Ala Leu  Arg Asp Arg
    1685             1690             1695

Arg Leu  Glu Phe Arg Tyr Asp  Leu Gly Lys Gly Ala  Ala Val Ile
    1700             1705             1710

Arg Ser  Arg Glu Pro Val Thr  Leu Gly Ala Trp Thr  Arg Val Ser
    1715             1720             1725

Leu Glu  Arg Asn Gly Arg Lys  Gly Ala Leu Arg Val  Gly Asp Gly
    1730             1735             1740

Pro Arg  Val Leu Gly Glu Ser  Pro Lys Ser Arg Lys  Val Pro His
    1745             1750             1755

Thr Val  Leu Asn Leu Lys Glu  Pro Leu Tyr Val Gly  Gly Ala Pro
    1760             1765             1770

Asp Phe  Ser Lys Leu Ala Arg  Ala Ala Ala Val Ser  Ser Gly Phe
    1775             1780             1785

Asp Gly  Ala Ile Gln Leu Val  Ser Leu Gly Gly Arg  Gln Leu Leu
    1790             1795             1800

Thr Pro  Glu His Val Leu Arg  Gln Val Asp Val Thr  Ser Phe Ala
    1805             1810             1815

Gly His  Pro Cys Thr Arg Ala  Ser Gly His Pro Cys  Leu Asn Gly
    1820             1825             1830

Ala Ser  Cys Val Pro Arg Glu  Ala Ala Tyr Val Cys  Leu Cys Pro
    1835             1840             1845

Gly Gly  Phe Ser Gly Pro His  Cys Glu Lys Gly Leu  Val Glu Lys
    1850             1855             1860

Ser Ala  Gly Asp Val Asp Thr  Leu Ala Phe Asp Gly  Arg Thr Phe
    1865             1870             1875

Val Glu  Tyr Leu Asn Ala Val  Thr Glu Ser Glu Leu  Ala Asn Glu
    1880             1885             1890

Ile Pro  Val Pro Glu Thr Leu  Asp Ser Gly Ala Leu  His Ser Glu
    1895             1900             1905

Lys Ala  Leu Gln Ser Asn His  Phe Glu Leu Ser Leu  Arg Thr Glu
    1910             1915             1920

Ala Thr  Gln Gly Leu Val Leu  Trp Ser Gly Lys Ala  Thr Glu Arg
    1925             1930             1935

Ala Asp  Tyr Val Ala Leu Ala  Ile Val Asp Gly His  Leu Gln Leu
    1940             1945             1950

Ser Tyr  Asn Leu Gly Ser Gln  Pro Val Val Leu Arg  Ser Thr Val
    1955             1960             1965

Pro Val  Asn Thr Asn Arg Trp  Leu Arg Val Val Ala  His Arg Glu
    1970             1975             1980

Gln Arg  Glu Gly Ser Leu Gln  Val Gly Asn Glu Ala  Pro Val Thr
    1985             1990             1995

Gly Ser  Ser Pro Leu Gly Ala  Thr Gln Leu Asp Thr  Asp Gly Ala
    2000             2005             2010

Leu Trp  Leu Gly Gly Leu Pro  Glu Leu Pro Val Gly  Pro Ala Leu
    2015             2020             2025

Pro Lys  Ala Tyr Gly Thr Gly  Phe Val Gly Cys Leu  Arg Asp Val
    2030             2035             2040

Val Val  Gly Arg His Pro Leu  His Leu Leu Glu Asp  Ala Val Thr
    2045             2050             2055

Lys Pro  Glu Leu Arg Pro Cys  Pro Thr Pro
```

-continued

```
                2060                  2065

<210> SEQ ID NO 5
<211> LENGTH: 1964
<212> TYPE: PRT
<213> ORGANISM: Artificial Sequence
<220> FEATURE:
<223> OTHER INFORMATION: polypeptide sequence corresponding to splice
      variant of human agrin corresponding to UniProt accession no.
      O00468-2
<220> FEATURE:
<221> NAME/KEY: misc_feature
<222> LOCATION: (3)..(3)
<223> OTHER INFORMATION: Xaa can be any naturally occurring amino acid

<400> SEQUENCE: 5

Met Pro Xaa Leu Ala Val Ala Arg Asp Thr Arg Gln Pro Ala Gly Ala
1               5                   10                  15

Ser Leu Leu Val Arg Gly Phe Met Val Pro Cys Asn Ala Cys Leu Ile
            20                  25                  30

Leu Leu Ala Thr Ala Thr Leu Gly Phe Ala Val Leu Leu Phe Leu Asn
            35                  40                  45

Asn Tyr Asp Lys Pro Gly Thr His Phe Thr Pro Val Pro Pro Thr Pro
      50                  55                  60

Pro Asp Ala Cys Arg Gly Met Leu Cys Gly Phe Gly Ala Val Cys Glu
65                  70                  75                  80

Pro Asn Ala Glu Gly Pro Gly Arg Ala Ser Cys Val Cys Lys Lys Ser
                85                  90                  95

Pro Cys Pro Ser Val Val Ala Pro Val Cys Gly Ser Asp Ala Ser Thr
            100                 105                 110

Tyr Ser Asn Glu Cys Glu Leu Gln Arg Ala Gln Cys Ser Gln Gln Arg
            115                 120                 125

Arg Ile Arg Leu Leu Ser Arg Gly Pro Cys Gly Ser Arg Asp Pro Cys
      130                 135                 140

Ser Asn Val Thr Cys Ser Phe Gly Ser Thr Cys Ala Arg Ser Ala Asp
145                 150                 155                 160

Gly Leu Thr Ala Ser Cys Leu Cys Pro Ala Thr Cys Arg Gly Ala Pro
                165                 170                 175

Glu Gly Thr Val Cys Gly Ser Asp Gly Ala Asp Tyr Pro Gly Glu Cys
            180                 185                 190

Gln Leu Leu Arg Arg Ala Cys Ala Arg Gln Glu Asn Val Phe Lys Lys
            195                 200                 205

Phe Asp Gly Pro Cys Asp Pro Cys Gln Gly Ala Leu Pro Asp Pro Ser
      210                 215                 220

Arg Ser Cys Arg Val Asn Pro Arg Thr Arg Arg Pro Glu Met Leu Leu
225                 230                 235                 240

Arg Pro Glu Ser Cys Pro Ala Arg Gln Ala Pro Val Cys Gly Asp Asp
                245                 250                 255

Gly Val Thr Tyr Glu Asn Asp Cys Val Met Gly Arg Ser Gly Ala Ala
            260                 265                 270

Arg Gly Leu Leu Leu Gln Lys Val Arg Ser Gly Gln Cys Gln Gly Arg
            275                 280                 285

Asp Gln Cys Pro Glu Pro Cys Arg Phe Asn Ala Val Cys Leu Ser Arg
      290                 295                 300

Arg Gly Arg Pro Arg Cys Ser Cys Asp Arg Val Thr Cys Asp Gly Ala
305                 310                 315                 320

Tyr Arg Pro Val Cys Ala Gln Asp Gly Arg Thr Tyr Asp Ser Asp Cys
```

-continued

```
              325                  330                  335

Trp Arg Gln Gln Ala Glu Cys Arg Gln Gln Arg Ala Ile Pro Ser Lys
        340                  345                  350

His Gln Gly Pro Cys Asp Gln Ala Pro Ser Pro Cys Leu Gly Val Gln
        355                  360                  365

Cys Ala Phe Gly Ala Thr Cys Ala Val Lys Asn Gly Gln Ala Ala Cys
    370                  375                  380

Glu Cys Leu Gln Ala Cys Ser Ser Leu Tyr Asp Pro Val Cys Gly Ser
385                  390                  395                  400

Asp Gly Val Thr Tyr Gly Ser Ala Cys Glu Leu Glu Ala Thr Ala Cys
            405                  410                  415

Thr Leu Gly Arg Glu Ile Gln Val Ala Arg Lys Gly Pro Cys Asp Arg
            420                  425                  430

Cys Gly Gln Cys Arg Phe Gly Ala Leu Cys Glu Ala Glu Thr Gly Arg
        435                  440                  445

Cys Val Cys Pro Ser Glu Cys Val Ala Leu Ala Gln Pro Val Cys Gly
    450                  455                  460

Ser Asp Gly His Thr Tyr Pro Ser Glu Cys Met Leu His Val His Ala
465                  470                  475                  480

Cys Thr His Gln Ile Ser Leu His Val Ala Ser Ala Gly Pro Cys Glu
                485                  490                  495

Thr Cys Gly Asp Ala Val Cys Ala Phe Gly Ala Val Cys Ser Ala Gly
            500                  505                  510

Gln Cys Val Cys Pro Arg Cys Glu His Pro Pro Pro Gly Pro Val Cys
            515                  520                  525

Gly Ser Asp Gly Val Thr Tyr Gly Ser Ala Cys Glu Leu Arg Glu Ala
        530                  535                  540

Ala Cys Leu Gln Gln Thr Gln Ile Glu Glu Ala Arg Ala Gly Pro Cys
545                  550                  555                  560

Glu Gln Ala Glu Cys Gly Ser Gly Gly Ser Gly Ser Gly Glu Asp Gly
                565                  570                  575

Asp Cys Glu Gln Glu Leu Cys Arg Gln Arg Gly Gly Ile Trp Asp Glu
            580                  585                  590

Asp Ser Glu Asp Gly Pro Cys Val Cys Asp Phe Ser Cys Gln Ser Val
            595                  600                  605

Pro Gly Ser Pro Val Cys Gly Ser Asp Gly Val Thr Tyr Ser Thr Glu
    610                  615                  620

Cys Glu Leu Lys Lys Ala Arg Cys Glu Ser Gln Arg Gly Leu Tyr Val
625                  630                  635                  640

Ala Ala Gln Gly Ala Cys Arg Gly Pro Thr Phe Ala Pro Leu Pro Pro
            645                  650                  655

Val Ala Pro Leu His Cys Ala Gln Thr Pro Tyr Gly Cys Cys Gln Asp
            660                  665                  670

Asn Ile Thr Ala Ala Arg Gly Val Gly Leu Ala Gly Cys Pro Ser Ala
        675                  680                  685

Cys Gln Cys Asn Pro His Gly Ser Tyr Gly Gly Thr Cys Asp Pro Ala
    690                  695                  700

Thr Gly Gln Cys Ser Cys Arg Pro Gly Val Gly Gly Leu Arg Cys Asp
705                  710                  715                  720

Arg Cys Glu Pro Gly Phe Trp Asn Phe Arg Gly Ile Val Thr Asp Gly
            725                  730                  735

Arg Ser Gly Cys Thr Pro Cys Ser Cys Asp Pro Gln Gly Ala Val Arg
        740                  745                  750
```

```
Asp Asp Cys Glu Gln Met Thr Gly Leu Cys Ser Cys Lys Pro Gly Val
        755                 760                 765

Ala Gly Pro Lys Cys Gly Gln Cys Pro Asp Gly Arg Ala Leu Gly Pro
        770                 775                 780

Ala Gly Cys Glu Ala Asp Ala Ser Ala Pro Ala Thr Cys Ala Glu Met
785                 790                 795                 800

Arg Cys Glu Phe Gly Ala Arg Cys Val Glu Glu Ser Gly Ser Ala His
                805                 810                 815

Cys Val Cys Pro Met Leu Thr Cys Pro Glu Ala Asn Ala Thr Lys Val
                820                 825                 830

Cys Gly Ser Asp Gly Val Thr Tyr Gly Asn Glu Cys Gln Leu Lys Thr
        835                 840                 845

Ile Ala Cys Arg Gln Gly Leu Gln Ile Ser Ile Gln Ser Leu Gly Pro
        850                 855                 860

Cys Gln Glu Ala Val Ala Pro Ser Thr His Pro Thr Ser Ala Ser Val
865                 870                 875                 880

Thr Val Thr Thr Pro Gly Leu Leu Leu Ser Gln Ala Leu Pro Ala Pro
                885                 890                 895

Pro Gly Ala Leu Pro Leu Ala Pro Ser Ser Thr Ala His Ser Gln Thr
                900                 905                 910

Thr Pro Pro Pro Ser Ser Arg Pro Arg Thr Thr Ala Ser Val Pro Arg
        915                 920                 925

Thr Thr Val Trp Pro Val Leu Thr Val Pro Pro Thr Ala Pro Ser Pro
        930                 935                 940

Ala Pro Ser Leu Val Ala Ser Ala Phe Gly Glu Ser Gly Ser Thr Asp
945                 950                 955                 960

Gly Ser Ser Asp Glu Glu Leu Ser Gly Asp Gln Glu Ala Ser Gly Gly
                965                 970                 975

Gly Ser Gly Gly Leu Glu Pro Leu Glu Gly Ser Ser Val Ala Thr Pro
                980                 985                 990

Gly Pro Pro Val Glu Arg Ala Ser  Cys Tyr Asn Ser Ala  Leu Gly Cys
        995                 1000                1005

Cys Ser  Asp Gly Lys Thr Pro  Ser Leu Asp Ala Glu  Gly Ser Asn
        1010                1015                1020

Cys Pro  Ala Thr Lys Val Phe  Gln Gly Val Leu Glu  Leu Glu Gly
        1025                1030                1035

Val Glu  Gly Gln Glu Leu Phe  Tyr Thr Pro Glu Met  Ala Asp Pro
        1040                1045                1050

Lys Ser  Glu Leu Phe Gly Glu  Thr Ala Arg Ser Ile  Glu Ser Thr
        1055                1060                1065

Leu Asp  Asp Leu Phe Arg Asn  Ser Asp Val Lys Lys  Asp Phe Arg
        1070                1075                1080

Ser Val  Arg Leu Arg Asp Leu  Gly Pro Gly Lys Ser  Val Arg Ala
        1085                1090                1095

Ile Val  Asp Val His Phe Asp  Pro Thr Thr Ala Phe  Arg Ala Pro
        1100                1105                1110

Asp Val  Ala Arg Ala Leu Leu  Arg Gln Ile Gln Val  Ser Arg Arg
        1115                1120                1125

Arg Ser  Leu Gly Val Arg Arg  Pro Leu Gln Glu His  Val Arg Phe
        1130                1135                1140

Met Asp  Phe Asp Trp Phe Pro  Ala Phe Ile Thr Gly  Ala Thr Ser
        1145                1150                1155
```

-continued

```
Gly Ala  Ile Ala Ala Gly Ala  Thr Ala Arg Ala Thr  Thr Ala Ser
    1160              1165              1170

Arg Leu  Pro Ser Ser Ala Val  Thr Pro Arg Ala Pro  His Pro Ser
    1175              1180              1185

His Thr  Ser Gln Pro Val Ala  Lys Thr Thr Ala Ala  Pro Thr Thr
    1190              1195              1200

Arg Arg  Pro Pro Thr Thr Ala  Pro Ser Arg Val Pro  Gly Arg Arg
    1205              1210              1215

Pro Pro  Ala Pro Gln Gln Pro  Pro Lys Pro Cys Asp  Ser Gln Pro
    1220              1225              1230

Cys Phe  His Gly Gly Thr Cys  Gln Asp Trp Ala Leu  Gly Gly Gly
    1235              1240              1245

Phe Thr  Cys Ser Cys Pro Ala  Gly Arg Gly Gly Ala  Val Cys Glu
    1250              1255              1260

Lys Val  Leu Gly Ala Pro Val  Pro Ala Phe Glu Gly  Arg Ser Phe
    1265              1270              1275

Leu Ala  Phe Pro Thr Leu Arg  Ala Tyr His Thr Leu  Arg Leu Ala
    1280              1285              1290

Leu Glu  Phe Arg Ala Leu Glu  Pro Gln Gly Leu Leu  Leu Tyr Asn
    1295              1300              1305

Gly Asn  Ala Arg Gly Lys Asp  Phe Leu Ala Leu Ala  Leu Leu Asp
    1310              1315              1320

Gly Arg  Val Gln Leu Arg Phe  Asp Thr Gly Ser Gly  Pro Ala Val
    1325              1330              1335

Leu Thr  Ser Ala Val Pro Val  Glu Pro Gly Gln Trp  His Arg Leu
    1340              1345              1350

Glu Leu  Ser Arg His Trp Arg  Arg Gly Thr Leu Ser  Val Asp Gly
    1355              1360              1365

Glu Thr  Pro Val Leu Gly Glu  Ser Pro Ser Gly Thr  Asp Gly Leu
    1370              1375              1380

Asn Leu  Asp Thr Asp Leu Phe  Val Gly Gly Val Pro  Glu Asp Gln
    1385              1390              1395

Ala Ala  Val Ala Leu Glu Arg  Thr Phe Val Gly Ala  Gly Leu Arg
    1400              1405              1410

Gly Cys  Ile Arg Leu Leu Asp  Val Asn Asn Gln Arg  Leu Glu Leu
    1415              1420              1425

Gly Ile  Gly Pro Gly Ala Ala  Thr Arg Gly Ser Gly  Val Gly Glu
    1430              1435              1440

Cys Gly  Asp His Pro Cys Leu  Pro Asn Pro Cys His  Gly Gly Ala
    1445              1450              1455

Pro Cys  Gln Asn Leu Glu Ala  Gly Arg Phe His Cys  Gln Cys Pro
    1460              1465              1470

Pro Gly  Arg Val Gly Pro Thr  Cys Ala Asp Glu Lys  Ser Pro Cys
    1475              1480              1485

Gln Pro  Asn Pro Cys His Gly  Ala Ala Pro Cys Arg  Val Leu Pro
    1490              1495              1500

Glu Gly  Gly Ala Gln Cys Glu  Cys Pro Leu Gly Arg  Glu Gly Thr
    1505              1510              1515

Phe Cys  Gln Thr Ala Ser Gly  Gln Asp Gly Ser Gly  Pro Phe Leu
    1520              1525              1530

Ala Asp  Phe Asn Gly Phe Ser  His Leu Glu Leu Arg  Gly Leu His
    1535              1540              1545

Thr Phe  Ala Arg Asp Leu Gly  Glu Lys Met Ala Leu  Glu Val Val
```

-continued

```
          1550                1555                1560

Phe Leu  Ala Arg Gly Pro Ser  Gly Leu Leu Leu Tyr  Asn Gly Gln
     1565                1570                1575

Lys Thr  Asp Gly Lys Gly Asp  Phe Val Ser Leu Ala  Leu Arg Asp
     1580                1585                1590

Arg Arg  Leu Glu Phe Arg Tyr  Asp Leu Gly Lys Gly  Ala Ala Val
     1595                1600                1605

Ile Arg  Ser Arg Glu Pro Val  Thr Leu Gly Ala Trp  Thr Arg Val
     1610                1615                1620

Ser Leu  Glu Arg Asn Gly Arg  Lys Gly Ala Leu Arg  Val Gly Asp
     1625                1630                1635

Gly Pro  Arg Val Leu Gly Glu  Ser Pro Lys Ser Arg  Lys Val Pro
     1640                1645                1650

His Thr  Val Leu Asn Leu Lys  Glu Pro Leu Tyr Val  Gly Gly Ala
     1655                1660                1665

Pro Asp  Phe Ser Lys Leu Ala  Arg Ala Ala Ala Val  Ser Ser Gly
     1670                1675                1680

Phe Asp  Gly Ala Ile Gln Leu  Val Ser Leu Gly Gly  Arg Gln Leu
     1685                1690                1695

Leu Thr  Pro Glu His Val Leu  Arg Gln Val Asp Val  Thr Ser Phe
     1700                1705                1710

Ala Gly  His Pro Cys Thr Arg  Ala Ser Gly His Pro  Cys Leu Asn
     1715                1720                1725

Gly Ala  Ser Cys Val Pro Arg  Glu Ala Ala Tyr Val  Cys Leu Cys
     1730                1735                1740

Pro Gly  Gly Phe Ser Gly Pro  His Cys Glu Lys Gly  Leu Val Glu
     1745                1750                1755

Lys Ser  Ala Gly Asp Val Asp  Thr Leu Ala Phe Asp  Gly Arg Thr
     1760                1765                1770

Phe Val  Glu Tyr Leu Asn Ala  Val Thr Glu Ser Glu  Leu Ala Asn
     1775                1780                1785

Glu Ile  Pro Val Pro Glu Thr  Leu Asp Ser Gly Ala  Leu His Ser
     1790                1795                1800

Glu Lys  Ala Leu Gln Ser Asn  His Phe Glu Leu Ser  Leu Arg Thr
     1805                1810                1815

Glu Ala  Thr Gln Gly Leu Val  Leu Trp Ser Gly Lys  Ala Thr Glu
     1820                1825                1830

Arg Ala  Asp Tyr Val Ala Leu  Ala Ile Val Asp Gly  His Leu Gln
     1835                1840                1845

Leu Ser  Tyr Asn Leu Gly Ser  Gln Pro Val Val Leu  Arg Ser Thr
     1850                1855                1860

Val Pro  Val Asn Thr Asn Arg  Trp Leu Arg Val Val  Ala His Arg
     1865                1870                1875

Glu Gln  Arg Glu Gly Ser Leu  Gln Val Gly Asn Glu  Ala Pro Val
     1880                1885                1890

Thr Gly  Ser Ser Pro Leu Gly  Ala Thr Gln Leu Asp  Thr Asp Gly
     1895                1900                1905

Ala Leu  Trp Leu Gly Gly Leu  Pro Glu Leu Pro Val  Gly Pro Ala
     1910                1915                1920

Leu Pro  Lys Ala Tyr Gly Thr  Gly Phe Val Gly Cys  Leu Arg Asp
     1925                1930                1935

Val Val  Val Gly Arg His Pro  Leu His Leu Leu Glu  Asp Ala Val
     1940                1945                1950
```

```
Thr Lys  Pro Glu Leu Arg Pro  Cys Pro Thr Pro
    1955               1960
```

<210> SEQ ID NO 6
<211> LENGTH: 2049
<212> TYPE: PRT
<213> ORGANISM: Artificial Sequence
<220> FEATURE:
<223> OTHER INFORMATION: Polypeptide sequence corresponding to splice
      variant of human agrin corresponding to UniProt accession no.
      O00468-3

<400> SEQUENCE: 6

```
Met Ala Gly Arg Ser His Pro Gly Pro Leu Arg Pro Leu Leu Pro Leu
1               5                   10                  15

Leu Val Val Ala Ala Cys Val Leu Pro Gly Ala Gly Gly Thr Cys Pro
            20                  25                  30

Glu Arg Ala Leu Glu Arg Arg Glu Glu Glu Ala Asn Val Val Leu Thr
        35                  40                  45

Gly Thr Val Glu Glu Ile Leu Asn Val Asp Pro Val Gln His Thr Tyr
    50                  55                  60

Ser Cys Lys Val Arg Val Trp Arg Tyr Leu Lys Gly Lys Asp Leu Val
65                  70                  75                  80

Ala Arg Glu Ser Leu Leu Asp Gly Gly Asn Lys Val Val Ile Ser Gly
            85                  90                  95

Phe Gly Asp Pro Leu Ile Cys Asp Asn Gln Val Ser Thr Gly Asp Thr
            100                 105                 110

Arg Ile Phe Phe Val Asn Pro Ala Pro Pro Tyr Leu Trp Pro Ala His
            115                 120                 125

Lys Asn Glu Leu Met Leu Asn Ser Ser Leu Met Arg Ile Thr Leu Arg
        130                 135                 140

Asn Leu Glu Glu Val Glu Phe Cys Val Glu Asp Lys Pro Gly Thr His
145                 150                 155                 160

Phe Thr Pro Val Pro Pro Thr Pro Pro Asp Ala Cys Arg Gly Met Leu
                165                 170                 175

Cys Gly Phe Gly Ala Val Cys Glu Pro Asn Ala Glu Gly Pro Gly Arg
            180                 185                 190

Ala Ser Cys Val Cys Lys Lys Ser Pro Cys Pro Ser Val Val Ala Pro
            195                 200                 205

Val Cys Gly Ser Asp Ala Ser Thr Tyr Ser Asn Glu Cys Glu Leu Gln
    210                 215                 220

Arg Ala Gln Cys Ser Gln Gln Arg Arg Ile Arg Leu Leu Ser Arg Gly
225                 230                 235                 240

Pro Cys Gly Ser Arg Asp Pro Cys Ser Asn Val Thr Cys Ser Phe Gly
                245                 250                 255

Ser Thr Cys Ala Arg Ser Ala Asp Gly Leu Thr Ala Ser Cys Leu Cys
            260                 265                 270

Pro Ala Thr Cys Arg Gly Ala Pro Glu Gly Thr Val Cys Gly Ser Asp
            275                 280                 285

Gly Ala Asp Tyr Pro Gly Glu Cys Gln Leu Leu Arg Arg Ala Cys Ala
    290                 295                 300

Arg Gln Glu Asn Val Phe Lys Lys Phe Asp Gly Pro Cys Asp Pro Cys
305                 310                 315                 320

Gln Gly Ala Leu Pro Asp Pro Ser Arg Ser Cys Arg Val Asn Pro Arg
                325                 330                 335
```

-continued

```
Thr Arg Arg Pro Glu Met Leu Leu Arg Pro Glu Ser Cys Pro Ala Arg
            340                 345                 350

Gln Ala Pro Val Cys Gly Asp Asp Gly Val Thr Tyr Glu Asn Asp Cys
            355                 360                 365

Val Met Gly Arg Ser Gly Ala Ala Arg Gly Leu Leu Leu Gln Lys Val
    370                 375                 380

Arg Ser Gly Gln Cys Gln Gly Arg Asp Gln Cys Pro Glu Pro Cys Arg
385                 390                 395                 400

Phe Asn Ala Val Cys Leu Ser Arg Arg Gly Arg Pro Arg Cys Ser Cys
                405                 410                 415

Asp Arg Val Thr Cys Asp Gly Ala Tyr Arg Pro Val Cys Ala Gln Asp
            420                 425                 430

Gly Arg Thr Tyr Asp Ser Asp Cys Trp Arg Gln Gln Ala Glu Cys Arg
            435                 440                 445

Gln Gln Arg Ala Ile Pro Ser Lys His Gln Gly Pro Cys Asp Gln Ala
    450                 455                 460

Pro Ser Pro Cys Leu Gly Val Gln Cys Ala Phe Gly Ala Thr Cys Ala
465                 470                 475                 480

Val Lys Asn Gly Gln Ala Ala Cys Glu Cys Leu Gln Ala Cys Ser Ser
                485                 490                 495

Leu Tyr Asp Pro Val Cys Gly Ser Asp Gly Val Thr Tyr Gly Ser Ala
                500                 505                 510

Cys Glu Leu Glu Ala Thr Ala Cys Thr Leu Gly Arg Glu Ile Gln Val
            515                 520                 525

Ala Arg Lys Gly Pro Cys Asp Arg Cys Gly Gln Cys Arg Phe Gly Ala
    530                 535                 540

Leu Cys Glu Ala Glu Thr Gly Arg Cys Val Cys Pro Ser Glu Cys Val
545                 550                 555                 560

Ala Leu Ala Gln Pro Val Cys Gly Ser Asp Gly His Thr Tyr Pro Ser
                565                 570                 575

Glu Cys Met Leu His Val His Ala Cys Thr His Gln Ile Ser Leu His
            580                 585                 590

Val Ala Ser Ala Gly Pro Cys Glu Thr Cys Gly Asp Ala Val Cys Ala
    595                 600                 605

Phe Gly Ala Val Cys Ser Ala Gly Gln Cys Val Cys Pro Arg Cys Glu
    610                 615                 620

His Pro Pro Pro Gly Pro Val Cys Gly Ser Asp Gly Val Thr Tyr Gly
625                 630                 635                 640

Ser Ala Cys Glu Leu Arg Glu Ala Ala Cys Leu Gln Gln Thr Gln Ile
                645                 650                 655

Glu Glu Ala Arg Ala Gly Pro Cys Glu Gln Ala Glu Cys Gly Ser Gly
            660                 665                 670

Gly Ser Gly Ser Gly Glu Asp Gly Asp Cys Glu Gln Glu Leu Cys Arg
            675                 680                 685

Gln Arg Gly Gly Ile Trp Asp Glu Asp Ser Glu Asp Gly Pro Cys Val
    690                 695                 700

Cys Asp Phe Ser Cys Gln Ser Val Pro Gly Ser Pro Val Cys Gly Ser
705                 710                 715                 720

Asp Gly Val Thr Tyr Ser Thr Glu Cys Glu Leu Lys Lys Ala Arg Cys
                725                 730                 735

Glu Ser Gln Arg Gly Leu Tyr Val Ala Ala Gln Gly Ala Cys Arg Gly
            740                 745                 750

Pro Thr Phe Ala Pro Leu Pro Pro Val Ala Pro Leu His Cys Ala Gln
```

-continued

```
         755                760                765
Thr Pro Tyr Gly Cys Cys Gln Asp Asn Ile Thr Ala Ala Arg Gly Val
    770                775                780
Gly Leu Ala Gly Cys Pro Ser Ala Cys Gln Cys Asn Pro His Gly Ser
785                790                795                800
Tyr Gly Gly Thr Cys Asp Pro Ala Thr Gly Gln Cys Ser Cys Arg Pro
                805                810                815
Gly Val Gly Gly Leu Arg Cys Asp Arg Cys Glu Pro Gly Phe Trp Asn
            820                825                830
Phe Arg Gly Ile Val Thr Asp Gly Arg Ser Gly Cys Thr Pro Cys Ser
            835                840                845
Cys Asp Pro Gln Gly Ala Val Arg Asp Asp Cys Glu Gln Met Thr Gly
    850                855                860
Leu Cys Ser Cys Lys Pro Gly Val Ala Gly Pro Lys Cys Gly Gln Cys
865                870                875                880
Pro Asp Gly Arg Ala Leu Gly Pro Ala Gly Cys Glu Ala Asp Ala Ser
                885                890                895
Ala Pro Ala Thr Cys Ala Glu Met Arg Cys Glu Phe Gly Ala Arg Cys
                900                905                910
Val Glu Glu Ser Gly Ser Ala His Cys Val Cys Pro Met Leu Thr Cys
                915                920                925
Pro Glu Ala Asn Ala Thr Lys Val Cys Gly Ser Asp Gly Val Thr Tyr
    930                935                940
Gly Asn Glu Cys Gln Leu Lys Thr Ile Ala Cys Arg Gln Gly Leu Gln
945                950                955                960
Ile Ser Ile Gln Ser Leu Gly Pro Cys Gln Glu Ala Val Ala Pro Ser
                965                970                975
Thr His Pro Thr Ser Ala Ser Val Thr Val Thr Thr Pro Gly Leu Leu
            980                985                990
Leu Ser Gln Ala Leu Pro Ala Pro  Pro Gly Ala Leu Pro  Leu Ala Pro
        995                1000                1005
Ser Ser  Thr Ala His Ser Gln  Thr Thr Pro Pro Pro  Ser Ser Arg
    1010                1015                1020
Pro Arg  Thr Thr Ala Ser Val  Pro Arg Thr Thr Val  Trp Pro Val
    1025                1030                1035
Leu Thr  Val Pro Pro Thr Ala  Pro Ser Pro Ala Pro  Ser Leu Val
    1040                1045                1050
Ala Ser  Ala Phe Gly Glu Ser  Gly Ser Thr Asp Gly  Ser Ser Asp
    1055                1060                1065
Glu Glu  Leu Ser Gly Asp Gln  Glu Ala Ser Gly Gly  Gly Ser Gly
    1070                1075                1080
Gly Leu  Glu Pro Leu Glu Gly  Ser Ser Val Ala Thr  Pro Gly Pro
    1085                1090                1095
Pro Val  Glu Arg Ala Ser Cys  Tyr Asn Ser Ala Leu  Gly Cys Cys
    1100                1105                1110
Ser Asp  Gly Lys Thr Pro Ser  Leu Asp Ala Glu Gly  Ser Asn Cys
    1115                1120                1125
Pro Ala  Thr Lys Val Phe Gln  Gly Val Leu Glu Leu  Glu Gly Val
    1130                1135                1140
Glu Gly  Gln Glu Leu Phe Tyr  Thr Pro Glu Met Ala  Asp Pro Lys
    1145                1150                1155
Ser Glu  Leu Phe Gly Glu Thr  Ala Arg Ser Ile Glu  Ser Thr Leu
    1160                1165                1170
```

Asp Asp Leu Phe Arg Asn Ser  Asp Val Lys Lys Asp  Phe Arg Ser
    1175            1180            1185

Val Arg Leu Arg Asp Leu Gly  Pro Gly Lys Ser Val  Arg Ala Ile
    1190            1195            1200

Val Asp Val His Phe Asp Pro  Thr Thr Ala Phe Arg  Ala Pro Asp
    1205            1210            1215

Val Ala Arg Ala Leu Leu Arg  Gln Ile Gln Val Ser  Arg Arg Arg
    1220            1225            1230

Ser Leu Gly Val Arg Arg Pro  Leu Gln Glu His Val  Arg Phe Met
    1235            1240            1245

Asp Phe Asp Trp Phe Pro Ala  Phe Ile Thr Gly Ala  Thr Ser Gly
    1250            1255            1260

Ala Ile Ala Ala Gly Ala Thr  Ala Arg Ala Thr Thr  Ala Ser Arg
    1265            1270            1275

Leu Pro Ser Ser Ala Val Thr  Pro Arg Ala Pro His  Pro Ser His
    1280            1285            1290

Thr Ser Gln Pro Val Ala Lys  Thr Thr Ala Ala Pro  Thr Thr Arg
    1295            1300            1305

Arg Pro Pro Thr Thr Ala Pro  Ser Arg Val Pro Gly  Arg Arg Pro
    1310            1315            1320

Pro Ala Pro Gln Gln Pro Pro  Lys Pro Cys Asp Ser  Gln Pro Cys
    1325            1330            1335

Phe His Gly Gly Thr Cys Gln  Asp Trp Ala Leu Gly  Gly Gly Phe
    1340            1345            1350

Thr Cys Ser Cys Pro Ala Gly  Arg Gly Gly Ala Val  Cys Glu Lys
    1355            1360            1365

Val Leu Gly Ala Pro Val Pro  Ala Phe Glu Gly Arg  Ser Phe Leu
    1370            1375            1380

Ala Phe Pro Thr Leu Arg Ala  Tyr His Thr Leu Arg  Leu Ala Leu
    1385            1390            1395

Glu Phe Arg Ala Leu Glu Pro  Gln Gly Leu Leu Leu  Tyr Asn Gly
    1400            1405            1410

Asn Ala Arg Gly Lys Asp Phe  Leu Ala Leu Ala Leu  Leu Asp Gly
    1415            1420            1425

Arg Val Gln Leu Arg Phe Asp  Thr Gly Ser Gly Pro  Ala Val Leu
    1430            1435            1440

Thr Ser Ala Val Pro Val Glu  Pro Gly Gln Trp His  Arg Leu Glu
    1445            1450            1455

Leu Ser Arg His Trp Arg Arg  Gly Thr Leu Ser Val  Asp Gly Glu
    1460            1465            1470

Thr Pro Val Leu Gly Glu Ser  Pro Ser Gly Thr Asp  Gly Leu Asn
    1475            1480            1485

Leu Asp Thr Asp Leu Phe Val  Gly Gly Val Pro Glu  Asp Gln Ala
    1490            1495            1500

Ala Val Ala Leu Glu Arg Thr  Phe Val Gly Ala Gly  Leu Arg Gly
    1505            1510            1515

Cys Ile Arg Leu Leu Asp Val  Asn Asn Gln Arg Leu  Glu Leu Gly
    1520            1525            1530

Ile Gly Pro Gly Ala Ala Thr  Arg Gly Ser Gly Val  Gly Glu Cys
    1535            1540            1545

Gly Asp His Pro Cys Leu Pro  Asn Pro Cys His Gly  Gly Ala Pro
    1550            1555            1560

-continued

```
Cys Gln  Asn Leu Glu Ala Gly  Arg Phe His Cys Gln  Cys Pro Pro
    1565              1570              1575

Gly Arg  Val Gly Pro Thr Cys  Ala Asp Glu Lys Ser  Pro Cys Gln
    1580              1585              1590

Pro Asn  Pro Cys His Gly Ala  Ala Pro Cys Arg Val  Leu Pro Glu
    1595              1600              1605

Gly Gly  Ala Gln Cys Glu Cys  Pro Leu Gly Arg Glu  Gly Thr Phe
    1610              1615              1620

Cys Gln  Thr Ala Ser Gly Gln  Asp Gly Ser Gly Pro  Phe Leu Ala
    1625              1630              1635

Asp Phe  Asn Gly Phe Ser His  Leu Glu Leu Arg Gly  Leu His Thr
    1640              1645              1650

Phe Ala  Arg Asp Leu Gly Glu  Lys Met Ala Leu Glu  Val Val Phe
    1655              1660              1665

Leu Ala  Arg Gly Pro Ser Gly  Leu Leu Leu Tyr Asn  Gly Gln Lys
    1670              1675              1680

Thr Asp  Gly Lys Gly Asp Phe  Val Ser Leu Ala Leu  Arg Asp Arg
    1685              1690              1695

Arg Leu  Glu Phe Arg Tyr Asp  Leu Gly Lys Gly Ala  Ala Val Ile
    1700              1705              1710

Arg Ser  Arg Glu Pro Val Thr  Leu Gly Ala Trp Thr  Arg Val Ser
    1715              1720              1725

Leu Glu  Arg Asn Gly Arg Lys  Gly Ala Leu Arg Val  Gly Asp Gly
    1730              1735              1740

Pro Arg  Val Leu Gly Glu Ser  Pro Lys Ser Arg Lys  Val Pro His
    1745              1750              1755

Thr Val  Leu Asn Leu Lys Glu  Pro Leu Tyr Val Gly  Gly Ala Pro
    1760              1765              1770

Asp Phe  Ser Lys Leu Ala Arg  Ala Ala Ala Val Ser  Ser Gly Phe
    1775              1780              1785

Asp Gly  Ala Ile Gln Leu Val  Ser Leu Gly Gly Arg  Gln Leu Leu
    1790              1795              1800

Thr Pro  Glu His Val Leu Arg  Gln Val Asp Val Thr  Ser Phe Ala
    1805              1810              1815

Gly His  Pro Cys Thr Arg Ala  Ser Gly His Pro Cys  Leu Asn Gly
    1820              1825              1830

Ala Ser  Cys Val Pro Arg Glu  Ala Ala Tyr Val Cys  Leu Cys Pro
    1835              1840              1845

Gly Gly  Phe Ser Gly Pro His  Cys Glu Lys Gly Leu  Val Glu Lys
    1850              1855              1860

Ser Ala  Gly Asp Val Asp Thr  Leu Ala Phe Asp Gly  Arg Thr Phe
    1865              1870              1875

Val Glu  Tyr Leu Asn Ala Val  Thr Glu Ser Glu Lys  Ala Leu Gln
    1880              1885              1890

Ser Asn  His Phe Glu Leu Ser  Leu Arg Thr Glu Ala  Thr Gln Gly
    1895              1900              1905

Leu Val  Leu Trp Ser Gly Lys  Ala Thr Glu Arg Ala  Asp Tyr Val
    1910              1915              1920

Ala Leu  Ala Ile Val Asp Gly  His Leu Gln Leu Ser  Tyr Asn Leu
    1925              1930              1935

Gly Ser  Gln Pro Val Val Leu  Arg Ser Thr Val Pro  Val Asn Thr
    1940              1945              1950

Asn Arg  Trp Leu Arg Val Val  Ala His Arg Glu Gln  Arg Glu Gly
```

-continued

```
      1955                1960                1965

Ser Leu  Gln Val Gly Asn Glu  Ala Pro Val Thr Gly  Ser Ser Pro
    1970                1975                1980

Leu Gly  Ala Thr Gln Leu Asp  Thr Asp Gly Ala Leu  Trp Leu Gly
    1985                1990                1995

Gly Leu  Pro Glu Leu Pro Val  Gly Pro Ala Leu Pro  Lys Ala Tyr
    2000                2005                2010

Gly Thr  Gly Phe Val Gly Cys  Leu Arg Asp Val Val  Val Gly Arg
    2015                2020                2025

His Pro  Leu His Leu Leu Glu  Asp Ala Val Thr Lys  Pro Glu Leu
    2030                2035                2040

Arg Pro  Cys Pro Thr Pro
    2045

<210> SEQ ID NO 7
<211> LENGTH: 2060
<212> TYPE: PRT
<213> ORGANISM: Artificial Sequence
<220> FEATURE:
<223> OTHER INFORMATION: Polypeptide sequence corresponding to splice
      variant of human agrin corresponding to UniProt accession no.
      O00468-4

<400> SEQUENCE: 7

Met Ala Gly Arg Ser His Pro Gly Pro Leu Arg Pro Leu Leu Pro Leu
1               5                   10                  15

Leu Val Val Ala Ala Cys Val Leu Pro Gly Ala Gly Gly Thr Cys Pro
                20                  25                  30

Glu Arg Ala Leu Glu Arg Arg Glu Glu Glu Ala Asn Val Val Leu Thr
            35                  40                  45

Gly Thr Val Glu Glu Ile Leu Asn Val Asp Pro Val Gln His Thr Tyr
        50                  55                  60

Ser Cys Lys Val Arg Val Trp Arg Tyr Leu Lys Gly Lys Asp Leu Val
65                  70                  75                  80

Ala Arg Glu Ser Leu Leu Asp Gly Gly Asn Lys Val Val Ile Ser Gly
                85                  90                  95

Phe Gly Asp Pro Leu Ile Cys Asp Asn Gln Val Ser Thr Gly Asp Thr
                100                 105                 110

Arg Ile Phe Phe Val Asn Pro Ala Pro Pro Tyr Leu Trp Pro Ala His
            115                 120                 125

Lys Asn Glu Leu Met Leu Asn Ser Ser Leu Met Arg Ile Thr Leu Arg
        130                 135                 140

Asn Leu Glu Glu Val Glu Phe Cys Val Glu Asp Lys Pro Gly Thr His
145                 150                 155                 160

Phe Thr Pro Val Pro Pro Thr Pro Pro Asp Ala Cys Arg Gly Met Leu
                165                 170                 175

Cys Gly Phe Gly Ala Val Cys Glu Pro Asn Ala Glu Gly Pro Gly Arg
            180                 185                 190

Ala Ser Cys Val Cys Lys Lys Ser Pro Cys Pro Ser Val Val Ala Pro
            195                 200                 205

Val Cys Gly Ser Asp Ala Ser Thr Tyr Ser Asn Glu Cys Glu Leu Gln
        210                 215                 220

Arg Ala Gln Cys Ser Gln Gln Arg Arg Ile Arg Leu Leu Ser Arg Gly
225                 230                 235                 240

Pro Cys Gly Ser Arg Asp Pro Cys Ser Asn Val Thr Cys Ser Phe Gly
                245                 250                 255
```

```
Ser Thr Cys Ala Arg Ser Ala Asp Gly Leu Thr Ala Ser Cys Leu Cys
        260                 265                 270

Pro Ala Thr Cys Arg Gly Ala Pro Glu Gly Thr Val Cys Gly Ser Asp
        275                 280                 285

Gly Ala Asp Tyr Pro Gly Glu Cys Gln Leu Leu Arg Arg Ala Cys Ala
        290                 295                 300

Arg Gln Glu Asn Val Phe Lys Lys Phe Asp Gly Pro Cys Asp Pro Cys
305                 310                 315                 320

Gln Gly Ala Leu Pro Asp Pro Ser Arg Ser Cys Arg Val Asn Pro Arg
                325                 330                 335

Thr Arg Arg Pro Glu Met Leu Leu Arg Pro Glu Ser Cys Pro Ala Arg
                340                 345                 350

Gln Ala Pro Val Cys Gly Asp Asp Gly Val Thr Tyr Glu Asn Asp Cys
        355                 360                 365

Val Met Gly Arg Ser Gly Ala Ala Arg Gly Leu Leu Leu Gln Lys Val
        370                 375                 380

Arg Ser Gly Gln Cys Gln Gly Arg Asp Gln Cys Pro Glu Pro Cys Arg
385                 390                 395                 400

Phe Asn Ala Val Cys Leu Ser Arg Arg Gly Arg Pro Arg Cys Ser Cys
                405                 410                 415

Asp Arg Val Thr Cys Asp Gly Ala Tyr Arg Pro Val Cys Ala Gln Asp
                420                 425                 430

Gly Arg Thr Tyr Asp Ser Asp Cys Trp Arg Gln Gln Ala Glu Cys Arg
                435                 440                 445

Gln Gln Arg Ala Ile Pro Ser Lys His Gln Gly Pro Cys Asp Gln Ala
        450                 455                 460

Pro Ser Pro Cys Leu Gly Val Gln Cys Ala Phe Gly Ala Thr Cys Ala
465                 470                 475                 480

Val Lys Asn Gly Gln Ala Ala Cys Glu Cys Leu Gln Ala Cys Ser Ser
                485                 490                 495

Leu Tyr Asp Pro Val Cys Gly Ser Asp Gly Val Thr Tyr Gly Ser Ala
                500                 505                 510

Cys Glu Leu Glu Ala Thr Ala Cys Thr Leu Gly Arg Glu Ile Gln Val
        515                 520                 525

Ala Arg Lys Gly Pro Cys Asp Arg Cys Gly Gln Cys Arg Phe Gly Ala
        530                 535                 540

Leu Cys Glu Ala Glu Thr Gly Arg Cys Val Cys Pro Ser Glu Cys Val
545                 550                 555                 560

Ala Leu Ala Gln Pro Val Cys Gly Ser Asp Gly His Thr Tyr Pro Ser
                565                 570                 575

Glu Cys Met Leu His Val His Ala Cys Thr His Gln Ile Ser Leu His
                580                 585                 590

Val Ala Ser Ala Gly Pro Cys Glu Thr Cys Gly Asp Ala Val Cys Ala
        595                 600                 605

Phe Gly Ala Val Cys Ser Ala Gly Gln Cys Val Cys Pro Arg Cys Glu
        610                 615                 620

His Pro Pro Pro Gly Pro Val Cys Gly Ser Asp Gly Val Thr Tyr Gly
625                 630                 635                 640

Ser Ala Cys Glu Leu Arg Glu Ala Ala Cys Leu Gln Gln Thr Gln Ile
                645                 650                 655

Glu Glu Ala Arg Ala Gly Pro Cys Glu Gln Ala Glu Cys Gly Ser Gly
                660                 665                 670
```

-continued

```
Gly Ser Gly Ser Gly Glu Asp Gly Asp Cys Glu Gln Glu Leu Cys Arg
        675             680             685

Gln Arg Gly Gly Ile Trp Asp Glu Asp Ser Glu Asp Gly Pro Cys Val
    690             695             700

Cys Asp Phe Ser Cys Gln Ser Val Pro Gly Ser Pro Val Cys Gly Ser
705             710             715             720

Asp Gly Val Thr Tyr Ser Thr Glu Cys Glu Leu Lys Lys Ala Arg Cys
            725             730             735

Glu Ser Gln Arg Gly Leu Tyr Val Ala Ala Gln Gly Ala Cys Arg Gly
            740             745             750

Pro Thr Phe Ala Pro Leu Pro Pro Val Ala Pro Leu His Cys Ala Gln
        755             760             765

Thr Pro Tyr Gly Cys Cys Gln Asp Asn Ile Thr Ala Ala Arg Gly Val
        770             775             780

Gly Leu Ala Gly Cys Pro Ser Ala Cys Gln Cys Asn Pro His Gly Ser
785             790             795             800

Tyr Gly Gly Thr Cys Asp Pro Ala Thr Gly Gln Cys Ser Cys Arg Pro
            805             810             815

Gly Val Gly Gly Leu Arg Cys Asp Arg Cys Glu Pro Gly Phe Trp Asn
        820             825             830

Phe Arg Gly Ile Val Thr Asp Gly Arg Ser Gly Cys Thr Pro Cys Ser
        835             840             845

Cys Asp Pro Gln Gly Ala Val Arg Asp Asp Cys Glu Gln Met Thr Gly
        850             855             860

Leu Cys Ser Cys Lys Pro Gly Val Ala Gly Pro Lys Cys Gly Gln Cys
865             870             875             880

Pro Asp Gly Arg Ala Leu Gly Pro Ala Gly Cys Glu Ala Asp Ala Ser
            885             890             895

Ala Pro Ala Thr Cys Ala Glu Met Arg Cys Glu Phe Gly Ala Arg Cys
            900             905             910

Val Glu Glu Ser Gly Ser Ala His Cys Val Cys Pro Met Leu Thr Cys
        915             920             925

Pro Glu Ala Asn Ala Thr Lys Val Cys Gly Ser Asp Gly Val Thr Tyr
    930             935             940

Gly Asn Glu Cys Gln Leu Lys Thr Ile Ala Cys Arg Gln Gly Leu Gln
945             950             955             960

Ile Ser Ile Gln Ser Leu Gly Pro Cys Gln Glu Ala Val Ala Pro Ser
            965             970             975

Thr His Pro Thr Ser Ala Ser Val Thr Val Thr Thr Pro Gly Leu Leu
        980             985             990

Leu Ser Gln Ala Leu Pro Ala Pro  Pro Gly Ala Leu Pro  Leu Ala Pro
        995             1000             1005

Ser Ser  Thr Ala His Ser Gln  Thr Thr Pro Pro Pro  Ser Ser Arg
    1010             1015             1020

Pro Arg  Thr Thr Ala Ser Val  Pro Arg Thr Thr Val  Trp Pro Val
    1025             1030             1035

Leu Thr  Val Pro Pro Thr Ala  Pro Ser Pro Ala Pro  Ser Leu Val
    1040             1045             1050

Ala Ser  Ala Phe Gly Glu Ser  Gly Ser Thr Asp Gly  Ser Ser Asp
    1055             1060             1065

Glu Glu  Leu Ser Gly Asp Gln  Glu Ala Ser Gly Gly  Gly Ser Gly
    1070             1075             1080

Gly Leu  Glu Pro Leu Glu Gly  Ser Ser Val Ala Thr  Pro Gly Pro
```

```
       1085                1090                1095

Pro Val  Glu Arg Ala Ser Cys  Tyr Asn Ser Ala Leu  Gly Cys Cys
    1100                1105                1110

Ser Asp  Gly Lys Thr Pro Ser  Leu Asp Ala Glu Gly  Ser Asn Cys
    1115                1120                1125

Pro Ala  Thr Lys Val Phe Gln  Gly Val Leu Glu Leu  Glu Gly Val
    1130                1135                1140

Glu Gly  Gln Glu Leu Phe Tyr  Thr Pro Glu Met Ala  Asp Pro Lys
    1145                1150                1155

Ser Glu  Leu Phe Gly Glu Thr  Ala Arg Ser Ile Glu  Ser Thr Leu
    1160                1165                1170

Asp Asp  Leu Phe Arg Asn Ser  Asp Val Lys Lys Asp  Phe Arg Ser
    1175                1180                1185

Val Arg  Leu Arg Asp Leu Gly  Pro Gly Lys Ser Val  Arg Ala Ile
    1190                1195                1200

Val Asp  Val His Phe Asp Pro  Thr Thr Ala Phe Arg  Ala Pro Asp
    1205                1210                1215

Val Ala  Arg Ala Leu Leu Arg  Gln Ile Gln Val Ser  Arg Arg Arg
    1220                1225                1230

Ser Leu  Gly Val Arg Arg Pro  Leu Gln Glu His Val  Arg Phe Met
    1235                1240                1245

Asp Phe  Asp Trp Phe Pro Ala  Phe Ile Thr Gly Ala  Thr Ser Gly
    1250                1255                1260

Ala Ile  Ala Ala Gly Ala Thr  Ala Arg Ala Thr Thr  Ala Ser Arg
    1265                1270                1275

Leu Pro  Ser Ser Ala Val Thr  Pro Arg Ala Pro His  Pro Ser His
    1280                1285                1290

Thr Ser  Gln Pro Val Ala Lys  Thr Thr Ala Ala Pro  Thr Thr Arg
    1295                1300                1305

Arg Pro  Pro Thr Thr Ala Pro  Ser Arg Val Pro Gly  Arg Arg Pro
    1310                1315                1320

Pro Ala  Pro Gln Gln Pro Pro  Lys Pro Cys Asp Ser  Gln Pro Cys
    1325                1330                1335

Phe His  Gly Gly Thr Cys Gln  Asp Trp Ala Leu Gly  Gly Gly Phe
    1340                1345                1350

Thr Cys  Ser Cys Pro Ala Gly  Arg Gly Gly Ala Val  Cys Glu Lys
    1355                1360                1365

Val Leu  Gly Ala Pro Val Pro  Ala Phe Glu Gly Arg  Ser Phe Leu
    1370                1375                1380

Ala Phe  Pro Thr Leu Arg Ala  Tyr His Thr Leu Arg  Leu Ala Leu
    1385                1390                1395

Glu Phe  Arg Ala Leu Glu Pro  Gln Gly Leu Leu Leu  Tyr Asn Gly
    1400                1405                1410

Asn Ala  Arg Gly Lys Asp Phe  Leu Ala Leu Ala Leu  Leu Asp Gly
    1415                1420                1425

Arg Val  Gln Leu Arg Phe Asp  Thr Gly Ser Gly Pro  Ala Val Leu
    1430                1435                1440

Thr Ser  Ala Val Pro Val Glu  Pro Gly Gln Trp His  Arg Leu Glu
    1445                1450                1455

Leu Ser  Arg His Trp Arg Arg  Gly Thr Leu Ser Val  Asp Gly Glu
    1460                1465                1470

Thr Pro  Val Leu Gly Glu Ser  Pro Ser Gly Thr Asp  Gly Leu Asn
    1475                1480                1485
```

-continued

```
Leu Asp Thr Asp Leu Phe Val  Gly Gly Val Pro Glu  Asp Gln Ala
    1490              1495               1500

Ala Val Ala Leu Glu Arg Thr  Phe Val Gly Ala Gly  Leu Arg Gly
    1505              1510               1515

Cys Ile Arg Leu Leu Asp Val  Asn Asn Gln Arg Leu  Glu Leu Gly
    1520              1525               1530

Ile Gly Pro Gly Ala Ala Thr  Arg Gly Ser Gly Val  Gly Glu Cys
    1535              1540               1545

Gly Asp His Pro Cys Leu Pro  Asn Pro Cys His Gly  Gly Ala Pro
    1550              1555               1560

Cys Gln Asn Leu Glu Ala Gly  Arg Phe His Cys Gln  Cys Pro Pro
    1565              1570               1575

Gly Arg Val Gly Pro Thr Cys  Ala Asp Glu Lys Ser  Pro Cys Gln
    1580              1585               1590

Pro Asn Pro Cys His Gly Ala  Ala Pro Cys Arg Val  Leu Pro Glu
    1595              1600               1605

Gly Gly Ala Gln Cys Glu Cys  Pro Leu Gly Arg Glu  Gly Thr Phe
    1610              1615               1620

Cys Gln Thr Ala Ser Gly Gln  Asp Gly Ser Gly Pro  Phe Leu Ala
    1625              1630               1635

Asp Phe Asn Gly Phe Ser His  Leu Glu Leu Arg Gly  Leu His Thr
    1640              1645               1650

Phe Ala Arg Asp Leu Gly Glu  Lys Met Ala Leu Glu  Val Val Phe
    1655              1660               1665

Leu Ala Arg Gly Pro Ser Gly  Leu Leu Leu Tyr Asn  Gly Gln Lys
    1670              1675               1680

Thr Asp Gly Lys Gly Asp Phe  Val Ser Leu Ala Leu  Arg Asp Arg
    1685              1690               1695

Arg Leu Glu Phe Arg Tyr Asp  Leu Gly Lys Gly Ala  Ala Val Ile
    1700              1705               1710

Arg Ser Arg Glu Pro Val Thr  Leu Gly Ala Trp Thr  Arg Val Ser
    1715              1720               1725

Leu Glu Arg Asn Gly Arg Lys  Gly Ala Leu Arg Val  Gly Asp Gly
    1730              1735               1740

Pro Arg Val Leu Gly Glu Ser  Pro Lys Ser Arg Lys  Val Pro His
    1745              1750               1755

Thr Val Leu Asn Leu Lys Glu  Pro Leu Tyr Val Gly  Gly Ala Pro
    1760              1765               1770

Asp Phe Ser Lys Leu Ala Arg  Ala Ala Ala Val Ser  Ser Gly Phe
    1775              1780               1785

Asp Gly Ala Ile Gln Leu Val  Ser Leu Gly Gly Arg  Gln Leu Leu
    1790              1795               1800

Thr Pro Glu His Val Leu Arg  Gln Val Asp Val Thr  Ser Phe Ala
    1805              1810               1815

Gly His Pro Cys Thr Arg Ala  Ser Gly His Pro Cys  Leu Asn Gly
    1820              1825               1830

Ala Ser Cys Val Pro Arg Glu  Ala Ala Tyr Val Cys  Leu Cys Pro
    1835              1840               1845

Gly Gly Phe Ser Gly Pro His  Cys Glu Lys Gly Leu  Val Glu Lys
    1850              1855               1860

Ser Ala Gly Asp Val Asp Thr  Leu Ala Phe Asp Gly  Arg Thr Phe
    1865              1870               1875
```

```
Val Glu  Tyr Leu Asn Ala Val  Thr Glu Ser Pro Glu  Thr Leu Asp
    1880                 1885              1890

Ser Gly  Ala Leu His Ser Glu  Lys Ala Leu Gln Ser  Asn His Phe
    1895                 1900              1905

Glu Leu  Ser Leu Arg Thr Glu  Ala Thr Gln Gly Leu  Val Leu Trp
    1910                 1915              1920

Ser Gly  Lys Ala Thr Glu Arg  Ala Asp Tyr Val Ala  Leu Ala Ile
    1925                 1930              1935

Val Asp  Gly His Leu Gln Leu  Ser Tyr Asn Leu Gly  Ser Gln Pro
    1940                 1945              1950

Val Val  Leu Arg Ser Thr Val  Pro Val Asn Thr Asn  Arg Trp Leu
    1955                 1960              1965

Arg Val  Val Ala His Arg Glu  Gln Arg Glu Gly Ser  Leu Gln Val
    1970                 1975              1980

Gly Asn  Glu Ala Pro Val Thr  Gly Ser Ser Pro Leu  Gly Ala Thr
    1985                 1990              1995

Gln Leu  Asp Thr Asp Gly Ala  Leu Trp Leu Gly Gly  Leu Pro Glu
    2000                 2005              2010

Leu Pro  Val Gly Pro Ala Leu  Pro Lys Ala Tyr Gly  Thr Gly Phe
    2015                 2020              2025

Val Gly  Cys Leu Arg Asp Val  Val Val Gly Arg His  Pro Leu His
    2030                 2035              2040

Leu Leu  Glu Asp Ala Val Thr  Lys Pro Glu Leu Arg  Pro Cys Pro
    2045                 2050              2055

Thr Pro
    2060
```

```
<210> SEQ ID NO 8
<211> LENGTH: 2057
<212> TYPE: PRT
<213> ORGANISM: Artificial Sequence
<220> FEATURE:
<223> OTHER INFORMATION: Polypeptide sequence corresponding to a splice
      variant of human agrin corresponding to UniProt accession no.
      O00468-5

<400> SEQUENCE: 8

Met Ala Gly Arg Ser His Pro Gly Pro Leu Arg Pro Leu Leu Pro Leu
1               5               10              15

Leu Val Val Ala Ala Cys Val Leu Pro Gly Ala Gly Gly Thr Cys Pro
            20              25              30

Glu Arg Ala Leu Glu Arg Arg Glu Glu Glu Ala Asn Val Val Leu Thr
        35              40              45

Gly Thr Val Glu Glu Ile Leu Asn Val Asp Pro Val Gln His Thr Tyr
    50              55              60

Ser Cys Lys Val Arg Val Trp Arg Tyr Leu Lys Gly Lys Asp Leu Val
65              70              75              80

Ala Arg Glu Ser Leu Leu Asp Gly Gly Asn Lys Val Val Ile Ser Gly
            85              90              95

Phe Gly Asp Pro Leu Ile Cys Asp Asn Gln Val Ser Thr Gly Asp Thr
            100             105             110

Arg Ile Phe Phe Val Asn Pro Ala Pro Pro Tyr Leu Trp Pro Ala His
        115             120             125

Lys Asn Glu Leu Met Leu Asn Ser Ser Leu Met Arg Ile Thr Leu Arg
    130             135             140

Asn Leu Glu Glu Val Glu Phe Cys Val Glu Asp Lys Pro Gly Thr His
```

```
145              150               155               160

Phe Thr Pro Val Pro Pro Thr Pro Pro Asp Ala Cys Arg Gly Met Leu
             165               170               175

Cys Gly Phe Gly Ala Val Cys Glu Pro Asn Ala Glu Gly Pro Gly Arg
             180               185               190

Ala Ser Cys Val Cys Lys Lys Ser Pro Cys Pro Ser Val Val Ala Pro
             195               200               205

Val Cys Gly Ser Asp Ala Ser Thr Tyr Ser Asn Glu Cys Glu Leu Gln
             210               215               220

Arg Ala Gln Cys Ser Gln Gln Arg Arg Ile Arg Leu Leu Ser Arg Gly
225               230               235               240

Pro Cys Gly Ser Arg Asp Pro Cys Ser Asn Val Thr Cys Ser Phe Gly
             245               250               255

Ser Thr Cys Ala Arg Ser Ala Asp Gly Leu Thr Ala Ser Cys Leu Cys
             260               265               270

Pro Ala Thr Cys Arg Gly Ala Pro Glu Gly Thr Val Cys Gly Ser Asp
             275               280               285

Gly Ala Asp Tyr Pro Gly Glu Cys Gln Leu Leu Arg Arg Ala Cys Ala
             290               295               300

Arg Gln Glu Asn Val Phe Lys Lys Phe Asp Gly Pro Cys Asp Pro Cys
305               310               315               320

Gln Gly Ala Leu Pro Asp Pro Ser Arg Ser Cys Arg Val Asn Pro Arg
             325               330               335

Thr Arg Arg Pro Glu Met Leu Leu Arg Pro Glu Ser Cys Pro Ala Arg
             340               345               350

Gln Ala Pro Val Cys Gly Asp Asp Gly Val Thr Tyr Glu Asn Asp Cys
             355               360               365

Val Met Gly Arg Ser Gly Ala Ala Arg Gly Leu Leu Leu Gln Lys Val
             370               375               380

Arg Ser Gly Gln Cys Gln Gly Arg Asp Gln Cys Pro Glu Pro Cys Arg
385               390               395               400

Phe Asn Ala Val Cys Leu Ser Arg Arg Gly Arg Pro Arg Cys Ser Cys
             405               410               415

Asp Arg Val Thr Cys Asp Gly Ala Tyr Arg Pro Val Cys Ala Gln Asp
             420               425               430

Gly Arg Thr Tyr Asp Ser Asp Cys Trp Arg Gln Gln Ala Glu Cys Arg
             435               440               445

Gln Gln Arg Ala Ile Pro Ser Lys His Gln Gly Pro Cys Asp Gln Ala
             450               455               460

Pro Ser Pro Cys Leu Gly Val Gln Cys Ala Phe Gly Ala Thr Cys Ala
465               470               475               480

Val Lys Asn Gly Gln Ala Ala Cys Glu Cys Leu Gln Ala Cys Ser Ser
             485               490               495

Leu Tyr Asp Pro Val Cys Gly Ser Asp Gly Val Thr Tyr Gly Ser Ala
             500               505               510

Cys Glu Leu Glu Ala Thr Ala Cys Thr Leu Gly Arg Glu Ile Gln Val
             515               520               525

Ala Arg Lys Gly Pro Cys Asp Arg Cys Gly Gln Cys Arg Phe Gly Ala
             530               535               540

Leu Cys Glu Ala Glu Thr Gly Arg Cys Val Cys Pro Ser Glu Cys Val
545               550               555               560

Ala Leu Ala Gln Pro Val Cys Gly Ser Asp Gly His Thr Tyr Pro Ser
             565               570               575
```

-continued

```
Glu Cys Met Leu His Val His Ala Cys Thr His Gln Ile Ser Leu His
            580                 585                 590

Val Ala Ser Ala Gly Pro Cys Glu Thr Cys Gly Asp Ala Val Cys Ala
            595                 600                 605

Phe Gly Ala Val Cys Ser Ala Gly Gln Cys Val Cys Pro Arg Cys Glu
            610                 615                 620

His Pro Pro Pro Gly Pro Val Cys Gly Ser Asp Gly Val Thr Tyr Gly
625                 630                 635                 640

Ser Ala Cys Glu Leu Arg Glu Ala Ala Cys Leu Gln Gln Thr Gln Ile
            645                 650                 655

Glu Glu Ala Arg Ala Gly Pro Cys Glu Gln Ala Glu Cys Gly Ser Gly
            660                 665                 670

Gly Ser Gly Ser Gly Glu Asp Gly Asp Cys Glu Gln Glu Leu Cys Arg
            675                 680                 685

Gln Arg Gly Gly Ile Trp Asp Glu Asp Ser Glu Asp Gly Pro Cys Val
            690                 695                 700

Cys Asp Phe Ser Cys Gln Ser Val Pro Gly Ser Pro Val Cys Gly Ser
705                 710                 715                 720

Asp Gly Val Thr Tyr Ser Thr Glu Cys Glu Leu Lys Lys Ala Arg Cys
            725                 730                 735

Glu Ser Gln Arg Gly Leu Tyr Val Ala Ala Gln Gly Ala Cys Arg Gly
            740                 745                 750

Pro Thr Phe Ala Pro Leu Pro Pro Val Ala Pro Leu His Cys Ala Gln
            755                 760                 765

Thr Pro Tyr Gly Cys Cys Gln Asp Asn Ile Thr Ala Ala Arg Gly Val
            770                 775                 780

Gly Leu Ala Gly Cys Pro Ser Ala Cys Gln Cys Asn Pro His Gly Ser
785                 790                 795                 800

Tyr Gly Gly Thr Cys Asp Pro Ala Thr Gly Gln Cys Ser Cys Arg Pro
            805                 810                 815

Gly Val Gly Gly Leu Arg Cys Asp Arg Cys Glu Pro Gly Phe Trp Asn
            820                 825                 830

Phe Arg Gly Ile Val Thr Asp Gly Arg Ser Gly Cys Thr Pro Cys Ser
            835                 840                 845

Cys Asp Pro Gln Gly Ala Val Arg Asp Asp Cys Glu Gln Met Thr Gly
850                 855                 860

Leu Cys Ser Cys Lys Pro Gly Val Ala Gly Pro Lys Cys Gly Gln Cys
865                 870                 875                 880

Pro Asp Gly Arg Ala Leu Gly Pro Ala Gly Cys Glu Ala Asp Ala Ser
            885                 890                 895

Ala Pro Ala Thr Cys Ala Glu Met Arg Cys Glu Phe Gly Ala Arg Cys
            900                 905                 910

Val Glu Glu Ser Gly Ser Ala His Cys Val Cys Pro Met Leu Thr Cys
            915                 920                 925

Pro Glu Ala Asn Ala Thr Lys Val Cys Gly Ser Asp Gly Val Thr Tyr
            930                 935                 940

Gly Asn Glu Cys Gln Leu Lys Thr Ile Ala Cys Arg Gln Gly Leu Gln
945                 950                 955                 960

Ile Ser Ile Gln Ser Leu Gly Pro Cys Gln Glu Ala Val Ala Pro Ser
            965                 970                 975

Thr His Pro Thr Ser Ala Ser Val Thr Val Thr Thr Pro Gly Leu Leu
            980                 985                 990
```

```
Leu Ser Gln Ala Leu Pro Ala Pro  Pro Gly Ala Leu Pro  Leu Ala Pro
        995            1000               1005

Ser Ser  Thr Ala His Ser Gln  Thr Thr Pro Pro Pro  Ser Ser Arg
    1010            1015            1020

Pro Arg  Thr Thr Ala Ser Val  Pro Arg Thr Thr Val  Trp Pro Val
    1025            1030            1035

Leu Thr  Val Pro Pro Thr Ala  Pro Ser Pro Ala Pro  Ser Leu Val
    1040            1045            1050

Ala Ser  Ala Phe Gly Glu Ser  Gly Ser Thr Asp Gly  Ser Ser Asp
    1055            1060            1065

Glu Glu  Leu Ser Gly Asp Gln  Glu Ala Ser Gly Gly  Gly Ser Gly
    1070            1075            1080

Gly Leu  Glu Pro Leu Glu Gly  Ser Ser Val Ala Thr  Pro Gly Pro
    1085            1090            1095

Pro Val  Glu Arg Ala Ser Cys  Tyr Asn Ser Ala Leu  Gly Cys Cys
    1100            1105            1110

Ser Asp  Gly Lys Thr Pro Ser  Leu Asp Ala Glu Gly  Ser Asn Cys
    1115            1120            1125

Pro Ala  Thr Lys Val Phe Gln  Gly Val Leu Glu Leu  Glu Gly Val
    1130            1135            1140

Glu Gly  Gln Glu Leu Phe Tyr  Thr Pro Glu Met Ala  Asp Pro Lys
    1145            1150            1155

Ser Glu  Leu Phe Gly Glu Thr  Ala Arg Ser Ile Glu  Ser Thr Leu
    1160            1165            1170

Asp Asp  Leu Phe Arg Asn Ser  Asp Val Lys Lys Asp  Phe Arg Ser
    1175            1180            1185

Val Arg  Leu Arg Asp Leu Gly  Pro Gly Lys Ser Val  Arg Ala Ile
    1190            1195            1200

Val Asp  Val His Phe Asp Pro  Thr Thr Ala Phe Arg  Ala Pro Asp
    1205            1210            1215

Val Ala  Arg Ala Leu Leu Arg  Gln Ile Gln Val Ser  Arg Arg Arg
    1220            1225            1230

Ser Leu  Gly Val Arg Arg Pro  Leu Gln Glu His Val  Arg Phe Met
    1235            1240            1245

Asp Phe  Asp Trp Phe Pro Ala  Phe Ile Thr Gly Ala  Thr Ser Gly
    1250            1255            1260

Ala Ile  Ala Ala Gly Ala Thr  Ala Arg Ala Thr Thr  Ala Ser Arg
    1265            1270            1275

Leu Pro  Ser Ser Ala Val Thr  Pro Arg Ala Pro His  Pro Ser His
    1280            1285            1290

Thr Ser  Gln Pro Val Ala Lys  Thr Thr Ala Ala Pro  Thr Thr Arg
    1295            1300            1305

Arg Pro  Pro Thr Thr Ala Pro  Ser Arg Val Pro Gly  Arg Arg Pro
    1310            1315            1320

Pro Ala  Pro Gln Gln Pro Pro  Lys Pro Cys Asp Ser  Gln Pro Cys
    1325            1330            1335

Phe His  Gly Gly Thr Cys Gln  Asp Trp Ala Leu Gly  Gly Gly Phe
    1340            1345            1350

Thr Cys  Ser Cys Pro Ala Gly  Arg Gly Gly Ala Val  Cys Glu Lys
    1355            1360            1365

Val Leu  Gly Ala Pro Val Pro  Ala Phe Glu Gly Arg  Ser Phe Leu
    1370            1375            1380

Ala Phe  Pro Thr Leu Arg Ala  Tyr His Thr Leu Arg  Leu Ala Leu
```

```
                1385              1390              1395

Glu Phe Arg Ala Leu Glu Pro Gln Gly Leu Leu Leu Tyr Asn Gly
    1400              1405              1410

Asn Ala Arg Gly Lys Asp Phe Leu Ala Leu Ala Leu Leu Asp Gly
    1415              1420              1425

Arg Val Gln Leu Arg Phe Asp Thr Gly Ser Gly Pro Ala Val Leu
    1430              1435              1440

Thr Ser Ala Val Pro Val Glu Pro Gly Gln Trp His Arg Leu Glu
    1445              1450              1455

Leu Ser Arg His Trp Arg Arg Gly Thr Leu Ser Val Asp Gly Glu
    1460              1465              1470

Thr Pro Val Leu Gly Glu Ser Pro Ser Gly Thr Asp Gly Leu Asn
    1475              1480              1485

Leu Asp Thr Asp Leu Phe Val Gly Gly Val Pro Glu Asp Gln Ala
    1490              1495              1500

Ala Val Ala Leu Glu Arg Thr Phe Val Gly Ala Gly Leu Arg Gly
    1505              1510              1515

Cys Ile Arg Leu Leu Asp Val Asn Asn Gln Arg Leu Glu Leu Gly
    1520              1525              1530

Ile Gly Pro Gly Ala Ala Thr Arg Gly Ser Gly Val Gly Glu Cys
    1535              1540              1545

Gly Asp His Pro Cys Leu Pro Asn Pro Cys His Gly Gly Ala Pro
    1550              1555              1560

Cys Gln Asn Leu Glu Ala Gly Arg Phe His Cys Gln Cys Pro Pro
    1565              1570              1575

Gly Arg Val Gly Pro Thr Cys Ala Asp Glu Lys Ser Pro Cys Gln
    1580              1585              1590

Pro Asn Pro Cys His Gly Ala Ala Pro Cys Arg Val Leu Pro Glu
    1595              1600              1605

Gly Gly Ala Gln Cys Glu Cys Pro Leu Gly Arg Glu Gly Thr Phe
    1610              1615              1620

Cys Gln Thr Ala Ser Gly Gln Asp Gly Ser Gly Pro Phe Leu Ala
    1625              1630              1635

Asp Phe Asn Gly Phe Ser His Leu Glu Leu Arg Gly Leu His Thr
    1640              1645              1650

Phe Ala Arg Asp Leu Gly Glu Lys Met Ala Leu Glu Val Val Phe
    1655              1660              1665

Leu Ala Arg Gly Pro Ser Gly Leu Leu Leu Tyr Asn Gly Gln Lys
    1670              1675              1680

Thr Asp Gly Lys Gly Asp Phe Val Ser Leu Ala Leu Arg Asp Arg
    1685              1690              1695

Arg Leu Glu Phe Arg Tyr Asp Leu Gly Lys Gly Ala Ala Val Ile
    1700              1705              1710

Arg Ser Arg Glu Pro Val Thr Leu Gly Ala Trp Thr Arg Val Ser
    1715              1720              1725

Leu Glu Arg Asn Gly Arg Lys Gly Ala Leu Arg Val Gly Asp Gly
    1730              1735              1740

Pro Arg Val Leu Gly Glu Ser Pro Lys Ser Arg Lys Val Pro His
    1745              1750              1755

Thr Val Leu Asn Leu Lys Glu Pro Leu Tyr Val Gly Gly Ala Pro
    1760              1765              1770

Asp Phe Ser Lys Leu Ala Arg Ala Ala Ala Val Ser Ser Gly Phe
    1775              1780              1785
```

```
Asp Gly  Ala Ile Gln Leu Val  Ser Leu Gly Gly Arg  Gln Leu Leu
    1790             1795              1800

Thr Pro  Glu His Val Leu Arg  Gln Val Asp Val Thr  Ser Phe Ala
    1805             1810              1815

Gly His  Pro Cys Thr Arg Ala  Ser Gly His Pro Cys  Leu Asn Gly
    1820             1825              1830

Ala Ser  Cys Val Pro Arg Glu  Ala Ala Tyr Val Cys  Leu Cys Pro
    1835             1840              1845

Gly Gly  Phe Ser Gly Pro His  Cys Glu Lys Gly Leu  Val Glu Lys
    1850             1855              1860

Ser Ala  Gly Asp Val Asp Thr  Leu Ala Phe Asp Gly  Arg Thr Phe
    1865             1870              1875

Val Glu  Tyr Leu Asn Ala Val  Thr Glu Ser Glu Leu  Ala Asn Glu
    1880             1885              1890

Ile Pro  Val Glu Lys Ala Leu  Gln Ser Asn His Phe  Glu Leu Ser
    1895             1900              1905

Leu Arg  Thr Glu Ala Thr Gln  Gly Leu Val Leu Trp  Ser Gly Lys
    1910             1915              1920

Ala Thr  Glu Arg Ala Asp Tyr  Val Ala Leu Ala Ile  Val Asp Gly
    1925             1930              1935

His Leu  Gln Leu Ser Tyr Asn  Leu Gly Ser Gln Pro  Val Val Leu
    1940             1945              1950

Arg Ser  Thr Val Pro Val Asn  Thr Asn Arg Trp Leu  Arg Val Val
    1955             1960              1965

Ala His  Arg Glu Gln Arg Glu  Gly Ser Leu Gln Val  Gly Asn Glu
    1970             1975              1980

Ala Pro  Val Thr Gly Ser Ser  Pro Leu Gly Ala Thr  Gln Leu Asp
    1985             1990              1995

Thr Asp  Gly Ala Leu Trp Leu  Gly Gly Leu Pro Glu  Leu Pro Val
    2000             2005              2010

Gly Pro  Ala Leu Pro Lys Ala  Tyr Gly Thr Gly Phe  Val Gly Cys
    2015             2020              2025

Leu Arg  Asp Val Val Val Gly  Arg His Pro Leu His  Leu Leu Glu
    2030             2035              2040

Asp Ala  Val Thr Lys Pro Glu  Leu Arg Pro Cys Pro  Thr Pro
    2045             2050              2055
```

```
<210> SEQ ID NO 9
<211> LENGTH: 2045
<212> TYPE: PRT
<213> ORGANISM: Artificial Sequence
<220> FEATURE:
<223> OTHER INFORMATION: Polypeptide sequence corresponding to a splice
      variant of human agrin corresponding to UniProt accession no.
      O00468-6

<400> SEQUENCE: 9

Met Ala Gly Arg Ser His Pro Gly Pro Leu Arg Pro Leu Leu Pro Leu
1               5                   10                  15

Leu Val Val Ala Ala Cys Val Leu Pro Gly Ala Gly Gly Thr Cys Pro
                20                  25                  30

Glu Arg Ala Leu Glu Arg Arg Glu Glu Glu Ala Asn Val Val Leu Thr
            35                  40                  45

Gly Thr Val Glu Glu Ile Leu Asn Val Asp Pro Val Gln His Thr Tyr
        50                  55                  60
```

```
Ser Cys Lys Val Arg Val Trp Arg Tyr Leu Lys Gly Lys Asp Leu Val
65                  70                  75                  80

Ala Arg Glu Ser Leu Leu Asp Gly Gly Asn Lys Val Val Ile Ser Gly
                85                  90                  95

Phe Gly Asp Pro Leu Ile Cys Asp Asn Gln Val Ser Thr Gly Asp Thr
            100                 105                 110

Arg Ile Phe Phe Val Asn Pro Ala Pro Pro Tyr Leu Trp Pro Ala His
            115                 120                 125

Lys Asn Glu Leu Met Leu Asn Ser Ser Leu Met Arg Ile Thr Leu Arg
    130                 135                 140

Asn Leu Glu Glu Val Glu Phe Cys Val Glu Asp Lys Pro Gly Thr His
145                 150                 155                 160

Phe Thr Pro Val Pro Pro Thr Pro Pro Asp Ala Cys Arg Gly Met Leu
                165                 170                 175

Cys Gly Phe Gly Ala Val Cys Glu Pro Asn Ala Glu Gly Pro Gly Arg
            180                 185                 190

Ala Ser Cys Val Cys Lys Lys Ser Pro Cys Pro Ser Val Val Ala Pro
            195                 200                 205

Val Cys Gly Ser Asp Ala Ser Thr Tyr Ser Asn Glu Cys Glu Leu Gln
    210                 215                 220

Arg Ala Gln Cys Ser Gln Gln Arg Arg Ile Arg Leu Leu Ser Arg Gly
225                 230                 235                 240

Pro Cys Gly Ser Arg Asp Pro Cys Ser Asn Val Thr Cys Ser Phe Gly
                245                 250                 255

Ser Thr Cys Ala Arg Ser Ala Asp Gly Leu Thr Ala Ser Cys Leu Cys
            260                 265                 270

Pro Ala Thr Cys Arg Gly Ala Pro Glu Gly Thr Val Cys Gly Ser Asp
            275                 280                 285

Gly Ala Asp Tyr Pro Gly Glu Cys Gln Leu Leu Arg Arg Ala Cys Ala
    290                 295                 300

Arg Gln Glu Asn Val Phe Lys Lys Phe Asp Gly Pro Cys Asp Pro Cys
305                 310                 315                 320

Gln Gly Ala Leu Pro Asp Pro Ser Arg Ser Cys Arg Val Asn Pro Arg
                325                 330                 335

Thr Arg Arg Pro Glu Met Leu Leu Arg Pro Glu Ser Cys Pro Ala Arg
            340                 345                 350

Gln Ala Pro Val Cys Gly Asp Asp Gly Val Thr Tyr Glu Asn Asp Cys
            355                 360                 365

Val Met Gly Arg Ser Gly Ala Ala Arg Gly Leu Leu Leu Gln Lys Val
    370                 375                 380

Arg Ser Gly Gln Cys Gln Gly Arg Asp Gln Cys Pro Glu Pro Cys Arg
385                 390                 395                 400

Phe Asn Ala Val Cys Leu Ser Arg Arg Gly Arg Pro Arg Cys Ser Cys
                405                 410                 415

Asp Arg Val Thr Cys Asp Gly Ala Tyr Arg Pro Val Cys Ala Gln Asp
            420                 425                 430

Gly Arg Thr Tyr Asp Ser Asp Cys Trp Arg Gln Gln Ala Glu Cys Arg
            435                 440                 445

Gln Gln Arg Ala Ile Pro Ser Lys His Gln Gly Pro Cys Asp Gln Ala
    450                 455                 460

Pro Ser Pro Cys Leu Gly Val Gln Cys Ala Phe Gly Ala Thr Cys Ala
465                 470                 475                 480

Val Lys Asn Gly Gln Ala Ala Cys Glu Cys Leu Gln Ala Cys Ser Ser
```

```
                    485              490                 495
Leu Tyr Asp Pro Val Cys Gly Ser Asp Gly Val Thr Tyr Gly Ser Ala
            500              505                 510

Cys Glu Leu Glu Ala Thr Ala Cys Thr Leu Gly Arg Glu Ile Gln Val
            515              520                 525

Ala Arg Lys Gly Pro Cys Asp Arg Cys Gly Gln Cys Arg Phe Gly Ala
        530              535                 540

Leu Cys Glu Ala Glu Thr Gly Arg Cys Val Cys Pro Ser Glu Cys Val
545              550                 555                 560

Ala Leu Ala Gln Pro Val Cys Gly Ser Asp Gly His Thr Tyr Pro Ser
                565              570                 575

Glu Cys Met Leu His Val His Ala Cys Thr His Gln Ile Ser Leu His
            580              585                 590

Val Ala Ser Ala Gly Pro Cys Glu Thr Cys Gly Asp Ala Val Cys Ala
            595              600                 605

Phe Gly Ala Val Cys Ser Ala Gly Gln Cys Val Cys Pro Arg Cys Glu
        610              615                 620

His Pro Pro Pro Gly Pro Val Cys Gly Ser Asp Gly Val Thr Tyr Gly
625              630              635                 640

Ser Ala Cys Glu Leu Arg Glu Ala Ala Cys Leu Gln Gln Thr Gln Ile
                645              650                 655

Glu Glu Ala Arg Ala Gly Pro Cys Glu Gln Ala Glu Cys Gly Ser Gly
            660              665                 670

Gly Ser Gly Ser Gly Glu Asp Gly Asp Cys Glu Gln Glu Leu Cys Arg
            675              680                 685

Gln Arg Gly Gly Ile Trp Asp Glu Asp Ser Glu Asp Gly Pro Cys Val
        690              695                 700

Cys Asp Phe Ser Cys Gln Ser Val Pro Gly Ser Pro Val Cys Gly Ser
705              710              715                 720

Asp Gly Val Thr Tyr Ser Thr Glu Cys Glu Leu Lys Lys Ala Arg Cys
            725              730                 735

Glu Ser Gln Arg Gly Leu Tyr Val Ala Ala Gln Gly Ala Cys Arg Gly
            740              745                 750

Pro Thr Phe Ala Pro Leu Pro Pro Val Ala Pro Leu His Cys Ala Gln
        755              760                 765

Thr Pro Tyr Gly Cys Cys Gln Asp Asn Ile Thr Ala Ala Arg Gly Val
        770              775                 780

Gly Leu Ala Gly Cys Pro Ser Ala Cys Gln Cys Asn Pro His Gly Ser
785              790              795                 800

Tyr Gly Gly Thr Cys Asp Pro Ala Thr Gly Gln Cys Ser Cys Arg Pro
                805              810                 815

Gly Val Gly Gly Leu Arg Cys Asp Arg Cys Glu Pro Gly Phe Trp Asn
            820              825                 830

Phe Arg Gly Ile Val Thr Asp Gly Arg Ser Gly Cys Thr Pro Cys Ser
        835              840                 845

Cys Asp Pro Gln Gly Ala Val Arg Asp Asp Cys Glu Gln Met Thr Gly
        850              855                 860

Leu Cys Ser Cys Lys Pro Gly Val Ala Gly Pro Lys Cys Gly Gln Cys
865              870              875                 880

Pro Asp Gly Arg Ala Leu Gly Pro Ala Gly Cys Glu Ala Asp Ala Ser
                885              890                 895

Ala Pro Ala Thr Cys Ala Glu Met Arg Cys Glu Phe Gly Ala Arg Cys
            900              905                 910
```

```
Val Glu Glu Ser Gly Ser Ala His Cys Val Cys Pro Met Leu Thr Cys
        915             920             925

Pro Glu Ala Asn Ala Thr Lys Val Cys Gly Ser Asp Gly Val Thr Tyr
    930             935             940

Gly Asn Glu Cys Gln Leu Lys Thr Ile Ala Cys Arg Gln Gly Leu Gln
945             950             955             960

Ile Ser Ile Gln Ser Leu Gly Pro Cys Gln Glu Ala Val Ala Pro Ser
            965             970             975

Thr His Pro Thr Ser Ala Ser Val Thr Val Thr Thr Pro Gly Leu Leu
            980             985             990

Leu Ser Gln Ala Leu Pro Ala Pro  Pro Gly Ala Leu Pro  Leu Ala Pro
            995             1000            1005

Ser Ser  Thr Ala His Ser Gln  Thr Thr Pro Pro Pro  Ser Ser Arg
    1010            1015            1020

Pro Arg  Thr Thr Ala Ser Val  Pro Arg Thr Thr Val  Trp Pro Val
    1025            1030            1035

Leu Thr  Val Pro Pro Thr Ala  Pro Ser Pro Ala Pro  Ser Leu Val
    1040            1045            1050

Ala Ser  Ala Phe Gly Glu Ser  Gly Ser Thr Asp Gly  Ser Ser Asp
    1055            1060            1065

Glu Glu  Leu Ser Gly Asp Gln  Glu Ala Ser Gly Gly  Gly Ser Gly
    1070            1075            1080

Gly Leu  Glu Pro Leu Glu Gly  Ser Ser Val Ala Thr  Pro Gly Pro
    1085            1090            1095

Pro Val  Glu Arg Ala Ser Cys  Tyr Asn Ser Ala Leu  Gly Cys Cys
    1100            1105            1110

Ser Asp  Gly Lys Thr Pro Ser  Leu Asp Ala Glu Gly  Ser Asn Cys
    1115            1120            1125

Pro Ala  Thr Lys Val Phe Gln  Gly Val Leu Glu Leu  Glu Gly Val
    1130            1135            1140

Glu Gly  Gln Glu Leu Phe Tyr  Thr Pro Glu Met Ala  Asp Pro Lys
    1145            1150            1155

Ser Glu  Leu Phe Gly Glu Thr  Ala Arg Ser Ile Glu  Ser Thr Leu
    1160            1165            1170

Asp Asp  Leu Phe Arg Asn Ser  Asp Val Lys Lys Asp  Phe Arg Ser
    1175            1180            1185

Val Arg  Leu Arg Asp Leu Gly  Pro Gly Lys Ser Val  Arg Ala Ile
    1190            1195            1200

Val Asp  Val His Phe Asp Pro  Thr Thr Ala Phe Arg  Ala Pro Asp
    1205            1210            1215

Val Ala  Arg Ala Leu Leu Arg  Gln Ile Gln Val Ser  Arg Arg Arg
    1220            1225            1230

Ser Leu  Gly Val Arg Arg Pro  Leu Gln Glu His Val  Arg Phe Met
    1235            1240            1245

Asp Phe  Asp Trp Phe Pro Ala  Phe Ile Thr Gly Ala  Thr Ser Gly
    1250            1255            1260

Ala Ile  Ala Ala Gly Ala Thr  Ala Arg Ala Thr Thr  Ala Ser Arg
    1265            1270            1275

Leu Pro  Ser Ser Ala Val Thr  Pro Arg Ala Pro His  Pro Ser His
    1280            1285            1290

Thr Ser  Gln Pro Val Ala Lys  Thr Thr Ala Ala Pro  Thr Thr Arg
    1295            1300            1305
```

```
Arg Pro  Pro Thr Thr Ala Pro  Ser Arg Val Pro Gly  Arg Arg Pro
    1310              1315              1320

Pro Ala  Pro Gln Gln Pro Pro  Lys Pro Cys Asp Ser  Gln Pro Cys
    1325              1330              1335

Phe His  Gly Gly Thr Cys Gln  Asp Trp Ala Leu Gly  Gly Gly Phe
    1340              1345              1350

Thr Cys  Ser Cys Pro Ala Gly  Arg Gly Gly Ala Val  Cys Glu Lys
    1355              1360              1365

Val Leu  Gly Ala Pro Val Pro  Ala Phe Glu Gly Arg  Ser Phe Leu
    1370              1375              1380

Ala Phe  Pro Thr Leu Arg Ala  Tyr His Thr Leu Arg  Leu Ala Leu
    1385              1390              1395

Glu Phe  Arg Ala Leu Glu Pro  Gln Gly Leu Leu Leu  Tyr Asn Gly
    1400              1405              1410

Asn Ala  Arg Gly Lys Asp Phe  Leu Ala Leu Ala Leu  Leu Asp Gly
    1415              1420              1425

Arg Val  Gln Leu Arg Phe Asp  Thr Gly Ser Gly Pro  Ala Val Leu
    1430              1435              1440

Thr Ser  Ala Val Pro Val Glu  Pro Gly Gln Trp His  Arg Leu Glu
    1445              1450              1455

Leu Ser  Arg His Trp Arg Arg  Gly Thr Leu Ser Val  Asp Gly Glu
    1460              1465              1470

Thr Pro  Val Leu Gly Glu Ser  Pro Ser Gly Thr Asp  Gly Leu Asn
    1475              1480              1485

Leu Asp  Thr Asp Leu Phe Val  Gly Gly Val Pro Glu  Asp Gln Ala
    1490              1495              1500

Ala Val  Ala Leu Glu Arg Thr  Phe Val Gly Ala Gly  Leu Arg Gly
    1505              1510              1515

Cys Ile  Arg Leu Leu Asp Val  Asn Asn Gln Arg Leu  Glu Leu Gly
    1520              1525              1530

Ile Gly  Pro Gly Ala Ala Thr  Arg Gly Ser Gly Val  Gly Glu Cys
    1535              1540              1545

Gly Asp  His Pro Cys Leu Pro  Asn Pro Cys His Gly  Gly Ala Pro
    1550              1555              1560

Cys Gln  Asn Leu Glu Ala Gly  Arg Phe His Cys Gln  Cys Pro Pro
    1565              1570              1575

Gly Arg  Val Gly Pro Thr Cys  Ala Asp Glu Lys Ser  Pro Cys Gln
    1580              1585              1590

Pro Asn  Pro Cys His Gly Ala  Ala Pro Cys Arg Val  Leu Pro Glu
    1595              1600              1605

Gly Gly  Ala Gln Cys Glu Cys  Pro Leu Gly Arg Glu  Gly Thr Phe
    1610              1615              1620

Cys Gln  Thr Ala Ser Gly Gln  Asp Gly Ser Gly Pro  Phe Leu Ala
    1625              1630              1635

Asp Phe  Asn Gly Phe Ser His  Leu Glu Leu Arg Gly  Leu His Thr
    1640              1645              1650

Phe Ala  Arg Asp Leu Gly Glu  Lys Met Ala Leu Glu  Val Val Phe
    1655              1660              1665

Leu Ala  Arg Gly Pro Ser Gly  Leu Leu Leu Tyr Asn  Gly Gln Lys
    1670              1675              1680

Thr Asp  Gly Lys Gly Asp Phe  Val Ser Leu Ala Leu  Arg Asp Arg
    1685              1690              1695

Arg Leu  Glu Phe Arg Tyr Asp  Leu Gly Lys Gly Ala  Ala Val Ile
```

-continued

```
        1700              1705                1710

Arg Ser  Arg Glu Pro Val Thr  Leu Gly Ala Trp Thr  Arg Val Ser
    1715              1720                1725

Leu Glu  Arg Asn Gly Arg Lys  Gly Ala Leu Arg Val  Gly Asp Gly
    1730              1735                1740

Pro Arg  Val Leu Gly Glu Ser  Pro Val Pro His Thr  Val Leu Asn
    1745              1750                1755

Leu Lys  Glu Pro Leu Tyr Val  Gly Gly Ala Pro Asp  Phe Ser Lys
    1760              1765                1770

Leu Ala  Arg Ala Ala Ala Val  Ser Ser Gly Phe Asp  Gly Ala Ile
    1775              1780                1785

Gln Leu  Val Ser Leu Gly Gly  Arg Gln Leu Leu Thr  Pro Glu His
    1790              1795                1800

Val Leu  Arg Gln Val Asp Val  Thr Ser Phe Ala Gly  His Pro Cys
    1805              1810                1815

Thr Arg  Ala Ser Gly His Pro  Cys Leu Asn Gly Ala  Ser Cys Val
    1820              1825                1830

Pro Arg  Glu Ala Ala Tyr Val  Cys Leu Cys Pro Gly  Gly Phe Ser
    1835              1840                1845

Gly Pro  His Cys Glu Lys Gly  Leu Val Glu Lys Ser  Ala Gly Asp
    1850              1855                1860

Val Asp  Thr Leu Ala Phe Asp  Gly Arg Thr Phe Val  Glu Tyr Leu
    1865              1870                1875

Asn Ala  Val Thr Glu Ser Glu  Lys Ala Leu Gln Ser  Asn His Phe
    1880              1885                1890

Glu Leu  Ser Leu Arg Thr Glu  Ala Thr Gln Gly Leu  Val Leu Trp
    1895              1900                1905

Ser Gly  Lys Ala Thr Glu Arg  Ala Asp Tyr Val Ala  Leu Ala Ile
    1910              1915                1920

Val Asp  Gly His Leu Gln Leu  Ser Tyr Asn Leu Gly  Ser Gln Pro
    1925              1930                1935

Val Val  Leu Arg Ser Thr Val  Pro Val Asn Thr Asn  Arg Trp Leu
    1940              1945                1950

Arg Val  Val Ala His Arg Glu  Gln Arg Glu Gly Ser  Leu Gln Val
    1955              1960                1965

Gly Asn  Glu Ala Pro Val Thr  Gly Ser Ser Pro Leu  Gly Ala Thr
    1970              1975                1980

Gln Leu  Asp Thr Asp Gly Ala  Leu Trp Leu Gly Gly  Leu Pro Glu
    1985              1990                1995

Leu Pro  Val Gly Pro Ala Leu  Pro Lys Ala Tyr Gly  Thr Gly Phe
    2000              2005                2010

Val Gly  Cys Leu Arg Asp Val  Val Val Gly Arg His  Pro Leu His
    2015              2020                2025

Leu Leu  Glu Asp Ala Val Thr  Lys Pro Glu Leu Arg  Pro Cys Pro
    2030              2035                2040

Thr Pro
    2045
```

<210> SEQ ID NO 10
<211> LENGTH: 2064
<212> TYPE: PRT
<213> ORGANISM: Artificial Sequence
<220> FEATURE:
<223> OTHER INFORMATION: Polypeptide sequence corresponding to a splice
      variant of human agrin corresponding to UniProt accession no.

-continued

```
          000468-7

<400> SEQUENCE: 10

Met Ala Gly Arg Ser His Pro Gly Pro Leu Arg Pro Leu Leu Pro Leu
1               5                   10                  15

Leu Val Val Ala Ala Cys Val Leu Pro Gly Ala Gly Gly Thr Cys Pro
                20                  25                  30

Glu Arg Ala Leu Glu Arg Arg Glu Glu Glu Ala Asn Val Val Leu Thr
            35                  40                  45

Gly Thr Val Glu Glu Ile Leu Asn Val Asp Pro Val Gln His Thr Tyr
        50                  55                  60

Ser Cys Lys Val Arg Val Trp Arg Tyr Leu Lys Gly Lys Asp Leu Val
65                  70                  75                  80

Ala Arg Glu Ser Leu Leu Asp Gly Gly Asn Lys Val Val Ile Ser Gly
                85                  90                  95

Phe Gly Asp Pro Leu Ile Cys Asp Asn Gln Val Ser Thr Gly Asp Thr
                100                 105                 110

Arg Ile Phe Phe Val Asn Pro Ala Pro Pro Tyr Leu Trp Pro Ala His
            115                 120                 125

Lys Asn Glu Leu Met Leu Asn Ser Ser Leu Met Arg Ile Thr Leu Arg
    130                 135                 140

Asn Leu Glu Glu Val Glu Phe Cys Val Glu Asp Lys Pro Gly Thr His
145                 150                 155                 160

Phe Thr Pro Val Pro Pro Thr Pro Pro Asp Ala Cys Arg Gly Met Leu
                165                 170                 175

Cys Gly Phe Gly Ala Val Cys Glu Pro Asn Ala Glu Gly Pro Gly Arg
            180                 185                 190

Ala Ser Cys Val Cys Lys Lys Ser Pro Cys Pro Ser Val Val Ala Pro
            195                 200                 205

Val Cys Gly Ser Asp Ala Ser Thr Tyr Ser Asn Glu Cys Glu Leu Gln
    210                 215                 220

Arg Ala Gln Cys Ser Gln Gln Arg Arg Ile Arg Leu Leu Ser Arg Gly
225                 230                 235                 240

Pro Cys Gly Ser Arg Asp Pro Cys Ser Asn Val Thr Cys Ser Phe Gly
                245                 250                 255

Ser Thr Cys Ala Arg Ser Ala Asp Gly Leu Thr Ala Ser Cys Leu Cys
            260                 265                 270

Pro Ala Thr Cys Arg Gly Ala Pro Glu Gly Thr Val Cys Gly Ser Asp
            275                 280                 285

Gly Ala Asp Tyr Pro Gly Glu Cys Gln Leu Leu Arg Arg Ala Cys Ala
    290                 295                 300

Arg Gln Glu Asn Val Phe Lys Lys Phe Asp Gly Pro Cys Asp Pro Cys
305                 310                 315                 320

Gln Gly Ala Leu Pro Asp Pro Ser Arg Ser Cys Arg Val Asn Pro Arg
            325                 330                 335

Thr Arg Arg Pro Glu Met Leu Leu Arg Pro Glu Ser Cys Pro Ala Arg
            340                 345                 350

Gln Ala Pro Val Cys Gly Asp Asp Gly Val Thr Tyr Glu Asn Asp Cys
            355                 360                 365

Val Met Gly Arg Ser Gly Ala Ala Arg Gly Leu Leu Leu Gln Lys Val
    370                 375                 380

Arg Ser Gly Gln Cys Gln Gly Arg Asp Gln Cys Pro Glu Pro Cys Arg
385                 390                 395                 400
```

```
Phe Asn Ala Val Cys Leu Ser Arg Arg Gly Arg Pro Arg Cys Ser Cys
                405                 410                 415

Asp Arg Val Thr Cys Asp Gly Ala Tyr Arg Pro Val Cys Ala Gln Asp
            420                 425                 430

Gly Arg Thr Tyr Asp Ser Asp Cys Trp Arg Gln Gln Ala Glu Cys Arg
            435                 440                 445

Gln Gln Arg Ala Ile Pro Ser Lys His Gln Gly Pro Cys Asp Gln Ala
    450                 455                 460

Pro Ser Pro Cys Leu Gly Val Gln Cys Ala Phe Gly Ala Thr Cys Ala
465                 470                 475                 480

Val Lys Asn Gly Gln Ala Ala Cys Glu Cys Leu Gln Ala Cys Ser Ser
            485                 490                 495

Leu Tyr Asp Pro Val Cys Gly Ser Asp Gly Val Thr Tyr Gly Ser Ala
            500                 505                 510

Cys Glu Leu Glu Ala Thr Ala Cys Thr Leu Gly Arg Glu Ile Gln Val
            515                 520                 525

Ala Arg Lys Gly Pro Cys Asp Arg Cys Gly Gln Cys Arg Phe Gly Ala
    530                 535                 540

Leu Cys Glu Ala Glu Thr Gly Arg Cys Val Cys Pro Ser Glu Cys Val
545                 550                 555                 560

Ala Leu Ala Gln Pro Val Cys Gly Ser Asp Gly His Thr Tyr Pro Ser
            565                 570                 575

Glu Cys Met Leu His Val His Ala Cys Thr His Gln Ile Ser Leu His
            580                 585                 590

Val Ala Ser Ala Gly Pro Cys Glu Thr Cys Gly Asp Ala Val Cys Ala
            595                 600                 605

Phe Gly Ala Val Cys Ser Ala Gly Gln Cys Val Cys Pro Arg Cys Glu
    610                 615                 620

His Pro Pro Gly Pro Val Cys Gly Ser Asp Gly Val Thr Tyr Gly
625                 630                 635                 640

Ser Ala Cys Glu Leu Arg Glu Ala Ala Cys Leu Gln Gln Thr Gln Ile
            645                 650                 655

Glu Glu Ala Arg Ala Gly Pro Cys Glu Gln Ala Glu Cys Gly Ser Gly
            660                 665                 670

Gly Ser Gly Ser Gly Glu Asp Gly Asp Cys Glu Gln Glu Leu Cys Arg
            675                 680                 685

Gln Arg Gly Gly Ile Trp Asp Glu Asp Ser Glu Asp Gly Pro Cys Val
    690                 695                 700

Cys Asp Phe Ser Cys Gln Ser Val Pro Gly Ser Pro Val Cys Gly Ser
705                 710                 715                 720

Asp Gly Val Thr Tyr Ser Thr Glu Cys Glu Leu Lys Lys Ala Arg Cys
            725                 730                 735

Glu Ser Gln Arg Gly Leu Tyr Val Ala Ala Gln Gly Ala Cys Arg Gly
            740                 745                 750

Pro Thr Phe Ala Pro Leu Pro Pro Val Ala Pro Leu His Cys Ala Gln
            755                 760                 765

Thr Pro Tyr Gly Cys Cys Gln Asp Asn Ile Thr Ala Ala Arg Gly Val
            770                 775                 780

Gly Leu Ala Gly Cys Pro Ser Ala Cys Gln Cys Asn Pro His Gly Ser
785                 790                 795                 800

Tyr Gly Gly Thr Cys Asp Pro Ala Thr Gly Gln Cys Ser Cys Arg Pro
            805                 810                 815

Gly Val Gly Gly Leu Arg Cys Asp Arg Cys Glu Pro Gly Phe Trp Asn
```

-continued

```
              820              825              830
Phe Arg Gly Ile Val Thr Asp Gly Arg Ser Gly Cys Thr Pro Cys Ser
         835              840              845

Cys Asp Pro Gln Gly Ala Val Arg Asp Asp Cys Glu Gln Met Thr Gly
    850              855              860

Leu Cys Ser Cys Lys Pro Gly Val Ala Gly Pro Lys Cys Gly Gln Cys
865              870              875              880

Pro Asp Gly Arg Ala Leu Gly Pro Ala Gly Cys Glu Ala Asp Ala Ser
              885              890              895

Ala Pro Ala Thr Cys Ala Glu Met Arg Cys Glu Phe Gly Ala Arg Cys
         900              905              910

Val Glu Glu Ser Gly Ser Ala His Cys Val Cys Pro Met Leu Thr Cys
         915              920              925

Pro Glu Ala Asn Ala Thr Lys Val Cys Gly Ser Asp Gly Val Thr Tyr
    930              935              940

Gly Asn Glu Cys Gln Leu Lys Thr Ile Ala Cys Arg Gln Gly Leu Gln
945              950              955              960

Ile Ser Ile Gln Ser Leu Gly Pro Cys Gln Glu Ala Val Ala Pro Ser
              965              970              975

Thr His Pro Thr Ser Ala Ser Val Thr Val Thr Thr Pro Gly Leu Leu
         980              985              990

Leu Ser Gln Ala Leu Pro Ala Pro  Pro Gly Ala Leu Pro  Leu Ala Pro
         995              1000             1005

Ser Ser  Thr Ala His Ser Gln  Thr Thr Pro Pro Pro  Ser Ser Arg
    1010             1015             1020

Pro Arg  Thr Thr Ala Ser Val  Pro Arg Thr Thr Val  Trp Pro Val
    1025             1030             1035

Leu Thr  Val Pro Pro Thr Ala  Pro Ser Pro Ala Pro  Ser Leu Val
    1040             1045             1050

Ala Ser  Ala Phe Gly Glu Ser  Gly Ser Thr Asp Gly  Ser Ser Asp
    1055             1060             1065

Glu Glu  Leu Ser Gly Asp Gln  Glu Ala Ser Gly Gly  Gly Ser Gly
    1070             1075             1080

Gly Leu  Glu Pro Leu Glu Gly  Ser Ser Val Ala Thr  Pro Gly Pro
    1085             1090             1095

Pro Val  Glu Arg Ala Ser Cys  Tyr Asn Ser Ala Leu  Gly Cys Cys
    1100             1105             1110

Ser Asp  Gly Lys Thr Pro Ser  Leu Asp Ala Glu Gly  Ser Asn Cys
    1115             1120             1125

Pro Ala  Thr Lys Val Phe Gln  Gly Val Leu Glu Leu  Glu Gly Val
    1130             1135             1140

Glu Gly  Gln Glu Leu Phe Tyr  Thr Pro Glu Met Ala  Asp Pro Lys
    1145             1150             1155

Ser Glu  Leu Phe Gly Glu Thr  Ala Arg Ser Ile Glu  Ser Thr Leu
    1160             1165             1170

Asp Asp  Leu Phe Arg Asn Ser  Asp Val Lys Lys Asp  Phe Arg Ser
    1175             1180             1185

Val Arg  Leu Arg Asp Leu Gly  Pro Gly Lys Ser Val  Arg Ala Ile
    1190             1195             1200

Val Asp  Val His Phe Asp Pro  Thr Thr Ala Phe Arg  Ala Pro Asp
    1205             1210             1215

Val Ala  Arg Ala Leu Leu Arg  Gln Ile Gln Val Ser  Arg Arg Arg
    1220             1225             1230
```

-continued

```
Ser Leu  Gly Val Arg Arg Pro  Leu Gln Glu His Val  Arg Phe Met
    1235              1240              1245

Asp Phe  Asp Trp Phe Pro Ala  Phe Ile Thr Gly Ala  Thr Ser Gly
    1250              1255              1260

Ala Ile  Ala Ala Gly Ala Thr  Ala Arg Ala Thr Thr  Ala Ser Arg
    1265              1270              1275

Leu Pro  Ser Ser Ala Val Thr  Pro Arg Ala Pro His  Pro Ser His
    1280              1285              1290

Thr Ser  Gln Pro Val Ala Lys  Thr Thr Ala Ala Pro  Thr Thr Arg
    1295              1300              1305

Arg Pro  Pro Thr Thr Ala Pro  Ser Arg Val Pro Gly  Arg Arg Pro
    1310              1315              1320

Pro Ala  Pro Gln Gln Pro Pro  Lys Pro Cys Asp Ser  Gln Pro Cys
    1325              1330              1335

Phe His  Gly Gly Thr Cys Gln  Asp Trp Ala Leu Gly  Gly Gly Phe
    1340              1345              1350

Thr Cys  Ser Cys Pro Ala Gly  Arg Gly Gly Ala Val  Cys Glu Lys
    1355              1360              1365

Val Leu  Gly Ala Pro Val Pro  Ala Phe Glu Gly Arg  Ser Phe Leu
    1370              1375              1380

Ala Phe  Pro Thr Leu Arg Ala  Tyr His Thr Leu Arg  Leu Ala Leu
    1385              1390              1395

Glu Phe  Arg Ala Leu Glu Pro  Gln Gly Leu Leu Leu  Tyr Asn Gly
    1400              1405              1410

Asn Ala  Arg Gly Lys Asp Phe  Leu Ala Leu Ala Leu  Leu Asp Gly
    1415              1420              1425

Arg Val  Gln Leu Arg Phe Asp  Thr Gly Ser Gly Pro  Ala Val Leu
    1430              1435              1440

Thr Ser  Ala Val Pro Val Glu  Pro Gly Gln Trp His  Arg Leu Glu
    1445              1450              1455

Leu Ser  Arg His Trp Arg Arg  Gly Thr Leu Ser Val  Asp Gly Glu
    1460              1465              1470

Thr Pro  Val Leu Gly Glu Ser  Pro Ser Gly Thr Asp  Gly Leu Asn
    1475              1480              1485

Leu Asp  Thr Asp Leu Phe Val  Gly Gly Val Pro Glu  Asp Gln Ala
    1490              1495              1500

Ala Val  Ala Leu Glu Arg Thr  Phe Val Gly Ala Gly  Leu Arg Gly
    1505              1510              1515

Cys Ile  Arg Leu Leu Asp Val  Asn Asn Gln Arg Leu  Glu Leu Gly
    1520              1525              1530

Ile Gly  Pro Gly Ala Ala Thr  Arg Gly Ser Gly Val  Gly Glu Cys
    1535              1540              1545

Gly Asp  His Pro Cys Leu Pro  Asn Pro Cys His Gly  Gly Ala Pro
    1550              1555              1560

Cys Gln  Asn Leu Glu Ala Gly  Arg Phe His Cys Gln  Cys Pro Pro
    1565              1570              1575

Gly Arg  Val Gly Pro Thr Cys  Ala Asp Glu Lys Ser  Pro Cys Gln
    1580              1585              1590

Pro Asn  Pro Cys His Gly Ala  Ala Pro Cys Arg Val  Leu Pro Glu
    1595              1600              1605

Gly Gly  Ala Gln Cys Glu Cys  Pro Leu Gly Arg Glu  Gly Thr Phe
    1610              1615              1620
```

```
Cys Gln Thr Ala Ser Gly Gln Asp Gly Ser Gly Pro Phe Leu Ala
1625            1630            1635

Asp Phe Asn Gly Phe Ser His Leu Glu Leu Arg Gly Leu His Thr
1640            1645            1650

Phe Ala Arg Asp Leu Gly Glu Lys Met Ala Leu Glu Val Val Phe
1655            1660            1665

Leu Ala Arg Gly Pro Ser Gly Leu Leu Leu Tyr Asn Gly Gln Lys
1670            1675            1680

Thr Asp Gly Lys Gly Asp Phe Val Ser Leu Ala Leu Arg Asp Arg
1685            1690            1695

Arg Leu Glu Phe Arg Tyr Asp Leu Gly Lys Gly Ala Ala Val Ile
1700            1705            1710

Arg Ser Arg Glu Pro Val Thr Leu Gly Ala Trp Thr Arg Val Ser
1715            1720            1725

Leu Glu Arg Asn Gly Arg Lys Gly Ala Leu Arg Val Gly Asp Gly
1730            1735            1740

Pro Arg Val Leu Gly Glu Ser Pro Val Pro His Thr Val Leu Asn
1745            1750            1755

Leu Lys Glu Pro Leu Tyr Val Gly Gly Ala Pro Asp Phe Ser Lys
1760            1765            1770

Leu Ala Arg Ala Ala Ala Val Ser Ser Gly Phe Asp Gly Ala Ile
1775            1780            1785

Gln Leu Val Ser Leu Gly Gly Arg Gln Leu Leu Thr Pro Glu His
1790            1795            1800

Val Leu Arg Gln Val Asp Val Thr Ser Phe Ala Gly His Pro Cys
1805            1810            1815

Thr Arg Ala Ser Gly His Pro Cys Leu Asn Gly Ala Ser Cys Val
1820            1825            1830

Pro Arg Glu Ala Ala Tyr Val Cys Leu Cys Pro Gly Gly Phe Ser
1835            1840            1845

Gly Pro His Cys Glu Lys Gly Leu Val Glu Lys Ser Ala Gly Asp
1850            1855            1860

Val Asp Thr Leu Ala Phe Asp Gly Arg Thr Phe Val Glu Tyr Leu
1865            1870            1875

Asn Ala Val Thr Glu Ser Glu Leu Ala Asn Glu Ile Pro Val Pro
1880            1885            1890

Glu Thr Leu Asp Ser Gly Ala Leu His Ser Glu Lys Ala Leu Gln
1895            1900            1905

Ser Asn His Phe Glu Leu Ser Leu Arg Thr Glu Ala Thr Gln Gly
1910            1915            1920

Leu Val Leu Trp Ser Gly Lys Ala Thr Glu Arg Ala Asp Tyr Val
1925            1930            1935

Ala Leu Ala Ile Val Asp Gly His Leu Gln Leu Ser Tyr Asn Leu
1940            1945            1950

Gly Ser Gln Pro Val Val Leu Arg Ser Thr Val Pro Val Asn Thr
1955            1960            1965

Asn Arg Trp Leu Arg Val Val Ala His Arg Glu Gln Arg Glu Gly
1970            1975            1980

Ser Leu Gln Val Gly Asn Glu Ala Pro Val Thr Gly Ser Ser Pro
1985            1990            1995

Leu Gly Ala Thr Gln Leu Asp Thr Asp Gly Ala Leu Trp Leu Gly
2000            2005            2010

Gly Leu Pro Glu Leu Pro Val Gly Pro Ala Leu Pro Lys Ala Tyr
```

-continued

```
        2015                 2020                 2025

Gly Thr  Gly Phe Val Gly Cys  Leu Arg Asp Val Val  Val Gly Arg
        2030                 2035                 2040

His Pro  Leu His Leu Leu Glu  Asp Ala Val Thr Lys  Pro Glu Leu
        2045                 2050                 2055

Arg Pro  Cys Pro Thr Pro
        2060
```

```
<210> SEQ ID NO 11
<211> LENGTH: 786
<212> TYPE: PRT
<213> ORGANISM: Artificial Sequence
<220> FEATURE:
<223> OTHER INFORMATION: Polypeptide sequence corresponding to amino
      acid residues 1260-2045 of human wild type agrin

<400> SEQUENCE: 11

Ala Thr Ser Gly Ala Ile Ala Ala Gly Ala Thr Ala Arg Ala Thr Thr
1               5                   10                  15

Ala Ser Arg Leu Pro Ser Ser Ala Val Thr Pro Arg Ala Pro His Pro
            20                  25                  30

Ser His Thr Ser Gln Pro Val Ala Lys Thr Thr Ala Ala Pro Thr Thr
            35                  40                  45

Arg Arg Pro Pro Thr Thr Ala Pro Ser Arg Val Pro Gly Arg Arg Pro
    50                  55                  60

Pro Ala Pro Gln Gln Pro Pro Lys Pro Cys Asp Ser Gln Pro Cys Phe
65                  70                  75                  80

His Gly Gly Thr Cys Gln Asp Trp Ala Leu Gly Gly Gly Phe Thr Cys
                85                  90                  95

Ser Cys Pro Ala Gly Arg Gly Gly Ala Val Cys Glu Lys Val Leu Gly
            100                 105                 110

Ala Pro Val Pro Ala Phe Glu Gly Arg Ser Phe Leu Ala Phe Pro Thr
            115                 120                 125

Leu Arg Ala Tyr His Thr Leu Arg Leu Ala Leu Glu Phe Arg Ala Leu
    130                 135                 140

Glu Pro Gln Gly Leu Leu Leu Tyr Asn Gly Asn Ala Arg Gly Lys Asp
145                 150                 155                 160

Phe Leu Ala Leu Ala Leu Leu Asp Gly Arg Val Gln Leu Arg Phe Asp
            165                 170                 175

Thr Gly Ser Gly Pro Ala Val Leu Thr Ser Ala Val Pro Val Glu Pro
            180                 185                 190

Gly Gln Trp His Arg Leu Glu Leu Ser Arg His Trp Arg Arg Gly Thr
            195                 200                 205

Leu Ser Val Asp Gly Glu Thr Pro Val Leu Gly Glu Ser Pro Ser Gly
    210                 215                 220

Thr Asp Gly Leu Asn Leu Asp Thr Asp Leu Phe Val Gly Gly Val Pro
225                 230                 235                 240

Glu Asp Gln Ala Ala Val Ala Leu Glu Arg Thr Phe Val Gly Ala Gly
            245                 250                 255

Leu Arg Gly Cys Ile Arg Leu Leu Asp Val Asn Asn Gln Arg Leu Glu
            260                 265                 270

Leu Gly Ile Gly Pro Gly Ala Ala Thr Arg Gly Ser Gly Val Gly Glu
            275                 280                 285

Cys Gly Asp His Pro Cys Leu Pro Asn Pro Cys His Gly Gly Ala Pro
    290                 295                 300
```

-continued

```
Cys Gln Asn Leu Glu Ala Gly Arg Phe His Cys Gln Cys Pro Pro Gly
305                 310                 315                 320

Arg Val Gly Pro Thr Cys Ala Asp Glu Lys Ser Pro Cys Gln Pro Asn
                325                 330                 335

Pro Cys His Gly Ala Ala Pro Cys Arg Val Leu Pro Glu Gly Gly Ala
                340                 345                 350

Gln Cys Glu Cys Pro Leu Gly Arg Glu Gly Thr Phe Cys Gln Thr Ala
                355                 360                 365

Ser Gly Gln Asp Gly Ser Gly Pro Phe Leu Ala Asp Phe Asn Gly Phe
                370                 375                 380

Ser His Leu Glu Leu Arg Gly Leu His Thr Phe Ala Arg Asp Leu Gly
385                 390                 395                 400

Glu Lys Met Ala Leu Glu Val Val Phe Leu Ala Arg Gly Pro Ser Gly
                405                 410                 415

Leu Leu Leu Tyr Asn Gly Gln Lys Thr Asp Gly Lys Gly Asp Phe Val
                420                 425                 430

Ser Leu Ala Leu Arg Asp Arg Arg Leu Glu Phe Arg Tyr Asp Leu Gly
                435                 440                 445

Lys Gly Ala Ala Val Ile Arg Ser Arg Glu Pro Val Thr Leu Gly Ala
                450                 455                 460

Trp Thr Arg Val Ser Leu Glu Arg Asn Gly Arg Lys Gly Ala Leu Arg
465                 470                 475                 480

Val Gly Asp Gly Pro Arg Val Leu Gly Glu Ser Pro Val Pro His Thr
                485                 490                 495

Val Leu Asn Leu Lys Glu Pro Leu Tyr Val Gly Gly Ala Pro Asp Phe
                500                 505                 510

Ser Lys Leu Ala Arg Ala Ala Ala Val Ser Ser Gly Phe Asp Gly Ala
                515                 520                 525

Ile Gln Leu Val Ser Leu Gly Gly Arg Gln Leu Leu Thr Pro Glu His
                530                 535                 540

Val Leu Arg Gln Val Asp Val Thr Ser Phe Ala Gly His Pro Cys Thr
545                 550                 555                 560

Arg Ala Ser Gly His Pro Cys Leu Asn Gly Ala Ser Cys Val Pro Arg
                565                 570                 575

Glu Ala Ala Tyr Val Cys Leu Cys Pro Gly Gly Phe Ser Gly Pro His
                580                 585                 590

Cys Glu Lys Gly Leu Val Glu Lys Ser Ala Gly Asp Val Asp Thr Leu
                595                 600                 605

Ala Phe Asp Gly Arg Thr Phe Val Glu Tyr Leu Asn Ala Val Thr Glu
                610                 615                 620

Ser Glu Lys Ala Leu Gln Ser Asn His Phe Glu Leu Ser Leu Arg Thr
625                 630                 635                 640

Glu Ala Thr Gln Gly Leu Val Leu Trp Ser Gly Lys Ala Thr Glu Arg
                645                 650                 655

Ala Asp Tyr Val Ala Leu Ala Ile Val Asp Gly His Leu Gln Leu Ser
                660                 665                 670

Tyr Asn Leu Gly Ser Gln Pro Val Val Leu Arg Ser Thr Val Pro Val
                675                 680                 685

Asn Thr Asn Arg Trp Leu Arg Val Val Ala His Arg Glu Gln Arg Glu
                690                 695                 700

Gly Ser Leu Gln Val Gly Asn Glu Ala Pro Val Thr Gly Ser Ser Pro
705                 710                 715                 720

Leu Gly Ala Thr Gln Leu Asp Thr Asp Gly Ala Leu Trp Leu Gly Gly
```

```
                725             730             735

Leu Pro Glu Leu Pro Val Gly Pro Ala Leu Pro Lys Ala Tyr Gly Thr
            740             745             750

Gly Phe Val Gly Cys Leu Arg Asp Val Val Val Gly Arg His Pro Leu
        755             760             765

His Leu Leu Glu Asp Ala Val Thr Lys Pro Glu Leu Arg Pro Cys Pro
    770             775             780

Thr Pro
785

<210> SEQ ID NO 12
<211> LENGTH: 6
<212> TYPE: PRT
<213> ORGANISM: Artificial Sequence
<220> FEATURE:
<223> OTHER INFORMATION: Amino acid sequence of MMP3 cleavage
      recognition sequence

<400> SEQUENCE: 12

Pro His Thr Val Leu Asn
1               5

<210> SEQ ID NO 13
<211> LENGTH: 3936
<212> TYPE: DNA
<213> ORGANISM: Artificial Sequence
<220> FEATURE:
<223> OTHER INFORMATION: Polynucleotide sequence

<400> SEQUENCE: 13
cacgtgcgat ttatggactt tgactggttt cctgcgttta tcacgggggc cacgtcagga      60
gccattgctg cgggagccac ggccagagcc accactgcat cgcgcctgcc gtcctctgct     120
gtgacccctc gggccccgca ccccagtcac acaagccagc ccgttgccaa gaccacggca     180
gcccccacca cacgtcggcc ccccaccact gcccccagcc gtgtgcccgg acgtcggccc     240
ccggcccccc agcagcctcc aaagccctgt gactcacagc cctgcttcca cggggggacc     300
tgccaggact gggcattggg cggggggcttc acctgcagct gcccggcagg caggggaggc     360
gccgtctgtg agaaggtgct tggcgcccct gtgccggcct tcgagggccg ctccttcctg     420
gccttcccca ctctccgcgc ctaccacacg ctgcgcctgg cactggaatt ccgggcgctg     480
gagcctcagg ggctgctgct gtacaatggc aacgcccggg caaggactt cctggcattg     540 gcgctgctag atggccgcgt gcagctcagg tttgacacag gttcggggcc ggcggtgctg     600
accagtgccg tgccggtaga gccgggccag tggcaccgcc tggagctgtc ccggcactgg     660
cgccggggca ccctctcggt ggatggtgag acccctgttc tgggcgagag tcccagtggc     720
accgacggcc tcaacctgga cacagacctc tttgtgggcg cgtacccga ggaccaggct     780 gccgtggcgc tggagcggac cttcgtgggc gccggcctga gggggtgcat ccgtttgctg     840
gacgtcaaca accagcgcct ggagcttggc attgggccgg gggctgccac ccgaggctct     900
ggcgtgggcg agtgcgggga ccaccctgc ctgcccaacc cctgccatgg cggggcccca     960
tgccagaacc tggaggctgg aaggttccat tgccagtgcc cgcccggccg cgtcggacca    1020
acctgtgccg atgagaagag cccctgccag cccaaccect gccatgggggc ggcgccctgc    1080 cgtgtgctgc cgagggtgg tgctcagtgc gagtgccccc tggggcgtga gggcaccttc    1140
tgccagacag cctcggggca ggacggctct gggcccttcc tggctgactt caacggcttc    1200
tcccacctgg agctgagagg cctgcacacc tttgcacggg acctggggga gaagatggcg    1260
```

```
ctggaggtcg tgttcctggc acgaggcccc agcggcctcc tgctctacaa cgggcagaag      1320
acggacggca aggggggactt cgtgtcgctg gcactgcggg accgccgcct ggagttccgc      1380
tacgacctgg gcaagggggc agcggtcatc aggagcaggg agccagtcac cctgggagcc      1440
tggaccaggg tctcactgga gcgaaacggc cgcaagggtg ccctgcgtgt gggcgacggc      1500
ccccgtgtgt tgggggagtc cccggttccg cacaccgtcc tcaacctgaa ggagccgctc      1560
tacgtagggg gcgctcccga cttcagcaag ctggcccgtg ctgctgccgt gtcctctggc      1620
ttcgacggtg ccatccagct ggtctccctc ggaggccgcc agctgctgac cccggagcac      1680
gtgctgcggc aggtggacgt cacgtccttt gcaggtcacc cctgcacccg ggcctcaggc      1740
cacccctgcc tcaatggggc ctcctgcgtc ccgagggagg ctgcctatgt gtgcctgtgt      1800
cccgggggat tctcaggacc gcactgcgag aaggggctgg tggagaagtc agcggggggac      1860 gtggatacct tggcctttga cgggcggacc tttgtcgagt acctcaacgc tgtgaccgag      1920
agcgagaagg cactgcagag caaccacttt gaactgagcc tgcgcactga ggccacgcag      1980
gggctggtgc tctggagtgg caaggccacg gagcgggcag actatgtggc actggccatt      2040
gtggacgggc acctgcaact gagctacaac ctgggctccc agcccgtggt gctgcgttcc      2100
accgtgcccg tcaacaccaa ccgctggttg cgggtcgtgg cacataggga gcagagggaa      2160
ggttccctgc aggtgggcaa tgaggcccct gtgaccggct cctccccgct gggcgccacg      2220
cagctggaca ctgatggagc cctgtggctt gggggcctgc cggagctgcc cgtgggccca      2280
gcactgccca aggcctacgg cacaggcttt gtgggctgct tgcgggacgt ggtggtgggc      2340
cggcacccgc tgcacctgct ggaggacgcc gtcaccaagc cagagctgcg gccctgcccc      2400
accccagacg atgacgacaa gatcatccca gttgaggagg agaacccgga cttctggaac      2460
cgcgaggcag ccgaggccct gggtgccgcc aagaagctgc agcctgcaca gacagccgcc      2520
aagaacctca tcatcttcct gggcgatggg atgggggtgt ctacggtgac agctgccagg      2580
atcctaaaag ggcagaagaa ggacaaactg gggcctgaga tacccctggc catggaccgc      2640
ttcccatatg tggctctgtc caagacatac aatgtagaca aacatgtgcc agacagtgga      2700
gccacagcca cggcctacct gtgcggggtc aagggcaact tccagaccat tggcttgagt      2760
gcagccgccc gctttaacca gtgcaacacg cacgcggca acgaggtcat ctccgtgatg      2820
aatcgggcca agaaagcagg gaagtcagtg ggagtggtaa ccaccacacg agtgcagcac      2880
gcctcgccag ccggcaccta cgcccacacg gtgaaccgca actggtactc ggacgccgac      2940
gtgcctgcct cggcccgcca ggagggggtgc caggacatcg ctacgcagct catctccaac      3000
atggacattg acgtgatcct aggtggaggc cgaaagtaca tgtttcgcat gggaaccccca      3060 gaccctgagt acccagatga ctacagccaa ggtgggacca ggctggacgg gaagaatctg      3120
gtgcaggaat ggctggcgaa gcgccagggt gcccggtatg tgtggaaccg cactgagctc      3180
atgcaggctt ccctggaccc gtctgtgacc catctcatgg gtctctttga gcctggagac      3240
atgaaatacg agatccaccg agactccaca ctggaccccct ccctgatgga gatgacagag      3300
gctgccctgc gcctgctgag caggaacccc cgcggcttct tcctcttcgt ggagggtggt      3360
cgcatcgacc atggtcatca tgaaagcagg gcttaccggg cactgactga gacgatcatg      3420
ttcgacgacg ccattgagag ggcgggccag ctcaccagcg aggaggacac gctgagcctc      3480
gtcactgccg accactccca cgtcttctcc ttcggaggct accccctgcg agggagctcc      3540
atcttcgggc tggcccctgg caaggcccgg gacaggaagg cctacacggt cctcctatac      3600
```

-continued

```
ggaaacggtc caggctatgt gctcaaggac ggcgcccggc cggatgttac cgagagcgag      3660
agcgggagcc ccgagtatcg gcagcagtca gcagtgcccc tggacgaaga gacccacgca      3720
ggcgaggacg tggcggtgtt cgcgcgcggc ccgcaggcgc acctggttca cggcgtgcag      3780
gagcagacct tcatagcgca cgtcatggcc ttcgccgcct gcctggagcc ctacaccgcc      3840
tgcgacctgg cgccccccgc cggcaccacc gacgccgcgc acccgggtga acaaaaactc      3900
atctcagaag aggatctgca tcaccatcac catcac                                3936
```

<210> SEQ ID NO 14
<211> LENGTH: 1312
<212> TYPE: PRT
<213> ORGANISM: Artificial Sequence
<220> FEATURE:
<223> OTHER INFORMATION: Polypeptide sequence

<400> SEQUENCE: 14

```
His Val Arg Phe Met Asp Phe Asp Trp Phe Pro Ala Phe Ile Thr Gly
1               5                   10                  15

Ala Thr Ser Gly Ala Ile Ala Ala Gly Ala Thr Ala Arg Ala Thr Thr
            20                  25                  30

Ala Ser Arg Leu Pro Ser Ser Ala Val Thr Pro Arg Ala Pro His Pro
        35                  40                  45

Ser His Thr Ser Gln Pro Val Ala Lys Thr Thr Ala Ala Pro Thr Thr
    50                  55                  60

Arg Arg Pro Pro Thr Thr Ala Pro Ser Arg Val Pro Gly Arg Arg Pro
65                  70                  75                  80

Pro Ala Pro Gln Gln Pro Pro Lys Pro Cys Asp Ser Gln Pro Cys Phe
                85                  90                  95

His Gly Gly Thr Cys Gln Asp Trp Ala Leu Gly Gly Gly Phe Thr Cys
            100                 105                 110

Ser Cys Pro Ala Gly Arg Gly Gly Ala Val Cys Glu Lys Val Leu Gly
        115                 120                 125

Ala Pro Val Pro Ala Phe Glu Gly Arg Ser Phe Leu Ala Phe Pro Thr
    130                 135                 140

Leu Arg Ala Tyr His Thr Leu Arg Leu Ala Leu Glu Phe Arg Ala Leu
145                 150                 155                 160

Glu Pro Gln Gly Leu Leu Leu Tyr Asn Gly Asn Ala Arg Gly Lys Asp
                165                 170                 175

Phe Leu Ala Leu Ala Leu Leu Asp Gly Arg Val Gln Leu Arg Phe Asp
            180                 185                 190

Thr Gly Ser Gly Pro Ala Val Leu Thr Ser Ala Val Pro Val Glu Pro
        195                 200                 205

Gly Gln Trp His Arg Leu Glu Leu Ser Arg His Trp Arg Arg Gly Thr
    210                 215                 220

Leu Ser Val Asp Gly Glu Thr Pro Val Leu Gly Glu Ser Pro Ser Gly
225                 230                 235                 240

Thr Asp Gly Leu Asn Leu Asp Thr Asp Leu Phe Val Gly Gly Val Pro
                245                 250                 255

Glu Asp Gln Ala Ala Val Ala Leu Glu Arg Thr Phe Val Gly Ala Gly
            260                 265                 270

Leu Arg Gly Cys Ile Arg Leu Leu Asp Val Asn Asn Gln Arg Leu Glu
        275                 280                 285

Leu Gly Ile Gly Pro Gly Ala Ala Thr Arg Gly Ser Gly Val Gly Glu
    290                 295                 300
```

Cys Gly Asp His Pro Cys Leu Pro Asn Pro Cys His Gly Gly Ala Pro
305                 310                 315                 320

Cys Gln Asn Leu Glu Ala Gly Arg Phe His Cys Gln Cys Pro Pro Gly
                325                 330                 335

Arg Val Gly Pro Thr Cys Ala Asp Glu Lys Ser Pro Cys Gln Pro Asn
                340                 345                 350

Pro Cys His Gly Ala Ala Pro Cys Arg Val Leu Pro Glu Gly Gly Ala
                355                 360                 365

Gln Cys Glu Cys Pro Leu Gly Arg Glu Gly Thr Phe Cys Gln Thr Ala
370                 375                 380

Ser Gly Gln Asp Gly Ser Gly Pro Phe Leu Ala Asp Phe Asn Gly Phe
385                 390                 395                 400

Ser His Leu Glu Leu Arg Gly Leu His Thr Phe Ala Arg Asp Leu Gly
                405                 410                 415

Glu Lys Met Ala Leu Glu Val Val Phe Leu Ala Arg Gly Pro Ser Gly
                420                 425                 430

Leu Leu Leu Tyr Asn Gly Gln Lys Thr Asp Gly Lys Gly Asp Phe Val
                435                 440                 445

Ser Leu Ala Leu Arg Asp Arg Arg Leu Glu Phe Arg Tyr Asp Leu Gly
450                 455                 460

Lys Gly Ala Ala Val Ile Arg Ser Arg Glu Pro Val Thr Leu Gly Ala
465                 470                 475                 480

Trp Thr Arg Val Ser Leu Glu Arg Asn Gly Arg Lys Gly Ala Leu Arg
                485                 490                 495

Val Gly Asp Gly Pro Arg Val Leu Gly Glu Ser Pro Val Pro His Thr
                500                 505                 510

Val Leu Asn Leu Lys Glu Pro Leu Tyr Val Gly Gly Ala Pro Asp Phe
                515                 520                 525

Ser Lys Leu Ala Arg Ala Ala Ala Val Ser Ser Gly Phe Asp Gly Ala
530                 535                 540

Ile Gln Leu Val Ser Leu Gly Gly Arg Gln Leu Leu Thr Pro Glu His
545                 550                 555                 560

Val Leu Arg Gln Val Asp Val Thr Ser Phe Ala Gly His Pro Cys Thr
                565                 570                 575

Arg Ala Ser Gly His Pro Cys Leu Asn Gly Ala Ser Cys Val Pro Arg
                580                 585                 590

Glu Ala Ala Tyr Val Cys Leu Cys Pro Gly Gly Phe Ser Gly Pro His
                595                 600                 605

Cys Glu Lys Gly Leu Val Glu Lys Ser Ala Gly Asp Val Asp Thr Leu
610                 615                 620

Ala Phe Asp Gly Arg Thr Phe Val Glu Tyr Leu Asn Ala Val Thr Glu
625                 630                 635                 640

Ser Glu Lys Ala Leu Gln Ser Asn His Phe Glu Leu Ser Leu Arg Thr
                645                 650                 655

Glu Ala Thr Gln Gly Leu Val Leu Trp Ser Gly Lys Ala Thr Glu Arg
                660                 665                 670

Ala Asp Tyr Val Ala Leu Ala Ile Val Asp Gly His Leu Gln Leu Ser
                675                 680                 685

Tyr Asn Leu Gly Ser Gln Pro Val Val Leu Arg Ser Thr Val Pro Val
                690                 695                 700

Asn Thr Asn Arg Trp Leu Arg Val Val Ala His Arg Glu Gln Arg Glu
705                 710                 715                 720

Gly Ser Leu Gln Val Gly Asn Glu Ala Pro Val Thr Gly Ser Ser Pro

-continued

```
              725              730              735

Leu Gly Ala Thr Gln Leu Asp Thr Asp Gly Ala Leu Trp Leu Gly Gly
              740              745              750

Leu Pro Glu Leu Pro Val Gly Pro Ala Leu Pro Lys Ala Tyr Gly Thr
              755              760              765

Gly Phe Val Gly Cys Leu Arg Asp Val Val Val Gly Arg His Pro Leu
    770              775              780

His Leu Leu Glu Asp Ala Val Thr Lys Pro Glu Leu Arg Pro Cys Pro
785              790              795              800

Thr Pro Asp Asp Asp Lys Ile Ile Pro Val Glu Glu Glu Asn Pro
              805              810              815

Asp Phe Trp Asn Arg Glu Ala Ala Glu Ala Leu Gly Ala Ala Lys Lys
              820              825              830

Leu Gln Pro Ala Gln Thr Ala Ala Lys Asn Leu Ile Ile Phe Leu Gly
              835              840              845

Asp Gly Met Gly Val Ser Thr Val Thr Ala Ala Arg Ile Leu Lys Gly
    850              855              860

Gln Lys Lys Asp Lys Leu Gly Pro Glu Ile Pro Leu Ala Met Asp Arg
865              870              875              880

Phe Pro Tyr Val Ala Leu Ser Lys Thr Tyr Asn Val Asp Lys His Val
              885              890              895

Pro Asp Ser Gly Ala Thr Ala Thr Ala Tyr Leu Cys Gly Val Lys Gly
              900              905              910

Asn Phe Gln Thr Ile Gly Leu Ser Ala Ala Ala Arg Phe Asn Gln Cys
              915              920              925

Asn Thr Thr Arg Gly Asn Glu Val Ile Ser Val Met Asn Arg Ala Lys
    930              935              940

Lys Ala Gly Lys Ser Val Gly Val Val Thr Thr Thr Arg Val Gln His
945              950              955              960

Ala Ser Pro Ala Gly Thr Tyr Ala His Thr Val Asn Arg Asn Trp Tyr
              965              970              975

Ser Asp Ala Asp Val Pro Ala Ser Ala Arg Gln Glu Gly Cys Gln Asp
              980              985              990

Ile Ala Thr Gln Leu Ile Ser Asn  Met Asp Ile Asp Val  Ile Leu Gly
    995              1000              1005

Gly Gly Arg Lys Tyr Met Phe  Arg Met Gly Thr Pro  Asp Pro Glu
    1010              1015              1020

Tyr Pro Asp Asp Tyr Ser Gln  Gly Gly Thr Arg Leu  Asp Gly Lys
    1025              1030              1035

Asn Leu  Val Gln Glu Trp Leu  Ala Lys Arg Gln Gly  Ala Arg Tyr
    1040              1045              1050

Val Trp  Asn Arg Thr Glu Leu  Met Gln Ala Ser Leu  Asp Pro Ser
    1055              1060              1065

Val Thr  His Leu Met Gly Leu  Phe Glu Pro Gly Asp  Met Lys Tyr
    1070              1075              1080

Glu Ile  His Arg Asp Ser Thr  Leu Asp Pro Ser Leu  Met Glu Met
    1085              1090              1095

Thr Glu  Ala Ala Leu Arg Leu  Leu Ser Arg Asn Pro  Arg Gly Phe
    1100              1105              1110

Phe Leu  Phe Val Glu Gly Gly  Arg Ile Asp His Gly  His His Glu
    1115              1120              1125

Ser Arg  Ala Tyr Arg Ala Leu  Thr Glu Thr Ile Met  Phe Asp Asp
    1130              1135              1140
```

```
Ala Ile  Glu Arg Ala Gly Gln  Leu Thr Ser Glu Glu  Asp Thr Leu
    1145             1150              1155

Ser Leu  Val Thr Ala Asp His  Ser His Val Phe Ser  Phe Gly Gly
    1160             1165              1170

Tyr Pro  Leu Arg Gly Ser Ser  Ile Phe Gly Leu Ala  Pro Gly Lys
    1175             1180              1185

Ala Arg  Asp Arg Lys Ala Tyr  Thr Val Leu Leu Tyr  Gly Asn Gly
    1190             1195              1200

Pro Gly  Tyr Val Leu Lys Asp  Gly Ala Arg Pro Asp  Val Thr Glu
    1205             1210              1215

Ser Glu  Ser Gly Ser Pro Glu  Tyr Arg Gln Gln Ser  Ala Val Pro
    1220             1225              1230

Leu Asp  Glu Glu Thr His Ala  Gly Glu Asp Val Ala  Val Phe Ala
    1235             1240              1245

Arg Gly  Pro Gln Ala His Leu  Val His Gly Val Gln  Glu Gln Thr
    1250             1255              1260

Phe Ile  Ala His Val Met Ala  Phe Ala Ala Cys Leu  Glu Pro Tyr
    1265             1270              1275

Thr Ala  Cys Asp Leu Ala Pro  Pro Ala Gly Thr Thr  Asp Ala Ala
    1280             1285              1290

His Pro  Gly Glu Gln Lys Leu  Ile Ser Glu Glu Asp  Leu His His
    1295             1300              1305

His His  His His
    1310
```

<210> SEQ ID NO 15
<211> LENGTH: 2406
<212> TYPE: DNA
<213> ORGANISM: Artificial Sequence
<220> FEATURE:
<223> OTHER INFORMATION: Polynucleotide sequence

<400> SEQUENCE: 15

```
cacgtgcgat ttatggactt tgactggttt cctgcgttta tcacgggggc cacgtcagga      60
gccattgctg cgggagccac ggccagagcc accactgcat cgcgcctgcc gtcctctgct     120
gtgacccctc gggccccgca ccccagtcac acaagccagc ccgttgccaa gaccacggca     180
gcccccacca cacgtcggcc ccccaccact gcccccagcc gtgtgcccgg acgtcggccc     240
ccggcccccc agcagcctcc aaagccctgt gactcacagc cctgcttcca cggggggacc     300
tgccaggact gggcattggg cgggggcttc acctgcagct gcccggcagg cagggggaggc     360 gccgtctgtg agaaggtgct tggcgcccct gtgccggcct cgagggccg ctccttcctg     420 gccttcccca ctctccgcgc ctaccacacg ctgcgcctgg cactggaatt ccgggcgctg     480
gagcctcagg ggctgctgct gtacaatggc aacgcccggg gcaaggactt cctggcattg     540
gcgctgctag atggccgcgt gcagctcagg tttgacacag gttcggggcc ggcggtgctg     600
accagtgccg tgccggtaga gccgggccag tggcaccgcc tggagctgtc ccggcactgg     660 cgccgggggca ccctctcggt ggatggtgag acccctgttc tgggcgagag tcccagtggc     720
accgacggcc tcaacctgga cacagacctc tttgtgggcg cgtacccga ggaccaggct     780 gccgtggcgc tggagcggac cttcgtgggc gccggcctga gggggtgcat ccgtttgctg     840
gacgtcaaca accagcgcct ggagcttggc attgggccgg gggctgccac ccgaggctct     900
ggcgtgggcg agtgcggga ccacccctgc ctgcccaacc cctgccatgg cggggccccca     960
```

```
tgccagaacc tggaggctgg aaggttccat tgccagtgcc cgcccggccg cgtcggacca    1020
acctgtgccg atgagaagag cccctgccag cccaacccct gccatggggc ggcgccctgc    1080
cgtgtgctgc ccgagggtgg tgctcagtgc gagtgccccc tggggcgtga gggcaccttc    1140
tgccagacag cctcggggca ggacggctct gggcccttcc tggctgactt caacggcttc    1200
tcccacctgg agctgagagg cctgcacacc tttgcacggg acctggggga aagatggcg    1260 ctggaggtcg tgttcctggc acgaggcccc agcggcctcc tgctctacaa cgggcagaag    1320
acggacggca agggggactt cgtgtcgctg gcactgcggg accgccgcct ggagttccgc    1380
tacgacctgg gcaagggggc agcggtcatc aggagcaggg agccagtcac cctgggagcc    1440
tggaccaggg tctcactgga gcgaaacggc cgcaagggtg ccctgcgtgt gggcgacggc    1500
ccccgtgtgt ggggggagtc cccggttccg cacaccgtcc tcaacctgaa ggagccgctc    1560
tacgtagggg gcgctcccga cttcagcaag ctggcccgtg ctgctgccgt gtcctctggc    1620
ttcgacggtg ccatccagct ggtctccctc ggaggccgcc agctgctgac cccggagcac    1680
gtgctgcggc aggtggacgt cacgtccttt gcaggtcacc cctgcacccg ggcctcaggc    1740
cacccctgcc tcaatggggc ctcctgcgtc ccgagggagg ctgcctatgt gtgcctgtgt    1800
cccgggggat tctcaggacc gcactgcgag aaggggctgg tggagaagtc agcggggac    1860 gtggatacct tggcctttga cgggcggacc tttgtcgagt acctcaacgc tgtgaccgag    1920
agcgagaagg cactgcagag caaccacttt gaactgagcc tgcgcactga ggccacgcag    1980
gggctggtgc tctggagtgg caaggccacg gagcgggcag actatgtggc actggccatt    2040
gtggacgggc acctgcaact gagctacaac ctgggctccc agcccgtggt gctgcgttcc    2100
accgtgcccg tcaacaccaa ccgctggttg cgggtcgtgg cacataggga gcagagggaa    2160
ggttccctgc aggtgggcaa tgaggcccct gtgaccggct cctccccgct gggcgccacg    2220
cagctggaca ctgatggagc cctgtggctt gggggcctgc cggagctgcc cgtgggccca    2280
gcactgccca aggcctacgg cacaggcttt gtgggctgct tgcgggacgt ggtggtgggc    2340
cggcacccgc tgcacctgct ggaggacgcc gtcaccaagc agagctgcg gccctgcccc    2400 acccca                                                                2406
```

```
<210> SEQ ID NO 16
<211> LENGTH: 3948
<212> TYPE: DNA
<213> ORGANISM: Artificial Sequence
<220> FEATURE:
<223> OTHER INFORMATION: Polynucleotide sequence

<400> SEQUENCE: 16
cacgtgcgat ttatggactt tgactggttt cctgcgttta tcacgggggc cacgtcagga      60
gccattgctg cgggagccac ggccagagcc accactgcat cgcgcctgcc gtcctctgct     120
gtgacccctc gggccccgca ccccagtcac acaagccagc ccgttgccaa gaccacggca     180
gcccccacca cacgtcggcc ccccaccact gcccccagcc gtgtgcccgg acgtcggccc     240
ccggcccccc agcagcctcc aaagccctgt gactcacagc cctgcttcca cggggggacc     300
tgccaggact gggcattggg cggggggcttc acctgcagct gcccggcagg cagggggaggc     360 gccgtctgtg agaaggtgct tggcgcccct gtgccggcct tcgagggccg ctccttcctg     420
gccttcccca ctctccgcgc ctaccacacg ctgcgcctgg cactggaatt ccgggcgctg     480
gagcctcagg ggctgctgct gtacaatggc aacgcccggg gcaaggactt cctgcattg      540 gcgctgctag atggccgcgt gcagctcagg tttgacacag gttcggggcc ggcggtgctg     600
```

```
accagtgccg tgccggtaga gccgggccag tggcaccgcc tggagctgtc ccggcactgg    660
cgccggggca ccctctcggt ggatggtgag acccctgttc tgggcgagag tcccagtggc    720
accgacggcc tcaacctgga cacagacctc tttgtgggcg gcgtacccga ggaccaggct    780
gccgtggcgc tggagcggac cttcgtgggc gccggcctga gggggtgcat ccgtttgctg    840
gacgtcaaca accagcgcct ggagcttggc attgggccgg gggctgccac ccgaggctct    900
ggcgtgggcg agtgcgggga ccacccctgc ctgcccaacc cctgccatgg cggggcccca    960
tgccagaacc tggaggctgg aaggttccat tgccagtgcc cgcccggccg cgtcggacca   1020
acctgtgcca atgagaagag cccctgccag cccaacccct gccatggggc ggcgccctgc   1080
cgtgtgctgc ccgagggtgg tgctcagtgc gagtgccccc tggggcgtga gggcaccttc   1140
tgccagacag cctcggggca ggacggctct gggcccttcc tggctgactt caacggcttc   1200
tcccacctgg agctgagagg cctgcacacc tttgcacggg acctggggga gaagatggcg   1260
ctggaggtcg tgttcctggc acgaggcccc agcggcctcc tgctctacaa cgggcagaag   1320
acggacggca aggggggactt cgtgtcgctg gcactgcggg accgccgcct ggagttccgc   1380
tacgacctgg gcaaggggc agcggtcatc aggagcaggg agccagtcac cctgggagcc   1440
tggaccaggg tctcactgga gcgaaacggc cgcaagggtg ccctgcgtgt gggcgacggc   1500
ccccgtgtgt tggggggagtc cccggttccg gggggggggg tcaacctgaa ggagccgctc   1560
tacgtagggg gcgctcccga cttcagcaag ctggcccgtg ctgctgccgt gtcctctggc   1620
ttcgacggtg ccatccagct ggtctccctc ggaggccgcc agctgctgac cccggagcac   1680
gtgctgcggc aggtggacgt cacgtccttt gcaggtcacc cctgcacccg ggcctcaggc   1740
cacccctgcc tcaatggggc ctcctgcgtc ccgagggagg ctgcctatgt gtgcctgtgt   1800 cccggggggat tctcaggacc gcactgcgag aaggggctgg tggagaagtc agcggggggac   1860 gtggatacct tggcctttga cgggcggacc tttgtcgagt acctcaacgc tgtgaccgag   1920
agcgagaagg cactgcagag caaccacttt gaactgagcc tgcgcactga ggccacgcag   1980
gggctggtgc tctggagtgg caaggccacg gagcgggcag actatgtggc actggccatt   2040
gtggacgggc acctgcaact gagctacaac ctgggctccc agcccgtggt gctgcgttcc   2100
accgtgcccg tcaacaccaa ccgctggttg cgggtcgtgg cacatataggga gcagagggaa   2160 ggttccctgc aggtgggcaa tgaggccct gtgaccggct cctccccgct gggcgccacg   2220
cagctggaca ctgatggagc cctgtggctt ggggggcctgc cggagctgcc cgtgggccca   2280
gcactgccca aggcctacgg cacaggcttt gtgggctgct tgcgggacgt ggtggtgggc   2340
cggcacccgc tgcacctgct ggaggacgcc gtcaccaagc cagagctgcg gccctgcccc   2400
accccagacg atgacgacaa gatcatccca gttgaggagg agaacccgga cttctggaac   2460
cgcgaggcag ccgaggccct gggtgccgcc aagaagctgc agcctgcaca gacagccgcc   2520
aagaacctca tcatcttcct gggcgatggg atggggggtgt ctacggtgac agctgccagg   2580
atcctaaaag ggcagaagaa ggacaaactg gggcctgaga taccctggc catggaccgc   2640 ttcccatatg tggctctgtc caagacatac aatgtagaca aacatgtgcc agacagtgga   2700
gccacagcca cggcctacct gtgcggggtc aagggcaact tccagaccat tggcttgagt   2760
gcagccgccc gctttaacca gtgcaacacg acacgcggca acgaggtcat ctccgtgatg   2820
aatcgggcca agaaagcagg gaagtcagtg ggagtggtaa ccaccacacg agtgcagcac   2880
gcctcgccag ccggcaccta cgcccacacg gtgaaccgca actggtactc ggacgccgac   2940
```

```
gtgcctgcct cggcccgcca ggaggggtgc caggacatcg ctacgcagct catctccaac   3000
atggacattg acgtgatcct aggtggaggc cgaaagtaca tgtttcgcat gggaacccca   3060
gaccctgagt acccagatga ctacagccaa ggtgggacca ggctggacgg gaagaatctg   3120
gtgcaggaat ggctggcgaa cgcgccaggg tcccggtatg tgtggaaccg cactgagctc   3180
atgcaggctt ccctggaccc gtctgtgacc catctcatgg gtctctttga gcctggagac   3240
atgaaatacg agatccaccg agactccaca ctggacccct ccctgatgga gatgacagag   3300
gctgccctgc gcctgctgag caggaacccc cgcggcttct tcctcttcgt ggagggtggt   3360
cgcatcgacc atggtcatca tgaaagcagg gcttaccggg cactgactga gacgatcatg   3420
ttcgacgacg ccattgagag ggcgggccag ctcaccagcg aggaggacac gctgagcctc   3480
gtcactgccg accactccca cgtcttctcc ttcggaggct accccctgcg agggagctcc   3540
atcttcgggc tggcccctgg caaggcccgg gacaggaagg cctacacggt cctcctatac   3600
ggaaacggtc caggctatgt gctcaaggac ggcgcccggc cggatgttac cgagagcgag   3660
agcgggagcc ccgagtatcg gcagcagtca gcagtgcccc tggacgaaga gacccacgca   3720
ggcgaggacg tggcggtgtt cgcgcgcggc ccgcaggcgc acctggttca cggcgtgcag   3780
gagcagacct tcatagcgca cgtcatggcc ttcgccgcct gcctggagcc ctacaccgcc   3840
tgcgacctgg cgcccccgc cggcaccacc gacgccgcgc acccgggtga acaaaaactc   3900
atctcagaag aggatctgca ccaccaccat caccatcatc accaccac               3948
```

<210> SEQ ID NO 17
<211> LENGTH: 1316
<212> TYPE: PRT
<213> ORGANISM: Artificial Sequence
<220> FEATURE:
<223> OTHER INFORMATION: Polypeptide sequence

<400> SEQUENCE: 17

```
His Val Arg Phe Met Asp Phe Asp Trp Phe Pro Ala Phe Ile Thr Gly
1               5                   10                  15

Ala Thr Ser Gly Ala Ile Ala Ala Gly Ala Thr Ala Arg Ala Thr Thr
            20                  25                  30

Ala Ser Arg Leu Pro Ser Ser Ala Val Thr Pro Arg Ala Pro His Pro
        35                  40                  45

Ser His Thr Ser Gln Pro Val Ala Lys Thr Thr Ala Ala Pro Thr Thr
    50                  55                  60

Arg Arg Pro Pro Thr Thr Ala Pro Ser Arg Val Pro Gly Arg Arg Pro
65                  70                  75                  80

Pro Ala Pro Gln Gln Pro Pro Lys Pro Cys Asp Ser Gln Pro Cys Phe
                85                  90                  95

His Gly Gly Thr Cys Gln Asp Trp Ala Leu Gly Gly Gly Phe Thr Cys
            100                 105                 110

Ser Cys Pro Ala Gly Arg Gly Gly Ala Val Cys Glu Lys Val Leu Gly
        115                 120                 125

Ala Pro Val Pro Ala Phe Glu Gly Arg Ser Phe Leu Ala Phe Pro Thr
    130                 135                 140

Leu Arg Ala Tyr His Thr Leu Arg Leu Ala Leu Glu Phe Arg Ala Leu
145                 150                 155                 160

Glu Pro Gln Gly Leu Leu Leu Tyr Asn Gly Asn Ala Arg Gly Lys Asp
                165                 170                 175

Phe Leu Ala Leu Ala Leu Leu Asp Gly Arg Val Gln Leu Arg Phe Asp
            180                 185                 190
```

```
Thr Gly Ser Gly Pro Ala Val Leu Thr Ser Ala Val Pro Val Glu Pro
        195                 200                 205

Gly Gln Trp His Arg Leu Glu Leu Ser Arg His Trp Arg Arg Gly Thr
    210                 215                 220

Leu Ser Val Asp Gly Glu Thr Pro Val Leu Gly Glu Ser Pro Ser Gly
225                 230                 235                 240

Thr Asp Gly Leu Asn Leu Asp Thr Asp Leu Phe Val Gly Gly Val Pro
                245                 250                 255

Glu Asp Gln Ala Ala Val Ala Leu Glu Arg Thr Phe Val Gly Ala Gly
                260                 265                 270

Leu Arg Gly Cys Ile Arg Leu Leu Asp Val Asn Asn Gln Arg Leu Glu
        275                 280                 285

Leu Gly Ile Gly Pro Gly Ala Ala Thr Arg Gly Ser Gly Val Gly Glu
        290                 295                 300

Cys Gly Asp His Pro Cys Leu Pro Asn Pro Cys His Gly Gly Ala Pro
305                 310                 315                 320

Cys Gln Asn Leu Glu Ala Gly Arg Phe His Cys Gln Cys Pro Pro Gly
                325                 330                 335

Arg Val Gly Pro Thr Cys Ala Asp Glu Lys Ser Pro Cys Gln Pro Asn
        340                 345                 350

Pro Cys His Gly Ala Ala Pro Cys Arg Val Leu Pro Glu Gly Gly Ala
        355                 360                 365

Gln Cys Glu Cys Pro Leu Gly Arg Glu Gly Thr Phe Cys Gln Thr Ala
        370                 375                 380

Ser Gly Gln Asp Gly Ser Gly Pro Phe Leu Ala Asp Phe Asn Gly Phe
385                 390                 395                 400

Ser His Leu Glu Leu Arg Gly Leu His Thr Phe Ala Arg Asp Leu Gly
                405                 410                 415

Glu Lys Met Ala Leu Glu Val Val Phe Leu Ala Arg Gly Pro Ser Gly
                420                 425                 430

Leu Leu Leu Tyr Asn Gly Gln Lys Thr Asp Gly Lys Gly Asp Phe Val
        435                 440                 445

Ser Leu Ala Leu Arg Asp Arg Arg Leu Glu Phe Arg Tyr Asp Leu Gly
        450                 455                 460

Lys Gly Ala Ala Val Ile Arg Ser Arg Glu Pro Val Thr Leu Gly Ala
465                 470                 475                 480

Trp Thr Arg Val Ser Leu Glu Arg Asn Gly Arg Lys Gly Ala Leu Arg
                485                 490                 495

Val Gly Asp Gly Pro Arg Val Leu Gly Glu Ser Pro Val Pro Gly Gly
                500                 505                 510

Gly Leu Asn Leu Lys Glu Pro Leu Tyr Val Gly Gly Ala Pro Asp Phe
        515                 520                 525

Ser Lys Leu Ala Arg Ala Ala Ala Val Ser Ser Gly Phe Asp Gly Ala
        530                 535                 540

Ile Gln Leu Val Ser Leu Gly Gly Arg Gln Leu Leu Thr Pro Glu His
545                 550                 555                 560

Val Leu Arg Gln Val Asp Val Thr Ser Phe Ala Gly His Pro Cys Thr
                565                 570                 575

Arg Ala Ser Gly His Pro Cys Leu Asn Gly Ala Ser Cys Val Pro Arg
        580                 585                 590

Glu Ala Ala Tyr Val Cys Leu Cys Pro Gly Gly Phe Ser Gly Pro His
        595                 600                 605
```

-continued

```
Cys Glu Lys Gly Leu Val Glu Lys Ser Ala Gly Asp Val Asp Thr Leu
    610             615             620

Ala Phe Asp Gly Arg Thr Phe Val Glu Tyr Leu Asn Ala Val Thr Glu
625             630             635             640

Ser Glu Lys Ala Leu Gln Ser Asn His Phe Glu Leu Ser Leu Arg Thr
            645             650             655

Glu Ala Thr Gln Gly Leu Val Leu Trp Ser Gly Lys Ala Thr Glu Arg
            660             665             670

Ala Asp Tyr Val Ala Leu Ala Ile Val Asp Gly His Leu Gln Leu Ser
            675             680             685

Tyr Asn Leu Gly Ser Gln Pro Val Val Leu Arg Ser Thr Val Pro Val
    690             695             700

Asn Thr Asn Arg Trp Leu Arg Val Val Ala His Arg Glu Gln Arg Glu
705             710             715             720

Gly Ser Leu Gln Val Gly Asn Glu Ala Pro Val Thr Gly Ser Ser Pro
            725             730             735

Leu Gly Ala Thr Gln Leu Asp Thr Asp Gly Ala Leu Trp Leu Gly Gly
            740             745             750

Leu Pro Glu Leu Pro Val Gly Pro Ala Leu Pro Lys Ala Tyr Gly Thr
    755             760             765

Gly Phe Val Gly Cys Leu Arg Asp Val Val Val Gly Arg His Pro Leu
    770             775             780

His Leu Leu Glu Asp Ala Val Thr Lys Pro Glu Leu Arg Pro Cys Pro
785             790             795             800

Thr Pro Asp Asp Asp Asp Lys Ile Ile Pro Val Glu Glu Glu Asn Pro
            805             810             815

Asp Phe Trp Asn Arg Glu Ala Ala Glu Ala Leu Gly Ala Ala Lys Lys
            820             825             830

Leu Gln Pro Ala Gln Thr Ala Ala Lys Asn Leu Ile Ile Phe Leu Gly
    835             840             845

Asp Gly Met Gly Val Ser Thr Val Thr Ala Ala Arg Ile Leu Lys Gly
    850             855             860

Gln Lys Lys Asp Lys Leu Gly Pro Glu Ile Pro Leu Ala Met Asp Arg
865             870             875             880

Phe Pro Tyr Val Ala Leu Ser Lys Thr Tyr Asn Val Asp Lys His Val
            885             890             895

Pro Asp Ser Gly Ala Thr Ala Thr Ala Tyr Leu Cys Gly Val Lys Gly
            900             905             910

Asn Phe Gln Thr Ile Gly Leu Ser Ala Ala Ala Arg Phe Asn Gln Cys
    915             920             925

Asn Thr Thr Arg Gly Asn Glu Val Ile Ser Val Met Asn Arg Ala Lys
    930             935             940

Lys Ala Gly Lys Ser Val Gly Val Val Thr Thr Thr Arg Val Gln His
945             950             955             960

Ala Ser Pro Ala Gly Thr Tyr Ala His Thr Val Asn Arg Asn Trp Tyr
            965             970             975

Ser Asp Ala Asp Val Pro Ala Ser Ala Arg Gln Glu Gly Cys Gln Asp
            980             985             990

Ile Ala Thr Gln Leu Ile Ser Asn  Met Asp Ile Asp Val  Ile Leu Gly
    995             1000             1005

Gly Gly  Arg Lys Tyr Met Phe  Arg Met Gly Thr Pro  Asp Pro Glu
    1010             1015             1020

Tyr Pro  Asp Asp Tyr Ser Gln  Gly Gly Thr Arg Leu  Asp Gly Lys
```

```
        1025                1030                1035

Asn Leu  Val Gln Glu Trp Leu  Ala Lys Arg Gln Gly  Ala Arg Tyr
    1040                1045                1050

Val Trp  Asn Arg Thr Glu Leu  Met Gln Ala Ser Leu  Asp Pro Ser
    1055                1060                1065

Val Thr  His Leu Met Gly Leu  Phe Glu Pro Gly Asp  Met Lys Tyr
    1070                1075                1080

Glu Ile  His Arg Asp Ser Thr  Leu Asp Pro Ser Leu  Met Glu Met
    1085                1090                1095

Thr Glu  Ala Ala Leu Arg Leu  Leu Ser Arg Asn Pro  Arg Gly Phe
    1100                1105                1110

Phe Leu  Phe Val Glu Gly Gly  Arg Ile Asp His Gly  His His Glu
    1115                1120                1125

Ser Arg  Ala Tyr Arg Ala Leu  Thr Glu Thr Ile Met  Phe Asp Asp
    1130                1135                1140

Ala Ile  Glu Arg Ala Gly Gln  Leu Thr Ser Glu Glu  Asp Thr Leu
    1145                1150                1155

Ser Leu  Val Thr Ala Asp His  Ser His Val Phe Ser  Phe Gly Gly
    1160                1165                1170

Tyr Pro  Leu Arg Gly Ser Ser  Ile Phe Gly Leu Ala  Pro Gly Lys
    1175                1180                1185

Ala Arg  Asp Arg Lys Ala Tyr  Thr Val Leu Leu Tyr  Gly Asn Gly
    1190                1195                1200

Pro Gly  Tyr Val Leu Lys Asp  Gly Ala Arg Pro Asp  Val Thr Glu
    1205                1210                1215

Ser Glu  Ser Gly Ser Pro Glu  Tyr Arg Gln Gln Ser  Ala Val Pro
    1220                1225                1230

Leu Asp  Glu Glu Thr His Ala  Gly Glu Asp Val Ala  Val Phe Ala
    1235                1240                1245

Arg Gly  Pro Gln Ala His Leu  Val His Gly Val Gln  Glu Gln Thr
    1250                1255                1260

Phe Ile  Ala His Val Met Ala  Phe Ala Ala Cys Leu  Glu Pro Tyr
    1265                1270                1275

Thr Ala  Cys Asp Leu Ala Pro  Pro Ala Gly Thr Thr  Asp Ala Ala
    1280                1285                1290

His Pro  Gly Glu Gln Lys Leu  Ile Ser Glu Glu Asp  Leu His His
    1295                1300                1305

His His  His His His His His  His
    1310                1315
```

<210> SEQ ID NO 18
<211> LENGTH: 2406
<212> TYPE: DNA
<213> ORGANISM: Artificial Sequence
<220> FEATURE:
<223> OTHER INFORMATION: Polynucleotide sequence

<400> SEQUENCE: 18

```
cacgtgcgat ttatggactt tgactggttt cctgcgttta tcacggggggc cacgtcagga      60 gccattgctg cgggagccac ggccagagcc accactgcat cgcgcctgcc gtcctctgct     120
gtgacccctc gggccccgca ccccagtcac acaagccagc ccgttgccaa gaccacggca     180
gcccccacca cacgtcggcc ccccaccact gcccccagcc gtgtgcccgg acgtcggccc     240
ccggcccccc agcagcctcc aaagccctgt gactcacagc cctgcttcca cggggggacc     300
```

-continued

```
tgccaggact gggcattggg cgggggcttc acctgcagct gcccggcagg caggggaggc    360
gccgtctgtg agaaggtgct tggcgcccct gtgccggcct tcgagggccg ctccttcctg    420
gccttcccca ctctccgcgc ctaccacacg ctgcgcctgg cactggaatt ccgggcgctg    480
gagcctcagg ggctgctgct gtacaatggc aacgcccggg gcaaggactt cctggcattg    540
gcgctgctag atggccgcgt gcagctcagg tttgacacag gttcggggcc ggcggtgctg    600
accagtgccg tgccggtaga gccgggccag tggcaccgcc tggagctgtc ccggcactgg    660
cgccggggca ccctctcggt ggatggtgag acccctgttc tgggcgagag tcccagtggc    720
accgacggcc tcaacctgga cacagacctc tttgtgggcg cgtacccga ggaccaggct     780 gccgtggcgc tggagcggac cttcgtgggc gccggcctga gggggtgcat ccgtttgctg    840
gacgtcaaca accagcgcct ggagcttggc attgggccgg gggctgccac ccgaggctct    900
ggcgtgggcg agtgcgggga ccacccctgc ctgcccaacc cctgccatgg cggggcccca    960
tgccagaacc tggaggctgg aaggttccat tgccagtgcc cgcccggccg cgtcggacca    1020
acctgtgccg atgagaagag cccctgccag cccaacccct gccatggggc ggcgccctgc    1080
cgtgtgctgc ccgagggtgg tgctcagtgc gagtgccccc tggggcgtga gggcaccttc    1140
tgccagacag cctcggggca ggacggctct gggcccttcc tggctgactt caacggcttc    1200
tcccacctgg agctgagagg cctgcacacc tttgcacggg acctggggga gaagatggcg    1260
ctggaggtcg tgttcctggc acgaggcccc agcggcctcc tgctctacaa cgggcagaag    1320
acggacggca aggggggactt cgtgtcgctg gcactgcggg accgccgcct ggagttccgc    1380
tacgacctgg caagggggc agcggtcatc aggagcaggg agccagtcac cctgggagcc    1440
tggaccaggg tctcactgga gcgaaacggc cgcaagggtg ccctgcgtgt gggcgacggc    1500
ccccgtgtgt tgggggagtc cccggttccg gggggggggc tcaacctgaa ggagccgctc    1560
tacgtagggg gcgctcccga cttcagcaag ctggcccgtg ctgctgccgt gtcctctggc    1620
ttcgacggtg ccatccagct ggtctccctc ggaggccgcc agctgctgac cccggagcac    1680
gtgctgcggc aggtggacgt cacgtccttt gcaggtcacc cctgcacccg ggcctcaggc    1740 caccctgcc tcaatggggc ctcctgcgtc ccgaggagg ctgcctatgt gtgcctgtgt      1800
cccgggggat tctcaggacc gcactgcgag aaggggctgg tggagaagtc agcgggggac    1860
gtggatacct tggcctttga cgggcggacc tttgtcgagt acctcaacgc tgtgaccgag    1920
agcgagaagg cactgcagag caaccacttt gaactgagcc tgcgcactga ggccacgcag    1980
gggctggtgc tctggagtgg caaggccacg gagcgggcag actatgtggc actggccatt    2040
gtggacgggc acctgcaact gagctacaac ctgggctccc agcccgtggt gctgcgttcc    2100
accgtgcccg tcaacaccaa ccgctggttg cgggtcgtgg cacataggga gcagagggaa    2160
ggttccctgc aggtgggcaa tgaggcccct gtgaccggct cctccccgct gggcgccacg    2220
cagctggaca ctgatggagc cctgtggctt gggggcctgc cggagctgcc cgtgggccca    2280
gcactgccca aggcctacgg cacaggcttt gtgggctgct tgcgggacgt ggtggtgggc    2340
cggcacccgc tgcacctgct ggaggacgcc gtcaccaagc agagctgcg ccctgccccc    2400 acccca                                                                2406
```

```
<210> SEQ ID NO 19
<211> LENGTH: 802
<212> TYPE: PRT
<213> ORGANISM: Artificial Sequence
<220> FEATURE:
<223> OTHER INFORMATION: Polypeptide sequence
```

<400> SEQUENCE: 19

His Val Arg Phe Met Asp Phe Asp Trp Phe Pro Ala Phe Ile Thr Gly
1               5                   10                  15

Ala Thr Ser Gly Ala Ile Ala Ala Gly Ala Thr Ala Arg Ala Thr Thr
            20                  25                  30

Ala Ser Arg Leu Pro Ser Ser Ala Val Thr Pro Arg Ala Pro His Pro
        35                  40                  45

Ser His Thr Ser Gln Pro Val Ala Lys Thr Thr Ala Ala Pro Thr Thr
    50                  55                  60

Arg Arg Pro Pro Thr Thr Ala Pro Ser Arg Val Pro Gly Arg Arg Pro
65                  70                  75                  80

Pro Ala Pro Gln Gln Pro Pro Lys Pro Cys Asp Ser Gln Pro Cys Phe
                85                  90                  95

His Gly Gly Thr Cys Gln Asp Trp Ala Leu Gly Gly Gly Phe Thr Cys
            100                 105                 110

Ser Cys Pro Ala Gly Arg Gly Gly Ala Val Cys Glu Lys Val Leu Gly
        115                 120                 125

Ala Pro Val Pro Ala Phe Glu Gly Arg Ser Phe Leu Ala Phe Pro Thr
    130                 135                 140

Leu Arg Ala Tyr His Thr Leu Arg Leu Ala Leu Glu Phe Arg Ala Leu
145                 150                 155                 160

Glu Pro Gln Gly Leu Leu Leu Tyr Asn Gly Asn Ala Arg Gly Lys Asp
                165                 170                 175

Phe Leu Ala Leu Ala Leu Leu Asp Gly Arg Val Gln Leu Arg Phe Asp
            180                 185                 190

Thr Gly Ser Gly Pro Ala Val Leu Thr Ser Ala Val Pro Val Glu Pro
        195                 200                 205

Gly Gln Trp His Arg Leu Glu Leu Ser Arg His Trp Arg Arg Gly Thr
    210                 215                 220

Leu Ser Val Asp Gly Glu Thr Pro Val Leu Gly Glu Ser Pro Ser Gly
225                 230                 235                 240

Thr Asp Gly Leu Asn Leu Asp Thr Asp Leu Phe Val Gly Gly Val Pro
            245                 250                 255

Glu Asp Gln Ala Ala Val Ala Leu Glu Arg Thr Phe Val Gly Ala Gly
            260                 265                 270

Leu Arg Gly Cys Ile Arg Leu Leu Asp Val Asn Asn Gln Arg Leu Glu
        275                 280                 285

Leu Gly Ile Gly Pro Gly Ala Ala Thr Arg Gly Ser Gly Val Gly Glu
    290                 295                 300

Cys Gly Asp His Pro Cys Leu Pro Asn Pro Cys His Gly Gly Ala Pro
305                 310                 315                 320

Cys Gln Asn Leu Glu Ala Gly Arg Phe His Cys Gln Cys Pro Pro Gly
            325                 330                 335

Arg Val Gly Pro Thr Cys Ala Asp Glu Lys Ser Pro Cys Gln Pro Asn
            340                 345                 350

Pro Cys His Gly Ala Ala Pro Cys Arg Val Leu Pro Glu Gly Gly Ala
        355                 360                 365

Gln Cys Glu Cys Pro Leu Gly Arg Glu Gly Thr Phe Cys Gln Thr Ala
    370                 375                 380

Ser Gly Gln Asp Gly Ser Gly Pro Phe Leu Ala Asp Phe Asn Gly Phe
385                 390                 395                 400

Ser His Leu Glu Leu Arg Gly Leu His Thr Phe Ala Arg Asp Leu Gly

-continued

```
                  405                 410                 415
Glu Lys Met Ala Leu Glu Val Val Phe Leu Ala Arg Gly Pro Ser Gly
            420                 425                 430
Leu Leu Leu Tyr Asn Gly Gln Lys Thr Asp Gly Lys Gly Asp Phe Val
            435                 440                 445
Ser Leu Ala Leu Arg Asp Arg Arg Leu Glu Phe Arg Tyr Asp Leu Gly
        450                 455                 460
Lys Gly Ala Ala Val Ile Arg Ser Arg Glu Pro Val Thr Leu Gly Ala
465                 470                 475                 480
Trp Thr Arg Val Ser Leu Glu Arg Asn Gly Arg Lys Gly Ala Leu Arg
                485                 490                 495
Val Gly Asp Gly Pro Arg Val Leu Gly Glu Ser Pro Val Pro Gly Gly
            500                 505                 510
Gly Leu Asn Leu Lys Glu Pro Leu Tyr Val Gly Gly Ala Pro Asp Phe
            515                 520                 525
Ser Lys Leu Ala Arg Ala Ala Ala Val Ser Ser Gly Phe Asp Gly Ala
        530                 535                 540
Ile Gln Leu Val Ser Leu Gly Gly Arg Gln Leu Leu Thr Pro Glu His
545                 550                 555                 560
Val Leu Arg Gln Val Asp Val Thr Ser Phe Ala Gly His Pro Cys Thr
                565                 570                 575
Arg Ala Ser Gly His Pro Cys Leu Asn Gly Ala Ser Cys Val Pro Arg
            580                 585                 590
Glu Ala Ala Tyr Val Cys Leu Cys Pro Gly Gly Phe Ser Gly Pro His
            595                 600                 605
Cys Glu Lys Gly Leu Val Glu Lys Ser Ala Gly Asp Val Asp Thr Leu
        610                 615                 620
Ala Phe Asp Gly Arg Thr Phe Val Glu Tyr Leu Asn Ala Val Thr Glu
625                 630                 635                 640
Ser Glu Lys Ala Leu Gln Ser Asn His Phe Glu Leu Ser Leu Arg Thr
                645                 650                 655
Glu Ala Thr Gln Gly Leu Val Leu Trp Ser Gly Lys Ala Thr Glu Arg
                660                 665                 670
Ala Asp Tyr Val Ala Leu Ala Ile Val Asp Gly His Leu Gln Leu Ser
            675                 680                 685
Tyr Asn Leu Gly Ser Gln Pro Val Val Leu Arg Ser Thr Val Pro Val
            690                 695                 700
Asn Thr Asn Arg Trp Leu Arg Val Val Ala His Arg Glu Gln Arg Glu
705                 710                 715                 720
Gly Ser Leu Gln Val Gly Asn Glu Ala Pro Val Thr Gly Ser Ser Pro
                725                 730                 735
Leu Gly Ala Thr Gln Leu Asp Thr Asp Gly Ala Leu Trp Leu Gly Gly
                740                 745                 750
Leu Pro Glu Leu Pro Val Gly Pro Ala Leu Pro Lys Ala Tyr Gly Thr
                755                 760                 765
Gly Phe Val Gly Cys Leu Arg Asp Val Val Val Gly Arg His Pro Leu
            770                 775                 780
His Leu Leu Glu Asp Ala Val Thr Lys Pro Glu Leu Arg Pro Cys Pro
785                 790                 795                 800
Thr Pro
```

The invention claimed is:

1. A soluble polypeptide comprising the amino acid sequence of SEQ ID NO: 3 or a variant thereof having at least 98% sequence identity to SEQ ID NO: 3, wherein the soluble polypeptide is a fragment of human agrin or a variant of human agrin and consists of up to 900 consecutive amino acids of said human agrin or said variant of human agrin; and wherein the soluble polypeptide has the ability to induce chondrocyte differentiation and/or chondrogenesis.

2. The soluble polypeptide of claim 1, consisting of up to 850 or 802 consecutive amino acids of said human agrin or said variant of human agrin.

3. The soluble polypeptide of claim 1, comprising or consisting of the amino acid sequence of SEQ ID NO: 3.

4. The soluble polypeptide of claim 1, wherein the soluble polypeptide is resistant to cleavage by MMP3.

5. The soluble polypeptide of claim 4, wherein at least one amino acid selected from the amino acids corresponding to positions 1753, 1754, 1755, 1756, 1757 and 1758 of SEQ ID NO: 1 is deleted or substituted with another amino acid.

6. The soluble polypeptide of claim 1, wherein the soluble polypeptide is a recombinant polypeptide.

7. The soluble polypeptide of claim 1, wherein the soluble polypeptide retains:

a) an ability to promote differentiation of chondrocytes;

b) an ability to induce chondrogenesis in mesenchymal stem cells;

c) an inability to induce MMP-13 or COL10A1 expression;

d) an ability to induce SOX9 expression;

e) an ability to induce COL2A1 expression;

f) an ability to induce aggrecan expression;

g) an ability to induce cartilage production; and/or h) an ability to induce the differentiation of mesenchymal stem cells of synovial membrane origin or mesenchymal stem cells of GDF5 lineage, as compared to the human agrin of SEQ ID NO: 1.

8. A polynucleotide encoding the soluble polypeptide of claim 1.

9. A composition comprising the soluble polypeptide of claim 1 and at least one pharmaceutically acceptable diluent, carrier, or preservative.

10. A method of treating osteoarthritis or an osteochondral defect in a subject, the method comprising administering to the subject the composition of claim 9.

11. The method of claim 10, wherein administering the composition comprises intra-articular or systemic delivery.

12. A method for inducing chondrogenic differentiation of mesenchymal stem cells, comprising contacting the mesenchymal stem cells with the soluble polypeptide of claim 1.

13. The method of claim 12, wherein the mesenchymal stem cells are of GDF5 lineage.

14. The method of claim 12, wherein the mesenchymal stem cells are of synovial membrane origin.

* * * * *